US011535887B2

(12) United States Patent
Gallant et al.

(10) Patent No.: US 11,535,887 B2
(45) Date of Patent: Dec. 27, 2022

(54) METHODS FOR SPATIAL ANALYSIS USING TARGETED RNA DEPLETION

(71) Applicant: 10x Genomics, Inc., Pleasanton, CA (US)

(72) Inventors: Caroline Julie Gallant, Stockholm (SE); Linda Kvastad, Solna (SE)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

(21) Appl. No.: 17/546,625

(22) Filed: Dec. 9, 2021

(65) Prior Publication Data

US 2022/0090181 A1  Mar. 24, 2022

Related U.S. Application Data

(63) Continuation of application No. PCT/US2021/028397, filed on Apr. 21, 2021.

(60) Provisional application No. 63/014,054, filed on Apr. 22, 2020.

(51) Int. Cl.
*C12Q 1/6837* (2018.01)

(52) U.S. Cl.
CPC ................ *C12Q 1/6837* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 5,002,882 A | 3/1991 | Lunnen |
| 5,130,238 A | 7/1992 | Malek |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,582,977 A | 12/1996 | Yue |
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,750,341 A | 5/1998 | Macevicz |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 5,925,545 A | 7/1999 | Reznikoff et al. |
| 5,958,775 A | 9/1999 | Wickstrrom |
| 5,965,443 A | 10/1999 | Reznikoff et al. |
| 6,013,440 A | 1/2000 | Lipshutz |
| 6,027,889 A | 2/2000 | Barany et al. |
| 6,060,240 A | 5/2000 | Kamb et al. |
| 6,130,073 A | 10/2000 | Eggerding |
| 6,143,496 A | 11/2000 | Brown |
| 6,153,389 A | 11/2000 | Haarer |
| 6,159,736 A | 12/2000 | Reznikoff et al. |
| 6,165,714 A | 12/2000 | Lane et al. |
| 6,210,891 B1 | 4/2001 | Nyren |
| 6,210,894 B1 | 4/2001 | Brennan |
| 6,214,587 B1 | 4/2001 | Dattagupta |
| 6,251,639 B1 | 6/2001 | Kura |
| 6,258,568 B1 | 7/2001 | Nyren |
| 6,266,459 B1 | 7/2001 | Walt |
| 6,268,148 B1 | 7/2001 | Barany et al. |
| 6,274,320 B1 | 8/2001 | Rothberg |
| 6,291,180 B1 | 9/2001 | Chu |
| 6,300,063 B1 | 10/2001 | Lipshutz et al. |
| 6,309,824 B1 | 10/2001 | Drmanac |
| 6,344,316 B1 | 2/2002 | Lockhart |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |

(Continued)

FOREIGN PATENT DOCUMENTS

| | | |
|---|---|---|
| CN | 1680604 | 10/2005 |
| CN | 101221182 | 7/2008 |

(Continued)

OTHER PUBLICATIONS

Schwers et al., "A High-Sensitivity, Medium-Density, and Target Amplification-Free Planar Waveguide Microarray System for Gene Expression Analysis of Formalin-Fixed and Paraffin-Embedded Tissue" 55(11) Clinical Chemistry 1995-2003 (Year: 2009).*
U.S. Appl. No. 60/416,118, filed Oct. 3, 2002, Fan et al.
U.S. Appl. No. 61/267,363, filed Dec. 7, 2009, Fan et al.
[No Author Listed], "Chromium Next GEM Single Cell 3' Reagent Kits v3.1—User Guide," 10x Genomics, Document No. CG000204, Nov. 2019, 58 pages.
[No Author Listed], "HuSNP Mapping Assay User's Manual," Affymetrix Part No. 90094 (Affymetrix, Santa Clara, Calif.), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).
[No Author Listed], "Proseek® Multiplex 96x96 User Manual," Olink Proteomics, Olink Bioscience, Uppsala, Sweden, 2017, 20 pages.

(Continued)

*Primary Examiner* — Nancy J Leith
(74) *Attorney, Agent, or Firm* — Fish & Richardson P.C.

(57) ABSTRACT

Provided herein are methods for spatial analysis using targeted RNA depletion.

30 Claims, 32 Drawing Sheets

Specification includes a Sequence Listing.

(56) References Cited

U.S. PATENT DOCUMENTS

| | | |
|---|---|---|
| 6,544,732 B1 | 4/2003 | Chee |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,890,741 B2 | 5/2005 | Fan et al. |
| 6,897,023 B2 | 5/2005 | Fu |
| 6,913,881 B1 | 7/2005 | Aizenstein et al. |
| 6,942,968 B1 | 9/2005 | Dickinson et al. |
| 7,011,944 B2 | 3/2006 | Prudent et al. |
| 7,057,026 B2 | 6/2006 | Barnes |
| 7,083,980 B2 | 8/2006 | Reznikoff et al. |
| 7,115,400 B1 | 10/2006 | Adessi |
| 7,118,883 B2 | 10/2006 | Inoue |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 | 8/2007 | Lao |
| 7,258,976 B2 | 8/2007 | Mitsuhashi |
| 7,282,328 B2 | 10/2007 | Kong et al. |
| 7,297,518 B2 | 11/2007 | Quake |
| 7,329,492 B2 | 2/2008 | Hardin |
| 7,358,047 B2 | 4/2008 | Hafner et al. |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,537,897 B2 | 5/2009 | Brenner |
| 7,563,576 B2 | 7/2009 | Chee |
| 7,579,153 B2 | 8/2009 | Brenner |
| 7,582,420 B2 | 9/2009 | Oliphant et al. |
| 7,601,492 B2 | 10/2009 | Fu et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,709,198 B2 | 5/2010 | Luo et al. |
| 7,776,547 B2 | 8/2010 | Roth |
| 7,776,567 B2 | 8/2010 | Mao |
| 7,803,943 B2 | 9/2010 | Mao |
| 7,888,009 B2 | 2/2011 | Barany et al. |
| 7,892,747 B2 | 2/2011 | Barany et al. |
| 7,914,981 B2 | 3/2011 | Barany et al. |
| 7,955,794 B2 | 6/2011 | Shen et al. |
| 7,960,119 B2 | 6/2011 | Chee |
| 8,003,354 B2 | 8/2011 | Shen et al. |
| 8,076,063 B2 | 12/2011 | Fan |
| 8,092,784 B2 | 1/2012 | Mao |
| 8,148,068 B2 | 4/2012 | Brenner |
| 8,206,917 B2 | 6/2012 | Chee |
| 8,288,103 B2 | 10/2012 | Oliphant |
| 8,383,338 B2 | 2/2013 | Kitzman |
| 8,460,865 B2 | 6/2013 | Chee |
| 8,481,257 B2 | 7/2013 | Van Eijk |
| 8,481,292 B2 | 7/2013 | Casbon |
| 8,481,698 B2 | 7/2013 | Lieberman et al. |
| 8,507,204 B2 | 8/2013 | Pierce et al. |
| 8,551,710 B2 | 10/2013 | Bernitz et al. |
| 8,568,979 B2 | 10/2013 | Stuelpnagel et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,685,889 B2 | 4/2014 | Van Eijk |
| 8,741,564 B2 | 6/2014 | Seligmann |
| 8,741,606 B2 | 6/2014 | Casbon |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 9,005,891 B2 | 4/2015 | Sinicropi et al. |
| 9,023,768 B2 | 5/2015 | Van Eijk |
| 9,062,348 B1 | 6/2015 | Van Eijk |
| 9,080,210 B2 | 7/2015 | Van Eijk |
| 9,194,001 B2 | 11/2015 | Brenner |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,598 B2 | 6/2016 | Chee |
| 9,376,716 B2 | 6/2016 | Van Eijk |
| 9,376,719 B2 | 6/2016 | Van Eijk |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,574,230 B2 | 2/2017 | Van Eijk |
| 9,593,365 B2 | 3/2017 | Frisen et al. |
| 9,598,728 B2 | 3/2017 | Barany et al. |
| 9,657,335 B2 | 5/2017 | Van Eijk |
| 9,670,542 B2 | 6/2017 | Van Eijk |
| 9,702,004 B2 | 7/2017 | Van Eijk |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,991 B2 | 2/2018 | Sinicropi et al. |
| 9,938,566 B2 | 4/2018 | Shepard et al. |
| 9,957,550 B2 | 5/2018 | Yeakley et al. |
| 10,002,316 B2 | 6/2018 | Fodor et al. |
| 10,023,907 B2 | 7/2018 | Van Eijk |
| 10,030,261 B2 | 7/2018 | Frisen et al. |
| 10,041,949 B2 | 8/2018 | Bendall et al. |
| 10,059,989 B2 | 8/2018 | Giresi et al. |
| 10,059,990 B2 | 8/2018 | Boyden et al. |
| 10,095,832 B2 | 10/2018 | Van Eijk |
| 10,144,966 B2 | 12/2018 | Cantor |
| 10,208,982 B2 | 2/2019 | Bannish et al. |
| 10,273,541 B2 | 4/2019 | Hindson et al. |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,550,429 B2 | 2/2020 | Harada et al. |
| 10,633,648 B2 | 4/2020 | Seelig et al. |
| 10,724,078 B2 | 7/2020 | Van Driel et al. |

(56) References Cited

U.S. PATENT DOCUMENTS

| | | |
|---|---|---|
| 10,774,372 B2 | 9/2020 | Chee et al. |
| 10,774,374 B2 | 9/2020 | Frisen et al. |
| 10,787,701 B2 | 9/2020 | Chee |
| 10,829,803 B2 | 11/2020 | Terbrueggen et al. |
| 10,913,975 B2 | 2/2021 | So et al. |
| 10,914,730 B2 | 2/2021 | Chee et al. |
| 10,927,403 B2 | 2/2021 | Chee et al. |
| 11,008,607 B2 | 5/2021 | Chee |
| 11,046,996 B1 | 6/2021 | Chee et al. |
| 11,067,567 B2 | 7/2021 | Chee |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 2001/0055764 A1 | 12/2001 | Empendocles et al. |
| 2002/0040275 A1 | 4/2002 | Cravatt |
| 2002/0048766 A1 | 4/2002 | Doyle et al. |
| 2002/0055100 A1 | 5/2002 | Kawashima |
| 2002/0086441 A1 | 7/2002 | Baranov et al. |
| 2002/0164611 A1 | 11/2002 | Bamdad |
| 2003/0017451 A1 | 1/2003 | Wang |
| 2003/0022207 A1 | 1/2003 | Balasubramanian |
| 2003/0064398 A1 | 4/2003 | Barnes |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0215936 A1 | 11/2003 | Kallioniemi et al. |
| 2003/0224419 A1 | 12/2003 | Corcoran |
| 2003/0232348 A1 | 12/2003 | Jones et al. |
| 2003/0232382 A1 | 12/2003 | Brennan |
| 2004/0019005 A1 | 1/2004 | Van Ness |
| 2004/0033499 A1 | 2/2004 | Ilsley et al. |
| 2004/0067492 A1 | 4/2004 | Peng et al. |
| 2004/0067493 A1 | 4/2004 | Matsuzaki |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0224326 A1 | 11/2004 | Kim et al. |
| 2004/0235103 A1 | 11/2004 | Reznikoff et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0100900 A1 | 5/2005 | Kawashima et al. |
| 2005/0130173 A1 | 6/2005 | Leamon et al. |
| 2005/0136414 A1 | 6/2005 | Gunderson et al. |
| 2005/0164292 A1 | 7/2005 | Farooqui |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0260653 A1 | 11/2005 | LaBaer |
| 2005/0266417 A1 | 12/2005 | Barany et al. |
| 2006/0046313 A1 | 3/2006 | Roth |
| 2006/0084078 A1 | 4/2006 | Zhao |
| 2006/0105352 A1 | 5/2006 | Qiao et al. |
| 2006/0188901 A1 | 8/2006 | Barnes et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0026430 A1 | 2/2007 | Andersen et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0166705 A1 | 7/2007 | Milton et al. |
| 2007/0172873 A1 | 7/2007 | Brenner et al. |
| 2007/0207482 A1 | 9/2007 | Church et al. |
| 2007/0254305 A1 | 11/2007 | Paik et al. |
| 2007/0269805 A1 | 11/2007 | Hogers |
| 2008/0003586 A1 | 1/2008 | Hyde et al. |
| 2008/0009420 A1 | 1/2008 | Schroth et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0153086 A1 | 6/2008 | Wong |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0000052 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu |
| 2009/0127589 A1 | 5/2009 | Rothberg et al. |
| 2009/0155781 A1 | 6/2009 | Drmanac et al. |
| 2009/0170713 A1 | 7/2009 | van Eijk et al. |
| 2009/0233802 A1 | 9/2009 | Bignell et al. |
| 2009/0253581 A1 | 10/2009 | van Eijk et al. |
| 2009/0283407 A1 | 11/2009 | Van Eijk |
| 2009/0291854 A1 | 11/2009 | Weisinger-Mayr et al. |
| 2009/0312193 A1 | 12/2009 | Kim et al. |
| 2010/0035249 A1 | 2/2010 | Hayashizaki et al. |
| 2010/0069263 A1 | 3/2010 | Shendure et al. |
| 2010/0105052 A1 | 4/2010 | Drmanac et al. |
| 2010/0120043 A1 | 5/2010 | Sood et al. |
| 2010/0120097 A1 | 5/2010 | Matz et al. |
| 2010/0120098 A1 | 5/2010 | Grunenwald et al. |
| 2010/0129874 A1 | 5/2010 | Mitra et al. |
| 2010/0145037 A1 | 6/2010 | Brive et al. |
| 2010/0173384 A1 | 7/2010 | Johnsson et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1 | 10/2010 | May et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0111409 A1 | 5/2011 | Sinicropi et al. |
| 2011/0152111 A1 | 6/2011 | Illumina |
| 2011/0245101 A1 | 10/2011 | Chee et al. |
| 2011/0245111 A1 | 10/2011 | Chee |
| 2011/0287435 A1 | 11/2011 | Grunenwald et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | van Eijk et al. |
| 2012/0202698 A1 | 8/2012 | van Eijk et al. |
| 2012/0202704 A1 | 8/2012 | Fan et al. |
| 2012/0252702 A1 | 10/2012 | Muratani et al. |
| 2012/0258871 A1 | 10/2012 | Kozlov et al. |
| 2012/0289414 A1 | 11/2012 | Mita et al. |
| 2013/0005594 A1 | 1/2013 | Terbrueggen et al. |
| 2013/0005600 A1 | 1/2013 | Olek |
| 2013/0035239 A1 | 2/2013 | Kong et al. |

(56) References Cited

U.S. PATENT DOCUMENTS

| | | |
|---|---|---|
| 2013/0079232 A1 | 3/2013 | Kain et al. |
| 2013/0171621 A1 | 7/2013 | Luo et al. |
| 2013/0244884 A1 | 9/2013 | Jacobson |
| 2013/0261019 A1 | 10/2013 | Lin et al. |
| 2013/0338042 A1 | 12/2013 | Shen et al. |
| 2014/0066318 A1 | 3/2014 | Frisen et al. |
| 2014/0121118 A1 | 5/2014 | Warner |
| 2014/0274731 A1 | 9/2014 | Raymond et al. |
| 2014/0323330 A1 | 10/2014 | Glezer et al. |
| 2014/0342921 A1 | 11/2014 | Weiner |
| 2015/0000854 A1 | 1/2015 | Gann-Fetter et al. |
| 2016/0019337 A1 | 1/2016 | Roberts et al. |
| 2016/0024576 A1 | 1/2016 | Chee |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0333403 A1 | 11/2016 | Chee |
| 2017/0016053 A1 | 1/2017 | Beechem et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg et al. |
| 2017/0166962 A1 | 6/2017 | van Eijk et al. |
| 2017/0220733 A1 | 8/2017 | Zhuang et al. |
| 2017/0233722 A1 | 8/2017 | Seelig et al. |
| 2017/0241911 A1 | 8/2017 | Rockel et al. |
| 2017/0335410 A1 | 11/2017 | Driscoll et al. |
| 2017/0349940 A1 | 12/2017 | Morin et al. |
| 2018/0051322 A1 | 2/2018 | Church et al. |
| 2018/0057873 A1 | 3/2018 | Zhou et al. |
| 2018/0094316 A1 | 4/2018 | Oliphant et al. |
| 2018/0112209 A1 | 4/2018 | Eshoo |
| 2018/0112261 A1 | 4/2018 | Van Driel et al. |
| 2018/0163265 A1 | 6/2018 | Zhang et al. |
| 2018/0179591 A1 | 6/2018 | van Eijk |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0237864 A1 | 8/2018 | Imler et al. |
| 2018/0245142 A1 | 8/2018 | So et al. |
| 2018/0247017 A1 | 8/2018 | van Eijk et al. |
| 2018/0291439 A1 | 10/2018 | van Eijk et al. |
| 2018/0305681 A1 | 10/2018 | Jovanovich et al. |
| 2018/0312822 A1 | 11/2018 | Lee et al. |
| 2019/0055594 A1 | 2/2019 | Samusik et al. |
| 2019/0085383 A1 | 3/2019 | Church et al. |
| 2019/0145982 A1 | 5/2019 | Chee et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0194709 A1 | 6/2019 | Church et al. |
| 2019/0203275 A1 | 7/2019 | Frisen et al. |
| 2019/0218276 A1 | 7/2019 | Regev et al. |
| 2019/0262831 A1 | 8/2019 | West et al. |
| 2019/0264268 A1 | 8/2019 | Frisen et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0330617 A1 | 10/2019 | Church et al. |
| 2019/0360043 A1* | 11/2019 | Pham ............... C12Q 1/6874 |
| 2019/0367969 A1 | 12/2019 | Belhocine et al. |
| 2020/0010891 A1 | 1/2020 | Beechem et al. |
| 2020/0024641 A1 | 1/2020 | Nolan et al. |
| 2020/0048690 A1 | 2/2020 | Chee |
| 2020/0063195 A1 | 2/2020 | Chee |
| 2020/0063196 A1 | 2/2020 | Chee |
| 2020/0080136 A1 | 3/2020 | Zhang et al. |
| 2020/0109443 A1 | 4/2020 | Chee |
| 2020/0199565 A1 | 6/2020 | Chen et al. |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0095331 A1 | 4/2021 | Fan et al. |
| 2021/0123040 A1 | 4/2021 | Macosko et al. |
| 2021/0140982 A1 | 5/2021 | Uytingco et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0049294 A1 | 2/2022 | Uytingco et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0098576 A1 | 3/2022 | Dadhwal |
| 2022/0098661 A1 | 3/2022 | Chew et al. |
| 2022/0106632 A1 | 4/2022 | Galonska et al. |

(56) References Cited

U.S. PATENT DOCUMENTS

| | | |
|---|---|---|
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |

FOREIGN PATENT DOCUMENTS

| | | |
|---|---|---|
| CN | 108949924 | 12/2018 |
| EP | 1782737 | 5/2007 |
| EP | 1910562 | 4/2008 |
| EP | 1923471 | 5/2008 |
| EP | 2002017 | 12/2008 |
| EP | 2292788 | 3/2011 |
| EP | 2302070 | 3/2011 |
| EP | 2881465 | 6/2015 |
| EP | 3013984 | 5/2016 |
| EP | 3511423 | 7/2019 |
| EP | 3541956 | 9/2019 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 2000/17390 | 3/2000 |
| WO | WO 2001/06012 | 1/2001 |
| WO | WO 2001/009363 | 2/2001 |
| WO | WO 2001/042796 | 6/2001 |
| WO | WO 2001/090415 | 11/2001 |
| WO | WO 2001/096608 | 12/2001 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/124771 | 11/2006 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/022332 | 2/2008 |
| WO | WO 2008/069906 | 6/2008 |
| WO | WO 2009/032167 | 3/2009 |
| WO | WO 2009/152928 | 12/2009 |
| WO | WO 2010/019826 | 2/2010 |
| WO | WO 2010/027870 | 3/2010 |
| WO | WO 2010/126614 | 11/2010 |
| WO | WO 2011/008502 | 1/2011 |
| WO | WO 2011/062933 | 5/2011 |
| WO | WO 2011/068088 | 6/2011 |
| WO | WO 2012/049316 | 4/2012 |
| WO | WO 2012/071428 | 5/2012 |
| WO | WO 2012/129242 | 9/2012 |
| WO | WO 2012/159089 | 11/2012 |
| WO | WO 2013/123442 | 8/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2014/044724 | 3/2014 |
| WO | WO 2014/144713 | 9/2014 |
| WO | WO 2014/152397 | 9/2014 |
| WO | WO 2014/210223 | 12/2014 |
| WO | WO 2014/210225 | 12/2014 |
| WO | WO 2015/161173 | 10/2015 |
| WO | WO 2016/138496 | 9/2016 |
| WO | WO 2016/138500 | 9/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/075293 | 5/2017 |
| WO | WO 2017/096158 | 7/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/045181 | 3/2018 |
| WO | WO 2018/064640 | 4/2018 |
| WO | WO 2018/085599 | 5/2018 |
| WO | WO 2018/091676 | 5/2018 |
| WO | WO 2018/102577 | 6/2018 |
| WO | WO 2018/136856 | 7/2018 |
| WO | WO 2018/144582 | 8/2018 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/113457 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2020/028194 | 2/2020 |
| WO | WO 2020/047002 | 3/2020 |
| WO | WO 2020/047005 | 3/2020 |
| WO | WO 2020/047010 | 3/2020 |
| WO | WO 2020/053655 | 3/2020 |
| WO | WO 2020/056381 | 3/2020 |
| WO | WO 2020/061064 | 3/2020 |
| WO | WO 2020/061066 | 3/2020 |
| WO | WO 2020/061108 | 3/2020 |
| WO | WO 2020/076979 | 4/2020 |
| WO | WO 2020/112604 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/176788 | 9/2020 |
| WO | WO 2020/190509 | 9/2020 |
| WO | WO 2020/206285 | 10/2020 |
| WO | WO 2020/219901 | 10/2020 |
| WO | WO 2020/243579 | 12/2020 |
| WO | WO 2021/041974 | 3/2021 |
| WO | WO 2021/067246 | 4/2021 |
| WO | WO 2021/091611 | 5/2021 |
| WO | WO 2021/092433 | 5/2021 |
| WO | WO 2021/097255 | 5/2021 |
| WO | WO 2021/119320 | 6/2021 |
| WO | WO 2021/133849 | 7/2021 |
| WO | WO 2021/168261 | 8/2021 |

(56) References Cited

FOREIGN PATENT DOCUMENTS

| | | |
|---|---|---|
| WO | WO 2021/168278 | 8/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/087273 | 4/2022 |
| WO | WO 2022/099037 | 5/2022 |
| WO | WO 2022/109181 | 5/2022 |

OTHER PUBLICATIONS

10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 69 pages.

10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0cH17rEk0UXwdl9It/e54d99fb08a8f1500aba503005a04a56/CG000238_VisiumSpatialTissueOptimizationUserGuide_RevD.pdf>, 42 pages.

Adessi et al., "Solid phase DNA amplification: characterisation of primer attachment and amplification mechanisms," Nucl. Acids Res., 2000, 28(20):E87, 8 pages.

Adiconis et al., "Comparative analysis of RNA sequencing methods for degraded or low-input samples," Nat Methods, Jul. 2013, 10(7):623-9.

Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.

Affymetrix, "Human Genome U95Av2," Internet Citation, retrieved from the internet: on the World Wide Web affymetrix.com, retrieved on Oct. 2, 2002, 1 page.

Alam, "Proximity Ligation Assay (PLA)," Curr Protoc Immunol., Nov. 2018, 123(1):e58, 8 pages.

Albretsen et al., "Applications of magnetic beads with covalently attached oligonucleotides in hybridization: Isolation and detection of specific measles virus mRNA from a crude cell lysate," Anal. Biochem., 1990, 189(1):40-50.

Allawi et al., "Thermodynamics and NMR of Internal GâT Mismatches in DNA," Biochemistry, 1996, 36(34):10581-10594.

Andresen et al., "Helicase-dependent amplification: use in OnChip amplification and potential for point-of-care diagnostics," Expert Rev Mol Diagn., Oct. 2009, 9(7):645-650.

Aran et al., "xCell: digitally portraying the tissue cellular heterogeneity landscape," Genome Biol., Nov. 2017, 18(1):220, 14 pages.

Archer et al., "Selective and flexible depletion of problematic sequences from RNA-seq libraries at the cDNA stage," BMC Genomics, May 2014, 15(1):401, 9 pages.

Armani et al, "2D-PCR: a method of mapping DNA in tissue sections," Lab Chip, 2009, 9(24):3526-34.

Atkinson el al., "An Updated Protocol for High Throughput Plant Tissue Sectioning," Front Plant Sci, 2017, 8:1721, 8 pages.

Atkinson, "Overview of Translation: Lecture Manuscript," U of Texas, 2000, DD, pp. 6.1-6.8.

Bains et al., "A novel method for nucleic acid sequence determination," Journal of Theoretical Biology, 1988, 135(3), 303-7.

Barnes, "PCR amplification of up to 35-kb DNA with high fidelity and high yield from lambda bacteriophage templates," Proc. Natl. Acad. Sci USA, 1994, 91(6):2216-2220.

Bartosovic et al., "Single-cell CUT&Tag profiles histone modifications and transcription factors in complex tissues," Nat Biotechnol., Jul. 2021, 39(7):825-835, Abstract.

Baugh et al., "Quantitative analysis of mRNA amplification by in vitro transcription," Nucleic Acids Res., 2001, 29(5):e29, 9 pages.

Beattie et al., "Advances in genosensor research," Clin Chem., May 1995, 41(5):700-6.

Beechem et al., "High-Plex Spatially Resolved RNA and Protein Detection Using Digital Spatial Profiling: A Technology Designed for Immuno-oncology Biomatker Discovery and Translational Research," Methods Mol Biol, 2020, Chapter 25, 2055:563-583.

Bell, "A simple way to treat PCR products prior to sequencing using ExoSAP-IT," Biotechniques, 2008, 44(6):834, 1 page.

Bentley et al., "Accurate whole human genome sequencing using reversible terminator chemistry," Nature, 2008, 456(7218):53-59.

Birney et al., "Identification and analysis of functional elements in 1% of the human genome by the ENCODE pilot project," Nature, 2007, 447(7146):799-816.

Blanchard et al., "High-density oligonucleotide arrays," Biosensors & Bioelectronics, 1996, 11(6-7):687-690.

Blokzijl et al., "Profiling protein expression and interactions: proximity ligation as a tool for personalized medicine," J Intern. Med., 2010, 268(3):232-245.

Blow, "Tissue Issues," Nature, 2007, 448(7156):959-962.

Bolognesi et al., "Multiplex Staining by Sequential Immunostaining and Antibody Removal on Routine Tissue Sections," J. Histochem. Cytochem., Aug. 2017, 65(8):431-444.

Brandon et al., "Mitochondrial mutations in cancer," Oncogene, 2006, 25(34):4647-4662.

Brenner et al., "Gene expression analysis by massively parallel signature sequencing (MPSS) on microbead arrays," Nat. Biotech., 2000, 18(6):630-634.

Brenner et al., "In vitro cloning of complex mixtures of DNA on microbeads: physical separation of differentially expressed cDNAs," Proc. Natl. Acad. Sci. USA, 2000, 97(4):1665-1670.

Brow, "35—The Cleavase I enzyme for mutation and polymorphism scanning," PCR Applications Protocols for Functional Genomics, 1999, pp. 537-550.

Brown et al., "Retroviral integration: structure of the initial covalent product and its precursor, and a role for the viral IN protein," Proc Natl Acad Sci USA, Apr. 1989, 86(8):2525-9.

Buenrostro et al., "Transposition of native chromatin for multimodal regulatory analysis and personal epigenomics," Nat Methods, Dec. 2013, 10(12):1213-1218.

Bullard et al., "Direct comparison of nick-joining activity of the nucleic acid ligases from bacteriophage T4," Biochem. J. 2006, 398(1):135-144.

Burgess, "A space for transcriptomics," Nature Reviews Genetics, 2016, 17(8):436-7.

Burgess, "Finding structure in gene expression," Nature Reviews Genetics, 2018, 19(5):249, 1 page.

Burton et al., "Coverslip Mounted-Immersion Cycled in Situ RT-PCR for the Localization of mRNA in Tissue Sections," Biotechniques, 1998, 24(1):92-100.

Cha et al., "Specificity, efficiency, and fidelity of PCR," Genome Res., 1993, 3(3):S18-29.

Chandra et al., "Cell-free synthesis-based protein microarrays and their applications," Proteomics, 2009, 5(6):717-30.

Chatterjee et al., "Mitochondrial DNA mutations in human cancer. Oncogene," 2006, 25(34):4663-4674.

Chen et al., "DNA hybridization detection in a microfluidic Channel using two fluorescently labelled nucleic acid probes," Biosensors and Bioelectronics, 2008, 23(12):1878-1882.

Chen et al., "Expansion microscopy," Science, 2015, 347(6221):543-548.

Chen et al., "Nanoscale imaging of RNA with expansion microscopy," Nat Methods, Aug. 2016, 13(8):679-84.

(56) References Cited

OTHER PUBLICATIONS

Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "Spatially resolved, highly multiplexed RNA profiling in single cells," Science, 2015, 348(6233):aaa6090, 21 pages.
Chen et al., "μCB-seq: microfluidic cell barcoding and sequencing for high-resolution imaging and sequencing of single cells," Lab Chip, Nov. 2020, 20(21):3899-3913.
Chrisey et al., "Covalent attachment of synthetic DNA to self-assembled monolayer films," Nucleic Acids Res., Aug. 1996, 24(15):3031-9.
Constantine et al., "Use of genechip high-density oligonucleotide arrays for gene expression monitoring," Life Sceience News, Amersham Life Science, 1998, pp. 11-14.
Corces et al., "An improved ATAC-seq protocol reduces background and enables interrogation of frozen tissues," Nat. Methods, 2017, 14(10):959-962.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cujec et al., "Selection of v-abl tyrosine kinase substrate sequences from randomized peptide and cellular proteomic libraries using mRNA display," Chemistry and Biology, 2002, 9(2):253-264.
Dahl et al., "Circle-to-circle amplification for precise and sensitive DNA analysis," Proc. Natl. Acad. Sci., 2004, 101(13):4548-4553.
Darmanis et al., "ProteinSeq: High-Performance Proteomic Analyses by Proximity, Ligation and Next Generation Sequencing," PLos One, 2011, 6(9):e25583, 10 pages.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Deamer et al., "Characterization of nucleic acids by nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.
Deng et al., "Spatial Epigenome Sequencing at Tissue Scale and Cellular Level," BioRxiv, Mar. 2021, 40 pages.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides," Anal. Biochem., 1988, 169(1):104-108.
Eberwine, "Amplification of mRNA populations using aRNA generated from immobilized oligo(dT)-T7 primed cDNA," BioTechniques, 1996, 20(4):584-91.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12): 1153-1155.

Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Counting individual DNA molecules by the stochastic attachment of diverse labels," PNAS, 2011, 108(22):9026-9031.
Fu et al., "Repeat subtraction-mediated sequence capture from a complex genome," Plant J., Jun. 2010, 62(5):898-909.
Fu et al., "Continuous Polony Gels for Tissue Mapping with High Resolution and RNA Capture Efficiency," bioRxiv, 2021, 20 pages.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gao et al., "Q&A: Expansion microscopy", BMC Biology, 15:50, 9 pages, 2017.
GenBank Accession No. M10098.1, "Human 18S rRNA gene, complete," Aug. 3, 1993, 2 pages.
GenBank Accession No. M11167.1, "Human 28S ribosomal RNA gene," Aug. 3, 1993, 2 pages.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gill et al., "Nucleic acid isothermal amplification technologies: a review," Nucleosides Nucleotides Nucleic Acids, Mar. 2008, 27(3):224-43.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goryshin et al., "Tn5 in vitro transposition," J Biol Chem., Mar. 1998, 273(13):7367-74.
Gracia Villacampa et al., "Genome-wide Spatial Expression Profiling in FFPE Tissues," bioRxiv, 2020, pp. 38 pages.
Grokhovsky, "Specificity of DNA cleavage by ultrasound," Molecular Biology, 2006, 40(2):276-283.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.
Guo et al.. "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hahnke et al., "Striptease on glass: validation of an improved stripping procedure for in situ microarrays," J Biotechnol., Jan. 2007, 128(1):1-13.

(56) References Cited

OTHER PUBLICATIONS

Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hejatko et al., "In situ hybridization technique for mRNA detection in whole mount *Arabidopsis* samples," Nature Protocols, 2006, 1(4):1939-1946.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains," PNAS, Oct. 2002, 99(20):12709-14.
Hu et al., "High reproducibility using sodium hydroxide-stripped long oligonucleotide DNA microarrays," Biotechniques, Jan. 2005, 38(1):121-4.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Kalinka et al., "Comparison of ethylene carbonate and formamide as components of the hybridization mixture in FISH," Scientia Agricola, 2021, 78(4):e20190315, 5 pages.
Kap et al., "Histological assessment of PAXgene tissue fixation and stabilization reagents," PLoS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistry, Aug. 3, 2015, 7(9):752-758.
Kaya-Okur et al., "CUT&Tag for efficient epigenomic profiling of small samples and single cells," Apr. 2019, 10(1):1930, 10 pages.
Kennedy-Darling et al., "Measuring the Formaldehyde Protein-DNA Cross-Link Reversal Rate," Analytical Chemistry, 2014, 86(12):5678-5681.
Kent et al., "Polymerase θ is a robust terminal transferase that oscillates between three different mechanisms during end-joining" Elife, Jun. 2016, 5:e13740, 25 pages.
Kirby et al., "Cryptic plasmids of *Mycobacterium avium*: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Korbel et al., "Paired-end mapping reveals extensive structural variation in the human genome," Science, 2007, 318(5849):420-426.
Kozlov et al., "A highly scalable peptide-based assay system for proteomics," PLoS ONE, 2012, 7(6):e37441, 10 pages.

Kozlov et al., "A method for rapid protease substrate evaluation and optimization," Comb Chem High Throughput Screen, 2006, 9(6):481-87.
Kristensen et al., "High-Throughput Methods for Detection of Genetic Variation," BioTechniques, Feb. 2001, 30(2):318-332.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lage et al., "Whole genome analysis of genetic alterations in small DNA samples using hyperbranched strand displacement amplification and array-CGH," Genome Research, 2003, 13(2):294-307.
Lampe et al., "A purified mariner transposase is sufficient to mediate transposition in vitro," Embo J., Oct. 1996, 15(19):5470-9.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Sensitive, multiplex and direct quantification of RNA sequences using a modified RASL assay," Nucleic Acids Research, 2014, 42(14):9146-9157.
Lee et al., "Fluorescent in situ sequencing (FISSEQ) of RNA for gene expression profiling in intact cells and tissues," Nature Protocols, 2015, 10(3):442-458.
Lee et al., "Improving the efficiency of genomic loci capture using oligonucleotide arrays for high throughput resequencing," BMC Genomics, Dec. 2009, 10:646, 12 pages.
Leriche et al., "Cleavable linkers in chemical biology," Bioorganic & Medicinal Chemistry, 2012, 20:571-582.
Li et al., "A photocleavable fluorescent nucleotide for DNA sequencing and analysis," Proc. Natl. Acad. Sci., 2003, 100(2):414-419.
Li et al., "An activity-dependent proximity ligation platform for spatially resolved quantification of active enzymes in single cells," Nat Commun, Nov. 2017, 8(1):1775, 12 pages.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Lin et al., "Highly multiplexed imaging of single cells using a high-throughput cyclic immunofluorescence method," Nat Commun., Sep. 2015, 6:8390, 7 pages.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Lizardi et al., "Mutation detection and single-molecule counting using isothermal rolling-circle amplification," Nat. Genet., 1998, 19(3):225-232.
Lovatt et al., "Transcriptome in vivo analysis (TIVA) of spatially defined single cells in live tissue," Nature Methods, 2013, 11(2):190-196.
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus," Gene, 1991, 108(1):1-6.
Lundberg et al., "Homogeneous antibody-based proximity extension assays provide sensitive and specific detection of low-abundant proteins in human blood," Nucleic Acids Res., 2011, 39(15):e102, 8 pages.
Lundberg et al., "Multiplexed homogeneous proximity ligation assays for high-throughput protein biomarker research in serological material," Mol Cell Proteomics, 2011, 10(4):M110.004978, 11 pages.

(56) References Cited

OTHER PUBLICATIONS

Lundin et al., "Increased throughput by parallelization of library preparation for massive sequencing," PLoS One, Apr. 2010, 5(4):e10029, 7 pages.
Lyck el al., "Immunohistochemical markers for quantitative studies of neurons and glia in human neocortex," J Histochem Cytochem, 2008, 56(3):201-21.
MacIntyre, "Unmasking antigens for immunohistochemistry.," Br J Biomed Sci., 2001, 58(3):190-6.
Marx, "Method of the Year: spatially resolved transcriptomics," Nature Methods, 2021, 18(1):9-14.
McCloskey et al., "Encoding PCR products with batch-stamps and barcodes," Biochem. Genet., 2007, 45(11-12):761-767.
Meers et al., "Improved CUT&RUN chromatin profiling tools," Elife, Jun. 2019, 8:e46314, 16 pages.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miele et al., "Mapping cis- and trans-chromatin interaction networks using chromosome conformation capture (3C)," Methods Mol Biol., 2009, 464:105-21.
Miller et al., "Basic concepts of microarrays and potential applications in clinical microbiology," Clinical Microbiology Reviews, 2009, 22(4):611-633.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Mizusawa et al., "A bacteriophage lambda vector for cloning with BamHI and Sau3A," Gene, 1982, 20(3):317-322.
Morlan et al., "Selective depletion of rRNA enables whole transcriptome profiling of archival fixed tissue," PLoS One, Aug. 2012, 7(8):e42882, 8 pages.
Motea et al., "Terminal deoxynucleotidyl transferase: the story of a misguided DNA polymerase," Biochim Biophys Acta., May 2010, 1804(5):1151-66.
Nandakumar et al., "How an RNA Ligase Discriminates RNA versus DNA Damage," Molecular Cell, 2004, 16:211-221.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Ng et al., "Gene identification signature (GIS) analysis for transcriptome characterization and genome annotation," Nature Methods, 2005, 2(2):105-111.
Nichols et al., "RNA Ligases," Curr Protoc Mol Biol., Oct. 2008, 84(1):3.15.1-3.15.4.
Nikiforov et al., "The use of 96-well polystyrene plates for DNA hybridization-based assays: an evaluation of different approaches to oligonucleotide immobilization," Anal Biochem, May 1995, 227(1):201-9.
Niklas et al., "Selective permeabilization for the high-throughput measurement of compartmented enzyme activities in mammalian cells," Anal Biochem, Sep. 2011, 416(2):218-27.
Nowak et al., "Entering the Postgenome Era," Science, 1995, 270(5235):368-71.
Ohtsubo et al., "Bacterial insertion sequences," Curr Top Microbiol Immunol., 1996, 204:1-26.
Pandey et al., "Inhibition of terminal deoxynucleotidyl transferase by adenine dinucleotides. Unique inhibitory action of Ap5A," FEBS Lett., Mar. 1987, 213(1):204-8.
Park et al., "Single cell trapping in larger microwells capable of supporting cell spreading and proliferation," Microfluid Nanofluid, 2010, 8:263-268.

PCT International Search Report and Written Opinion in International Appln. No. PCT/US2021/028397, dated Sep. 29, 2021, 20 pages.
PCT Invitation to Pay Additional Fees in International Appln. No. PCT/US2021/028397, dated Aug. 11, 2021, 12 pages.
PCT Invitation to Pay Additional Fees in International Appln. No. PCT/US2021/028397, dated Jun. 30, 2021, 14 pages.
Pemov et al., "DNA analysis with multiplex microarray-enhanced PCR," Nucl. Acids Res., Jan. 2005, 33(2):e11, 9 pages.
Perler et al., "Intervening sequences in an Archaea DNA polymerase gen," Proc Natl Acad Sci USA, Jun. 1992, 89(12):5577-5581.
Petterson et al., "Generations of sequencing technologies," Genomics, 2009, 93(2):105-111.
Picelli et al. "Tn5 transposase and tagmentation procedures for massively scaled sequencing projects," Genome Res., Dec. 2014, 24(12):2033-40.
Pipenburg et al., "DNA detection using recombination proteins," PLoS Biol., Jul. 2006, 4(7):e204, 7 pages.
Pirici et al., "Antibody elution method for multiple immunohistochemistry on primary antibodies raised in the same species and of the same subtypem," J. Histochem. Cytochem., Jun. 2009, 57(6):567-75.
Plasterk, "The Tcl/mariner transposon family," Curr Top Microbiol Immunol., 1996, 204:125-43.
Plongthongkum et al., "Advances in the profiling of DNA modifications: cytosine methylation and beyond," Nature Reviews Genetics, Aug. 2014, 15(10):647-661.
Polsky-Cynkin et al., "Use of DNA immobilized on plastic and agarose supports to detect DNA by sandwich hybridization," Clin. Chem., 1985, 31(9):1438-1443.
U.S. Appl. No. 61/267,363, filed Dec. 7, 2009, 33 pages.
Raab et al., "Human tRNA genes function as chromatin insulators," EMBO J., Jan. 2012, 31(2):330-50.
Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Reznikoff, "Tn5 as a model for understanding DNA transposition," Mol Microbiol., Mar. 2003, 47(5):1199-206.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Rouhanifard et al., "ClampFISH detects individual nucleic acid molecules using click chemistry-based amplification," Nat Biotechnol., Nov. 2018, 11 pages.
Roy et al., "Assessing long-distance RNA sequence connectivity via RNA-templated DNA-DNA ligation," eLife, 2015, 4:e03700, 21 pages.
Salmén et al., "Barcoded solid-phase RNA capture for Spatial Transcriptomics profiling in mammalian tissue sections," Nature Protocols, Oct. 2018, 13(11):2501-2534.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Schweitzer et al., "Multiplexed protein profiling on microarrays by rolling-circle amplification," Nature Biotechnology, Apr. 2002, 20(4):359-365.

(56) References Cited

OTHER PUBLICATIONS

Shalon et al., "A DNA microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Simonis et al., "Nuclear organization of active and inactive chromatin domains uncovered by chromosome conformation capture-on-chip (4C)," Nat Genet., Nov. 2006, 38(11):1348-54.
Skene et al., "An efficient targeted nuclease strategy for high-resolution mapping of DNA binding sites," Elife, Jan. 2017, 6:e21856, 35 pages.
Spitale et al., "Structural imprints in vivo decode RNA regulatorv mechanisms," Nature, 2015, 519(7544):486-90.
Stahl et al., "Visualization and analysis of gene expression in tissue sections by spatial transcriptomics," Science, Jun. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Trejo et al., "Extraction-free whole transcriptome gene expression analysis of FFPE sections and histology-directed subareas of tissue," PLoS ONE, Feb. 2019, 14(2):e0212031, 22 pages.
Twyman et al., "Techniques Patents for SNP Genotyping," Pharmacogenomics, Jan. 2003, 4(1):67-79.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Vandernoot et al., "cDNA normalization bv hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Velculescu et al., "Serial analysis of gene expression," Science, Oct. 1995, 270(5235):484-7.
Vickovic et al., "High-definition spatial transcriptomics for in situ tissue profiling," Nat Methods, Oct. 2019, 16(10):987-990.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "Imaging-based pooled CRISPR screening reveals regulators of lncRNA localization," Proc Natl Acad Sci USA, May 2019, 116(22):10842-10851.
Wang et al., "High-fidelity mRNA amplification for gene profiling," Nature Biotechnology, Apr. 2000, 18(4):457-459.
Wang, "RNA amplification for successful gene profiling analysis," J Transl Med., Jul. 2005, 3:28, 11 pages.
Weinreich et al., "Evidence that the cis Preference of the Tn5 Transposase is Caused by Nonproductive Multimerization," Genes and Development, Oct. 1994, 8(19):2363-2374.
Wiedmann et al., "Ligase chain reaction (LCR)—overview and applications," PCR Methods Appl., Feb. 1994, 3(4):S51-64.
Wilson et al., "New transposon delivery plasmids for insertional mutagenesis in Bacillus anthracis," J Microbiol Methods, Dec. 2007, 71(3):332-5.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.
Worthington et al., "Cloning of random oligonucleotides to create single-insert plasmid libraries," Anal Biochem, 2001, 294(2):169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Yeakley et al, "Profiling alternative splicing on fiber-optic arrays," Nature biotechnology, 2002, 20:353-358.
Yeakley et al., "A trichostatin A expression signature identified by TempO-Seq targeted whole transcriptome profiling," PLoS One, May 2017, 12(5):e0178302, 22 pages.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase," PNAS, 2005, 102(44):15815-20.
Zhang et al., "Archaeal RNA ligase from thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Multiplex ligation-dependent probe amplification (MLPA) for ultrasensitive multiplexed microRNA detection using ribonucleotide-modified DNA probes†," Chem. Commun., 2013, 49:10013-10015.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.

(56) References Cited

OTHER PUBLICATIONS

Zhu et al., "Reverse transcriptase template switching: a SMART approach for full-length cDNA library construction," Biotechniques, Apr. 2001, 30(4):892-897.
[No Author Listed], "Chromium Next GEM Single Cell 3' Reagent Kits v3.1 (Dual Index)—User Guide," 10x Genomics, Mar. 2021, Document No. CG000315, 61 pages.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw51ee9/6a2ac61cf6388a72564eeb9 6bc294967/CG000238_VisiumSpatialTissueOptimizationUserGuide_Rev_A.pdf>, 46 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0cH17rEk0UXwdl9It/e54d99fb08a8f1500aba503 005a04a56/CG000238_VisiumSpatialTissueOptimizationUserGuide_RevD.pdf>, 43 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVha1pexR/8baa08d9007157592b65 b2cdc7130990/CG000239_VisiumSpatialGeneExpression_UserGuide_RevD.pdf>, 70 pages.
Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Blanco et al., "A practical approach to FRET-based PNA fluorescence in situ hybridization," Methods, Dec. 2010, 52(4):343-51.
Cruz et al., "Methylation in cell-free DNA for early cancer detection," Ann Oncol., Jun. 2018, 29(6):1351-1353.
Czarnik, "Encoding methods for combinatorial chemistry," Curr Opin Chem Biol., Jun. 1997, 1(1):60-6.
Hamaguchi et al. "Direct reverse transcription-PCR on oligo(dT)-immobilized polypropylene microplates after capturing total mRNA from crude cell lysates," Clin Chem., Nov. 1998, 44(11):2256-63.
Ke et al., "In situ sequencing for RNA analysis in preserved tissue and cells," Nat Methods., Sep. 2013, Supplementary Materials, 29 pages.
MacBeath et al., "Printing proteins as microarrays for high-throughput function determination," Science, Sep. 2000, 289(5485):1760-1763.
Miner et al., "Molecular barcodes detect redundancy and contamination in hairpin-bisulfite PCR," Nucleic Acids Res., Sep. 2004, 32(17):e135, 4 pages.
Pellestor el al., "The peptide nucleic acids (PNAs), powerful tools for molecular genetics and cytogenetics," Eur J Hum Genet., Sep. 2004, 12(9):694-700.
Wang et al., "Tagmentation-based whole-genome bisulfite sequencing," Nature Protocols, Oct. 2013, 8(10):2022-2032.
U.S. Appl. No. 16/353,937, Frisen et al., filed Mar. 14, 2019.
U.S. Appl. No. 17/707,189, Chell el al., filed Mar. 29, 2022.
Wang et al., "Optimization of Process Conditions for Infected Animal Tissues by Alkaline Hydrolysis Technology," Procedia Environmental Sciences, 2016, 31:366-374.
Dalma-Weiszhausz et al., "The affymetrix GeneChip platform: an overview," Methods Enzymol., 2006, 410:3-28.
Fehlmann et al., "cPAS-based sequencing on the BGISEQ-500 to explore small non-coding RNAs," Clin Epigenetics, Nov. 2016, 8:123, 11 pages.
Illumina.com [online], "Ribo-Zero® rRNA Removal Kit Reference Guide," Aug. 2016, retrieved on Apr. 26. 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Lahiani et al., "Enabling Histopathological Annotations on Immunofluorescent Images through Virtualization of Hematoxylin and Eosin," J Pathol Inform., Feb. 2018, 9:1, 8 pages.
Lou et al., "A review of room temperature storage of biospecimen tissue and nucleic acids for anatomic pathology laboratories and biorepositories," Clin Biochem., Mar. 2014, 47(4-5):267-73.
Lykidis et al., "Novel zinc-based fixative for high quality DNA, RNA and protein analysis," Nucleic Acids Res., Jun. 2007, 35(12):e85, 10 pages.
Miller et al., "Chapter 11—Solid and Suspension Microarrays for Microbial Diagnostics," Methods in Microbiology, 2015, 42:395-431.
Nadji et al., "Immunohistochemistry of tissue prepared by a molecular-friendly fixation and processing system," Appl Immunohistochem Mol Morphol., Sep. 2005, 13(3):277-82.
Niedringhaus et al., "Landscape of next-generation sequencing technologies," Anal Chem., Jun. 2011, 83(12):4327-41.
Passow et al., "RNAlater and flash freezing storage methods nonrandomly influence observed gene expression in RNAseq experiments," bioRxiv, Jul. 2018, 28 pages.
Porreca et al., "Polony DNA sequencing," Curr Protoc Mol Biol., Nov. 2006, Chapter 7, Unit 7.8, pp. 7.8.1-7.8.22.
Qiu et al., "Combination probes with intercalating anchors and proximal fluorophores for DNA and RNA detection," Nucleic Acids Research, Sep. 2016, 44(17):e138, 12 pages.
Vickovic et al., "SM-Omics: An automated Platform for High-Throughput Spatial Multi-Omics," bioRxiv, Oct. 2020, 40 pages.
Wohnhaas et al., "DMSO cryopreservation is the method of choice to preserve cells for droplet-based single-cell RNA sequencing," Scientific Reports, Jul. 2019, 9(1):10699, 14 pages.
Zhao et al., "Isothermal Amplification of Nucleic Acids," Chemical Reviews, Nov. 2015, 115(22):12491-12545.
Asp et al., "Spatially Resolved Transcriptomes-Next Generation Tools for Tissue Exploration," Bioessays, Oct. 2020, 42(10):e1900221, 16 pages.
Balakrishnan et al., "Flap endonuclease 1," Annu Rev Biochem., Jun. 2013, 82:119-138.
Bergenstråhle et al., "Seamless integration of image and molecular analysis for spatial transcriptomics workflows," BMC Genomics, Jul. 2020, 21(1):482, 7 pages.
Berger et al., "Universal bases for hybridization, replication and chain termination," Nucleic Acid Res., Aug. 2000, 28(15):2911-2914.
Blair et al., "Microarray temperature optimization using hybridizition kinetics," Methods Mol Biol., 2009, 529:171-96.
Bolotin et al., "MiXCR: software for comprehensive adaptive immunity profiling," Nat Methods., May 2015, 12(5):380-1.
Chen et al., "Parallel single nucleotide polymorphism genotyping by surface invasive cleavage with universal detection," Anal Chem., Apr. 2005, 77(8):2400-5.
Chester et al., "Dimethyl sulfoxide-mediated primer Tm reduction: a method for analyzing the role of renaturation temperature in the polymerase chain reaction," Anal Biochem, Mar. 1993, 209(2):284-90.
Ciaccio et al., "Systems analysis of EGF receptor signaling dynamics with microwestern arrays," Nat Methods., Feb. 2010, 7(2):148-55.
Gerard et al., "Excess dNTPs minimize RNA hydrolysis during reverse transcription," Biotechniques, Nov. 2002, 33(5):984, 986, 988, 990.
Hessner et al., "Genotyping of factor V G1691A (Leiden) without the use of PCR by invasive cleavage of oligonucleotide probes," Clin Chem., Aug. 2000, 46(8 Pt 1):1051-6.
Hoffman et al., "Formaldehyde crosslinking: a tool for the study of chromatin complexes," J Biol Chem., Oct. 2015, 290(44):26404-11.
Hughes et al., "Microfluidic Western blotting," PNAS, Dec. 2012, 109(52):21450-21455.
Jucá et al., "Effect of dimethyl sulfoxide on reverse transcriptase activity," Braz. J. Med. Biol. Res., Mar. 1995, 28(3):285-90.

(56) References Cited

OTHER PUBLICATIONS

Kalantari et al., "Deparaffinization of formalin-fixed paraffin-embedded tissue blocks using hot water instead of xylene," Anal Biochem., Aug. 2016, 507:71-3.

Krzywkowski et al., "Chimeric padlock and iLock probes for increased efficiency of targeted RNA detection," RNA, Jan. 2019, 25(1):82-89.

Krzywkowski et al., "Fidelity of RNA templated end-joining by chlorella virus DNA ligase and a novel iLock assay with improved direct RNA detection accuracy," Nucleic Acids Research, Oct. 2017, 45(18):e161, 9 pages.

Lyamichev et al., "Invader assay for SNP genotyping," Methods Mol Biol., 2003, 212:229-40.

Lyamichev et al., "Polymorphism identification and quantitative detection of genomic DNA by invasive cleavage of oligonucleotide probes," Nat Biotechnol., Mar. 1999, 17(3):292-6.

Nilsson et al., "RNA-templated DNA ligation for transcript analysis," Nucleic Acids Res., Jan. 2001, 29(2):578-81.

Olivier, "The Invader assay for SNP genotyping," Mutat. Res., Jun. 2005, 573(1-2):103-110.

Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.

Perocchi et al., "Antisense artifacts in transcriptome microarray experiments are resolved by actinomycin D," Nucleic Acids Res., 2007, 35(19):e128, 7 pages.

Picelli et al., "Full-length RNA-seq from single cells using Smart-seq2," Nat Protoc., Jan. 2014, 9(1):171-81.

Schouten et al., "Relative quantification of 40 nucleic acid sequences by multiplex ligation-dependent probe amplification," Nucleic Acids Res., Jun. 2002, 30(12):e57, 13 pages.

Singh et al., "High-throughput targeted long-read single cell sequencing reveals the clonal and transcriptional landscape of lymphocytes," Nat Commun., Jul. 2019, 10(1):3120, 13 pages.

Sountoulidis et al., "SCRINSHOT, a spatial method for single-cell resolution mapping of cell states in tissue sections," PLoS Biol., Nov. 2020, 18(11):e3000675, 32 pages.

Spiess et al., "A highly efficient method for long-chain cDNA synthesis using trehalose and betaine," Anal. Biochem., Feb. 2002, 301(2):168-74.

Sutherland et al., "Utility of formaldehyde cross-linking and mass spectrometry in the study of protein-protein interactions," J. Mass Spectrom., Jun. 2008, 43(6):699-715.

Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.

Tu et al., "TCR sequencing paired with massively parallel 3' RNA-seq reveals clonotypic T cell signatures," Nature Immunology, Dec. 2019, 20(12):1692-1699.

Vázquez Bernat et al., "High-Quality Library Preparation for NGS-Based Immunoglobulin Germline Gene Inference and Repertoire Expression Analysis," Front Immunol., Apr. 2019, 10:660, 12 pages.

Wu et al., "RollFISH achieves robust quantification of single-molecule RNA biomarkers in paraffin-embedded tumor tissue samples," Commun Biol., Nov. 2018, 1:209, 8 pages.

Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.

Burgess, "Spatial transcriptomics coming of age," Nat Rev Genet., Jun. 2019, 20(6):317, 1 page.

Kumar et al., "Template-directed oligonucleotide strand ligation, covalent intramolecular DNA circularization and catenation using click chemistry," J Am Chem Soc., May 2007, 129(21):6859-64.

Ozsolak et al., "Digital transcriptome profiling from attomole-level RNA samples," Genome Res., Apr. 2010, 20(4):519-25.

* cited by examiner

SEQUENCE LISTING

<160> NUMBER OF SEQ ID NOS: 195

<210> SEQ ID NO 1
<211> LENGTH: 50
<212> TYPE: DNA
<213> ORGANISM: Artificial
<220> FEATURE:
<223> OTHER INFORMATION: Synthetic probe AG9327_18_1

<400> SEQUENCE: 1
taatgatcct tccgcaggtt cacctacgga aaccttgtta cgactttac      50

<210> SEQ ID NO 2
<211> LENGTH: 50
<212> TYPE: DNA
<213> ORGANISM: Artificial
<220> FEATURE:
<223> OTHER INFORMATION: Synthetic probe AG9328_18_2

<400> SEQUENCE: 2
ttcctctaga tagtcaagtt cgaccgtctt ctcagcgctc cgccagggcc      50

<210> SEQ ID NO 3
<211> LENGTH: 50
<212> TYPE: DNA
<213> ORGANISM: Artificial
<220> FEATURE:
<223> OTHER INFORMATION: Synthetic probe AG9329_18_3

<400> SEQUENCE: 3
gtgggccgac cccggcgggg ccgatccgag ggcctcacta aaccatccaa      50

<210> SEQ ID NO 4
<211> LENGTH: 50

```
<212> TYPE: DNA
<213> ORGANISM: Artificial
<220> FEATURE:
<223> OTHER INFORMATION: Synthetic probe AG9330_18_4

<400> SEQUENCE: 4
tcggtagtag cgacgggcgg tgtgtacaaa gggcagggac ttaatcaacg        50

<210> SEQ ID NO 5
<211> LENGTH: 50
<212> TYPE: DNA
<213> ORGANISM: Artificial
<220> FEATURE:
<223> OTHER INFORMATION: Synthetic probe AG9331_18_5

<400> SEQUENCE: 5
caagcttatg acccgcactt actcgggaat tccctcgttc atggggaata        50

<210> SEQ ID NO 6
<211> LENGTH: 50
<212> TYPE: DNA
<213> ORGANISM: Artificial
<220> FEATURE:
<223> OTHER INFORMATION: Synthetic probe AG9332_18_6

<400> SEQUENCE: 6
attgcaatcc ccgatcccca tcacgaatgg ggttcaacgg gttacccgcg        50

<210> SEQ ID NO 7
<211> LENGTH: 50
<212> TYPE: DNA
<213> ORGANISM: Artificial
<220> FEATURE:
<223> OTHER INFORMATION: Synthetic probe AG9333_18_7

<400> SEQUENCE: 7
cctgccggcg tagggtaggc acacgctgag ccagtcagtg tagcgcgcgt        50

<210> SEQ ID NO 8
<211> LENGTH: 50
<212> TYPE: DNA
<213> ORGANISM: Artificial
<220> FEATURE:
<223> OTHER INFORMATION: Synthetic probe AG9334_18_8

<400> SEQUENCE: 8
gcagccccgg acatctaagg gcatcacaga cctgttattg ctcaatctcg        50

<210> SEQ ID NO 9
<211> LENGTH: 50
<212> TYPE: DNA
<213> ORGANISM: Artificial
<220> FEATURE:
<223> OTHER INFORMATION: Synthetic probe AG9335_18_9

<400> SEQUENCE: 9
ggtggctgaa cgccacttgt ccctctaaga agttggggga cgccgaccgc        50

<210> SEQ ID NO 10
<211> LENGTH: 50
<212> TYPE: DNA
<213> ORGANISM: Artificial
<220> FEATURE:
<223> OTHER INFORMATION: Synthetic probe AG9336_18_10

<400> SEQUENCE: 10
``` tcggggtcg cgtaactagt tagcatgcca gagtctcgtt cgttatcgga                50

<210> SEQ ID NO 11
<211> LENGTH: 50
<212> TYPE: DNA
<213> ORGANISM: Artificial
<220> FEATURE:
<223> OTHER INFORMATION: Synthetic probe AG9337_18_11

<400> SEQUENCE: 11
attaaccaga caaatcgctc caccaactaa gaacggccat gcaccaccac                50

<210> SEQ ID NO 12
<211> LENGTH: 50
<212> TYPE: DNA
<213> ORGANISM: Artificial
<220> FEATURE:
<223> OTHER INFORMATION: Synthetic probe AG9338_18_12

<400> SEQUENCE: 12
ccacggaatc gagaaagagc tatcaatctg tcaatcctgt ccgtgtccgg                50

<210> SEQ ID NO 13
<211> LENGTH: 50
<212> TYPE: DNA
<213> ORGANISM: Artificial
<220> FEATURE:
<223> OTHER INFORMATION: Synthetic probe AG9339_18_13

<400> SEQUENCE: 13
gccgggtgag gtttcccgtg ttgagtcaaa ttaagccgca ggctccactc                50

<210> SEQ ID NO 14
<211> LENGTH: 50
<212> TYPE: DNA
<213> ORGANISM: Artificial
<220> FEATURE:
<223> OTHER INFORMATION: Synthetic probe AG9340_18_14

<400> SEQUENCE: 14
ctggtggtgc ccttccgtca attcctttaa gtttcagctt tgcaaccata                50

<210> SEQ ID NO 15
<211> LENGTH: 50
<212> TYPE: DNA
<213> ORGANISM: Artificial
<220> FEATURE:
<223> OTHER INFORMATION: Synthetic probe AG9341_18_15

<400> SEQUENCE: 15
ctccccccgg aacccaaaga ctttggtttc ccggaagctg cccggcgggt                50

<210> SEQ ID NO 16
<211> LENGTH: 50
<212> TYPE: DNA
<213> ORGANISM: Artificial
<220> FEATURE:
<223> OTHER INFORMATION: Synthetic probe AG9342_18_16

<400> SEQUENCE: 16
catgggaata acgccgccgc atcgccggtc ggcatcgttt atggtcggaa                50

<210> SEQ ID NO 17
<211> LENGTH: 50
<212> TYPE: DNA
<213> ORGANISM: Artificial

```
<220> FEATURE:
<223> OTHER INFORMATION: Synthetic probe AG9343_18_17

<400> SEQUENCE: 17
ctacgacggt atctgatcgt cttcgaacct ccgactttcg ttcttgatta            50

<210> SEQ ID NO 18
<211> LENGTH: 50
<212> TYPE: DNA
<213> ORGANISM: Artificial
<220> FEATURE:
<223> OTHER INFORMATION: Synthetic probe AG9344_18_18

<400> SEQUENCE: 18
atgaaaacat tcttggcaaa tgctttcgct ctggtccgtc ttgcgccggt            50

<210> SEQ ID NO 19
<211> LENGTH: 50
<212> TYPE: DNA
<213> ORGANISM: Artificial
<220> FEATURE:
<223> OTHER INFORMATION: Synthetic probe AG9345_18_19

<400> SEQUENCE: 19
ccaagaattt cacctctagc ggcgcaatac gaatgccccc ggccgtccct            50

<210> SEQ ID NO 20
<211> LENGTH: 50
<212> TYPE: DNA
<213> ORGANISM: Artificial
<220> FEATURE:
<223> OTHER INFORMATION: Synthetic probe AG9346_18_20

<400> SEQUENCE: 20
cttaatcatg gcctcagttc cgaaaaccaa caaaatagaa ccgcggtcct            50

<210> SEQ ID NO 21
<211> LENGTH: 50
<212> TYPE: DNA
<213> ORGANISM: Artificial
<220> FEATURE:
<223> OTHER INFORMATION: Synthetic probe AG9347_18_21

<400> SEQUENCE: 21
attccattat tcctagctgc ggtatccagg cggctcgggc ctgctttgaa            50

<210> SEQ ID NO 22
<211> LENGTH: 50
<212> TYPE: DNA
<213> ORGANISM: Artificial
<220> FEATURE:
<223> OTHER INFORMATION: Synthetic probe AG9348_18_22

<400> SEQUENCE: 22
cactctaatt ttttcaaagt aaacgcttcg ggcccgcgg  gacactcagc            50

<210> SEQ ID NO 23
<211> LENGTH: 50
<212> TYPE: DNA
<213> ORGANISM: Artificial
<220> FEATURE:
<223> OTHER INFORMATION: Synthetic probe AG9349_18_23

<400> SEQUENCE: 23
taagagcatc gagggggcgc cgagaggcaa ggggcgggga cgggcggtgg            50
```

<210> SEQ ID NO 24
<211> LENGTH: 50
<212> TYPE: DNA
<213> ORGANISM: Artificial
<220> FEATURE:
<223> OTHER INFORMATION: Synthetic probe AG9350_18_24

<400> SEQUENCE: 24
ctcgcctcgc ggcggaccgc ccgcccgctc ccaagatcca actacgagct          50

<210> SEQ ID NO 25
<211> LENGTH: 50
<212> TYPE: DNA
<213> ORGANISM: Artificial
<220> FEATURE:
<223> OTHER INFORMATION: Synthetic probe AG9351_18_25

<400> SEQUENCE: 25
ttttaactgc agcaacttta atatacgcta ttggagctgg aattaccgcg          50

<210> SEQ ID NO 26
<211> LENGTH: 50
<212> TYPE: DNA
<213> ORGANISM: Artificial
<220> FEATURE:
<223> OTHER INFORMATION: Synthetic probe AG9352_18_26

<400> SEQUENCE: 26
gctgctggca ccagacttgc cctccaatgg atcctcgtta aaggatttaa          50

<210> SEQ ID NO 27
<211> LENGTH: 50
<212> TYPE: DNA
<213> ORGANISM: Artificial
<220> FEATURE:
<223> OTHER INFORMATION: Synthetic probe AG9353_18_27

<400> SEQUENCE: 27
agtggactca ttccaattac agggcctcga aagagtcctg tattgttatt          50

<210> SEQ ID NO 28
<211> LENGTH: 50
<212> TYPE: DNA
<213> ORGANISM: Artificial
<220> FEATURE:
<223> OTHER INFORMATION: Synthetic probe AG9354_18_28

<400> SEQUENCE: 28
tttcgtcact acctccccgg gtcgggagtg ggtaatttgc gcgcctgctg          50

<210> SEQ ID NO 29
<211> LENGTH: 50
<212> TYPE: DNA
<213> ORGANISM: Artificial
<220> FEATURE:
<223> OTHER INFORMATION: Synthetic probe AG9355_18_29

<400> SEQUENCE: 29
ccttccttgg atgtggtagc cgtttctcag gctccctctc cggaatcgaa          50

<210> SEQ ID NO 30
<211> LENGTH: 50
<212> TYPE: DNA
<213> ORGANISM: Artificial
<220> FEATURE:
<223> OTHER INFORMATION: Synthetic probe AG9356_18_30

```
<400> SEQUENCE: 30
ccctgattcc ccgtcacccg tggtcaccat ggtaggcacg gcgactacca         50

<210> SEQ ID NO 31
<211> LENGTH: 48
<212> TYPE: DNA
<213> ORGANISM: Artificial
<220> FEATURE:
<223> OTHER INFORMATION: Synthetic probe AG9357_18_31

<400> SEQUENCE: 31
tcgaaagttg atagggcaga cgttcgaatg ggtcgtcgcc gccacggg           48

<210> SEQ ID NO 32
<211> LENGTH: 50
<212> TYPE: DNA
<213> ORGANISM: Artificial
<220> FEATURE:
<223> OTHER INFORMATION: Synthetic probe AG9358_18_32

<400> SEQUENCE: 32
gcgtgcgatc ggcccgaggt tatctagagt caccaaagcc gccggcgccc         50

<210> SEQ ID NO 33
<211> LENGTH: 50
<212> TYPE: DNA
<213> ORGANISM: Artificial
<220> FEATURE:
<223> OTHER INFORMATION: Synthetic probe AG9359_18_33

<400> SEQUENCE: 33 gcccccggc cggggccgga gaggggctga ccgggttggt tttgatctga          50

<210> SEQ ID NO 34
<211> LENGTH: 50
<212> TYPE: DNA
<213> ORGANISM: Artificial
<220> FEATURE:
<223> OTHER INFORMATION: Synthetic probe AG9360_18_34

<400> SEQUENCE: 34
taaatgcacg catccccccc gcgaaggggg tcagcgcccg tcggcatgta         50

<210> SEQ ID NO 35
<211> LENGTH: 50
<212> TYPE: DNA
<213> ORGANISM: Artificial
<220> FEATURE:
<223> OTHER INFORMATION: Synthetic probe AG9361_18_35

<400> SEQUENCE: 35
ttagctctag aattaccaca gttatccaag taggagagga gcgagcgacc         50

<210> SEQ ID NO 36
<211> LENGTH: 50
<212> TYPE: DNA
<213> ORGANISM: Artificial
<220> FEATURE:
<223> OTHER INFORMATION: Synthetic probe AG9362_18_36

<400> SEQUENCE: 36
aaaggaacca taactgattt aatgagccat tcgcagtttc actgtaccgg         50

<210> SEQ ID NO 37
```

<211> LENGTH: 50
<212> TYPE: DNA
<213> ORGANISM: Artificial
<220> FEATURE:
<223> OTHER INFORMATION: Synthetic probe AG9363_18_37

<400> SEQUENCE: 37
ccgtgcgtac ttagacatgc atggcttaat ctttgagaca agcatatgct            50

<210> SEQ ID NO 38
<211> LENGTH: 50
<212> TYPE: DNA
<213> ORGANISM: Artificial
<220> FEATURE:
<223> OTHER INFORMATION: Synthetic probe AG9364_18_38

<400> SEQUENCE: 38
tggcttaatc tttgagacaa gcatatgcta ctggcaggat caaccaggta            50

<210> SEQ ID NO 39
<211> LENGTH: 50
<212> TYPE: DNA
<213> ORGANISM: Artificial
<220> FEATURE:
<223> OTHER INFORMATION: Synthetic probe AG9365_28_1

<400> SEQUENCE: 39
gacaaaccct tgtgtcgagg gctgactttc aatagatcgc agcgagggag            50

<210> SEQ ID NO 40
<211> LENGTH: 50
<212> TYPE: DNA
<213> ORGANISM: Artificial
<220> FEATURE:
<223> OTHER INFORMATION: Synthetic probe AG9366_28_2

<400> SEQUENCE: 40
ctgctctgct acgtacgaaa ccccgaccca gaagcaggtc gtctacgaat            50

<210> SEQ ID NO 41
<211> LENGTH: 49
<212> TYPE: DNA
<213> ORGANISM: Artificial
<220> FEATURE:
<223> OTHER INFORMATION: Synthetic probe AG9367_28_3

<400> SEQUENCE: 41
ggtttagcgc caggttcccc acgaacgtgc ggtgcgtgac gggcgaggg             49

<210> SEQ ID NO 42
<211> LENGTH: 50
<212> TYPE: DNA
<213> ORGANISM: Artificial
<220> FEATURE:
<223> OTHER INFORMATION: Synthetic probe AG9368_28_4

<400> SEQUENCE: 42
gcggccgcct ttccggccgc gccccgtttc ccaggacgaa gggcactccg            50

<210> SEQ ID NO 43
<211> LENGTH: 50
<212> TYPE: DNA
<213> ORGANISM: Artificial
<220> FEATURE:
<223> OTHER INFORMATION: Synthetic probe AG9369_28_5

<400> SEQUENCE: 43
caccggaccc cggtcccggc gcgcggcggg gcacgcgccc tcccgcggcg        50

<210> SEQ ID NO 44
<211> LENGTH: 49
<212> TYPE: DNA
<213> ORGANISM: Artificial
<220> FEATURE:
<223> OTHER INFORMATION: Synthetic probe AG9370_28_6

<400> SEQUENCE: 44
gggcgcgtgg agggggggcg gcccgccggc ggggacaggc gggggaccg         49

<210> SEQ ID NO 45
<211> LENGTH: 50
<212> TYPE: DNA
<213> ORGANISM: Artificial
<220> FEATURE:
<223> OTHER INFORMATION: Synthetic probe AG9371_28_7

<400> SEQUENCE: 45
gctatccgag gccaaccgag gctccgcggc gctgccgtat cgttcgcctg        50

<210> SEQ ID NO 46
<211> LENGTH: 50
<212> TYPE: DNA
<213> ORGANISM: Artificial
<220> FEATURE:
<223> OTHER INFORMATION: Synthetic probe AG9372_28_8

<400> SEQUENCE: 46
ggcgggattc tgacttagag gcgttcagtc ataatcccac agatggtagc        50

<210> SEQ ID NO 47
<211> LENGTH: 50
<212> TYPE: DNA
<213> ORGANISM: Artificial
<220> FEATURE:
<223> OTHER INFORMATION: Synthetic probe AG9373_28_9

<400> SEQUENCE: 47
ttcgccccat tggctcctca gccaagcaca tacaccaaat gtctgaacct        50

<210> SEQ ID NO 48
<211> LENGTH: 50
<212> TYPE: DNA
<213> ORGANISM: Artificial
<220> FEATURE:
<223> OTHER INFORMATION: Synthetic probe AG9374_28_10

<400> SEQUENCE: 48
gcggttcctc tcgtactgag caggattacc atggcaacaa cacatcatca        50

<210> SEQ ID NO 49
<211> LENGTH: 50
<212> TYPE: DNA
<213> ORGANISM: Artificial
<220> FEATURE:
<223> OTHER INFORMATION: Synthetic probe AG9375_28_11

<400> SEQUENCE: 49
gtagggtaaa actaacctgt ctcacgacgg tctaaaccca gctcacgttc        50

<210> SEQ ID NO 50
<211> LENGTH: 50
<212> TYPE: DNA

```
<213> ORGANISM: Artificial
<220> FEATURE:
<223> OTHER INFORMATION: Synthetic probe AG9376_28_12

<400> SEQUENCE: 50
cctattagtg ggtgaacaat ccaacgcttg gcgaattctg cttcacaatg        50

<210> SEQ ID NO 51
<211> LENGTH: 50
<212> TYPE: DNA
<213> ORGANISM: Artificial
<220> FEATURE:
<223> OTHER INFORMATION: Synthetic probe AG9377_28_13

<400> SEQUENCE: 51
ataggaagag ccgacatcga aggatcaaaa agcgacgtcg ctatgaacgc        50

<210> SEQ ID NO 52
<211> LENGTH: 50
<212> TYPE: DNA
<213> ORGANISM: Artificial
<220> FEATURE:
<223> OTHER INFORMATION: Synthetic probe AG9378_28_14

<400> SEQUENCE: 52
ttggccgcca caagccagtt atccctgtgg taactttcct gacacctcct        50

<210> SEQ ID NO 53
<211> LENGTH: 50
<212> TYPE: DNA
<213> ORGANISM: Artificial
<220> FEATURE:
<223> OTHER INFORMATION: Synthetic probe AG9379_28_15

<400> SEQUENCE: 53
gcttaaaacc caaaaggtca gaaggatcgt gaggccccgc tttcacggtc        50

<210> SEQ ID NO 54
<211> LENGTH: 50
<212> TYPE: DNA
<213> ORGANISM: Artificial
<220> FEATURE:
<223> OTHER INFORMATION: Synthetic probe AG9380_28_16

<400> SEQUENCE: 54
tgtattcgta ctgaaaatca agatcaagcg agcttttgcc cttctgctcc        50

<210> SEQ ID NO 55
<211> LENGTH: 50
<212> TYPE: DNA
<213> ORGANISM: Artificial
<220> FEATURE:
<223> OTHER INFORMATION: Synthetic probe AG9381_28_17

<400> SEQUENCE: 55
acgggaggtt tctgtcctcc ctgagctcgc cttaggacac ctgcgttacc        50

<210> SEQ ID NO 56
<211> LENGTH: 50
<212> TYPE: DNA
<213> ORGANISM: Artificial
<220> FEATURE:
<223> OTHER INFORMATION: Synthetic probe AG9382_28_18

<400> SEQUENCE: 56
gtttgacagg tgtaccgccc cagtcaaact ccccacctgg cactgtcccc        50
```

<210> SEQ ID NO 57
<211> LENGTH: 50
<212> TYPE: DNA
<213> ORGANISM: Artificial
<220> FEATURE:
<223> OTHER INFORMATION: Synthetic probe AG9383_28_19

<400> SEQUENCE: 57
ggagcgggtc gcgcccggcc gggcgggcgc ttggcgccag aagcgagagc    50

<210> SEQ ID NO 58
<211> LENGTH: 50
<212> TYPE: DNA
<213> ORGANISM: Artificial
<220> FEATURE:
<223> OTHER INFORMATION: Synthetic probe AG9384_28_20

<400> SEQUENCE: 58
ccctcgggct cgcccccccg cctcaccggg tcagtgaaaa aacgatcaga    50

<210> SEQ ID NO 59
<211> LENGTH: 50
<212> TYPE: DNA
<213> ORGANISM: Artificial
<220> FEATURE:
<223> OTHER INFORMATION: Synthetic probe AG9385_28_21

<400> SEQUENCE: 59
gtagtggtat ttcaccggcg gcccgcaggg ccgcggaccc cgccccgggc    50

<210> SEQ ID NO 60
<211> LENGTH: 49
<212> TYPE: DNA
<213> ORGANISM: Artificial
<220> FEATURE:
<223> OTHER INFORMATION: Synthetic probe AG9386_28_22

<400> SEQUENCE: 60
ccctcgcggg gacaccgggg ggcgccgggg gcctcccact tattctaca    49

<210> SEQ ID NO 61
<211> LENGTH: 50
<212> TYPE: DNA
<213> ORGANISM: Artificial
<220> FEATURE:
<223> OTHER INFORMATION: Synthetic probe AG9387_28_23

<400> SEQUENCE: 61
cctctcatgt ctcttcaccg tgccagacta gagtcaagct caacagggtc    50

<210> SEQ ID NO 62
<211> LENGTH: 50
<212> TYPE: DNA
<213> ORGANISM: Artificial
<220> FEATURE:
<223> OTHER INFORMATION: Synthetic probe AG9388_28_24

<400> SEQUENCE: 62
ttctttcccc gctgattccg ccaagcccgt tcccttggct gtggtttcgc    50

<210> SEQ ID NO 63
<211> LENGTH: 50
<212> TYPE: DNA
<213> ORGANISM: Artificial
<220> FEATURE:

<223> OTHER INFORMATION: Synthetic probe AG9389_28_25

<400> SEQUENCE: 63
tggatagtag gtagggacag tgggaatctc gttcatccat tcatgcgcgt        50

<210> SEQ ID NO 64
<211> LENGTH: 50
<212> TYPE: DNA
<213> ORGANISM: Artificial
<220> FEATURE:
<223> OTHER INFORMATION: Synthetic probe AG9390_28_26

<400> SEQUENCE: 64
cactaattag atgacgaggc atttggctac cttaagagag tcatagttac        50

<210> SEQ ID NO 65
<211> LENGTH: 50
<212> TYPE: DNA
<213> ORGANISM: Artificial
<220> FEATURE:
<223> OTHER INFORMATION: Synthetic probe AG9391_28_27

<400> SEQUENCE: 65
tcccgccgtt tacccgcgct tcattgaatt tcttcacttt gacattcaga        50

<210> SEQ ID NO 66
<211> LENGTH: 50
<212> TYPE: DNA
<213> ORGANISM: Artificial
<220> FEATURE:
<223> OTHER INFORMATION: Synthetic probe AG9392_28_28

<400> SEQUENCE: 66
gcactgggca gaaatcacat cgcgtcaaca cccgccgcgg gccttcgcga        50

<210> SEQ ID NO 67
<211> LENGTH: 50
<212> TYPE: DNA
<213> ORGANISM: Artificial
<220> FEATURE:
<223> OTHER INFORMATION: Synthetic probe AG9393_28_29

<400> SEQUENCE: 67
tgctttgttt taattaaaca gtcggattcc cctggtccgc accagttcta        50

<210> SEQ ID NO 68
<211> LENGTH: 50
<212> TYPE: DNA
<213> ORGANISM: Artificial
<220> FEATURE:
<223> OTHER INFORMATION: Synthetic probe AG9394_28_30

<400> SEQUENCE: 68
agtcggctgc taggcgccgg ccgaggcgag gcgcgcgcgg aaccgcggcc        50

<210> SEQ ID NO 69
<211> LENGTH: 49
<212> TYPE: DNA
<213> ORGANISM: Artificial
<220> FEATURE:
<223> OTHER INFORMATION: Synthetic probe AG9395_28_31

<400> SEQUENCE: 69 ccggggcgg acccggcggg gggaccggcc cgcggcccct ccgccgcct        49

```
<210> SEQ ID NO 70
<211> LENGTH: 50
<212> TYPE: DNA
<213> ORGANISM: Artificial
<220> FEATURE:
<223> OTHER INFORMATION: Synthetic probe AG9396_28_32

<400> SEQUENCE: 70
gccgccgccg ccgccgcgcg ccgaggagga gggggggaacg gggggcggac          50

<210> SEQ ID NO 71
<211> LENGTH: 48
<212> TYPE: DNA
<213> ORGANISM: Artificial
<220> FEATURE:
<223> OTHER INFORMATION: Synthetic probe AG9397_28_33

<400> SEQUENCE: 71
gggccggggg gtagggcggg gggacgaacc gccccgcccc gccgcccg             48

<210> SEQ ID NO 72
<211> LENGTH: 50
<212> TYPE: DNA
<213> ORGANISM: Artificial
<220> FEATURE:
<223> OTHER INFORMATION: Synthetic probe AG9398_28_34

<400> SEQUENCE: 72
ccgaccgccg ccgcccgacc gctcccgccc ccagcggacg cgcgcgcgac          50

<210> SEQ ID NO 73
<211> LENGTH: 50
<212> TYPE: DNA
<213> ORGANISM: Artificial
<220> FEATURE:
<223> OTHER INFORMATION: Synthetic probe AG9399_28_35

<400> SEQUENCE: 73
cgagacgtgg ggtgggggtg gggggcgcgc cgcgccgccg ccgggctccc          50

<210> SEQ ID NO 74
<211> LENGTH: 50
<212> TYPE: DNA
<213> ORGANISM: Artificial
<220> FEATURE:
<223> OTHER INFORMATION: Synthetic probe AG9400_28_36

<400> SEQUENCE: 74
cgggggcggc cgcgacgccc gccgcagctg gggcgatcca cgggaagggc          50

<210> SEQ ID NO 75
<211> LENGTH: 50
<212> TYPE: DNA
<213> ORGANISM: Artificial
<220> FEATURE:
<223> OTHER INFORMATION: Synthetic probe AG9401_28_37

<400> SEQUENCE: 75
ccggctcgcg tccagagtcc gcgccgccgc cggccccccg ggtccccggg          50

<210> SEQ ID NO 76
<211> LENGTH: 50
<212> TYPE: DNA
<213> ORGANISM: Artificial
<220> FEATURE:
<223> OTHER INFORMATION: Synthetic probe AG9402_28_38
```

<400> SEQUENCE: 76
gcccccctcg cggggacctg cccccgccgg ccgccccggc ggccgccgcg					50

<210> SEQ ID NO 77
<211> LENGTH: 50
<212> TYPE: DNA
<213> ORGANISM: Artificial
<220> FEATURE:
<223> OTHER INFORMATION: Synthetic probe AG9403_28_39

<400> SEQUENCE: 77 cggccctgc cgccccgacc cttctccccc cgccgcgccc ccacgcggcg					50

<210> SEQ ID NO 78
<211> LENGTH: 50
<212> TYPE: DNA
<213> ORGANISM: Artificial
<220> FEATURE:
<223> OTHER INFORMATION: Synthetic probe AG9404_28_40

<400> SEQUENCE: 78
ctcccccggg gagggggag dacggggagc gggggagaga gagagagaga					50

<210> SEQ ID NO 79
<211> LENGTH: 50
<212> TYPE: DNA
<213> ORGANISM: Artificial
<220> FEATURE:
<223> OTHER INFORMATION: Synthetic probe AG9405_28_41

<400> SEQUENCE: 79
gggcgcgggg tggggaggga gcgagcggcg cgcgcgggtg gggcgggga					50

<210> SEQ ID NO 80
<211> LENGTH: 49
<212> TYPE: DNA
<213> ORGANISM: Artificial
<220> FEATURE:
<223> OTHER INFORMATION: Synthetic probe AG9406_28_42

<400> SEQUENCE: 80
gggccgcgag gggggtgccc cgggcgtggg ggggcgcgcg cctcgtcca					49

<210> SEQ ID NO 81
<211> LENGTH: 50
<212> TYPE: DNA
<213> ORGANISM: Artificial
<220> FEATURE:
<223> OTHER INFORMATION: Synthetic probe AG9407_28_43

<400> SEQUENCE: 81
gccgcggcgc gcgcccagcc ccgcttcgcg ccccagcccg accgacccag					50

<210> SEQ ID NO 82
<211> LENGTH: 50
<212> TYPE: DNA
<213> ORGANISM: Artificial
<220> FEATURE:
<223> OTHER INFORMATION: Synthetic probe AG9408_28_44

<400> SEQUENCE: 82
cccttagagc caatccttat cccgaagtta cggatccggc ttgccgactt					50

<210> SEQ ID NO 83
<211> LENGTH: 50

```
<212> TYPE: DNA
<213> ORGANISM: Artificial
<220> FEATURE:
<223> OTHER INFORMATION: Synthetic probe AG9409_28_45

<400> SEQUENCE: 83
cccttaccta cattgttcca acatgccaga ggctgttcac cttggagacc      50

<210> SEQ ID NO 84
<211> LENGTH: 50
<212> TYPE: DNA
<213> ORGANISM: Artificial
<220> FEATURE:
<223> OTHER INFORMATION: Synthetic probe AG9410_28_46

<400> SEQUENCE: 84
tgctgcggat atgggtacgg cccggcgcga gatttacacc ctctccccg       50

<210> SEQ ID NO 85
<211> LENGTH: 50
<212> TYPE: DNA
<213> ORGANISM: Artificial
<220> FEATURE:
<223> OTHER INFORMATION: Synthetic probe AG9411_28_47

<400> SEQUENCE: 85
gattttcaag ggccagcgag agctcaccgg acgccgccgg aaccgcgacg      50

<210> SEQ ID NO 86
<211> LENGTH: 50
<212> TYPE: DNA
<213> ORGANISM: Artificial
<220> FEATURE:
<223> OTHER INFORMATION: Synthetic probe AG9412_28_48

<400> SEQUENCE: 86
ctttccaagg cacgggcccc tctctcgggg cgaacccatt ccagggcgcc      50

<210> SEQ ID NO 87
<211> LENGTH: 50
<212> TYPE: DNA
<213> ORGANISM: Artificial
<220> FEATURE:
<223> OTHER INFORMATION: Synthetic probe AG9413_28_49

<400> SEQUENCE: 87
ctgcccttca caaagaaaag agaactctcc ccggggctcc cgccggcttc      50

<210> SEQ ID NO 88
<211> LENGTH: 50
<212> TYPE: DNA
<213> ORGANISM: Artificial
<220> FEATURE:
<223> OTHER INFORMATION: Synthetic probe AG9414_28_50

<400> SEQUENCE: 88
tccgggatcg gtcgcgttac cgcactggac gcctcgcggc gcccatctcc      50

<210> SEQ ID NO 89
<211> LENGTH: 50
<212> TYPE: DNA
<213> ORGANISM: Artificial
<220> FEATURE:
<223> OTHER INFORMATION: Synthetic probe AG9415_28_51

<400> SEQUENCE: 89
```
gccactccgg attcggggat ctgaacccga ctcccttttcg atcggccgag        50

<210> SEQ ID NO 90
<211> LENGTH: 50
<212> TYPE: DNA
<213> ORGANISM: Artificial
<220> FEATURE:
<223> OTHER INFORMATION: Synthetic probe AG9416_28_52

<400> SEQUENCE: 90
ggcaacggag gccatcgccc gtcccttcgg aacggcgctc gcccatctct        50

<210> SEQ ID NO 91
<211> LENGTH: 50
<212> TYPE: DNA
<213> ORGANISM: Artificial
<220> FEATURE:
<223> OTHER INFORMATION: Synthetic probe AG9417_28_53

<400> SEQUENCE: 91
caggaccgac tgacccatgt tcaactgctg ttcacatgga acccttctcc        50

<210> SEQ ID NO 92
<211> LENGTH: 50
<212> TYPE: DNA
<213> ORGANISM: Artificial
<220> FEATURE:
<223> OTHER INFORMATION: Synthetic probe AG9418_28_54

<400> SEQUENCE: 92
acttcggcct tcaaagttct cgtttgaata tttgctacta ccaccaagat        50

<210> SEQ ID NO 93
<211> LENGTH: 50
<212> TYPE: DNA
<213> ORGANISM: Artificial
<220> FEATURE:
<223> OTHER INFORMATION: Synthetic probe AG9419_28_55

<400> SEQUENCE: 93
ctgcacctgc ggcggctcca cccgggcccg cgccctaggc ttcaaggctc        50

<210> SEQ ID NO 94
<211> LENGTH: 50
<212> TYPE: DNA
<213> ORGANISM: Artificial
<220> FEATURE:
<223> OTHER INFORMATION: Synthetic probe AG9420_28_56

<400> SEQUENCE: 94
accgcagcgg ccctcctact cgtcgcggcg tagcgtccgc ggggctccgg        50

<210> SEQ ID NO 95
<211> LENGTH: 45
<212> TYPE: DNA
<213> ORGANISM: Artificial
<220> FEATURE:
<223> OTHER INFORMATION: Synthetic probe AG9421_28_57

<400> SEQUENCE: 95
gggcggggag cggggcgtgg gcgggaggag gggaggaggc gtggg        45

<210> SEQ ID NO 96
<211> LENGTH: 50
<212> TYPE: DNA
<213> ORGANISM: Artificial

```
<220> FEATURE:
<223> OTHER INFORMATION: Synthetic probe AG9422_28_58

<400> SEQUENCE: 96
gggcggggga aggacccccac accccccgccg ccgccgccgc cgccgccctc          50

<210> SEQ ID NO 97
<211> LENGTH: 50
<212> TYPE: DNA
<213> ORGANISM: Artificial
<220> FEATURE:
<223> OTHER INFORMATION: Synthetic probe AG9423_28_59

<400> SEQUENCE: 97
cgacgcacac cacacgcgcg cgcgcgcgcg ccgcccccgc cgctcccgtc          50

<210> SEQ ID NO 98
<211> LENGTH: 50
<212> TYPE: DNA
<213> ORGANISM: Artificial
<220> FEATURE:
<223> OTHER INFORMATION: Synthetic probe AG9424_28_60

<400> SEQUENCE: 98
cactctcgac tgccggcgac ggccgggtat gggcccgacg ctccagcgcc          50

<210> SEQ ID NO 99
<211> LENGTH: 50
<212> TYPE: DNA
<213> ORGANISM: Artificial
<220> FEATURE:
<223> OTHER INFORMATION: Synthetic probe AG9425_28_61

<400> SEQUENCE: 99
atccattttc agggctagtt gattcggcag gtgagttgtt acacactcct          50

<210> SEQ ID NO 100
<211> LENGTH: 50
<212> TYPE: DNA
<213> ORGANISM: Artificial
<220> FEATURE:
<223> OTHER INFORMATION: Synthetic probe AG9426_28_62

<400> SEQUENCE: 100
tagcggattc cgacttccat ggccaccgtc ctgctgtcta tatcaaccaa          50

<210> SEQ ID NO 101
<211> LENGTH: 50
<212> TYPE: DNA
<213> ORGANISM: Artificial
<220> FEATURE:
<223> OTHER INFORMATION: Synthetic probe AG9427_28_63

<400> SEQUENCE: 101 cacctttct ggggtctgat gagcgtcggc atcgggcgcc ttaacccggc          50

<210> SEQ ID NO 102
<211> LENGTH: 50
<212> TYPE: DNA
<213> ORGANISM: Artificial
<220> FEATURE:
<223> OTHER INFORMATION: Synthetic probe AG9428_28_64

<400> SEQUENCE: 102
gttcggttca tcccgcagcg ccagttctgc ttaccaaaag tggcccacta          50
```

<210> SEQ ID NO 103
<211> LENGTH: 50
<212> TYPE: DNA
<213> ORGANISM: Artificial
<220> FEATURE:
<223> OTHER INFORMATION: Synthetic probe AG9429_28_65

<400> SEQUENCE: 103
ggcactcgca ttccacgccc ggctccacgc cagcgagccg ggcttcttac        50

<210> SEQ ID NO 104
<211> LENGTH: 50
<212> TYPE: DNA
<213> ORGANISM: Artificial
<220> FEATURE:
<223> OTHER INFORMATION: Synthetic probe AG9430_28_66

<400> SEQUENCE: 104
ccatttaaag tttgagaata ggttgagatc gtttcggccc caagacctct        50

<210> SEQ ID NO 105
<211> LENGTH: 50
<212> TYPE: DNA
<213> ORGANISM: Artificial
<220> FEATURE:
<223> OTHER INFORMATION: Synthetic probe AG9431_28_67

<400> SEQUENCE: 105
aatcattcgc tttaccggat aaaactgcgt ggcggggtg cgtcgggtct        50

<210> SEQ ID NO 106
<211> LENGTH: 50
<212> TYPE: DNA
<213> ORGANISM: Artificial
<220> FEATURE:
<223> OTHER INFORMATION: Synthetic probe AG9432_28_68

<400> SEQUENCE: 106
gcgagagcgc cagctatcct gagggaaact tcggagggaa ccagctacta        50

<210> SEQ ID NO 107
<211> LENGTH: 50
<212> TYPE: DNA
<213> ORGANISM: Artificial
<220> FEATURE:
<223> OTHER INFORMATION: Synthetic probe AG9433_28_69

<400> SEQUENCE: 107
gatggttcga ttagtctttc gcccctatac ccaggtcgga cgaccgattt        50

<210> SEQ ID NO 108
<211> LENGTH: 50
<212> TYPE: DNA
<213> ORGANISM: Artificial
<220> FEATURE:
<223> OTHER INFORMATION: Synthetic probe AG9434_28_70

<400> SEQUENCE: 108
gcacgtcagg accgctacgg acctccacca gagtttcctc tggcttcgcc        50

<210> SEQ ID NO 109
<211> LENGTH: 50
<212> TYPE: DNA
<213> ORGANISM: Artificial
<220> FEATURE:
<223> OTHER INFORMATION: Synthetic probe AG9435_28_71

<400> SEQUENCE: 109
ctgcccaggc atagttcacc atctttcggg tcctaacacg tgcgctcgtg    50

<210> SEQ ID NO 110
<211> LENGTH: 50
<212> TYPE: DNA
<213> ORGANISM: Artificial
<220> FEATURE:
<223> OTHER INFORMATION: Synthetic probe AG9436_28_72

<400> SEQUENCE: 110
ctccacctcc ccggcgcggc gggcgagacg ggccggtggt gcgccctcgg    50

<210> SEQ ID NO 111
<211> LENGTH: 50
<212> TYPE: DNA
<213> ORGANISM: Artificial
<220> FEATURE:
<223> OTHER INFORMATION: Synthetic probe AG9437_28_73

<400> SEQUENCE: 111
cggactggag aggcctcggg atcccacctc ggccggcgag cgcgccggcc    50

<210> SEQ ID NO 112
<211> LENGTH: 50
<212> TYPE: DNA
<213> ORGANISM: Artificial
<220> FEATURE:
<223> OTHER INFORMATION: Synthetic probe AG9438_28_74

<400> SEQUENCE: 112
ttcaccttca ttgcgccacg gcggctttcg tgcgagcccc cgactcgcgc    50

<210> SEQ ID NO 113
<211> LENGTH: 50
<212> TYPE: DNA
<213> ORGANISM: Artificial
<220> FEATURE:
<223> OTHER INFORMATION: Synthetic probe AG9439_28_75

<400> SEQUENCE: 113
acgtgttaga ctccttggtc cgtgtttcaa gacgggtcgg gtgggtagcc    50

<210> SEQ ID NO 114
<211> LENGTH: 49
<212> TYPE: DNA
<213> ORGANISM: Artificial
<220> FEATURE:
<223> OTHER INFORMATION: Synthetic probe AG9440_28_76

<400> SEQUENCE: 114
gacgtcgccg ccgaccccgt gcgctcgctc cgccgtcccc ctcttcggg    49

<210> SEQ ID NO 115
<211> LENGTH: 50
<212> TYPE: DNA
<213> ORGANISM: Artificial
<220> FEATURE:
<223> OTHER INFORMATION: Synthetic probe AG9441_28_77

<400> SEQUENCE: 115
gacgcgcgcg tggccccgag agaacctccc ccgggcccga cggcgcgacc    50

<210> SEQ ID NO 116

```
<211> LENGTH: 50
<212> TYPE: DNA
<213> ORGANISM: Artificial
<220> FEATURE:
<223> OTHER INFORMATION: Synthetic probe AG9442_28_78

<400> SEQUENCE: 116
cgcccggggc gcactgggga cagtccgccc cgccccccga cccgcgcgcg            50

<210> SEQ ID NO 117
<211> LENGTH: 50
<212> TYPE: DNA
<213> ORGANISM: Artificial
<220> FEATURE:
<223> OTHER INFORMATION: Synthetic probe AG9443_28_79

<400> SEQUENCE: 117 gcacccccc cgtcgccggg gcggggggcgc ggggaggagg ggtgggagag             50

<210> SEQ ID NO 118
<211> LENGTH: 50
<212> TYPE: DNA
<213> ORGANISM: Artificial
<220> FEATURE:
<223> OTHER INFORMATION: Synthetic probe AG9444_28_80

<400> SEQUENCE: 118
cggtcgcgcc gtgggagggg tggcccggcc ccccacgag gagacgccgg              50

<210> SEQ ID NO 119
<211> LENGTH: 50
<212> TYPE: DNA
<213> ORGANISM: Artificial
<220> FEATURE:
<223> OTHER INFORMATION: Synthetic probe AG9445_28_81

<400> SEQUENCE: 119
cgcgcccccg cggggagac ccccctcgcg ggggattccc cgcggggtg               50

<210> SEQ ID NO 120
<211> LENGTH: 50
<212> TYPE: DNA
<213> ORGANISM: Artificial
<220> FEATURE:
<223> OTHER INFORMATION: Synthetic probe AG9446_28_82

<400> SEQUENCE: 120
ggcgccggga gggggagag cgcggcgacg ggtctcgctc cctcggcccc             50

<210> SEQ ID NO 121
<211> LENGTH: 49
<212> TYPE: DNA
<213> ORGANISM: Artificial
<220> FEATURE:
<223> OTHER INFORMATION: Synthetic probe AG9447_28_83

<400> SEQUENCE: 121
gggattcggc gagtgctgct gccggggggg ctgtaacact cgggggggt              49

<210> SEQ ID NO 122
<211> LENGTH: 50
<212> TYPE: DNA
<213> ORGANISM: Artificial
<220> FEATURE:
<223> OTHER INFORMATION: Synthetic probe AG9448_28_84

<400> SEQUENCE: 122
```
ttcggtcccg ccgcccccgc cgccgccgcc accgccgccg ccgccgccgc        50

<210> SEQ ID NO 123
<211> LENGTH: 50
<212> TYPE: DNA
<213> ORGANISM: Artificial
<220> FEATURE:
<223> OTHER INFORMATION: Synthetic probe AG9449_28_85

<400> SEQUENCE: 123
cccgacccgc gcgccctccc gagggaggac gcggggccgg ggggcggaga        50

<210> SEQ ID NO 124
<211> LENGTH: 50
<212> TYPE: DNA
<213> ORGANISM: Artificial
<220> FEATURE:
<223> OTHER INFORMATION: Synthetic probe AG9450_28_86

<400> SEQUENCE: 124
cgggggagga ggaggacgga cggacggacg gggcccccg agccaccttc         50

<210> SEQ ID NO 125
<211> LENGTH: 50
<212> TYPE: DNA
<213> ORGANISM: Artificial
<220> FEATURE:
<223> OTHER INFORMATION: Synthetic probe AG9451_28_87

<400> SEQUENCE: 125
cccgccgggc cttcccagcc gtcccggagc cggtcgcggc gcaccgccgc        50

<210> SEQ ID NO 126
<211> LENGTH: 50
<212> TYPE: DNA
<213> ORGANISM: Artificial
<220> FEATURE:
<223> OTHER INFORMATION: Synthetic probe AG9452_28_88

<400> SEQUENCE: 126
ggtggaaatg cgcccggcgg cggccggtcg ccggtcgggg gacggtcccc        50

<210> SEQ ID NO 127
<211> LENGTH: 50
<212> TYPE: DNA
<213> ORGANISM: Artificial
<220> FEATURE:
<223> OTHER INFORMATION: Synthetic probe AG9453_28_89

<400> SEQUENCE: 127
cgccgacccc accccggcc ccgcccgccc accccgcac ccgccggagc          50

<210> SEQ ID NO 128
<211> LENGTH: 50
<212> TYPE: DNA
<213> ORGANISM: Artificial
<220> FEATURE:
<223> OTHER INFORMATION: Synthetic probe AG9454_28_90

<400> SEQUENCE: 128 ccgcccctc cggggaggag gaggagggc ggcgggggaa gggagggcgg          50

<210> SEQ ID NO 129
<211> LENGTH: 50
<212> TYPE: DNA

```
<213> ORGANISM: Artificial
<220> FEATURE:
<223> OTHER INFORMATION: Synthetic probe AG9455_28_91

<400> SEQUENCE: 129
gtggaggggt cgggaggaac gggggggcggg aaagatccgc cgggccgccg          50

<210> SEQ ID NO 130
<211> LENGTH: 50
<212> TYPE: DNA
<213> ORGANISM: Artificial
<220> FEATURE:
<223> OTHER INFORMATION: Synthetic probe AG9456_28_92

<400> SEQUENCE: 130
acacggccgg acccgccgcc gggttgaatc ctccgggcgg actgcgcgga          50

<210> SEQ ID NO 131
<211> LENGTH: 50
<212> TYPE: DNA
<213> ORGANISM: Artificial
<220> FEATURE:
<223> OTHER INFORMATION: Synthetic probe AG9457_28_93

<400> SEQUENCE: 131
ccccacccgt ttacctctta acggtttcac gccctcttga actctctctt          50

<210> SEQ ID NO 132
<211> LENGTH: 50
<212> TYPE: DNA
<213> ORGANISM: Artificial
<220> FEATURE:
<223> OTHER INFORMATION: Synthetic probe AG9458_28_94

<400> SEQUENCE: 132
caaagttctt ttcaactttc ccttacggta cttgttgact atcggtctcg          50

<210> SEQ ID NO 133
<211> LENGTH: 50
<212> TYPE: DNA
<213> ORGANISM: Artificial
<220> FEATURE:
<223> OTHER INFORMATION: Synthetic probe AG9459_28_95

<400> SEQUENCE: 133
tgccggtatt tagccttaga tggagtttac cacccgcttt gggctgcatt          50

<210> SEQ ID NO 134
<211> LENGTH: 50
<212> TYPE: DNA
<213> ORGANISM: Artificial
<220> FEATURE:
<223> OTHER INFORMATION: Synthetic probe AG9460_28_96

<400> SEQUENCE: 134
cccaagcaac ccgactccgg aagacccgg gcgcgcgccg ccgctaccg             50

<210> SEQ ID NO 135
<211> LENGTH: 50
<212> TYPE: DNA
<213> ORGANISM: Artificial
<220> FEATURE:
<223> OTHER INFORMATION: Synthetic probe AG9461_28_97

<400> SEQUENCE: 135
gcctcacacc gtccacgggc tgggcctcga tcagaaggac ttgggccccc          50
```

<210> SEQ ID NO 136
<211> LENGTH: 50
<212> TYPE: DNA
<213> ORGANISM: Artificial
<220> FEATURE:
<223> OTHER INFORMATION: Synthetic probe AG9462_28_98

<400> SEQUENCE: 136
cacgagcggc gccggggagc gggtcttccg tacgccacat gtcccgcgcc           50

<210> SEQ ID NO 137
<211> LENGTH: 50
<212> TYPE: DNA
<213> ORGANISM: Artificial
<220> FEATURE:
<223> OTHER INFORMATION: Synthetic probe AG9463_28_99

<400> SEQUENCE: 137
ccgcggggcg gggattcggc gctgggctct tccctgttca ctcgccgtta           50

<210> SEQ ID NO 138
<211> LENGTH: 50
<212> TYPE: DNA
<213> ORGANISM: Artificial
<220> FEATURE:
<223> OTHER INFORMATION: Synthetic probe AG9464_28_100

<400> SEQUENCE: 138
ctgagggaat cctggttagt ttcttttcct ccgctgacta atatgcttaa           50

<210> SEQ ID NO 139
<211> LENGTH: 50
<212> TYPE: DNA
<213> ORGANISM: Artificial
<220> FEATURE:
<223> OTHER INFORMATION: Synthetic probe AG9465_28_101

<400> SEQUENCE: 139
gactaatatg cttaaattca gcgggtcgcc acgtctgatc tgaggtcgcg           50

<210> SEQ ID NO 140
<211> LENGTH: 50
<212> TYPE: DNA
<213> ORGANISM: Artificial
<220> FEATURE:
<223> OTHER INFORMATION: Synthetic probe AG9466_5.8_1

<400> SEQUENCE: 140
aagcgacgct cagacaggcg tagccccggg aggaacccgg ggccgcaagt           50

<210> SEQ ID NO 141
<211> LENGTH: 50
<212> TYPE: DNA
<213> ORGANISM: Artificial
<220> FEATURE:
<223> OTHER INFORMATION: Synthetic probe AG9467_5.8_2

<400> SEQUENCE: 141
gcgttcgaag tgtcgatgat caatgtgtcc tgcaattcac attaattctc           50

<210> SEQ ID NO 142
<211> LENGTH: 50
<212> TYPE: DNA
<213> ORGANISM: Artificial
<220> FEATURE:

-continued

<223> OTHER INFORMATION: Synthetic probe AG9468_5.8_3

<400> SEQUENCE: 142
gcagctagct gcgttcttca tcgacgcacg agccgagtga tccaccgcta                   50

<210> SEQ ID NO 143
<211> LENGTH: 50
<212> TYPE: DNA
<213> ORGANISM: Artificial
<220> FEATURE:
<223> OTHER INFORMATION: Synthetic probe AG9469_16_1

<400> SEQUENCE: 143
aaaccctgtt cttgggtggg tgtgggtata atactaagtt gagatgatat                   50

<210> SEQ ID NO 144
<211> LENGTH: 50
<212> TYPE: DNA
<213> ORGANISM: Artificial
<220> FEATURE:
<223> OTHER INFORMATION: Synthetic probe AG9470_16_2

<400> SEQUENCE: 144
catttacggg ggaaggcgct ttgtgaagta ggccttattt ctcttgtcct                   50

<210> SEQ ID NO 145
<211> LENGTH: 50
<212> TYPE: DNA
<213> ORGANISM: Artificial
<220> FEATURE:
<223> OTHER INFORMATION: Synthetic probe AG9471_16_3
<220> FEATURE:
<221> NAME/KEY: misc_feature
<222> LOCATION: (23)..(23)
<223> OTHER INFORMATION: n is a, c, g, or t

<400> SEQUENCE: 145
ttcgtacagg gaggaatttg aangtagata gaaaccgacc tggattactc                   50

<210> SEQ ID NO 146
<211> LENGTH: 50
<212> TYPE: DNA
<213> ORGANISM: Artificial
<220> FEATURE:
<223> OTHER INFORMATION: Synthetic probe AG9472_16_4

<400> SEQUENCE: 146
cggtctgaac tcagatcacg taggacttta atcgttgaac aaacgaacct                   50

<210> SEQ ID NO 147
<211> LENGTH: 50
<212> TYPE: DNA
<213> ORGANISM: Artificial
<220> FEATURE:
<223> OTHER INFORMATION: Synthetic probe AG9473_16_5

<400> SEQUENCE: 147
ttaatagcgg ctgcaccatc gggatgtcct gatccaacat cgaggtcgta                   50

<210> SEQ ID NO 148
<211> LENGTH: 50
<212> TYPE: DNA
<213> ORGANISM: Artificial
<220> FEATURE:
<223> OTHER INFORMATION: Synthetic probe AG9474_16_6

<400> SEQUENCE: 148
aaccctattg ttgatatgga ctctagaata ggattgcgct gttatcccta            50

<210> SEQ ID NO 149
<211> LENGTH: 50
<212> TYPE: DNA
<213> ORGANISM: Artificial
<220> FEATURE:
<223> OTHER INFORMATION: Synthetic probe AG9475_16_7

<400> SEQUENCE: 149
gggtaacttg ttccgttggt caagttattg gatcaattga gtatagtagt            50

<210> SEQ ID NO 150
<211> LENGTH: 50
<212> TYPE: DNA
<213> ORGANISM: Artificial
<220> FEATURE:
<223> OTHER INFORMATION: Synthetic probe AG9476_16_8

<400> SEQUENCE: 150
tcgctttgac tggtgaagtc ttagcatgta ctgctcggag gttgggttct            50

<210> SEQ ID NO 151
<211> LENGTH: 50
<212> TYPE: DNA
<213> ORGANISM: Artificial
<220> FEATURE:
<223> OTHER INFORMATION: Synthetic probe AG9477_16_9

<400> SEQUENCE: 151
gctccgaggt cgccccaacc gaaatttta atgcaggttt ggtagtttag              50

<210> SEQ ID NO 152
<211> LENGTH: 50
<212> TYPE: DNA
<213> ORGANISM: Artificial
<220> FEATURE:
<223> OTHER INFORMATION: Synthetic probe AG9478_16_10

<400> SEQUENCE: 152
gacctgtggg tttgttaggt actgtttgca ttaataaatt aaagctccat            50

<210> SEQ ID NO 153
<211> LENGTH: 50
<212> TYPE: DNA
<213> ORGANISM: Artificial
<220> FEATURE:
<223> OTHER INFORMATION: Synthetic probe AG9479_16_11

<400> SEQUENCE: 153
agggtcttct cgtcttgctg tgttatgccc gcctcttcac gggcaggtca            50

<210> SEQ ID NO 154
<211> LENGTH: 50
<212> TYPE: DNA
<213> ORGANISM: Artificial
<220> FEATURE:
<223> OTHER INFORMATION: Synthetic probe AG9480_16_12

<400> SEQUENCE: 154
atttcactgg ttaaaagtaa gagacagctg aaccctcgtg gagccattca            50

<210> SEQ ID NO 155
<211> LENGTH: 50
<212> TYPE: DNA

-continued

<213> ORGANISM: Artificial
<220> FEATURE:
<223> OTHER INFORMATION: Synthetic probe AG9481_16_13

<400> SEQUENCE: 155
tacaggtccc tatttaagga acaagtgatt atgctacctt tgcacggtta            50

<210> SEQ ID NO 156
<211> LENGTH: 50
<212> TYPE: DNA
<213> ORGANISM: Artificial
<220> FEATURE:
<223> OTHER INFORMATION: Synthetic probe AG9482_16_14

<400> SEQUENCE: 156
gggtaccgcg gccgttaaac atgtgtcact gggcaggcgg tgcctctaat            50

<210> SEQ ID NO 157
<211> LENGTH: 50
<212> TYPE: DNA
<213> ORGANISM: Artificial
<220> FEATURE:
<223> OTHER INFORMATION: Synthetic probe AG9483_16_15

<400> SEQUENCE: 157
actggtgatg ctagaggtga tgtttttggt aaacaggcgg ggtaagattt            50

<210> SEQ ID NO 158
<211> LENGTH: 50
<212> TYPE: DNA
<213> ORGANISM: Artificial
<220> FEATURE:
<223> OTHER INFORMATION: Synthetic probe AG9484_16_16

<400> SEQUENCE: 158
gccgagttcc ttttactttt tttaacctttt ccttatgagc atgcctgtgt           50

<210> SEQ ID NO 159
<211> LENGTH: 50
<212> TYPE: DNA
<213> ORGANISM: Artificial
<220> FEATURE:
<223> OTHER INFORMATION: Synthetic probe AG9485_16_17

<400> SEQUENCE: 159
tgggttgaca gtgagggtaa taatgacttg ttggttgatt gtagatattg            50

<210> SEQ ID NO 160
<211> LENGTH: 50
<212> TYPE: DNA
<213> ORGANISM: Artificial
<220> FEATURE:
<223> OTHER INFORMATION: Synthetic probe AG9486_16_18

<400> SEQUENCE: 160
ggctgttaat tgtcagttca gtgttttaat ctgacgcagg cttatgcgga            50

<210> SEQ ID NO 161
<211> LENGTH: 50
<212> TYPE: DNA
<213> ORGANISM: Artificial
<220> FEATURE:
<223> OTHER INFORMATION: Synthetic probe AG9487_16_19

<400> SEQUENCE: 161
ggagaatgtt ttcatgttac ttatactaac attagttctt ctataggtg             50

<210> SEQ ID NO 162
<211> LENGTH: 50
<212> TYPE: DNA
<213> ORGANISM: Artificial
<220> FEATURE:
<223> OTHER INFORMATION: Synthetic probe AG9488_16_20

<400> SEQUENCE: 162
atagattggt ccaattgggt gtgaggagtt cagttatatg tttgggattt        50

<210> SEQ ID NO 163
<211> LENGTH: 50
<212> TYPE: DNA
<213> ORGANISM: Artificial
<220> FEATURE:
<223> OTHER INFORMATION: Synthetic probe AG9489_16_21

<400> SEQUENCE: 163
tttaggtagt gggtgttgag cttgaacgct ttcttaattg gtggctgctt        50

<210> SEQ ID NO 164
<211> LENGTH: 50
<212> TYPE: DNA
<213> ORGANISM: Artificial
<220> FEATURE:
<223> OTHER INFORMATION: Synthetic probe AG9490_16_22

<400> SEQUENCE: 164
ttaggcctac tatgggtgtt aaattttta ctctctctac aaggtttttt         50

<210> SEQ ID NO 165
<211> LENGTH: 50
<212> TYPE: DNA
<213> ORGANISM: Artificial
<220> FEATURE:
<223> OTHER INFORMATION: Synthetic probe AG9491_16_23

<400> SEQUENCE: 165
cctagtgtcc aaagagctgt tcctctttgg actaacagtt aaatttacaa        50

<210> SEQ ID NO 166
<211> LENGTH: 49
<212> TYPE: DNA
<213> ORGANISM: Artificial
<220> FEATURE:
<223> OTHER INFORMATION: Synthetic probe AG9492_16_24

<400> SEQUENCE: 166
gggatttaga ggttctgtg ggcaaattta aagttgaact aagattcta          49

<210> SEQ ID NO 167
<211> LENGTH: 50
<212> TYPE: DNA
<213> ORGANISM: Artificial
<220> FEATURE:
<223> OTHER INFORMATION: Synthetic probe AG9493_16_25

<400> SEQUENCE: 167
tcttggacaa ccagctatca ccaggctcgg taggtttgtc gcctctacct        50

<210> SEQ ID NO 168
<211> LENGTH: 50
<212> TYPE: DNA
<213> ORGANISM: Artificial
<220> FEATURE:

```
<223> OTHER INFORMATION: Synthetic probe AG9494_16_26

<400> SEQUENCE: 168
ataaatcttc ccactatttt gctacataga cgggtgtgct cttttagctg        50

<210> SEQ ID NO 169
<211> LENGTH: 50
<212> TYPE: DNA
<213> ORGANISM: Artificial
<220> FEATURE:
<223> OTHER INFORMATION: Synthetic probe AG9495_16_27

<400> SEQUENCE: 169
ttcttaggta gctcgtctgg tttcgggggt cttagctttg gctctccttg        50

<210> SEQ ID NO 170
<211> LENGTH: 50
<212> TYPE: DNA
<213> ORGANISM: Artificial
<220> FEATURE:
<223> OTHER INFORMATION: Synthetic probe AG9496_16_28

<400> SEQUENCE: 170
caaagttatt tctagttaat tcattatgca gaaggtatag gggttagtcc        50

<210> SEQ ID NO 171
<211> LENGTH: 50
<212> TYPE: DNA
<213> ORGANISM: Artificial
<220> FEATURE:
<223> OTHER INFORMATION: Synthetic probe AG9497_16_29

<400> SEQUENCE: 171
ttgctatatt atgcttggtt ataattttc atctttccct tgcggtacta         50

<210> SEQ ID NO 172
<211> LENGTH: 50
<212> TYPE: DNA
<213> ORGANISM: Artificial
<220> FEATURE:
<223> OTHER INFORMATION: Synthetic probe AG9498_16_30

<400> SEQUENCE: 172
tatctattgc gccaggtttc aatttctatc gcctatactt tatttgggta        50

<210> SEQ ID NO 173
<211> LENGTH: 50
<212> TYPE: DNA
<213> ORGANISM: Artificial
<220> FEATURE:
<223> OTHER INFORMATION: Synthetic probe AG9499_16_31

<400> SEQUENCE: 173
aatggtttgg ctaaggttgt ctggtagtaa ggtggagtgg gtttggggct        50

<210> SEQ ID NO 174
<211> LENGTH: 50
<212> TYPE: DNA
<213> ORGANISM: Artificial
<220> FEATURE:
<223> OTHER INFORMATION: Synthetic probe AG9500_12_1

<400> SEQUENCE: 174
gttcgtccaa gtgcactttc cagtacactt accatgttac gacttgtctc        50
```

```
<210> SEQ ID NO 175
<211> LENGTH: 50
<212> TYPE: DNA
<213> ORGANISM: Artificial
<220> FEATURE:
<223> OTHER INFORMATION: Synthetic probe AG9501_12_2

<400> SEQUENCE: 175
ctctatataa atgcgtaggg gttttagtta aatgtccttt gaagtatact              50

<210> SEQ ID NO 176
<211> LENGTH: 50
<212> TYPE: DNA
<213> ORGANISM: Artificial
<220> FEATURE:
<223> OTHER INFORMATION: Synthetic probe AG9502_12_3

<400> SEQUENCE: 176
tgaggagggt gacgggcggt gtgtacgcgc ttcagggccc tgttcaacta              50

<210> SEQ ID NO 177
<211> LENGTH: 50
<212> TYPE: DNA
<213> ORGANISM: Artificial
<220> FEATURE:
<223> OTHER INFORMATION: Synthetic probe AG9503_12_4

<400> SEQUENCE: 177
agcactctac tcttagttta ctgctaaatc caccttcgac ccttaagttt              50

<210> SEQ ID NO 178
<211> LENGTH: 50
<212> TYPE: DNA
<213> ORGANISM: Artificial
<220> FEATURE:
<223> OTHER INFORMATION: Synthetic probe AG9504_12_5

<400> SEQUENCE: 178
cataagggct atcgtagttt tctggggtag aaaatgtagc ccatttcttg              50

<210> SEQ ID NO 179
<211> LENGTH: 50
<212> TYPE: DNA
<213> ORGANISM: Artificial
<220> FEATURE:
<223> OTHER INFORMATION: Synthetic probe AG9505_12_6

<400> SEQUENCE: 179
ccacctcatg ggctacacct tgacctaacg tctttacgtg ggtacttgcg              50

<210> SEQ ID NO 180
<211> LENGTH: 50
<212> TYPE: DNA
<213> ORGANISM: Artificial
<220> FEATURE:
<223> OTHER INFORMATION: Synthetic probe AG9506_12_7

<400> SEQUENCE: 180
cttactttgt agccttcatc agggtttgct gaagatggcg gtatataggc              50

<210> SEQ ID NO 181
<211> LENGTH: 50
<212> TYPE: DNA
<213> ORGANISM: Artificial
<220> FEATURE:
<223> OTHER INFORMATION: Synthetic probe AG9507_12_8
```

<400> SEQUENCE: 181
tgagcaagag gtggtgaggt tgatcggggt ttatcgatta cagaacaggc            50

<210> SEQ ID NO 182
<211> LENGTH: 50
<212> TYPE: DNA
<213> ORGANISM: Artificial
<220> FEATURE:
<223> OTHER INFORMATION: Synthetic probe AG9508_12_9

<400> SEQUENCE: 182
tcctctagag ggatatgaag caccgccagg tcctttgagt tttaagctgt            50

<210> SEQ ID NO 183
<211> LENGTH: 50
<212> TYPE: DNA
<213> ORGANISM: Artificial
<220> FEATURE:
<223> OTHER INFORMATION: Synthetic probe AG9509_12_10

<400> SEQUENCE: 183
ggctcgtagt gttctggcga gcagttttgt tgatttaact gttgaggttt            50

<210> SEQ ID NO 184
<211> LENGTH: 50
<212> TYPE: DNA
<213> ORGANISM: Artificial
<220> FEATURE:
<223> OTHER INFORMATION: Synthetic probe AG9510_12_11

<400> SEQUENCE: 184
agggctaagc atagtggggt atctaatccc agtttgggtc ttagctattg            50

<210> SEQ ID NO 185
<211> LENGTH: 50
<212> TYPE: DNA
<213> ORGANISM: Artificial
<220> FEATURE:
<223> OTHER INFORMATION: Synthetic probe AG9511_12_12

<400> SEQUENCE: 185
tgtgttcaga tatgttaaag ccactttcgt agtctatttt gtgtcaactg            50

<210> SEQ ID NO 186
<211> LENGTH: 50
<212> TYPE: DNA
<213> ORGANISM: Artificial
<220> FEATURE:
<223> OTHER INFORMATION: Synthetic probe AG9512_12_13

<400> SEQUENCE: 186 gagttttta caactcaggt gagttttagc tttattgggg aggggtgat              50

<210> SEQ ID NO 187
<211> LENGTH: 50
<212> TYPE: DNA
<213> ORGANISM: Artificial
<220> FEATURE:
<223> OTHER INFORMATION: Synthetic probe AG9513_12_14

<400> SEQUENCE: 187
ctaaaacact ctttacgccg gcttctattg acttgggtta atcgtgtgac            50

<210> SEQ ID NO 188
<211> LENGTH: 50

```
<212> TYPE: DNA
<213> ORGANISM: Artificial
<220> FEATURE:
<223> OTHER INFORMATION: Synthetic probe AG9514_12_15

<400> SEQUENCE: 188
cgcggtggct ggcacgaaat tgaccaaccc tggggttagt atagcttagt            50

<210> SEQ ID NO 189
<211> LENGTH: 48
<212> TYPE: DNA
<213> ORGANISM: Artificial
<220> FEATURE:
<223> OTHER INFORMATION: Synthetic probe AG9515_12_16

<400> SEQUENCE: 189
taaactttcg tttattgcta aaggttaatc actgctgttt cccgtggg             48

<210> SEQ ID NO 190
<211> LENGTH: 50
<212> TYPE: DNA
<213> ORGANISM: Artificial
<220> FEATURE:
<223> OTHER INFORMATION: Synthetic probe AG9516_12_17

<400> SEQUENCE: 190
tgtggctagg ctaagcgttt tgagctgcat tgctgcgtgc ttgatgcttg            50

<210> SEQ ID NO 191
<211> LENGTH: 50
<212> TYPE: DNA
<213> ORGANISM: Artificial
<220> FEATURE:
<223> OTHER INFORMATION: Synthetic probe AG9517_12_18

<400> SEQUENCE: 191
ttccttttga tcgtggtgat ttagagggtg aactcactgg aacggggatg            50

<210> SEQ ID NO 192
<211> LENGTH: 50
<212> TYPE: DNA
<213> ORGANISM: Artificial
<220> FEATURE:
<223> OTHER INFORMATION: Synthetic probe AG9518_12_19

<400> SEQUENCE: 192
cttgcatgtg taatcttact aagagctaat agaaaggcta ggaccaaacc            50

<210> SEQ ID NO 193
<211> LENGTH: 50
<212> TYPE: DNA
<213> ORGANISM: Artificial
<220> FEATURE:
<223> OTHER INFORMATION: Synthetic probe AG9519_5_1

<400> SEQUENCE: 193
aaagcctaca gcacccggta ttcccaggcg gtctcccatc caagtactaa            50

<210> SEQ ID NO 194
<211> LENGTH: 50
<212> TYPE: DNA
<213> ORGANISM: Artificial
<220> FEATURE:
<223> OTHER INFORMATION: Synthetic probe AG9520_5_2

<400> SEQUENCE: 194
```

```
ccaggcccga ccctgcttag cttccgagat cagacgagat cgggcgcgtt            50

<210> SEQ ID NO 195
<211> LENGTH: 50
<212> TYPE: DNA
<213> ORGANISM: Artificial
<220> FEATURE:
<223> OTHER INFORMATION: Synthetic probe AG9521_5_3

<400> SEQUENCE: 195
ttccgagatc agacgagatc gggcgcgttc agggtggtat ggccgtagac            50
```

METHODS FOR SPATIAL ANALYSIS USING TARGETED RNA DEPLETION

CROSS-REFERENCE TO RELATED APPLICATIONS

Pursuant to 35 U.S.C. § 119(e), this application is a continuation of International Application PCT/US2021/028397, with an international filing date of Apr. 21, 2021, which claims priority to U.S. Provisional Patent Application No. 63/014,054, filed Apr. 22, 2020, which is incorporated herein by reference in its entirety.

SEQUENCE LISTING

The instant application contains a Sequence Listing which has been submitted on a compact disc and is hereby incorporated by reference in its entirety. Said Sequence Listing is called 0200001_SequenceListing.txt, is 37,954 bytes in size, and was created on Dec. 8, 2021.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the context of an intact tissue or a portion of a tissue, or provide a lot of analyte data for single cells, but fail to provide information regarding the position of the single cell in a parent biological sample (e.g., tissue sample).

Undesirable RNA (e.g, ribosomal RNA) constitutes a considerable proportion of the total nucleic acid pool from the biological sample, which can compete with hybridization of target analytes of interest. In certain settings, undesirable RNA is capable of hybridizing to randomers, poly-adenylated sequences, and even gene specific capture sequences, thus creating increased background signal that interferes with target analyte binding.

One option for decreasing background signal of undesirable RNA molecules is to add depletion probes during the reverse transcription step of the spatial array gene expression protocol. Depletion probes can be designed to tile various types of undesirable RNA molecules (e.g., both nuclear and mitochondrial RNA molecules). In this setting, by tiling rRNA molecules, the molecules are largely inhibited from interacting with the spatial capture array. However, one drawback could be that it is possible that a considerable fraction of rRNA are already interacting with the array when the depletion probes are added, thereby limited their utility. Thus, there is a need to remove such undesirable RNA.

RNA-templated ligation (RTL) is the process by which multiple oligonucleotides hybridize to an analyte at nearby or adjacent sequences followed by ligation of the oligonucleotides to create a ligation product. After hybridization and ligation, a DNA-RNA hybrid complex that includes the analyte of interest (e.g., RNA) and the ligated probe (made of DNA or DNA/RNA combination) is created. RTL utilizes a ribonuclease (e.g., RNAse H) to digest the DNA-RNA hybrid complex, freeing the ligated probe for downstream applications such as spatial array probe hybridization and sequencing. Here, Applicants have identified that undesirable RNA probes can also be added and hybridized to undesirable RNAs. Further, because the undesirable RNA probes/undesirable RNA complex creates a DNA-RNA hybrid complex, the same endonuclease step can digest the analyte also digests the undesirable RNA. Because there remains a need to remove such undesirable RNA, this approach simplifies the necessity for multiple enzymatic steps that could affect nucleic acid integrity and function.

SUMMARY

The present invention relates to methods of depleting undesirable RNA from nucleic acid samples. The invention is useful for preparing cDNA from the RNA-depleted nucleic acid samples, for example, from fixed paraffin embedded (FFPE) tissue samples.

In one aspect, provided herein is a method for identifying a location of an analyte in a biological sample, the method comprising: (a) contacting a biological sample with a first probe oligonucleotide, a second probe oligonucleotide, and a plurality of undesirable RNA depletion probes, wherein the first probe oligonucleotide and the second probe oligonucleotide are substantially complementary to adjacent sequences of the analyte, wherein the second probe oligonucleotide comprises a capture probe binding domain that is capable of binding to a capture domain of a capture probe, and wherein an undesirable RNA depletion probe of the plurality of undesirable RNA depletion probes is substantially complementary to a sequence of an undesirable RNA molecule in the biological sample; (b) hybridizing the first probe oligonucleotide and the second probe oligonucleotide to the analyte; (c) hybridizing the undesirable RNA depletion probe to the undesirable RNA molecule; (d) ligating the first probe oligonucleotide and the second probe oligonucleotide, thereby creating a ligated probe that is substantially complementary to the analyte; (e) removing the plurality of undesirable RNA depletion probe-undesirable RNA complexes and releasing the ligated probe from the analyte; (f) hybridizing the capture probe binding domain of the ligated probe to a capture domain of a capture probe that is affixed to the substrate; and (g) determining (i) all or a part of the sequence of the ligated probe specifically bound to the capture domain, or a complement thereof, and (ii) all or a part of the sequence of the spatial barcode, or a complement thereof, and using the determined sequence of (i) and (ii) to identify the location of the analyte in the biological sample.

In some embodiments, the first probe oligonucleotide comprises at least two ribonucleic acid bases at the 3' end.

In some embodiments, the first probe oligonucleotide further comprises a functional sequence. In some embodiments, the functional sequence is a primer sequence.

In some embodiments, the second probe oligonucleotide comprises a phosphorylated nucleotide at the 5' end.

In some embodiments, the method further comprises providing a capture probe binding domain blocking moiety that interacts with the capture probe binding domain.

In some embodiments, the method further comprises releasing the capture probe binding domain blocking moiety from the capture probe binding domain prior to step (f).

In some embodiments, the capture probe binding domain comprises a poly-adenylated (poly(A)) sequence or a complement thereof.

In some embodiments, the capture probe binding domain blocking moiety comprises a poly-uridine sequence, a poly-thymidine sequence, or both.

In some embodiments, releasing the poly-uridine sequence from the poly(A) sequence comprises denaturing the ligated probe or contacting the ligated probe with an endonuclease or exonuclease.

In some embodiments, the capture probe binding domain comprises a sequence that is complementary to all or a portion of the capture domain of the capture probe. In some embodiments, the capture probe binding domain comprises a degenerate sequence.

In some embodiments, the ligation step comprises ligating the first and second probe oligonucleotides using enzymatic ligation or chemical ligation. In some embodiments, the enzymatic ligation utilizes a ligase.

In some embodiments, the ligase is one or more of a T4 RNA ligase (Rnl2), a splintR ligase, a single stranded DNA ligase, or a T4 DNA ligase. In some embodiments, the ligase is a T4 RNA ligase 2 (Rnl2) ligase.

In some embodiments, the first probe oligonucleotide and the second probe oligonucleotide are DNA probes. In some embodiments, the undesirable RNA depletion probe is a DNA probe.

In some embodiments, the steps (b) and (c) each creates a RNA: DNA hybrid.

In some embodiments, step (e) comprises contacting the undesirable RNA depletion probe with a ribonuclease.

In some embodiments, the ribonuclease is RNase H. In some embodiments, the RNase H is RNase H1. In some embodiments, the RNase H is RNase H2. In some embodiments, the RNase H is a thermostable RNase.

In some embodiments, the method further comprises amplifying the ligated probe prior to step (f). In some embodiments, steps (b) and (c) are performed at substantially the same time.

In one aspect, provided herein is a method for identifying a location of an analyte in a biological sample, the method comprising: (a) contacting the biological sample with a substrate comprising a plurality of attached capture probes, wherein a capture probe of the plurality comprises (i) the spatial barcode and (ii) a capture domain that binds specifically to a sequence present in the analyte; and a plurality of undesirable RNA depletion probes, wherein an undesirable RNA depletion probe in the plurality of undesirable RNA depletion probes is substantially complementary to a sequence of an undesirable RNA molecule in the biological sample; (b) hybridizing the undesirable RNA depletion probe to the undesirable RNA; (c) removing the plurality of undesirable RNA depletion probe-undesirable RNA complexes; (d) hybridizing the analyte to a capture domain of a capture probe that is affixed to the substrate; (e) extending a 3' end of the capture probe using the analyte that is specifically bound to the capture domain as a template to generate an extended capture probe; and (f) amplifying the extended capture probe to produce a nucleic acid.

In some embodiments, provided herein is the method for identifying a location of an analyte in a biological sample, further comprising determining (i) all or a part of the sequence of the spatial barcode or the complement thereof, and (ii) all or a portion of the sequence of the analyte from the biological sample, and using the determined sequences of (i) and (ii) to identify the location of the analyte in the biological sample.

In one aspect, provided herein is a method for identifying a location of an analyte in a biological sample, the method comprising: (a) contacting the biological sample with a plurality of undesirable RNA depletion probes, wherein an undesirable RNA depletion probe in the plurality of undesirable RNA depletion probes is substantially complementary to a sequence of an undesirable RNA molecule in the biological sample; (b) hybridizing the undesirable RNA depletion probe to the undesirable RNA; (c) removing the plurality of undesirable RNA depletion probe-undesirable RNA complexes; (d) contacting a plurality of nucleic acids with a plurality of target oligonucleotide probes, wherein a nucleic acid of the plurality of nucleic acids comprises (i) a spatial barcode or a complement thereof, and (ii) a portion of a sequence of an analyte from a biological sample, or a complement thereof; and a target oligonucleotide probe of the plurality of target oligonucleotide probes comprises: a domain that binds specifically to (i) all or a portion of the spatial barcode or a complement thereof, and/or (ii) all or a portion of the sequence of the analyte from the biological sample, or a complement thereof, and a molecular tag; (e) enriching a complex of the target oligonucleotide probe specifically bound to the nucleic acid using a substrate comprising an agent that binds specifically to the molecular tag; and (f) determining (i) all or a portion of the sequence of the spatial barcode or the complement thereof, and (ii) all or a portion of the sequence of the analyte from the biological sample, and using the determined sequences of (i) and (ii) to identify the location of the analyte in the biological sample.

In some embodiments, the method further comprises generating the plurality of nucleic acids comprises: (a) contacting the biological sample with a substrate comprising a plurality of attached capture probes, wherein a capture probe of the plurality comprises (i) the spatial barcode and (ii) a capture domain that binds specifically to a sequence present in the analyte; (b) extending a 3' end of the capture probe using the analyte that is specifically bound to the capture domain as a template to generate an extended capture probe; and (c) amplifying the extended capture probe to produce the nucleic acid.

In some embodiments, the domain of the target oligonucleotide probe comprises a total of about 40 nucleotides to about 160 nucleotides.

In some embodiments, the molecular tag comprises a moiety. In some embodiments, the moiety is streptavidin, avidin, biotin, or a fluorophore.

In some embodiments, the molecular tag comprises a small molecule, a nucleic acid, or a carbohydrate.

In some embodiments, the molecular tag is positioned 5' or 3' to the domain in the target oligonucleotide probe.

In some embodiments, the agent that binds specifically to the molecular tag comprises a protein. In some embodiments, the protein is an antibody.

In some embodiments, the agent that binds specifically to the molecular tag comprises a nucleic acid. In some embodiments, the nucleic acid is DNA.

In some embodiments, the agent that binds specifically to the molecular tag comprises a small molecule.

In some embodiments, the analyte from the biological sample is associated with a disease or condition. In some embodiments, the analyte from the biological sample comprises a mutation. In some embodiments, the analyte from the biological sample comprises a single nucleotide polymorphism (SNP). In some embodiments, the analyte from the biological sample comprises a trinucleotide repeat.

In some embodiments, the biological sample is a tissue sample.

In some embodiments, the tissue sample is a formalin-fixed, paraffin-embedded (FFPE) tissue sample, a fresh or a frozen tissue sample. In some embodiments, the tissue sample is the FFPE tissue sample, and the tissue sample is decrosslinked.

In some embodiments, the biological sample was previously stained. In some embodiments, the biological sample was previously stained using hematoxylin and eosin (H&E). In some embodiments, the biological sample was previously stained using immunofluorescence or immunohistochemistry.

In some embodiments, the method further comprises contacting the biological sample with a permeabilization agent.

In some embodiments, the biological sample is a permeabilized biological sample that has been permeabilized with a permeabilization agent.

In some embodiments, the permeabilization agent is selected from an organic solvent, a detergent, and an enzyme, or a combination thereof. In some embodiments, the permeabilization agent is an endopeptidase or protease. In some embodiments, the endopeptidase is pepsin or proteinase K.

In some embodiments, the determining step comprises amplifying all or part of the ligated probe specifically bound to the capture domain.

In some embodiments, the amplifying is isothermal. In some embodiments, the amplifying is not isothermal.

In some embodiments, an amplifying product comprises (i) all or part of sequence of the ligated probe specifically bound to the capture domain, or a complement thereof, and (ii) all or a part of the sequence of the spatial barcode, or a complement thereof.

In some embodiments, the determining step comprises sequencing.

In some embodiments, the analyte is RNA. In some embodiments, the RNA is an mRNA.

In one aspect, provided herein is a method for enriching a target nucleic acid in a spatial array comprising (a) adding a plurality of undesirable RNA depletion probes to the spatial array, wherein an undesirable RNA depletion probe of the plurality of undesirable RNA depletion probes is substantially complementary to a sequence of an undesirable RNA molecule in the spatial array; (b) hybridizing an undesirable RNA depletion probe to the undesirable RNA; (c) removing the plurality of undesirable RNA depletion probe-undesirable RNA complexes; and (d) applying remaining nucleic acids to enrich the target nuclei acid.

In one aspect, provided herein is a method for depleting undesirable RNA molecules in a spatial array, comprising (a) adding a plurality of undesirable RNA depletion probes to the spatial array, wherein an undesirable RNA depletion probe of the plurality of undesirable RNA depletion probes is substantially complementary to a sequence of an undesirable RNA molecule in the spatial array; (b) hybridizing an undesirable RNA depletion probe to the undesirable RNA; and (c) removing the plurality of undesirable RNA depletion probe-undesirable RNA complexes to deplete the undesirable RNA molecules.

In some embodiments, the undesirable RNA depletion probe is a DNA probe.

In some embodiments, the hybridizing step comprises hybridizing the DNA probe with the undesirable RNA molecule that creates a RNA: DNA hybrid.

In some embodiments, the removing step comprises contacting the undesirable RNA depletion probe with a ribonuclease.

In some embodiments, the ribonuclease is RNase H. In some embodiments, the RNase H is RNase H1. In some embodiments, the RNase H is RNase H2. In some embodiments, the RNase H is a thermostable RNase.

In some embodiments, the undesirable RNA depletion probe is substantially complementary to all or a portion of the sequence of the undesirable RNA molecule in the biological sample.

In some embodiments, at least one undesirable RNA depletion probe specifically hybridizes to substantially one or more portions of the sequence of the undesirable RNA molecule.

In some embodiments, at least one undesirable RNA depletion probe specifically hybridizes to substantially the entire full length sequence of the undesirable RNA molecule.

In some embodiments, the undesirable RNA molecule is a transfer RNA (tRNA), a ribosomal RNA (rRNA), a messenger RNA (mRNA), or any combinations thereof.

In some embodiments, the undesirable RNA molecule is a mitochondrial RNA, nuclear RNA, or cytoplasmic RNA.

In some embodiments, the undesirable RNA depletion probe further comprises a capture moiety. In some embodiments, the removing step comprises using a capture moiety-binding agent that binds specifically to the capture moiety.

In some embodiments, the capture moiety is streptavidin, avidin, biotin, or a fluorophore. In some embodiments, the capture moiety is a biotin.

In some embodiments, the capture moiety comprises a small molecule, a nucleic acid, or a carbohydrate.

In some embodiments, the capture moiety is positioned 5' or 3' to the domain in the undesirable RNA depletion probe.

In some embodiments, a capture moiety-binding agent that binds specifically to the capture moiety comprises a protein.

In some embodiments, the protein is an antibody. In some embodiments, the protein is streptavidin.

In some embodiments, the capture moiety-binding agent that binds specifically to the capture moiety comprises a nucleic acid. In some embodiments, the nucleic acid is DNA.

In some embodiments, the capture moiety-binding agent that binds specifically to the capture moiety comprises a small molecule.

In some embodiments, the capture moiety-binding agent that binds specifically to the capture moiety is attached to a substrate.

In some embodiments, the substrate is a bead. In some embodiments, the bead is a magnetic bead. In some embodiments, the capture moiety is a biotin and the capture moiety-binding agent is streptavidin. In some embodiments, the streptavidin is attached to a magnetic bead that allows the undesirable RNA depletion probe-undesirable RNA complexes to be removed magnetically from the biological sample.

In some embodiments, the capture probes are capable of hybridizing to the ligated probe as described herein.

In some embodiments, the capture probes further comprises a functional sequence. In some embodiments, the functional sequence is primer sequence or a complement thereof. In some embodiments, the capture probe further comprises a unique molecular sequence or a complement thereof. In some embodiments, the capture probe further comprises an additional primer binding sequence or a complement thereof.

In one aspect, provided herein is a kit comprising (a) an array comprising a plurality of capture probes; (b) a plurality of probe oligonucleotides comprising a first probe oligonucleotide and a second oligonucleotide, wherein the first probe oligonucleotide and the second probe oligonucleotide are substantially complementary to adjacent sequences of an analyte, wherein the second probe oligonucleotide comprises a capture probe binding domain that is capable of binding to a capture domain of the capture probe; (c) a plurality of enzymes comprising a ribonuclease and a ligase; and (d) an instruction for using the kit.

In some embodiments, the ribonuclease is RNase H.

In some embodiments, the ligase is one or more of a T4 RNA ligase (Rnl2), a splintR ligase, a single stranded DNA ligase, or a T4 DNA ligase. In some embodiments, the ligase is a T4 RNA ligase 2 (Rnl2) ligase.

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

FIGS. 19B-19D show gene expression heat maps for samples 1-4 for Penk, Doc2g, and Kctd12, respectively.

FIGS. 20A and 20B show gene expression heat maps for house keeping genes: Actb and Gapdh, respectively. FIGS. 20C and 20D show gene expression heat maps for two targets of the ribosomal depletion probes: mt-Rn 1 and mt-Rnr2, respectively.

DETAILED DESCRIPTION

I. Introduction

Figure 1:
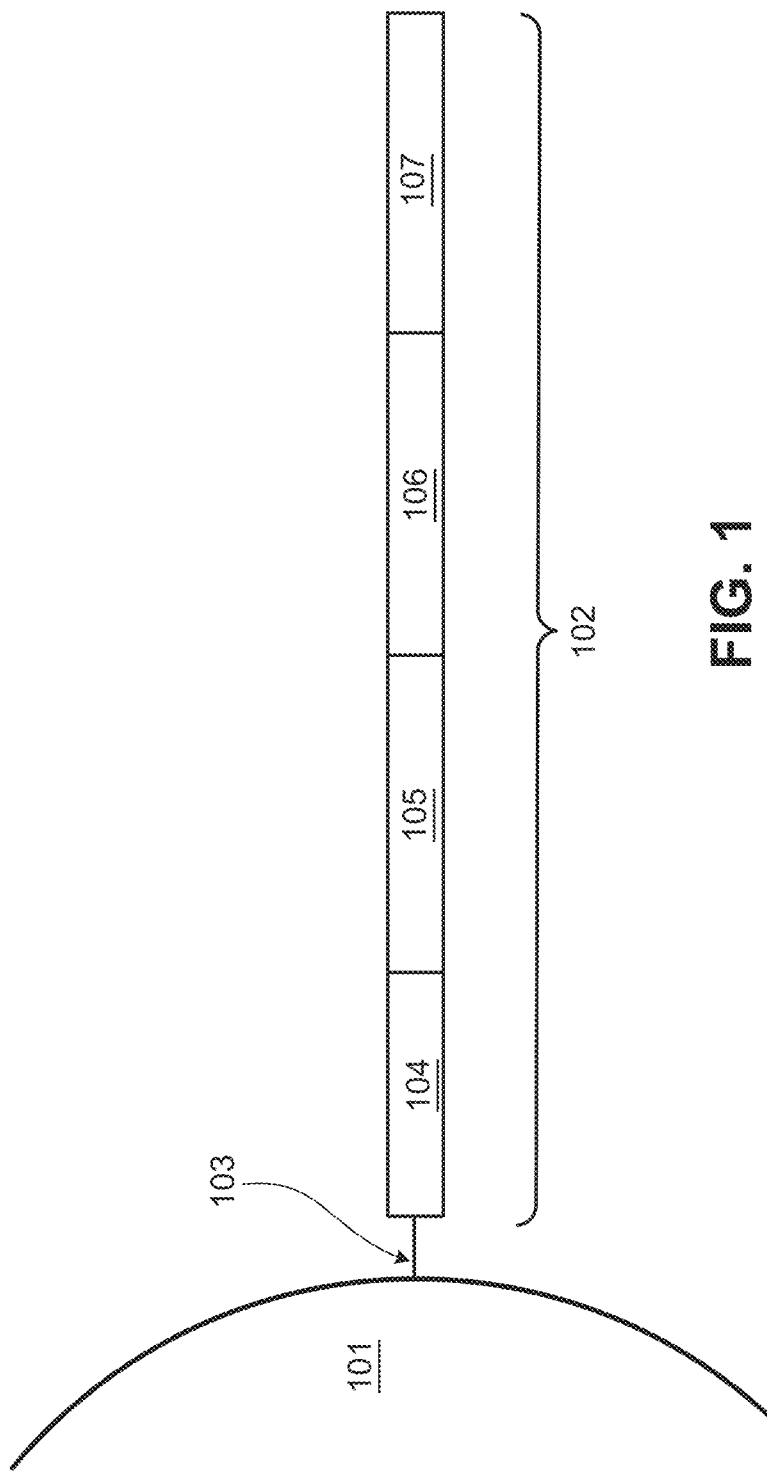
FIG. 1 is a schematic diagram showing an example of a barcoded capture probe, as described herein.

Disclosed herein are methods and compositions predicated on using targeted RNA depletion to remove one or more species of undesirable RNA molecules (e.g., ribosomal RNA and/or mitochondrial RNA) to reduce the pool and concentration of undesirable RNA molecules in a sample which could interfere with desired target detection (e.g., detection of mRNA). To achieve depletion, one or more probes are designed that hybridize to one or more undesirable RNA molecules. For example, in one embodiment, probes can be administered to a biological sample that selectively hybridize to ribosomal RNA (rRNA), thereby reducing the pool and concentration of rRNA in the sample. Here, this type of RNA depletion is combined with spatial analysis techniques in order to determine abundance and/or location of one or more analytes in a biological sample. The ability to reduce interference with detection of desired targets by removing undesirable RNA increases efficiency and sensitivity +y of the spatial analysis techniques. For example, subsequent or concurrent application of capture probes to the sample can result in improved capture of other types of RNA (e.g., mRNA or products of RNA-templated ligation) due to a reduction in undesirable RNA (e.g., down-selected RNA) present in the sample.

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodrigues et al., Science 363(6434):1463-1467, 2019; Lee et al., Nat. Protoc. 10(3):442-458, 2015; Trejo et al., PLoS ONE 14(2): e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a connected probe (e.g., a ligation product) or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)).

FIG. 1 is a schematic diagram showing an exemplary capture probe, as described herein. As shown, the capture probe 102 is optionally coupled to a feature 101 by a cleavage domain 103, such as a disulfide linker. The capture probe can include functional sequence 104 that is useful for subsequent processing. The functional sequence 104 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 105. The capture probe can also include a unique molecular identifier (UMI) sequence 106. While FIG. 1 shows the spatial barcode 105 as being located upstream (5') of UMI sequence 106, it is to be understood that capture probes wherein UMI sequence 106 is located upstream (5') of the spatial barcode 105 is also suitable for use in any of the methods described herein. The capture probe can also include a capture domain 107 to facilitate capture of a target analyte. The capture domain can have a sequence complementary to a sequence of a nucleic acid analyte. The capture domain can have a sequence complementary to a connected probe described herein. The capture domain can have a sequence complementary to a capture handle sequence present in an analyte capture agent. The capture domain can have a sequence complementary to a splint oligonucleotide. Such splint oligonucleotide, in addition to having a sequence complementary to a capture domain of a capture probe, can have a sequence of a nucleic acid analyte, a sequence complementary to a portion of a connected probe described herein, and/or a capture handle sequence described herein.

The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 105 and functional sequences 104 are common to all of the probes attached to a given feature. In some embodiments, the UMI sequence 106 of a capture probe attached to a given feature is different from the UMI sequence of a different capture probe attached to the given feature.

Figure 2:
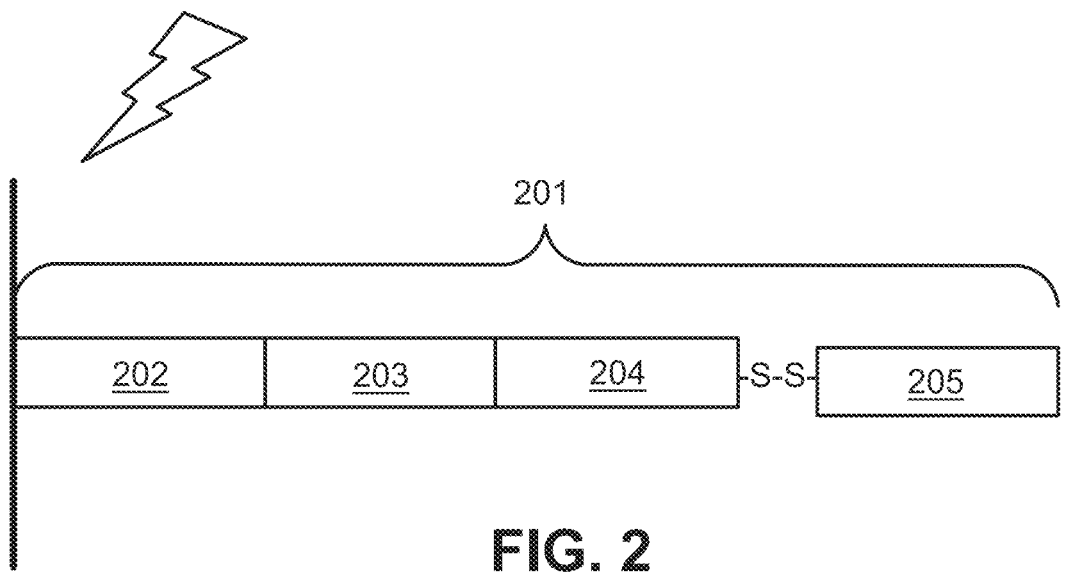
FIG. 2 is a schematic illustrating a cleavable capture probe, wherein the cleaved capture probe can enter into a non-permeabilized cell and bind to target analytes within the sample.

FIG. 2 is a schematic illustrating a cleavable capture probe, wherein the cleaved capture probe can enter into a non-permeabilized cell and bind to analytes within the sample. The capture probe 201 contains a cleavage domain 202, a cell penetrating peptide 203, a reporter molecule 204, and a disulfide bond (—S—S—). 205 represents all other parts of a capture probe, for example a spatial barcode and a capture domain.

Figure 3:
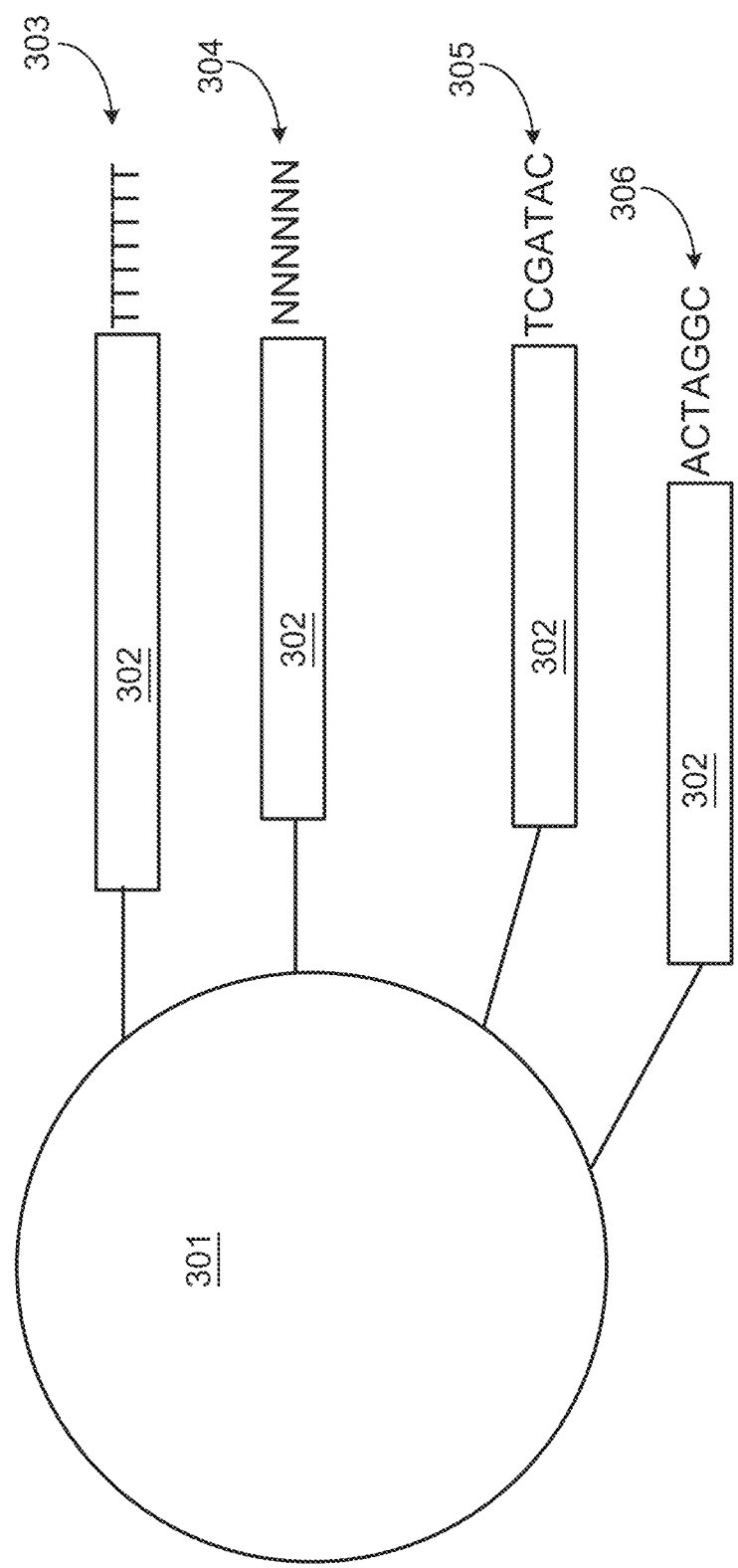
FIG. 3 is a schematic diagram of an exemplary multiplexed spatially-barcoded feature.

FIG. 3 is a schematic diagram of an exemplary multiplexed spatially-barcoded feature. In FIG. 3, the feature 301 can be coupled to spatially-barcoded capture probes, wherein the spatially-barcoded probes of a particular feature can possess the same spatial barcode, but have different capture domains designed to associate the spatial barcode of the feature with more than one target analyte. For example, a feature may be coupled to four different types of spatially-barcoded capture probes, each type of spatially-barcoded capture probe possessing the spatial barcode 302. One type of capture probe associated with the feature includes the spatial barcode 302 in combination with a poly(T) capture domain 303, designed to capture mRNA target analytes. A second type of capture probe associated with the feature includes the spatial barcode 302 in combination with a random N-mer capture domain 304 for gDNA analysis. A third type of capture probe associated with the feature includes the spatial barcode 302 in combination with a capture domain complementary to a capture handle sequence of an analyte capture agent of interest 305. A fourth type of capture probe associated with the feature includes the spatial barcode 302 in combination with a capture domain that can specifically bind a nucleic acid molecule 306 that can function in a CRISPR assay (e.g., CRISPR/Cas9). While only four different capture probe-barcoded constructs are shown in FIG. 3, capture-probe barcoded constructs can be tailored for analyses of any given analyte associated with a nucleic acid and capable of binding with such a construct. For example, the schemes shown in FIG. 3 can also be used for concurrent analysis of other analytes disclosed herein, including, but not limited to: (a) mRNA, a lineage tracing construct, cell surface or intracellular proteins and metabolites, and gDNA; (b) mRNA, accessible chromatin (e.g., ATAC-seq, DNase-seq, and/or MNase-seq) cell surface or intracellular proteins and metabolites, and a perturbation agent (e.g., a CRISPR crRNA/sgRNA, TALEN, zinc finger nuclease, and/or antisense oligonucleotide as described herein); (c) mRNA, cell surface or intracellular proteins and/or metabolites, a barcoded labelling agent (e.g., the MEW multimers described herein), and a V(D)J sequence of an immune cell receptor (e.g., T-cell receptor). In some embodiments, a perturbation agent can be a small molecule, an antibody, a drug, an aptamer, a miRNA, a physical environmental (e.g., temperature change), or any other known perturbation agents. See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) a capture handle sequence. As used herein, the term "analyte binding moiety barcode" refers to a barcode that is associated with or otherwise identifies the analyte binding moiety. As used herein, the term "analyte capture sequence" or "capture handle sequence" refers to a region or moiety configured to hybridize to, bind to, couple to, or otherwise interact with a capture domain of a capture probe. In some embodiments, a capture handle sequence is complementary to a capture domain of a capture probe. In some cases, an analyte binding moiety barcode (or portion thereof) may be able to be removed (e.g., cleaved) from the analyte capture agent.

Figure 4:
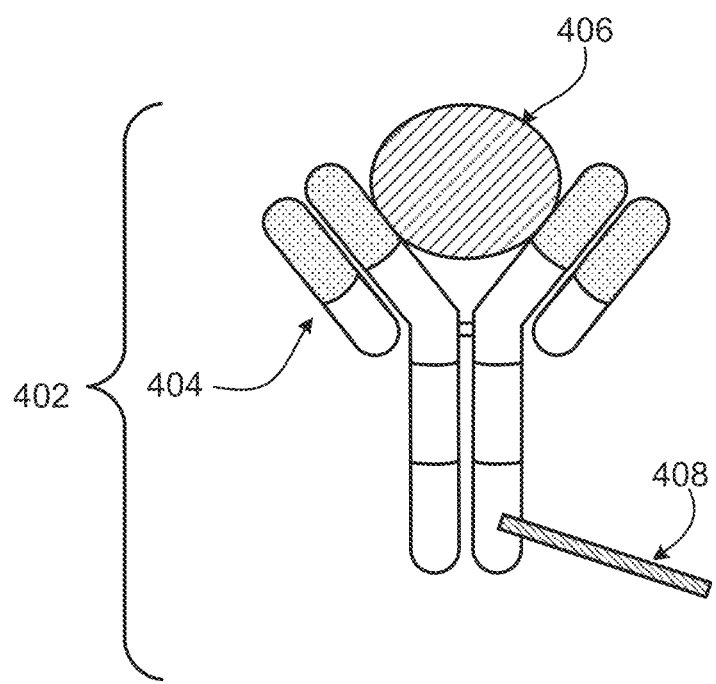
FIG. 4 is a schematic diagram of an exemplary analyte capture agent.

FIG. 4 is a schematic diagram of an exemplary analyte capture agent 402 comprised of an analyte-binding moiety 404 and an analyte-binding moiety barcode domain 408. The exemplary analyte-binding moiety 404 is a molecule capable of binding to an analyte 406 and the analyte capture agent is capable of interacting with a spatially-barcoded capture probe. The analyte-binding moiety can bind to the analyte 406 with high affinity and/or with high specificity. The analyte capture agent can include an analyte-binding moiety barcode domain 408, a nucleotide sequence (e.g., an oligonucleotide), which can hybridize to at least a portion or an entirety of a capture domain of a capture probe. The analyte-binding moiety barcode domain 408 can comprise an analyte binding moiety barcode and a capture handle sequence described herein. The analyte-binding moiety 404 can include a polypeptide and/or an aptamer. The analyte-binding moiety 404 can include an antibody or antibody fragment (e.g., an antigen-binding fragment).

Figure 5:
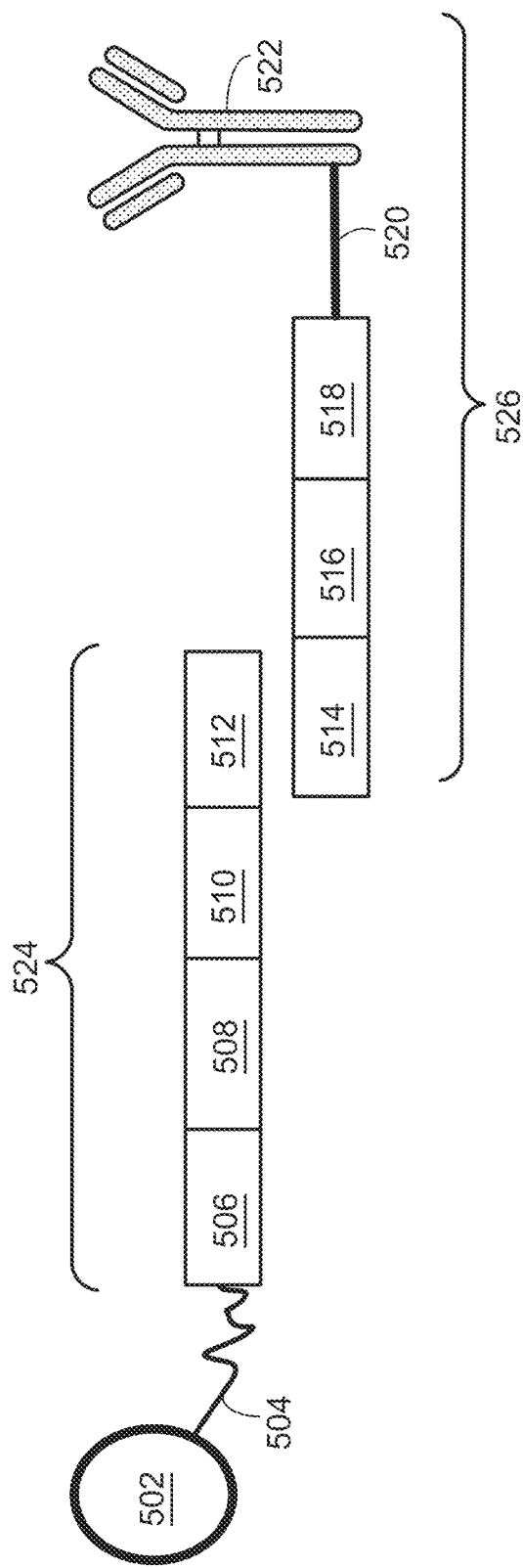
FIG. 5 is a schematic diagram depicting an exemplary interaction between a feature-immobilized capture probe 524 and an analyte capture agent 526.

FIG. 5 is a schematic diagram depicting an exemplary interaction between a feature-immobilized capture probe 524 and an analyte capture agent 526. The feature-immobilized capture probe 524 can include a spatial barcode 508 as well as functional sequences 506 and UMI 510, as described elsewhere herein. The capture probe can also include a capture domain 512 that is capable of binding to an analyte capture agent 526. The analyte capture agent 526 can include a functional sequence 518, analyte binding moiety barcode 516, and a capture handle sequence 514 that is capable of binding to the capture domain 512 of the capture probe 524. The analyte capture agent can also include a linker 520 that allows the capture agent barcode domain 516 to couple to the analyte binding moiety 522.

Figure 6A:
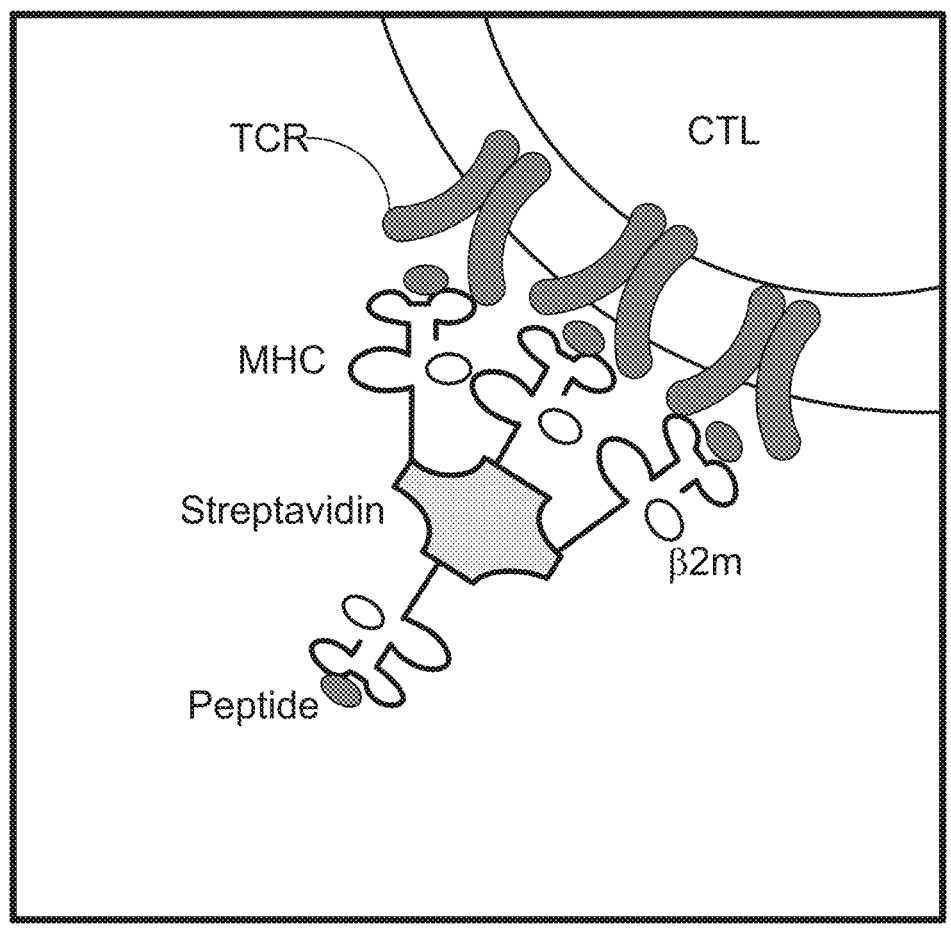
FIGS. 6A, 6B, and 6C are schematics illustrating how streptavidin cell tags can be utilized in an array-based system to produce spatially-barcoded cells or cellular contents.
Figure 6B:
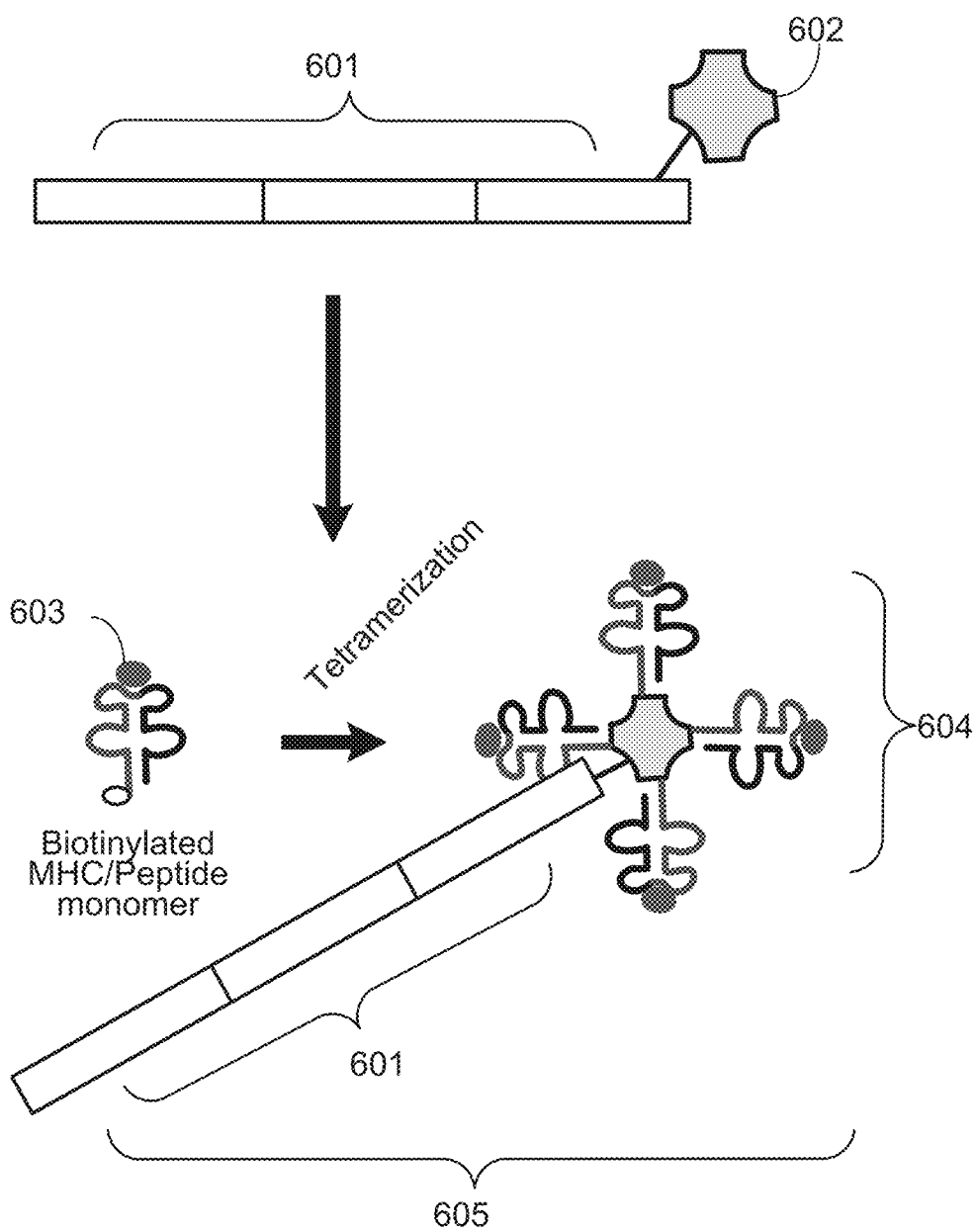
Figure 6C:
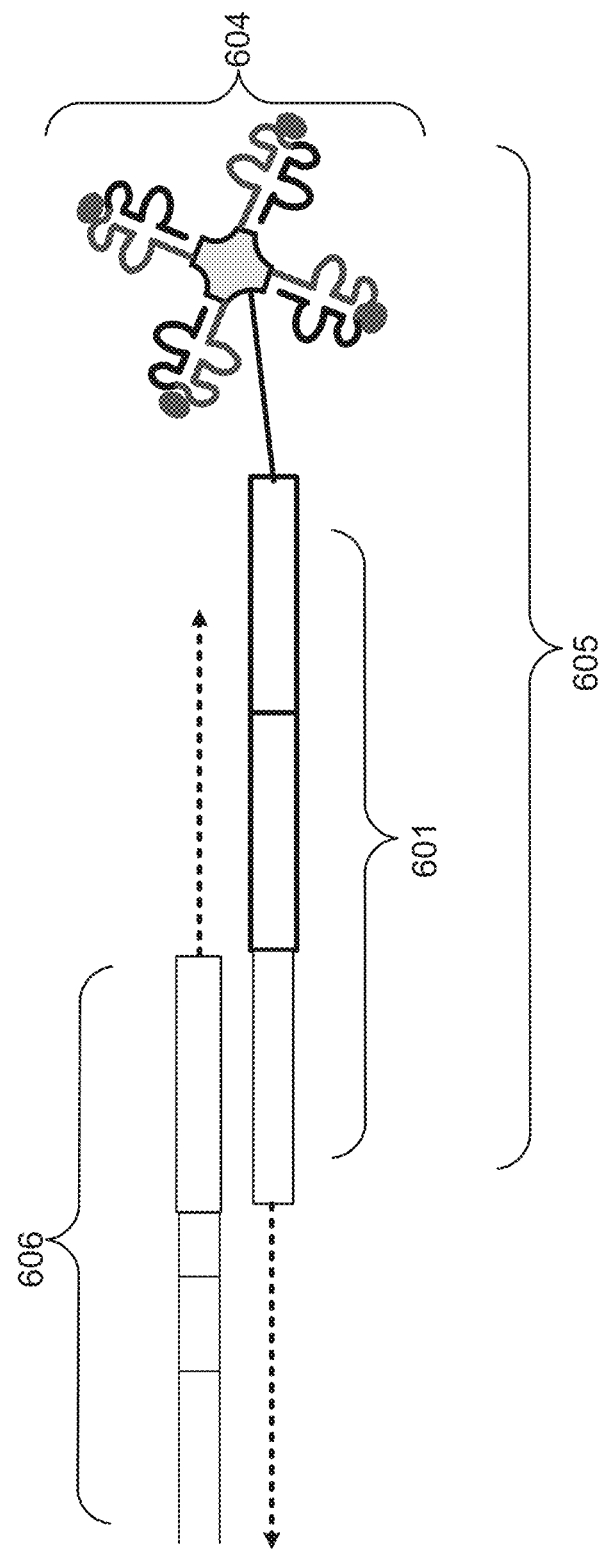

FIGS. 6A, 6B, and 6C are schematics illustrating how streptavidin cell tags can be utilized in an array-based system to produce a spatially-barcoded cell or cellular contents. For example, as shown in FIG. 6A, peptide-bound major histocompatibility complex (MHC) can be individually associated with biotin (β2m) and bound to a streptavidin moiety such that the streptavidin moiety comprises multiple pMHC moieties. Each of these moieties can bind to a TCR such that the streptavidin binds to a target T-cell via multiple MHC/TCR binding interactions. Multiple interactions synergize and can substantially improve binding affinity. Such improved affinity can improve labelling of T-cells and also reduce the likelihood that labels will dissociate from T-cell surfaces. As shown in FIG. 6B, a capture agent barcode domain 601 can be modified with streptavidin 602 and contacted with multiple molecules of biotinylated MHC 603 such that the biotinylated MHC 603 molecules are coupled with the streptavidin conjugated capture agent barcode domain 601. The result is a barcoded MHC multimer complex 605. As shown in FIG. 6B, the capture agent barcode domain sequence 601 can identify the MHC as its associated label and also includes optional functional sequences such as sequences for hybridization with other oligonucleotides. As shown in FIG. 6C, one example oligonucleotide is capture probe 606 that comprises a complementary sequence (e.g., rGrGrG corresponding to C C C), a barcode sequence and other functional sequences, such as, for example, a UMI, an adapter sequence (e.g., comprising a sequencing primer sequence (e.g., R1 or a partial R1 ("pR1"), R2), a flow cell attachment sequence (e.g., P5 or P7 or partial sequences thereof)), etc. In some cases, capture probe 606 may at first be associated with a feature (e.g., a gel bead) and released from the feature. In other embodiments, capture probe 606 can hybridize with a capture agent barcode domain 601 of the MHC-oligonucleotide complex 605. The hybridized oligonucleotides (Spacer C C C and Spacer rGrGrG) can then be extended in primer extension reactions such that constructs comprising sequences that correspond to each of the two spatial barcode sequences (the spatial barcode associated with the capture probe, and the barcode associated with the MHC-oligonucleotide complex) are generated. In some cases, one or both of the corresponding sequences may be a complement of the original sequence in capture probe 606 or capture agent barcode domain 601. In other embodiments, the capture probe and the capture agent barcode domain are ligated together. The resulting constructs can be optionally further processed (e.g., to add any additional sequences and/or for clean-up) and subjected to sequencing. As described elsewhere herein, a sequence derived from the capture probe 606 spatial barcode sequence may be used to identify a feature and the sequence derived from spatial barcode sequence on the capture agent barcode domain 601 may be used to identify the particular peptide MHC complex 604 bound on the surface of the cell (e.g., when using MHC-peptide libraries for screening immune cells or immune cell populations).

Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

In some cases, capture probes may be configured to prime, replicate, and consequently yield optionally barcoded extension products from a template (e.g., a DNA or RNA template, such as an analyte or an intermediate agent (e.g., a connected probe (e.g., a ligation product) or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form a connected probe (e.g., a ligation product) with a template (e.g., a DNA or RNA template, such as an analyte or an intermediate agent, or portion thereof), thereby creating ligations products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction). Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a connected probe (e.g., a ligation product). In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the connected probe (e.g., a ligation product) is released from the analyte. In some instances, the connected probe (e.g., a ligation product) is released using an endonuclease (e.g., RNAse H). The released connected probe (e.g., a ligation product) can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

II. Targeted RNA Depletion

Targeted RNA depletion allows for depletion or removal of one or more species of undesirable RNA molecules (e.g., ribosomal RNA and/or mitochondrial RNA), thereby reducing the pool and concentration of undesirable RNA molecules in the sample which could interfere with desired target detection (e.g., detection of mRNA). To achieve depletion, one or more probes are designed that hybridize to one or more undesirable RNA molecules. For example, in one embodiment, probes can be administered to a biological sample that selectively hybridize to ribosomal RNA (rRNA), thereby reducing the pool and concentration of rRNA in the sample. In one embodiment, probes can be administered to a biological sample that selectively hybridize to mitochondria RNA (mtRNA), thereby reducing the pool and concentration of mtRNA in the sample. Subsequent or concurrent application of capture probes to the sample can result in improved capture of other types of RNA due to a reduction in undesirable RNA (e.g., down-selected RNA) present in the sample.

A non-limiting example of a method for identifying a location of an analyte (e.g., any of the analytes described herein) in a biological sample using targeted RNA depletion includes: (a) contacting the biological sample with a plurality of undesirable RNA depletion probes (e.g., any of the undesirable RNA depletion probes described herein), wherein an undesirable RNA depletion probe in the plurality of undesirable RNA depletion probes is substantially complementary to all or a portion of the sequence of an undesirable RNA molecule (e.g., any of the undesirable RNA molecules described herein) in the biological sample; (b) hybridizing the undesirable RNA depletion probe to the undesirable RNA (e.g., using any of the methods for hybridizing the undesirable RNA depletion probe to the undesirable RNA described herein); (c) removing the plurality of undesirable RNA depletion probe-undesirable RNA complexes (e.g., using any of the methods for removing the plurality of undesirable RNA depletion probe-undesirable RNA complexes described herein); (d) contacting the biological sample with a substrate (e.g., any of the substrates described herein) comprising a plurality of attached capture probes (e.g., any of the capture probes described herein), wherein a capture probe of the plurality includes (i) the spatial barcode (e.g., any of the spatial barcode described herein) and (ii) a capture domain (e.g., any of the capture domains described herein) that binds specifically to a sequence present in the analyte; (e) extending a 3' end of the capture probe using the analyte that is specifically bound to the capture domain as a template to generate an extended capture probe; and (f) amplifying (e.g., using any of the methods for amplifying described herein) the extended capture probe to produce a nucleic acid.

A non-limiting example of a method for identifying a location of an analyte in a biological sample using RNA-templated ligation and targeted RNA depletion includes: (a) contacting a biological sample with a first probe oligonucleotide, a second probe oligonucleotide, and a plurality of undesirable RNA depletion probes, wherein the first probe oligonucleotide and the second probe oligonucleotide are substantially complementary to adjacent sequences of the analyte, wherein the second probe oligonucleotide includes a capture probe binding domain that is capable of binding to a capture domain of a capture probe, and wherein an undesirable RNA depletion probe of the plurality of undesirable RNA depletion probes is substantially complementary to a sequence of an undesirable RNA molecule in the biological sample (b) hybridizing the first probe oligonucleotide and the second probe oligonucleotide to the analyte; (c) hybridizing the undesirable RNA depletion probe to the undesirable RNA molecule; (d) ligating the first probe oligonucleotide and the second probe oligonucleotide, thereby creating a ligated probe that is substantially complementary to the analyte; (e) removing the plurality of undesirable RNA depletion probe-undesirable RNA complexes and releasing the ligated probe from the analyte; (f) hybridizing the capture probe binding domain of the ligated probe to a capture domain of a capture probe that is affixed to the substrate; and (g) determining (i) all or a part of the sequence of the ligated probe specifically bound to the capture domain, or a complement thereof, and (ii) all or a part of the sequence of the spatial barcode, or a complement thereof, and using the determined sequence of (i) and (ii) to identify the location of the analyte in the biological sample.

Figure 7:
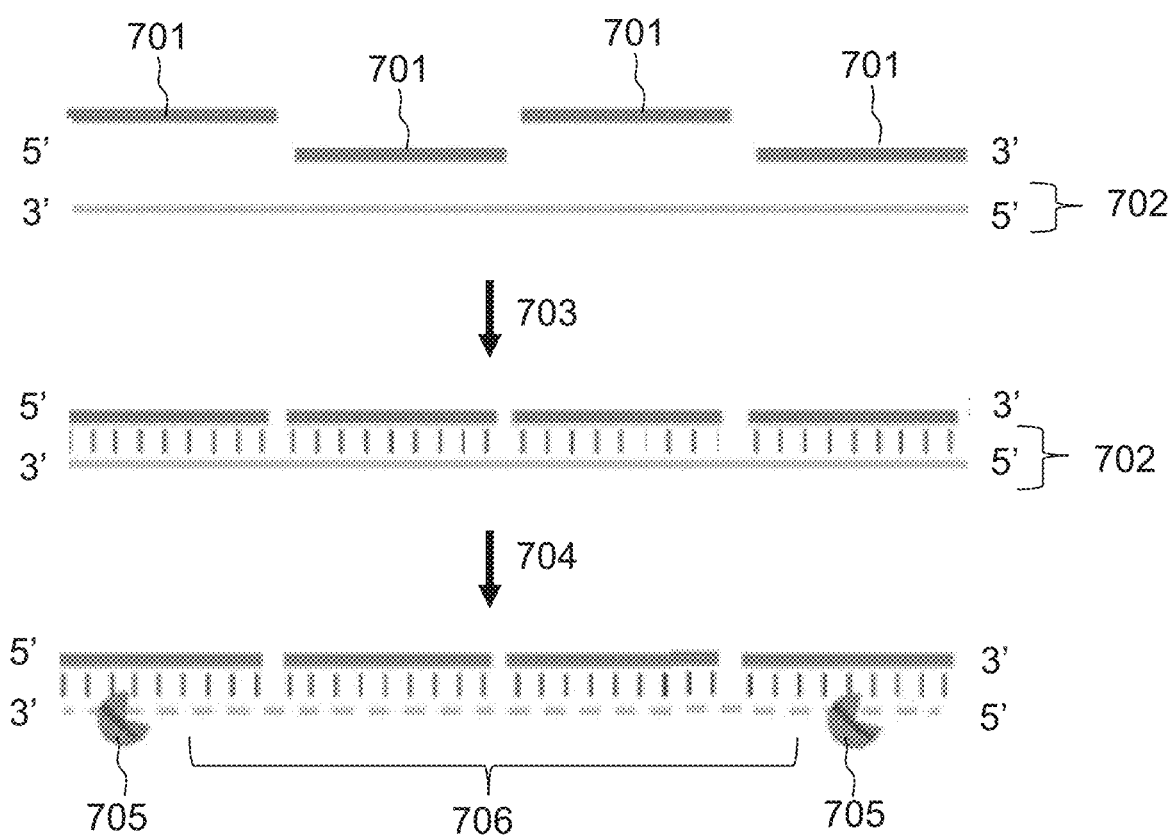
FIG. 7 shows a schematic workflow illustrating exemplary, non-limiting, non-exhaustive steps for in situ ribosomal RNA depletion.

A non-limiting example of the methods described herein using undesirable RNA depletion probes is shown in FIG. 7 A biological sample is contacted with undesirable RNA depletion probes 701 (e.g., ribosomal depletion probes) where the undesirable RNA depletion probes hybridize 703 to an undesirable RNA molecule 702 (e.g., rRNA). The RNA depletion probes can be ligated together, or not ligated together. The undesirable RNA that is bound to the undesirable RNA depletion probe are digested enzymatically 704 using RNAse H 705. Treatment with RNAse H results in digested undesirable RNA 706. In some embodiments where the RNA depletion probes are combined with RNA-template ligation, the method described in FIG. 7 can happen prior to or concurrent with RTL probe (e.g., RHS and LHS probes) hybridization and ligation reaction with the target mRNA. The RNase H digestion of the RNA of the RNA:DNA hybrids of the RNA depletion method can happened concurrent with that for the mRNA of the target mRNA:DNA probe hybrids created for the RNA templated ligation reaction. In some embodiments, the methods described in FIG. 7 can also be performed in any spatial analysis methodology which would benefit from the removal of undesirable RNA species. For example, RNA depletion as described herein could also be used in conjunction with the direct capture of a mRNA by the capture probe.

Upon depletion of the undesirable RNA, the sample will contain an enriched population of the RNA target of interest (e.g., an mRNA target). In some embodiments, the undesirable RNA comprises less than 20%, 19%, 18%, 17%, 16% 15%, 14%, 13%, 12%, 11% 10%, 9%, 8%, 7%, 6%, 5%, 4%, 3%, 2%, or 1%, or any range therein, of the total RNA in the sample after depletion of the undesirable RNA (i.e., less than 20%, 19%, 18%, 17%, 16% 15%, 14%, 13%, 12%, 11% 10%, 9%, 8%, 7%, 6%, 5%, 4%, 3%, 2%, or 1%, or any range therein compared to a sample that undergoes no depletion step). Consequently, the enriched population of the RNA target of interest may comprise at least 99%, 98%, 97%, 96%, 95%, 94%, 93%, 92%, 91%, 90%, 89%, 88%, 87%, 86%, 85%, 84%, 83%, 82%, 81%, or 80%, or any range therein, of the total RNA in the sample.

(a) Undesirable RNA Molecule(s)

As used herein, the term "undesirable RNA molecule", or "undesirable RNA", refers to an undesired RNA that is the target for depletion from the biological sample. In some embodiments, examples of the undesirable RNA include, but are not limited to, messenger RNA (mRNA), ribosomal RNA (rRNA), mitochondrial RNA (mtRNA), transfer RNA (tRNA), microRNA (miRNA), and viral RNA. In some embodiments, the undesirable RNA can be a transcript (e.g., present in a tissue section).

In some embodiments, the undesirable RNA molecule includes 5.8S ribosomal RNA (rRNA), 5S rRNA, transfer RNA (tRNA), microRNA (miRNA), a small nucleolar RNA (snoRNAs), Piwi-interacting RNA (piRNA), tRNA-derived small RNA (tsRNA), and small rDNA-derived RNA (srRNA), or mitochondrial RNA (mtRNA). In some embodiments, the undesirable RNA molecule includes an RNA molecule that is added (e.g., transfected) into a sample (e.g., a small interfering RNA (siRNA)). The undesirable RNA can be double-stranded RNA or single-stranded RNA. In embodiments where the undesirable RNA is double-stranded it is processed as a single-stranded RNA prior to depletion. In some embodiments, the undesirable RNA can be circular RNA. In some embodiments, the undesirable RNA can be a bacterial rRNA (e.g., 16s rRNA or 23s rRNA). In some embodiments, the undesirable RNA is from *E. coli*.

In some embodiments, the undesirable RNA molecule is rRNA. In some embodiments, the rRNA is eukaryotic rRNA. In some embodiments, the rRNA is cytoplasmic rRNA. In some embodiments, the rRNA is mitochondrial rRNA. Cytoplasmic rRNAs include, for example, 28S, 5.8S, 5S and 18S rRNAs. Mitochondrial rRNAs include, for example, 12S and 16S rRNAs. The rRNA may also be prokaryotic rRNA, which includes, for example, 5S, 16S, and 23S rRNA. The sequences for rRNAs are well known to those skilled in the art and can be readily found in sequence databases such as GenBank or may be found in the literature. For example, the sequence for the human 18S rRNA can be found in GenBank as Accession No. M10098 and the human 28S rRNA as Accession No. M11167.

In some embodiments, the undesirable RNA molecule is mitochondrial RNA. Mitochondrial RNAs include, for example, 12S rRNA (encoded by MT-RNR1), and 16S rRNA (encoded by MT-RNR2), RNAs encoding electron transport chain proteins (e.g., NADH dehydrogenase, coenzyme Q-cytochrome c reductase/cytochrome b, cytochrome c oxidase, ATP synthase, or humanin), and tRNAs (encoded by MT-TA, MT-TR, MT-TN, MT-TD, MT-TC, MT-TE, MT-TQ, MT-TG, MT-TH, MT-TI, MT-TL1, MT-TL2, MT-TK, MT-TM, MT-TF, MT-TP, MT-TS1, MT-TS2, MT-TT, MT-TW, MT-TY, or MT-TV).

In some embodiments, the undesirable RNA is transfer RNA (tRNA). In some embodiments, the undesirable RNA may be a particular mRNA. For example, it may be desirable to remove cellular transcripts that are usually present in abundance. Thus, the undesirable mRNA may include, but is not limited to, ACTB, GAPDH, and TUBB. Other sequences for tRNA and specific mRNA are well known to those skilled in the art and can be readily found in sequence databases such as GenBank or may be found in the literature.

In some embodiments, mRNA is not targeted for depletion by undesirable RNA probes. In some embodiments, one or more undesirable RNA depletion probes do not have a poly-dT that will hybridize to the poly-A tail of eukaryotic mRNA. In yet another particular embodiment, the undesirable RNA depletion probe targets and specifically hybridizes to human 18S or human 28S rRNA. Examples of the sequence of undesirable RNA depletion probes targeting the full length sequence of human 18S and human 28S rRNA are illustrated in, e.g., US Appl. Publ. No. 2011/0111409 A1, which is incorporated herein by reference.

In some embodiments, the one or more undesirable RNA molecules is a single species of RNA. For example, in some embodiments, the one or more undesirable RNA molecule hybridizes only ribosomal RNA molecules. In some embodiments, the one or more undesirable RNA molecule hybridizes only mitochondrial RNA molecules. In some embodiments, the undesirable RNA molecule can be a combination of two or more species of RNA. In some embodiments, the undesirable RNA molecule is an RNA fragment of one of the undesirable RNA molecules described herein. In some embodiments, the undesirable RNA molecule is a full length RNA molecule of one of the undesirable RNA molecules described herein.

(b) Design of Undesirable RNA Depletion Probes

In some embodiments, the one or more undesirable RNA depletion probes is a DNA probe. In some embodiments, the DNA probe includes a single-stranded DNA oligonucleotide having a sequence partially or completely complementary to an undesirable RNA and specifically hybridizes to the undesirable RNA. In some embodiments, the one or more undesirable RNA depletion probes are at least 70%, at least 75%, at least 80%, at least 85%, at least 90%, at least 91%, at least 92%, at least 93%, at least 94%, at least 95%, at least 96%, at least 97%, at least 98%, or at least 99% complementary to one or more undesirable RNA molecules. In some embodiments, the one or more undesirable RNA depletion probes is 100% (i.e., completely) complementary to one or more undesirable RNA molecules.

In some embodiments, probes used herein have been described in Morlan et al., PLoS One. 2012; 7(8):e42882, which is incorporated by reference in its entirety. In some embodiments, probes used herein have been described in U.S. Appl. Publ. No. 2011/0111409, which is incorporated by reference in its entirety. In some embodiments, probes used herein have been described in Adiconis et al., Nat Methods. 2013 July; 10(7):623-9, which is incorporated by reference in its entirety.

The DNA probe can be produced by techniques known in the art. For example, in some embodiments, a DNA probe is produced by chemical synthesis, by in vitro expression from recombinant nucleic acid molecules, or by in vivo expression from recombinant nucleic acid molecules. The undesirable RNA depletion probe may also be produced by amplification of the undesirable RNA, e.g., RT-PCR, asymmetric PCR, or rolling circle amplification.

In some embodiments, the methods of targeted RNA depletion as disclosed herein include multiple undesirable RNA depletion probes. In some embodiments, the undesirable RNA depletion probes include sequences that are complementary or substantially complementary to one or more undesirable RNA molecules. Methods provided herein may be applied to a single undesirable RNA molecule or a plurality of undesirable RNA molecules.

In some embodiments, the undesirable RNA depletion probe is about 20, about 21, about 22, about 23, about 24, about 25, about 26, about 27, about 28, about 29, about 30, about 31, about 32, about 33, about 34, about 35, about 36, about 37, about 38, about 39, about 40, about 40, about 41, about 42, about 43, about 44, about 45, about 46, about 47, about 48, about 49, about 50, about 51, about 52 about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 200, about 300, about 400, about 500, about 600, about 700, about 800, about 900, about 1000, about 1500, about 2000, about 3000, about 4000, or about 5000 nucleotides in length.

In some embodiments, a single undesirable RNA depletion probe spans the entire length of the undesirable RNA. In some embodiments, the undesirable RNA depletion probe has regions that are not complementary to un undesirable RNA, so long as such sequences do not substantially affect specific hybridization of the undesirable RNA depletion probe to the undesirable RNA. In some embodiments, the depletion probes are not contiguous, such that while they may collectively hybridize across a length of the undesirable RNA there may exist gaps between the individual depletion probes. For example, in some embodiments, the RNA depletion probes that target an undesirable RNA are spaced at least one, at least two, at least 5, at least 10, at least 20, at least 30, at least 50, at least 60 nucleotides apart along the length of the undesirable RNA. As such, there may be a plurality of RNA depletion probes that will hybridize adjacent to, or non-contiguous to, each other along the length, or partially along the length, of the undesirable RNA molecule.

In some embodiments, the undesirable RNA depletion probe is associated with (e.g., conjugated to) a detectable label, an optical label, and or a label as described herein. In some instances, the detectable label is a radioisotope, a fluorescent or chemiluminescent moiety, with an enzyme or ligand, which can be used for detection or confirmation that the probe has hybridized to the target sequence. The detectable label can be directly detectable by itself (e.g., radioisotope labels or fluorescent labels) or, in the case of an enzymatic label, can be indirectly detectable, e.g., by catalyzing chemical alterations of a chemical substrate compound or composition, which chemical substrate compound or composition is directly detectable. The detectable label can be qualitatively detected (e.g., optically or spectrally), or it can be quantified using methods known in the art and/or disclosed herein.

In some embodiments, the methods provided herein include a pool of two or more undesirable RNA depletion probes. In some embodiments, the pool of undesirable RNA depletion probes include about 100 nM, about 200 nM, about 300 nM, about 400 nM, about 500 nM, about 600 nM, about 700 nM, about 800 nM, about 900 nM, or about 1000 nM of each RNA depletion probe. In some embodiments, the pool of undesirable RNA depletion probes include about 1 µM, about 2 µM, about 3 µM, about 4 µM, about 5 µM, about 6 µM, about 7 µM, about 8 µM, about 9 µM, or about 10 µM, or more, of each RNA depletion probe. In some embodiments, the concentration of an RNA depletion probe in a pool of RNA depletion probes depends on the relative abundance of the undesirable RNA targeted by the specific RNA depletion probe. For example, ribosomal transcripts 18S and 28S can be highly abundant in a tissue sample. In this case, RNA depletion probes targeting 18S and/or 28S can be present in the pool of undesirable RNA depletion probes at a higher concentration that other RNA depletion probes present in the pool.

In some embodiments, an RNA depletion probe includes a nucleic acid sequence of any one of SEQ ID NOs: 1-195. In some embodiments, a pool of RNA depletion probes includes two or more probes each having a nucleic acid sequence selected from any one of SEQ ID NOs: 1-195.

(c) Hybridization of Undesirable RNA Depletion Probe to the Undesirable RNA Molecule In some embodiments, one or more undesirable RNA depletion probes hybridize to an undesirable RNA. In some embodiments, one or more undesirable RNA depletion probes hybridize to one or more portions of the sequence of the undesirable RNA molecule. In some embodiments, one or more undesirable RNA depletion probes hybridize to the complete sequence of the undesirable RNA molecule. Hybridization can occur at an undesirable RNA having a sequence that is 100% complementary to the probe oligonucleotide(s). In some embodiments, hybridization can occur at a target having a sequence that is at least (e.g., at least about) 80%, at least (e.g., at least about) 85%, at least (e.g., at least about) 90%, at least (e.g., at least about) 95%, at least (e.g., at least about) 96%, at least (e.g., at least about) 97%, at least (e.g., at least about) 98%, or at least (e.g., at least about) 99% complementary to the probe oligonucleotide(s).

In some embodiments, the undesirable RNA depletion probe may be complementary to all or part of an undesirable RNA sequence and therefore, there may be more than one undesirable RNA probe that specifically hybridizes to the undesirable RNA. For example, there may be at least 1, 2, 3, 4, 5, 6, 7, 8, 9, 10, or more undesirable RNA depletion probes that specifically hybridize to an undesirable RNA. In some embodiments, the undesirable RNA has a tertiary structure and the undesirable RNA depletion probe can be complementary to an exposed portion of the undesirable RNA sequence.

In some embodiments, one or more undesirable RNA depletion probes can hybridize to the undesirable RNA such that at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, at least about 99%, or 100% of the complete sequence of the undesirable RNA is hybridized by the undesirable RNA depletion probes.

In some embodiments, at least one undesirable RNA depletion probe specifically hybridizes to substantially the entire full length sequence of the undesirable RNA. As used herein, "substantially the entire full length sequence" refers to less than 100% but at least 80%, 81%, 82%, 83%, 84%, 85%, 86%, 87%, 88%, 89%, 90%, 91%, 92%, 93%, 94%, 95%, 96%, 97%, 98%, or 99%, or any range therein, of the full length sequence. In some embodiments, a multiplicity of undesirable RNA depletion probes specifically binds to substantially the entire full length sequence of the target RNA. In another embodiment, a multiplicity of DNA probes specifically binds to the entire full length sequence, or portions thereof, of the target RNA, either adjacent or in a non-contiguous manner.

In some embodiments, the undesirable RNA depletion probe specifically hybridizes to the undesirable RNA molecule and creates a RNA:DNA hybrid. As used herein, "specifically hybridizes" refers to a state where a specific DNA probe is able to hybridize with a target RNA, for example, rRNA, over other nucleic acids present in a nucleic acid sample. In some instances, the DNA probe is first denatured into single-stranded DNA by methods known in the art, for example, by heating or under alkaline conditions, and then hybridized to the target RNA by methods also known in the art, for example, by cooling the heated DNA in the presence of the target RNA. In some instances, the double-stranded DNA probe is heated to achieve denaturation to a single strand prior to being added to the biological sample. In some instances, the DNA probe is produced as a single-stranded DNA molecule, in which case no denaturation would be required. The condition under which a DNA probe specifically hybridizes with an RNA are well known to those of ordinary skill in the art and it will be appreciated that these conditions may vary depending upon factors including the GC content and length of the probe, the hybridization temperature, the composition of the hybridization reagent or solution, and the degree of hybridization specificity sought.

In some embodiments, the RNA:DNA hybrid is then depleted from the nucleic acid sample. For example, in some embodiments, a ribonuclease (RNase) that specifically targets RNA:DNA hybrids is used to deplete the RNA:DNA hybrid. In some embodiments, RNAse H is used to specifically hydrolyze the RNA in the RNA:DNA hybrid so that the RNA becomes degraded. The remaining DNA is then available to hybridize with another undesirable RNA sequence.

In some instances, after the RNA:DNA hybrid is created, no further steps are taken to remove the hybrid (e.g., ribonuclease digestion as described below does not occur). Thus, in some instances, hybridization serves to "block" (e.g., inhibit binding of) single-stranded undesirable RNA molecules (e.g., rRNA) from associating with probe sequences that target e.g., poly(A) tails or other targets of interest. Accordingly, in some aspects, spatial detection methods disclosed herein occur in the presence of the RNA:DNA hybrid. In instances where the RNA:DNA hybrid is created but not removed, detection of RNA molecules of interest is increased relative to a setting in which no hybrid is created. In some instances, detection of target RNA molecules of interest is increased by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95%, by about 1.5-fold, by about 2.0-fold, by about 2.5-fold, by about 3.0-fold, by about 3.5-fold, by about 4.0-fold, by about 4.5-fold, by about 5.0-fold, by about 6-fold, by about 7-fold, by about 8-fold, by about 9-fold, by about 10-fold, or more compared to a setting in which no hybrid is created.

(d) Removing the Plurality of Undesirable RNA Depletion Probe-Undesirable RNA Complexes.

(i) Ribonuclease Digestion

In some embodiments, the undesirable RNA depletion probe-undesirable RNA complex is removed. In some embodiments, the removing step includes the addition of RNAse H. In some embodiments, the removing step includes contacting the undesirable RNA depletion probe with a ribonuclease (e.g., RNAse H). In some embodiments, the ribonuclease is an endoribonuclease. In some embodiments (e.g., in the setting of RNA-templated ligation), an endoribonuclease also is used to release the probe from the analyte. In some embodiments, the endoribonuclease is one or more of RNase H, RNase A, RNase C, or RNase I, or any combinations thereof. In some embodiments, the endoribonuclease is RNase H. In some embodiments, the RNase H is RNase H1, RNase H2, or any combinations thereof. In some embodiments, the RNAse H is a thermostable RNAse H. Thermostable RNAse H may be obtained commercially, including, for example, Hybridase™ (Lucigen, Middleton, Wis.).

In some embodiments, the RNAse H degrades the RNA from a RNA:DNA hybrid at a temperature range of between 32° C. and 95° C. (e.g., using a thermostable RNAse H). In some embodiments, the RNAse H degrades the RNA from a RNA:DNA hybrid at a temperature range of between 32° C. and 60° C. In some embodiments, the RNAse H degrades the RNA from a RNA:DNA hybrid at a temperature range of between 37° C. and 60° C. In yet another embodiment, RNAse H degrades the RNA from a RNA:DNA hybrid at a temperature of about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C. or about 64° C.

In some embodiments, the hybridization step and RNA degradation with RNAse H is repeated more than once. In some instances, the hybridization step and RNA degradation step is repeated at least twice, at least three times, at least four times, at least five times, or more. In some instances, a wash step is performed between each step using methods and solutions (e.g., PBS, PBST) disclosed herein and known in the art.

In some embodiments, the ribonuclease can be inactivated by a permeabilization agent, for example concurrent inactivation and permeabilization of a biological sample. In some instances, the permeabilization agent is one or more of an organic solvent, a cross-linking agent, a detergent, and an enzyme known in the art. In some instances, the permeabilization agent is an endopeptidase or protease. In some instances, the endopeptidase is pepsin. In some instances, the endopeptidase is proteinase K. In some instances, the ribonuclease is heat inactivated. For example, in some instances, the ribonuclease (e.g., other than thermostable RNAse H) is heat inactivated at 65° C.

In some embodiments, DNA probes that have not hybridized with target undesirable RNA, or probes that have been released following RNase H degradation of the RNA from the RNA:DNA hybrid, can be removed at various stages of RNA isolation by DNA degrading enzymes or other techniques well known in the art. In some embodiments, the DNA degrading enzyme is an exonuclease that digests DNA from in a 5' to 3' direction. In some embodiments, the DNA degrading enzyme does not digest the capture probes attached on the substrate. In some embodiments, the DNA degrading enzyme is a RecJ exonuclease. A RecJ exonuclease degrades single-stranded DNA (ssDNA) in the 5'-3' direction and can participate in homologous recombination and mismatch repair. In some instances, the RecJ exonuclease is isolated from *Escherichia coli*. In some embodiments, DNA degrading enzyme can be inactivated by a permeabilization agent disclosed herein.

(ii) Removal of Undesirable RNA-Depletion Probe Complex

In some embodiments, the DNA:RNA complex that includes an undesirable RNA depletion probe and an undesirable RNA is removed using methods other than adding RNAse H. In some instances, the undesirable RNA depletion probe includes a capture moiety. As disclosed herein, a capture moiety of the undesirable RNA depletion probe is affixed to (e.g., conjugated to) the nucleic acid sequence of the undesirable RNA depletion probe. In some embodiments, the undesirable RNA depletion probe includes one or more capture moieties. In some embodiments, the capture moiety includes a label as described herein. In some embodiments, the label is used to identify and remove an undesirable RNA depletion probe, whether they are hybridized to undesirable RNA molecules or not. In some instances, using the label, the RNA depletion probe (including undesirable RNA depletion probes complexed with undesirable RNA) can be isolated and removed from the biological sample. In some embodiments, the label is directly associated with (i.e., conjugated to) the undesirable RNA depletion probe. The detectable label can be directly detectable by itself (e.g., radioisotope labels or fluorescent labels) or, in the case of an enzymatic label, can be indirectly detectable, e.g., by catalyzing chemical alterations of a chemical substrate compound or composition, which chemical substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

In some embodiments, the capture moiety includes a small molecule. In some embodiments, the capture moiety includes a nucleic acid. In some embodiments, the nucleic acid is single-stranded. In some embodiments, the nucleic acid is double-stranded. In some embodiments, the nucleic acid is RNA. In some embodiments, the nucleic acid is DNA. In some embodiments, the capture moiety includes a carbohydrate. In some embodiments, the capture moiety is positioned 5' to the domain in the undesirable RNA depletion probe. In some embodiments, the capture moiety is position 3' to the domain in the undesirable RNA depletion probe.

In some embodiments, the capture moiety-binding agent that binds specifically to the capture moiety includes a protein. In some embodiments, the protein is an antibody. In some embodiments, the capture moiety-binding agent that binds specifically to the capture moiety comprises a nucleic acid. In some embodiments, the capture moiety-binding agent that binds specifically to the capture moiety comprises a small molecule. In some embodiments, the capture moiety-binding agent that binds specifically to the capture moiety is attached to a substrate. In some embodiments, the substrate is a bead. In some embodiments, the substrate is a well. In some embodiments, the substrate is a slide. In some embodiments, the substrate is a magnetic bead, for example a paramagnetic particle, such that the undesirable RNA depletion probe-undesirable RNA complexes, or the undesirable RNA depletion probe alone, can be removed magnetically from the biological sample, for example by a rare earth magnet or other magnetic devices.

In some embodiments, the capture moiety is biotin. In some embodiments, a biotin molecule is directly associated with (i.e., conjugated to) the undesirable RNA depletion probe at the 3' end. In some embodiments, a biotin molecule is directly associated with (i.e., conjugated to) the undesirable RNA depletion probe at the 5' end. In some embodiments, the biotin molecule can be associated to (e.g., conjugated to) an avidin molecule, allowing pulldown of the undesirable RNA depletion probe-undesirable RNA complexes, or the undesirable RNA depletion probe. In some embodiments, and as disclosed below, the biotin molecule can be associated to (e.g., conjugated to) a streptavidin molecule, such that the undesirable RNA depletion probe-undesirable RNA complexes, or the undesirable RNA depletion probe conjugated to a biotin molecule can be captured by streptavidin or avidin and depleted from the biological sample.

(e) In Situ Spatial RNA-Templated Ligation (RTL) Using Targeted RNA Depletion

In some instances, the undesirable RNA depletion probe is used in the setting of (e.g., concurrently with) in situ spatial RNA-templated ligation (RTL). In the setting of RTL, removal of undesirable RNA can be achieved concurrently. In some instances, both RTL probe oligonucleotides and undesirable RNA depletion probes can be added at the same time. After ligation of the RTL probes, an endonuclease such as RNAse H is added to the sample. RNAse H digests both the RNA analyte and the undesirable RNA. In some instances, at least one of the RTL probes includes a probe capture sequence such as a poly-A sequence, an oligo-d(T) sequence, or a particular capture sequence (in the setting of targeted RNA analysis). As a result of this process, undesirable RNA molecules (e.g., rRNA; mtRNA) are digested and thus are not available to interfere with downstream applications such as probe capture of the poly-A sequence or a complement thereof that occurs during spatial array-based methods disclosed herein.

In one feature of the disclosure, provided are methods for identifying a location of an analyte in a biological sample, the method comprising (a) contacting a biological sample with a first probe oligonucleotide, a second probe oligonucleotide, and a plurality of undesirable RNA depletion probes; (b) hybridizing the first probe oligonucleotide and the second probe oligonucleotide to the analyte; (c) hybridizing the undesirable RNA depletion probe to the undesirable RNA molecule; (d) ligating the first probe oligonucleotide and the second probe oligonucleotide, thereby creating a ligated probe that is substantially complementary to the analyte; (e) removing the plurality of undesirable RNA depletion probe-undesirable RNA complexes and releasing the ligated probe from the analyte; (f) contacting the biological sample with a substrate, wherein the capture probe is affixed to the substrate, wherein the capture probe comprises a spatial barcode and the capture domain; (g) allowing the capture probe binding domain of the ligated probe to specifically bind to the capture domain; and (h) determining (i) all or a part of the sequence of the ligated probe specifically bound to the capture domain, or a complement thereof, and (ii) all or a part of the sequence of the spatial barcode, or a complement thereof, and using the determined sequence of (i) and (ii) to identify the location of the analyte in the biological sample.

In some embodiments, the methods as disclosed herein include hybridizing of one or more probe oligonucleotides (e.g., RTL probes) to a target analyte (e.g., RNA; e.g., mRNA) of interest. In some embodiments, the methods include hybridization of 2, 3, 4, or more probe oligonucleotides. In some embodiments, the methods include hybridization of two probe oligonucleotides. In some embodiments, the probe oligonucleotide includes sequences that are complementary or substantially complementary to an analyte. For example, in some embodiments, each probe oligonucleotide includes a sequence that is complementary or substantially complementary to an mRNA of interest (e.g., to a portion of the sequence of an mRNA of interest). Methods provided herein may be applied to hybridization of two or more probe oligonucleotides to a single nucleic acid molecule. In some embodiments, each target analyte includes a first target region and a second target region. In some instances, the methods include providing a plurality of first probe oligonucleotides and a plurality of second probe oligonucleotides. In some instances, a first probe oligonucleotide hybridizes to a first target region of the nucleic acid. In some instances, a second probe oligonucleotide hybridizes to a second target region of the nucleic acid.

In some instances, a first probe oligonucleotide sequence of a first probe oligonucleotide of the plurality of first probe oligonucleotides may comprise a first reactive moiety. One or more first probe oligonucleotides of the plurality of first probe oligonucleotides may comprise the same first probe oligonucleotide sequence and/or the same second probe oligonucleotide sequence. The plurality of second probe oligonucleotides may each comprise a third probe oligonucleotide sequence complementary to the sequence of a second target region of a nucleic acid molecule of the plurality of nucleic acid molecules. The plurality of second probe oligonucleotides may further comprise a fourth probe oligonucleotide sequence. A third probe oligonucleotide sequence of a second probe oligonucleotide of the plurality of second probe oligonucleotides may comprise a second reactive moiety. One or more probe oligonucleotides of the second probe oligonucleotides of the plurality of second probe oligonucleotides may comprise the same third probe oligonucleotide sequence and/or, if present, the same fourth probe oligonucleotide sequence. A first probe oligonucleotide sequence of a first probe oligonucleotide of the plurality of first probe oligonucleotides may hybridize to first target region of a nucleic acid molecule of the plurality of nucleic acid molecules. A third probe oligonucleotide sequence of a second probe oligonucleotide of the plurality of second probe oligonucleotides may hybridize to the second target region of a nucleic acid molecule of the plurality of nucleic acid molecules. The first and third probe oligonucleotide sequences hybridized to the first and second target regions, respectively, of a nucleic acid molecule of the plurality of nucleic acid molecules may be adjacent to one another such that a first reactive moiety of the first probe oligonucleotide sequence is adjacent to a second reactive moiety of the third probe oligonucleotide sequence. The first and second reactive moieties of the first and second probe oligonucleotides hybridized to nucleic acid molecules of the plurality of nucleic acid molecules may react to provide a plurality of probe oligonucleotide-linked nucleic acid molecules.

In some embodiments, one of the probe oligonucleotides includes a poly(A) sequence or a complement thereof. In some instances, the poly(A) sequence or a complement thereof is on the 5' end of one of the probe oligonucleotides. In some instances, the poly(A) sequence or a complement thereof is on the 3' end of one of the probe oligonucleotides. In some embodiments, one probe oligonucleotides includes a degenerate or UMI sequence. In some embodiments, the UMI sequence is specific to a particular target or set of targets. In some instances, the UMI sequence or a complement thereof is on the 5' end of one of the probe oligonucleotides. In some instances, the UMI sequence or a complement thereof is on the 3' end of one of the probe oligonucleotides.

In some instances, the first and second target regions of a nucleic acid molecule of the plurality of nucleic acid molecules are adjacent to one another. In some embodiments, the first and second probe oligonucleotides bind to complementary sequences on the same transcript. In some embodiments, the complementary sequences to which the first probe oligonucleotide and the second probe oligonucleotide bind are 1, 2, 3, 4, 5, 6, 7, 8, 9, 10, about 15, about 20, about 25, about 30, about 35, about 40, about 45, about 50, about 55, about 60, about 65, about 70, about 75, about 80, about 85, about 90, about 95, about 100, about 125, or about 150 nucleotides away from each other. Gaps between the probe oligonucleotides may first be filled prior to ligation, using, for example, dNTPs in combination with a polymerase such as Mu polymerase, DNA polymerase, RNA polymerase, reverse transcriptase, VENT polymerase, Taq polymerase, and/or any combinations, derivatives, and variants (e.g., engineered mutants) thereof. In some embodiments, when the first and second probe oligonucleotides are separated from each other by one or more nucleotides, deoxyribonucleotides are used to extend and ligate the first and second probe oligonucleotides.

In some instances, the first probe oligonucleotide and the second probe oligonucleotide hybridize to an analyte on the same transcript. In some instances, the first probe oligonucleotide and the second probe oligonucleotide hybridize to an analyte on the same exon. In some instances, the first probe oligonucleotide and the second probe oligonucleotide hybridize to an analyte on different exons. In some instances, the first probe oligonucleotide and the second probe oligonucleotide hybridize to an analyte that is the result of a translocation event (e.g., in the setting of cancer). The methods provided herein make it possible to identify alternative splicing events, translocation events, and mutations that change the hybridization rate of one or both probe oligonucleotides (e.g., single nucleotide polymorphisms, insertions, deletions, point mutations).

In some embodiments, the first and/or second probe as disclosed herein includes at least two ribonucleic acid bases at the 3' end; a functional sequence; a phosphorylated nucleotide at the 5' end; and/or a capture probe binding domain. In some embodiments, the functional sequence is a primer sequence. The capture probe binding domain is a sequence that is complementary to a particular capture domain present in a capture probe. In some embodiments, the capture probe binding domain includes a poly(A) sequence. In some embodiments, the capture probe binding domain includes a poly-uridine sequence, a poly-thymidine sequence, or a combination thereof. In some embodiments, the capture probe binding domain includes a random sequence (e.g., a random hexamer or octamer). In some embodiments, the capture probe binding domain is complementary to a capture domain in a capture probe that detects a particular target(s) of interest. In some embodiments, a capture probe binding domain blocking moiety that interacts with the capture probe binding domain is provided. In some embodiments, a capture probe binding domain blocking moiety includes a sequence that is complementary or substantially complementary to a capture probe binding domain. In some embodiments, a capture probe binding domain blocking moiety prevents the capture probe binding domain from binding the capture probe when present. In some embodiments, a capture probe binding domain blocking moiety is removed prior to binding the capture probe binding domain (e.g., present in a ligated probe) to a capture probe. In some embodiments, a capture probe binding domain blocking moiety comprises a poly-uridine sequence, a poly-thymidine sequence, or a combination thereof.

In some embodiments, the first probe oligonucleotide hybridizes to an analyte and a second probe oligonucleotide hybridizes to an analyte in proximity to the first probe oligonucleotide. Hybridization can occur at a target having a sequence that is 100% complementary to the probe oligonucleotide(s). In some embodiments, hybridization can occur at a target having a sequence that is at least (e.g., at least about) 80%, at least (e.g., at least about) 85%, at least (e.g., at least about) 90%, at least (e.g., at least about) 95%, at least (e.g., at least about) 96%, at least (e.g., at least about) 97%, at least (e.g., at least about) 98%, or at least (e.g., at least about) 99% complementary to the probe oligonucleotide(s). After hybridization, in some embodiments, the first probe oligonucleotide is extended. After hybridization, in some embodiments, the second probe oligonucleotide is extended. For example, in some instances a first probe oligonucleotide hybridizes to a target sequence upstream for a second oligonucleotide probe, whereas in other instances a first probe oligonucleotide hybridizes to a target sequence downstream of a second probe oligonucleotide.

The method disclosed herein include addition of undesirable RNA probes described herein. In some instances, the undesirable RNA probes are added at the same time as the first probe oligonucleotide and the second probe oligonucleotide. In some instances, the undesirable RNA probes are added before the first probe oligonucleotide and the second probe oligonucleotide. In some instances, the undesirable RNA probes are added after the first probe oligonucleotide and the second probe oligonucleotide.

In some embodiments, methods disclosed herein include a wash step after hybridizing the first and the second probe oligonucleotides and/or the undesirable RNA probes. The wash step removes any unbound oligonucleotides and can be performed using any technique known in the art. In some embodiments, a pre-Hybridization buffer is used to wash the sample. In some embodiments, a phosphate buffer is used. In some embodiments, multiple wash steps are performed to remove unbound oligonucleotides. For example, it is advantageous to decrease the amount of unhybridized probes present in a biological sample as they may interfere with downstream applications and methods.

In some embodiments, after hybridization of probe oligonucleotides (e.g., first and the second probe oligonucleotides) to the target analyte, the probe oligonucleotides (e.g., the first probe oligonucleotide and the second probe oligonucleotide) are ligated together, creating a single ligated probe that is complementary to the target analyte. Ligation can be performed enzymatically or chemically, as described herein. For example, the first and second probe oligonucleotides are hybridized to the first and second target regions of the analyte, and the probe oligonucleotides are subjected to a nucleic acid reaction to ligate them together. For example, the probes may be subjected to an enzymatic ligation reaction using a ligase (e.g., T4 RNA ligase (Rnl2), a SplintR ligase, or a T4 DNA ligase). See, e.g., Zhang L., et al.; Archaeal RNA ligase from *Thermoccocus kodakarensis* for template dependent ligation RNA Biol. 2017; 14(1): 36-44 for a description of KOD ligase.

In some embodiments, adenosine triphosphate (ATP) is added during the ligation reaction. DNA ligase-catalyzed sealing of nicked DNA substrates is first activated through ATP hydrolysis, resulting in covalent addition of an AMP group to the enzyme. After binding to a nicked site in a DNA duplex, the ligase transfers this AMP to the phosphorylated 5'-end at the nick, forming a 5'-5' pyrophosphate bond. Finally, the ligase catalyzes an attack on this pyrophosphate bond by the OH group at the 3'-end of the nick, thereby sealing it, whereafter ligase and AMP are released. If the ligase detaches from the substrate before the 3' attack, e.g., because of premature AMP reloading of the enzyme, then the 5' AMP is left at the 5'-end, blocking further ligation attempts. In some instances, ATP is added at a concentration of about 1 µM, about 10 µM about 100 µM about 1000 µM or about 10000 µM during the ligation reaction.

In some instances, cofactors that aid in joining of the probe oligonuclotides are added during the ligation process. In some instances, the cofactors include magnesium ions ($Mg^{2+}$). In some instances, the cofactors include manganese ions ($Mn^{2+}$). In some instances, Mg' is added in the form of $MgCl_2$. In some instances, $Mn^{2+}$ is added in the form of $MnCl_2$. In some instances, the concentration of $MgCl_2$ is at about 1 mM, at about 10 mM, at about 100 mM, or at about 1000 mM. In some instances, the concentration of $MnCl_2$ is at about 1 mM, at about 10 mM, at about 100 mM, or at about 1000 mM.

In some embodiments, the probe oligonucleotides (e.g., the first probe oligonucleotide and the second probe oligonucleotide) may each comprise a reactive moiety such that, upon hybridization to the target and exposure to appropriate ligation conditions, the probe oligonucleotides may ligate to one another. In some embodiments, probe oligonucleotides that include a reactive moiety are ligated chemically. For example, a probe oligonucleotide capable of hybridizing to a first target region of a nucleic acid molecule may comprise a first reactive moiety, and a probe oligonucleotide capable of hybridizing to a second target region of the nucleic acid molecule may comprise a second reactive moiety. When the first and second probe oligonucleotides are hybridized to the first and second target regions of the nucleic acid molecule, the first and second reactive moieties may be adjacent to one another. A reactive moiety of a probe may be selected from the non-limiting group consisting of azides, alkynes, nitrones (e.g., 1,3-nitrones), strained alkenes (e.g., trans-cycloalkenes such as cyclooctenes or oxanorbornadiene), tetrazines, tetrazoles, iodides, thioates (e.g., phorphorothioate), acids, amines, and phosphates. For example, the first reactive moiety of a first probe oligonucleotide may comprise an azide moiety, and a second reactive moiety of a second probe oligonucleotide may comprise an alkyne moiety. The first and second reactive moieties may react to form a linking moiety. A reaction between the first and second reactive moieties may be, for example, a cycloaddition reaction such as a strain-promoted azide-alkyne cycloaddition, a copper-catalyzed azide-alkyne cycloaddition, a strain-promoted alkyne-nitrone cycloaddition, a Diels-Alder reaction, a [3+2] cycloaddition, a [4+2] cycloaddition, or a [4+1] cycloaddition; a thiol-ene reaction; a nucleophilic substation reaction; or another reaction. In some instances, the ends of the probes are ligated together using bioorthogonal click chemistry, effectively locking the probes around the target. See Rouhanifard et al., Nat Biotechnol. 2018 Nov. 12; 10.1038/nbt.4286, which is incorporated by reference in its entirety. In some cases, reaction between the first and second reactive moieties may yield a triazole moiety or an isoxazoline moiety. A reaction between the first and second reactive moieties may involve subjecting the reactive moieties to suitable conditions such as a suitable temperature, pH, or pressure and providing one or more reagents or catalysts for the reaction. For example, a reaction between the first and second reactive moieties may be catalyzed by a copper catalyst, a ruthenium catalyst, or a strained species such as a difluorooctyne, dibenzylcyclooctyne, or biarylazacyclooctynone. Reaction between a first reactive moiety of a first probe oligonucleotide hybridized to a first target region of the nucleic acid molecule and a second reactive moiety of a third probe oligonucleotide hybridized to a second target region of the nucleic acid molecule may link the first probe oligonucleotide and the second probe oligonucleotide to provide a ligated probe. Accordingly, reaction of the first and second reactive moieties may comprise a chemical ligation reaction such as a copper-catalyzed 5' azide to 3' alkyne "click" chemistry reaction to form a triazole linkage between two probe oligonucleotides. In other non-limiting examples, an iodide moiety may be chemically ligated to a phosphorothioate moiety to form a phosphorothioate bond, an acid may be ligated to an amine to form an amide bond, and/or a phosphate and amine may be ligated to form a phosphoramidate bond.

In some embodiments, after ligation of the first and second probe oligonucleotides to create a ligated probe, the ligated probe is released from the analyte. At this stage of the method, (1) the ligated probe is created and is hybridized to the analyte, and (2) the undesirable RNA probe is hybridized to the undesirable RNA. To release the ligated probe is released from the analyte, an endoribonuclease is used. An endoribonuclease such as RNAse H specifically cleaves RNA in RNA:DNA hybrids. Thus, not only does RNAse H cleave the hybridization of the ligated probe to the analyte (releasing the ligated probe), RNAse H also cleaves the undesirable RNA. In some embodiments, the ligated probe is released enzymatically. In some embodiments, an endoribonuclease is used to release the probe from the analyte. In some embodiments, the endoribonuclease is one or more of RNase H. In some embodiments, the RNase H is RNase H1 or RNase H2.

In some embodiments, after creating a ligated probe from the probe oligonucleotides (e.g., a first probe oligonucleotide and second probe oligonucleotide), the biological sample is permeabilized. In some embodiments, permeabilization occurs using a protease. In some embodiments, the protease is an endopeptidase. Endopeptidases that can be used include but are not limited to trypsin, chymotrypsin, elastase, thermolysin, pepsin, clostripan, glutamyl endopeptidase (GluC), ArgC, peptidyl-asp endopeptidase (ApsN), endopeptidase LysC and endopeptidase LysN. In some embodiments, the endopeptidase is pepsin.

In some embodiments, the ligated probe includes a capture probe binding domain, which can hybridize to a capture probe (e.g., a capture probe immobilized, directly or indirectly, on a substrate). In some embodiments, methods provided herein include contacting a biological sample with a substrate, wherein the capture probe is affixed to the substrate (e.g., immobilized to the substrate, directly or indirectly). In some embodiments, the capture probe includes a spatial barcode and the capture domain. In some embodiments, the capture probe binding domain of the ligated probe specifically binds to the capture domain. After hybridization of the ligated probe to the capture probe, the ligated probe is extended at the 3' end to make a copy of the additional components (e.g., the spatial barcode) of the capture probe. In some embodiments, methods of ligated probe capture as provided herein include permeabilization of the biological sample such that the capture probe can more easily hybridize to the captured ligated probe (i.e., compared to no permeabilization). In some embodiments, reverse transcription (RT) reagents can be added to permeabilized biological samples. Incubation with the RT reagents can produce spatially-barcoded full-length cDNA from the captured analytes (e.g., polyadenylated mRNA). Second strand reagents (e.g., second strand primers, enzymes) can be added to the biological sample on the slide to initiate second strand synthesis.

The resulting cDNA can be denatured from the capture probe template and transferred (e.g., to a clean tube) for amplification, and/or library construction as described herein. The spatially-barcoded, full-length cDNA can be amplified via PCR prior to library construction. The cDNA can then be enzymatically fragmented and size-selected in order to optimize the cDNA amplicon size. P5, P7, i7, and i5 can be used as sample indexes, and TruSeq Read 2 can be added via End Repair, A-tailing, Adaptor Ligation, and PCR. The cDNA fragments can then be sequenced using paired-end sequencing using TruSeq Read 1 and TruSeq Read 2 as sequencing primer sites.

In some embodiments, the biological sample is contacted with the undesirable RNA depletion probes and the RTL probes (e.g., the first probe oligonucleotide and the second probe oligonucleotide) at substantially the same time. In some embodiments, the biological sample is contacted with the RTL probes (e.g., the first probe oligonucleotide and the second probe oligonucleotide) after the undesirable RNA depletion probes.

In some embodiments, the hybridization between the RTL probes (e.g., the first probe oligonucleotide and the second probe oligonucleotide) to the analyte and the hybridization between the undesirable RNA depletion probes to the undesirable RNA occurs at substantially the same time. In some embodiments, the hybridization between the RTL probes (e.g., the first probe oligonucleotide and the second probe oligonucleotide) to the analyte occurs after the hybridization between the undesirable RNA depletion probes to the undesirable RNA occurs substantially the same time.

In some embodiments, the step of removing the plurality of undesirable RNA depletion probe-undesirable RNA complexes and releasing the ligated probe from the analyte occur substantially the same time. In some embodiments, the step of removing the plurality of undesirable RNA depletion probe-undesirable RNA complexes occurs before releasing the ligated probe from the analyte.

In some embodiments, the RTL probes (e.g., the first and second probe oligonucleotides) and the analyte (e.g., the target mRNA) hybridize to form an RNA:DNA hybrid at substantially the same time when the undesirable RNA depletion probes and the undesirable RNA hybridize to form an RNA:DNA hybrid. In some embodiments, a ribonuclease (e.g., RNase H) digests the RNA strands of the RNA:DNA hybrids, where the RNA strands include the analyte and the undesirable RNA molecule.

Detailed descriptions of targeted RNA capture using RNA-templated ligation (RTL) has been disclosed in U.S. application No. 62/952,736, the entirety of which is incorporated herein by reference.

(f) Targeted Capture of Analytes Using Hybridization of Target Oligonucleotide Probes In some embodiments, one or more target oligonucleotide probes are designed to target and hybridize to a plurality of nucleic acids (e.g., to prepared spatial libraries; e.g., to prepared cDNA libraries). In this instance, before targeting one or more target nucleic acids of interest, in some embodiments, the biological sample is first contacted with the undesirable RNA depletion probes as described herein. In some embodiments, a complex of undesirable RNA depletion probes hybridized to an undesirable RNA molecule is formed. In some embodiments, a ribonuclease (e.g., RNase H) digests the RNA strands of the RNA:DNA hybrids, where the RNA strands undesirable RNA molecules (e.g., rRNA).

In some embodiments, disclosed herein are methods of depleting an unwanted RNA in a biological sample and include first contacting the biological sample with a plurality of undesirable RNA depletion probes, wherein an undesirable RNA depletion probe in the plurality of undesirable RNA depletion probes is substantially complementary to a sequence of an undesirable RNA molecule in the biological sample; hybridizing the undesirable RNA depletion probe to the undesirable RNA; and removing the plurality of undesirable RNA depletion probe-undesirable RNA complexes. After removal of the undesirable RNA depletion probe-undesirable RNA complexes, identification of an analyte can be pursued.

In some instances, to create a non-specific library of analytes from a sample whose unwanted RNA molecules was depleted, the methods (after unwanted RNA depletion) include hybridizing the analytes to a plurality to capture probes, each including a spatial barcode and a capture domain that binds specifically to a sequence present in the analyte. In some embodiments, the capture probe is extended using the analyte that is specifically bound to the capture domain as a template to generate an extended capture probe. After template production, the capture probe/analyte complex can be amplified to produce a cDNA library using methods disclosed herein.

After RNA depletion, particular target analytes can be analyzed. For example, in one instance disclosed herein, target oligonucleotide probes are part of a "panel" that includes hundreds or thousands of oligonucleotide probes specific for certain settings. For example, a panel of oligonucleotides can detect analytes dysregulated during cancer, during immune-dysregulation, during neurological development and disease progression, or acting in the same pathway. Panels and particular oligonucleotides are disclosed in U.S. Appl. No. 62/970,066; 62/929,686; 62/980,124; and 62/980,116, each of which is incorporated by reference in its entirety.

In some instances, the target oligonucleotide probes hybridize to a target analyte, and then they are selectively enriched e.g., by amplification and/or pulldown methods disclosed herein. In some embodiments, the target oligonucleotide probe does not include a moiety affixed to the sequence (i.e., the target oligonucleotide probe is a naked target oligonucleotide probe). In some instances, the oligonucleotide probes are associated with one or more moieties. In some embodiments, the moiety is biotin. In some embodiments, a biotin molecule is directly associated with (i.e., conjugated to) the target oligonucleotide probe at the 3' end. In some embodiments, a biotin molecule is directly associated with (i.e., conjugated to) the target oligonucleotide probe at the 5' end. In some embodiments, and as disclosed below, the biotin molecule can be associated to (e.g., conjugated to) an avidin molecule, allowing pulldown of an analyte. In some embodiments, and as disclosed below, the biotin molecule can be associated to (e.g., conjugated to) a streptavidin molecule, allowing pulldown of an analyte. After pulldown of the analytes of interest, the resulting analyte can be amplified, creating an enriched library of analytes. By "enriched," it is meant that there are increased concentrations of an analyte of interest compared to a sample of the same library of analytes that has not undergone the pulldown step.

(g) Methods of Targeted RNA Depletion

Provided herein are methods for identifying a location of an analyte (e.g., any of the analyte described herein) in a biological sample that include (a) contacting the biological sample with a substrate comprising a plurality of attached capture probes, wherein a capture probe of the plurality comprises (i) the spatial barcode and (ii) a capture domain that binds specifically to a capture probe capture domain; (b) contacting a biological sample with a first probe oligonucleotide, a second probe oligonucleotide, and a plurality of undesirable RNA depletion probes (e.g., any of the undesirable RNA depletion probes described herein), wherein the first probe oligonucleotide and the second probe oligonucleotide are substantially complementary to adjacent sequences of the analyte, wherein the second probe oligonucleotide comprises a capture probe binding domain (e.g., any of the capture probe binding domains described herein) that is capable of binding to a capture domain (e.g., any of the capture domains described herein) of a capture probe (e.g., any of the capture probes described herein), and wherein an undesirable RNA depletion probe of the plurality of undesirable RNA depletion probes is substantially complementary to all or a portion of the sequence of an undesirable RNA molecule (e.g., any of the undesirable RNA molecules described herein) in the biological sample; (c) hybridizing the first probe oligonucleotide and the second probe oligonucleotide to the analyte; (d) hybridizing the undesirable RNA depletion probe to the undesirable RNA molecule (e.g., using any of the methods for hybridizing the undesirable RNA depletion probe to the undesirable RNA described herein); (e) ligating the first probe oligonucleotide and the second probe oligonucleotide, thereby creating a ligated probe (e.g., using any of the methods for ligating described herein) that is substantially complementary to the analyte; (f) removing the plurality of undesirable RNA depletion probe-undesirable RNA complexes (e.g., using any of the methods for removing the plurality of undesirable RNA depletion probe-undesirable RNA complexes described herein) and releasing the ligated probe from the analyte (e.g., using any of the methods for releasing the ligated probe from the analyte described herein); (g) allowing the capture probe binding domain of the ligated probe to specifically bind to the capture domain; and (h) determining (i) all or a part of the sequence of the ligated probe specifically bound to the capture domain, or a complement thereof, and (ii) all or a part of the sequence of the spatial barcode, or a complement thereof, and using the determined sequence of (i) and (ii) to identify the location of the analyte in the biological sample.

Provided herein are methods for identifying a location of an analyte (e.g., any of the analyte described herein) in a biological sample that include (a) contacting the biological sample with a substrate (e.g., any of the substrates described herein) comprising a plurality of attached capture probes (e.g., any of the capture probes described herein), wherein a capture probe of the plurality comprises (i) the spatial barcode (e.g., any of the spatial barcode described herein) and (ii) a capture domain (e.g., any of the capture domain described herein) that binds specifically to a sequence present in the analyte; (b) contacting the biological sample with a plurality of undesirable RNA depletion probes (e.g., any of the undesirable RNA depletion probes described herein), wherein an undesirable RNA depletion probe in the plurality of undesirable RNA depletion probes is substantially complementary to all or a portion of the sequence of an undesirable RNA molecule (e.g., any of the undesirable RNA molecules described herein) in the biological sample; (c) hybridizing the undesirable RNA depletion probe to the undesirable RNA (e.g., using any of the methods for hybridizing the undesirable RNA depletion probe to the undesirable RNA described herein); (d) removing the plurality of undesirable RNA depletion probe-undesirable RNA complexes (e.g., using any of the methods for removing the plurality of undesirable RNA depletion probe-undesirable RNA complexes described herein); (e) extending a 3' end of the capture probe using the analyte that is specifically bound to the capture domain as a template to generate an extended capture probe; and (f) amplifying (e.g., using any of the methods for amplifying described herein) the extended capture probe to produce a nucleic acid.

Provided herein are methods for identifying a location of an analyte (e.g., any of the analyte described herein) in a biological sample that include (a) contacting the biological sample with a plurality of undesirable RNA depletion probes (e.g., any of the undesirable RNA depletion probes described herein), wherein an undesirable RNA depletion probe in the plurality of undesirable RNA depletion probes is substantially complementary to all or a portion of the sequence of an undesirable RNA molecule (e.g., any of the undesirable RNA molecule described herein) in the biological sample; (b) hybridizing the undesirable RNA depletion probe to the undesirable RNA (e.g., using any of the methods for hybridizing the undesirable RNA depletion probe to the undesirable RNA described herein); (c) removing the plurality of undesirable RNA depletion probe-undesirable RNA complexes (e.g., using any of the methods for removing the plurality of undesirable RNA depletion probe-undesirable RNA complexes described herein); (d) contacting a plurality of nucleic acids with a plurality of target oligonucleotide probes (e.g., any of the target oligonucleotide probes described herein), wherein: a nucleic acid of the plurality of nucleic acids comprises (i) a spatial barcode (e.g., any of the spatial barcode described herein) or a complement thereof, and (ii) a portion of a sequence of an analyte from a biological sample, or a complement thereof; and a target oligonucleotide probe of the plurality of target oligonucleotide probes comprises: a domain that binds specifically to (i) all or a portion of the spatial barcode or a complement thereof, and/or (ii) all or a portion of the sequence of the analyte from the biological sample, or a complement thereof, and a molecular tag; (e) enriching a complex of the target oligonucleotide probe specifically bound to the nucleic acid using a substrate comprising an agent (e.g., any of the agent described herein) that binds specifically to the molecular tag; and (f) determining (i) all or a portion of the sequence of the spatial barcode or the complement thereof, and (ii) all or a portion of the sequence of the analyte from the biological sample, and using the determined sequences of (i) and (ii) to identify the location of the analyte in the biological sample.

In some instances, the undesirable RNA depletion probes are used in a setting where a protein-DNA molecule is used as a target probe. In some instances, the undesirable RNA depletion probes can be used in any of the spatial analysis methods described herein. For example, undesirable RNA depletion probes can hybridize to an undesirable RNA molecule in the presence of an antibody or antigen binding fragment thereof that is associated with a nucleic acid molecule, as disclosed herein. In some instances, the molecule (e.g., a nucleic acid molecule) having a barcode (e.g., a spatial barcode) can be coupled (e.g., associated with; conjugated to) an antibody or antigen binding fragment thereof in a manner that facilitates attachment of the molecule (e.g., a nucleic acid molecule) having a barcode (e.g., a spatial barcode) to a biological sample (e.g., a cell; e.g., a surface of a cell) using the antibody or antigen binding fragment thereof. In some instances, the undesirable RNA depletion probes hybridize to undesirable RNA molecules, disallowing the undesirable RNA molecules from hybridizing to the nucleic acid molecule of the antibody or antigen binding fragment thereof. In some instances, detection of analytes of interest is increased by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95%, by about 1.5-fold, by about 2.0-fold, by about 2.5-fold, by about 3.0-fold, by about 3.5-fold, by about 4.0-fold, by about 4.5-fold, by about 5.0-fold, by about 6-fold, by about 7-fold, by about 8-fold, by about 9-fold, by about 10-fold, or more compared to a setting in which no hybrid of undesirable RNA depletion probe-undesirable RNA is created.

In some instances, the undesirable RNA depletion probe is an RNA molecule. In some instances, the RNA molecule hybridizes to a DNA molecule that is conjugated to protein (e.g., an antibody), wherein the antibody binds to a protein of interest. The RNA molecule is complementary to the DNA molecule that is conjugated to the protein (e.g., the antibody). In some instances, the following steps are performed: the antibody-DNA molecule binds to a protein of interest; the RNA molecules (i.e., the RNA depletion probes) hybridize to the DNA molecule, thereby blocking other nucleic acids from hybridizing to the DNA molecule.

In some instances, the antibody binds to the protein of interest after hybridizing the RNA molecule to the DNA molecule. In the latter setting, in one embodiment, the RNA molecule is complexed to the antibody-DNA molecule before the antibody-DNA molecule binds to the protein of interest. After the antibody hybridizes to the protein, RNAse H can be added to cleave the RNA molecule from the DNA molecule such that the DNA molecule is free to hybridize to any spatial capture array as described herein.

(h) Pre-Hybridization Methods (i) Imaging and Staining

Prior to addition of the probes (e.g., undesirable RNA depletion probes and/or RTL probes), in some instances, biological samples can be stained using a wide variety of stains and staining techniques. In some instances, the biological sample is a section on a slide (e.g., a 5 µm section, a 7 µm section, a 10 µm section, etc.). In some instances, the biological sample is dried after placement onto a glass slide. In some instances, the biological sample is dried at 42° C. In some instances, drying occurs for about 1 hour, about 2, hours, about 3 hours, or until the sections become transparent. In some instances, the biological sample can be dried overnight (e.g., in a desiccator at room temperature).

In some embodiments, a sample can be stained using any number of biological stains, including but not limited to, acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, or safranin. In some instances, the methods disclosed herein include imaging the biological sample. In some instances, imaging the sample occurs prior to deaminating the biological sample. In some instances, the sample can be stained using known staining techniques, including Can-Grunwald, Giemsa, hematoxylin and eosin (H&E), Jenner's, Leishman, Masson's trichrome, Papanicolaou, Romanowsky, silver, Sudan, Wright's, and/or Periodic Acid Schiff (PAS) staining techniques. PAS staining is typically performed after formalin or acetone fixation. In some instances, the stain is an H&E stain.

In some embodiments, the biological sample can be stained using a detectable label (e.g., radioisotopes, fluorophores, chemiluminescent compounds, bioluminescent compounds, and dyes) as described elsewhere herein. In some embodiments, a biological sample is stained using only one type of stain or one technique. In some embodiments, staining includes biological staining techniques such as H&E staining. In some embodiments, staining includes identifying analytes using fluorescently-conjugated antibodies. In some embodiments, a biological sample is stained using two or more different types of stains, or two or more different staining techniques. For example, a biological sample can be prepared by staining and imaging using one technique (e.g., H&E staining and brightfield imaging), followed by staining and imaging using another technique (e.g., IHC/IF staining and fluorescence microscopy) for the same biological sample.

In some embodiments, biological samples can be destained. Methods of destaining or discoloring a biological sample are known in the art, and generally depend on the nature of the stain(s) applied to the sample. For example, H&E staining can be destained by washing the sample in HCl, or any other acid (e.g., selenic acid, sulfuric acid, hydroiodic acid, benzoic acid, carbonic acid, malic acid, phosphoric acid, oxalic acid, succinic acid, salicylic acid, tartaric acid, sulfurous acid, trichloroacetic acid, hydrobromic acid, hydrochloric acid, nitric acid, orthophosphoric acid, arsenic acid, selenous acid, chromic acid, citric acid, hydrofluoric acid, nitrous acid, isocyanic acid, formic acid, hydrogen selenide, molybdic acid, lactic acid, acetic acid, carbonic acid, hydrogen sulfide, or combinations thereof). In some embodiments, destaining can include 1, 2, 3, 4, 5, or more washes in an acid (e.g., HCl). In some embodiments, destaining can include adding HCl to a downstream solution (e.g., permeabilization solution). In some embodiments, destaining can include dissolving an enzyme used in the disclosed methods (e.g., pepsin) in an acid (e.g., HCl) solution. In some embodiments, after destaining hematoxylin with an acid, other reagents can be added to the destaining solution to raise the pH for use in other applications. For example, SDS can be added to an acid destaining solution in order to raise the pH as compared to the acid destaining solution alone. As another example, in some embodiments, one or more immunofluorescence stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., J. Histochem. Cytochem. 2017; 65(8): 431-444, Lin et al., Nat Commun. 2015; 6:8390, Pirici et al., J. Histochem. Cytochem. 2009; 57:567-75, and Glass et al., J. Histochem. Cytochem. 2009; 57:899-905, the entire contents of each of which are incorporated herein by reference.

In some embodiments, immunofluorescence or immunohistochemistry protocols (direct and indirect staining techniques) can be performed as a part of, or in addition to, the exemplary spatial workflows presented herein. For example, tissue sections can be fixed according to methods described herein. The biological sample can be transferred to an array (e.g., capture probe array), wherein analytes (e.g., proteins) are probed using immunofluorescence protocols. For example, the sample can be rehydrated, blocked, and permeabilized (3×SSC, 2% BSA, 0.1% Triton X, 1 U/µl RNAse inhibitor for 10 minutes at 4° C.) before being stained with fluorescent primary antibodies (1:100 in 3×SSC, 2% BSA, 0.1% Triton X, 1 U/µl RNAse inhibitor for 30 minutes at 4° C.). The biological sample can be washed, coverslipped (in glycerol+1 U/µl RNAse inhibitor), imaged (e.g., using a confocal microscope or other apparatus capable of fluorescent detection), washed, and processed according to analyte capture or spatial workflows described herein.

In some instances, a glycerol solution and a cover slip can be added to the sample. In some instances, the glycerol solution can include a counterstain (e.g., DAPI).

As used herein, an antigen retrieval buffer can improve antibody capture in IF/IHC protocols. An exemplary protocol for antigen retrieval can be preheating the antigen retrieval buffer (e.g., to 95° C.), immersing the biological sample in the heated antigen retrieval buffer for a predetermined time, and then removing the biological sample from the antigen retrieval buffer and washing the biological sample.

In some embodiments, optimizing permeabilization can be useful for identifying intracellular analytes. Permeabilization optimization can include selection of permeabilization agents, concentration of permeabilization agents, and permeabilization duration. Tissue permeabilization is discussed elsewhere herein.

In some embodiments, blocking an array and/or a biological sample in preparation of labeling the biological sample decreases nonspecific binding of the antibodies to the array and/or biological sample (decreases background). Some embodiments provide for blocking buffers/blocking solutions that can be applied before and/or during application of the label, wherein the blocking buffer can include a blocking agent, and optionally a surfactant and/or a salt solution. In some embodiments, a blocking agent can be bovine serum albumin (BSA), serum, gelatin (e.g., fish gelatin), milk (e.g., non-fat dry milk), casein, polyethylene glycol (PEG), polyvinyl alcohol (PVA), or polyvinylpyrrolidone (PVP), biotin blocking reagent, a peroxidase blocking reagent, levamisole, Carnoy's solution, glycine, lysine, sodium borohydride, pontamine sky blue, Sudan Black, trypan blue, FITC blocking agent, and/or acetic acid. The blocking buffer/blocking solution can be applied to the array and/or biological sample prior to and/or during labeling (e.g., application of fluorophore-conjugated antibodies) to the biological sample.

(ii) Preparation of a Sample for Application of Probes

In some instances, the biological sample is deparaffinized. Deparaffinization can be achieved using any method known in the art. For example, in some instances, the biological samples is treated with a series of washes that include xylene and various concentrations of ethanol. In some instances, methods of deparaffinization include treatment of xylene (e.g., three washes at 5 minutes each). In some instances, the methods further include treatment with ethanol (e.g., 100% ethanol, two washes 10 minutes each; 95% ethanol, two washes 10 minutes each; 70% ethanol, two washes 10 minutes each; 50% ethanol, two washes 10 minutes each). In some instances, after ethanol washes, the biological sample can be washed with deionized water (e.g., two washes for 5 minutes each). It is appreciated that one skilled in the art can adjust these methods to optimize deparaffinization.

In some instances, the biological sample is decrosslinked. In some instances, the biological sample is decrosslinked in a solution containing TE buffer (comprising Tris and EDTA). In some instances, the TE buffer is basic (e.g., at a pH of about 9). In some instances, decrosslinking occurs at about 50° C. to about 80° C. In some instances, decrosslinking occurs at about 70° C. In some instances, decrosslinking occurs for about 1 hour at 70° C. Just prior to decrosslinking, the biological sample can be treated with an acid (e.g., 0.1M HCl for about 1 minute). After the decrosslinking step, the biological sample can be washed (e.g., with 1×PBST).

In some instances, the methods of preparing a biological sample for probe application include permeabilizing the sample. In some instances, the biological sample is permeabilized using a phosphate buffer. In some instances, the phosphate buffer is PBS (e.g., 1×PBS). In some instances, the phosphate buffer is PBST (e.g., 1×PBST). In some instances, the permeabilization step is performed multiple times (e.g., 3 times at 5 minutes each).

In some instances, the methods of preparing a biological sample for probe application include steps of equilibrating and blocking the biological sample. In some instances, equilibrating is performed using a pre-hybridization (pre-Hyb) buffer. In some instances, the pre-Hyb buffer is RNase-free. In some instances, the pre-Hyb buffer contains no bovine serum albumin (BSA), solutions like Denhardt's, or other potentially nuclease-contaminated biological materials.

In some instances, the equilibrating step is performed multiple times (e.g., 2 times at 5 minutes each; 3 times at 5 minutes each). In some instances, the biological sample is blocked with a blocking buffer. In some instances, the blocking buffer includes a carrier such as tRNA, for example yeast tRNA such as from brewer's yeast (e.g., at a final concentration of 10-20 µg/mL). In some instances, blocking can be performed for 5, 10, 15, 20, 25, or 30 minutes.

Any of the foregoing steps can be optimized for performance. For example, one can vary the temperature. In some instances, the pre-hybridization methods are performed at room temperature. In some instances, the pre-hybridization methods are performed at 4° C. (in some instances, varying the timeframes provided herein).

Hybridizing the Probes

In some embodiments, the methods described herein include hybridizing undesirable RNA depletion probes prior to or contemporaneously with targeted RNA capture that includes hybridizing a first probe oligonucleotide and a second probe oligonucleotide (e.g., a probe pair). In some instances, the first and second probe oligonucleotides for targeted RNA capture each include sequences that are substantially complementary to one or more sequences (e.g., one or more target sequences) of an analyte of interest. In some embodiments, the first probe and the second probe bind to complementary sequences that are completely adjacent (i.e., no gap of nucleotides) to one another or are on the same transcript.

In some instances, the methods include hybridization of probe sets, wherein the probe pairs are in a medium at a concentration of about 1 to about 100 nM. In some instances, the concentration of the probe pairs is about 1, 2, 3, 4, 5, 6, 7, 8, 9, 10, 15, 20, 25, 30, 35, 40, 45, 50, 60, 70, 80, 90, 100, 200, 300, 400, or 500 nM. In some instances, the concentration of the probe pairs is 5 nM. In some instances, the probe sets are diluted in a hybridization (Hyb) buffer. In some instances, the probe sets are at a concentration of 5 nM in Hyb buffer.

In some instances, probe hybridization (e.g., hybridizing the undesirable RNA depletion probes and/or the first and second probe oligonucleotides) occurs at about 50° C. In some instances, the temperature of probe hybridization ranges from about 30° C. to about 75° C., from about 35° C. to about 70° C., or from about 40° C. to about 65° C. In some embodiments, the temperature is about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., or about 70° C. In some instances, probe hybridization occurs for about 30 minutes, about 1 hour, about 2 hours, about 2.5 hours, about 3 hours, or more. In some instances, probe hybridization occurs for about 2.5 hours at 50° C.

In some instances, the hybridization buffer includes SSC (e.g., 1×SSC) or SSPE. In some instances, the hybridization buffer includes formamide or ethylene carbonate. In some instances, the hybridization buffer includes one or more salts, like Mg salt for example $MgCl_2$, Na salt for example NaCl, Mn salt for example $MnCl_2$. In some instances, the hybridization buffer includes Denhardt's solution, dextran sulfate, ficoll, PEG or other hybridization rate accelerators. In some instances, the hybridization buffer includes a carrier such as yeast tRNA, salmon sperm DNA, and/or lambda phage DNA. In some instances, the hybridization buffer includes one or more blockers. In some instances, the hybridization buffer includes RNase inhibitor(s). In some instances, the hybridization buffer can include BSA, sequence specific blockers, non-specific blockers, EDTA, RNase inhibitor(s), betaine, TMAC, or DMSO. In some instances, a hybridization buffer can further include detergents such as Tween, Triton-X 100, sarkosyl, and SDS. In some instances, the hybridization buffer includes nuclease-free water, DEPC water.

In some embodiments, the complementary sequences to which the first probe oligonucleotide and the second probe oligonucleotide bind are 1, 2, 3, 4, 5, 6, 7, 8, 9, 10, about 15, about 20, about 25, about 30, about 35, about 40, about 45, about 50, about 55, about 60, about 65, about 70, about 75, about 80, about 85, about 90, about 95, about 100, about 125, about 150, about 175, about 200, about 250, about 300, about 350, about 400, about 450, about 500, about 600, about 700, about 800, about 900, or about 1000 nucleotides away from each other. Gaps between the probe oligonucleotides may first be filled prior to ligation, using, for example, Mu polymerase, DNA polymerase, RNA polymerase, reverse transcriptase, VENT polymerase, Taq polymerase, and/or any combinations, derivatives, and variants (e.g., engineered mutants) thereof. In some embodiments, when the first and second probe oligonucleotides are separated from each other by one or more nucleotides, nucleotides are ligated between the first and second probe oligonucleotides. In some embodiments, when the first and second probe oligonucleotides are separated from each other by one or more nucleotides, deoxyribonucleotides are ligated between the first and second probe oligonucleotides.

In some instances, after hybridization, the biological sample is washed with a post-hybridization wash buffer. In some instances, the post-hybridization wash buffer includes one or more of SSC, yeast tRNA, formamide, ethylene carbonate, and nuclease-free water.

Additional embodiments regarding probe hybridization are further provided.

(i) Hybridizing Temperatures

In some embodiments, the method described utilizes oligonucleotides that include deoxyribonucleic acids (instead of strictly utilizing ribonucleotides) at the site of ligation. Utilizing deoxyribonucleic acids in the methods described herein create a more uniform efficiency that can be readily-controlled and flexible for various applications. In some embodiments, an undesirable RNA depletion probe includes deoxyribonucleic acids (instead of strictly utilizing ribonucleotides) at the site of ligation. In some embodiments, a first probe oligonucleotide and/or a second probe oligonucleotide include deoxyribonucleic acids (instead of strictly utilizing ribonucleotides) at the site of ligation.

In a non-limiting example, the methods disclosed herein include contacting a biological sample with a plurality of oligonucleotides (e.g., undesirable RNA depletion probes and/or RTL probes) including, an undesirable RNA depletion probe, a first oligonucleotide (e.g., a first probe) and a second oligonucleotide (e.g., a second probe), wherein the undesirable RNA depletion probe includes a sequence that is substantially complementary to at least a portion of an undesirable RNA, wherein the first oligonucleotide (e.g., the first probe) and the second oligonucleotide (e.g., the second probe) are complementary to a first sequence present in an analyte and a second sequence present in the analyte, respectively; hybridizing the undesirable RNA depletion probe, the first oligonucleotide (e.g., the first probe), and the second oligonucleotide (e.g., the second probe) to the analyte at a first temperature; hybridizing the undesirable RNA depletion probe, and the first oligonucleotide (e.g., the first probe) and the second oligonucleotide (e.g., the second probe) to a third oligonucleotide (e.g., a splint oligonucleotide) at a second temperature such that the first oligonucleotide (e.g., the first probe) and the second oligonucleotide (e.g., the second probe) abut each other; ligating the first oligonucleotide (e.g., the first probe) to the second oligonucleotide (e.g., the second probe) to create a ligation product; contacting the biological sample with a substrate, wherein a capture probe is immobilized on the substrate, wherein the capture probe includes a spatial barcode and a capture domain; allowing the ligation product to specifically bind to the capture domain; and determining (i) all or a part of the sequence of the ligation product specifically bound to the capture domain, or a complement thereof, and (ii) all or a part of the sequence of the spatial barcode, or a complement thereof, and using the determined sequence of (i) and (ii) to identify the location of the analyte in the biological sample; wherein the first oligonucleotide (e.g., the first probe), the second oligonucleotide (e.g., the second probe), and the third oligonucleotide are DNA oligonucleotides, and wherein the first temperature is a higher temperature than the second temperature.

In some embodiments, the undesirable RNA depletion probe, the first oligonucleotide (e.g., the first probe), and/or the second oligonucleotide (e.g., the second probe) hybridize to an analyte at a first temperature. In some embodiments, the first temperature ranges from about 50° C. to about 75° C., from about 55° C. to about 70° C., or from about 60° C. to about 65° C. In some embodiments, the first temperature is about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., or about 70° C.

In some embodiments, after the step of hybridizing the undesirable RNA depletion probe, first oligonucleotide (e.g., the first probe), and/or the second oligonucleotide (e.g., the second probe) to the analyte, a wash step is performed to remove unbound oligonucleotides (e.g., probes). The wash step can be performed using any of the wash methods and solutions described herein.

In some embodiments, after the step of hybridizing the first oligonucleotide (e.g., the first probe) and the second oligonucleotide (e.g., the second probe) to the analyte, a third oligonucleotide (e.g., a splint oligonucleotide) is added to the analyte. In some embodiments, the third oligonucleotide is an oligonucleotide. In some embodiments, the third oligonucleotide is a DNA oligonucleotide.

In some embodiments, the third oligonucleotide includes a sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to a portion of the first probe oligonucleotide (e.g., a portion of the first probe that is not hybridized to the analyte (e.g., an auxiliary sequence)). In some embodiments, the third oligonucleotide includes a sequence that is 100% complementary to a portion of the first oligonucleotide (e.g., the first probe). In some embodiments, the third oligonucleotide includes a sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to a portion of the second probe oligonucleotide (e.g., a portion of the second probe that is not hybridized to the analyte (e.g., an auxiliary sequence)). In some embodiments, the third oligonucleotide includes a sequence that is 100% complementary to a portion of the second oligonucleotide (e.g., the second probe). In some embodiments, the third oligonucleotide hybridizes to the first oligonucleotide (e.g., the first probe) at the complementary portion. In some embodiments, the third oligonucleotide hybridizes to the second oligonucleotide (e.g., the second probe) at the complementary portion.

In some embodiments, the third oligonucleotide hybridizes to the first oligonucleotide (e.g., the first probe) and to the second oligonucleotide (e.g., the second probe) at a second temperature. In some embodiments, the second temperature is lower than the first temperature at which the first and second oligonucleotides (e.g., the first and second probes) bind the analyte. In some embodiments, the second temperature ranges from about 15° C. to about 35° C., from about 20° C. to about 30° C., or from about 25° C. to about 30° C. In some embodiments, the first temperature is about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., or about 35° C. Methods including a third, or splint, oligonucleotide have been described in U.S. Patent Pub. No. 2019/0055594A1, which is herein incorporated by reference in its entirety.

In some embodiments, after the step of hybridizing the third oligonucleotide to the analyte, a wash step is performed to remove unbound third oligonucleotides. The wash step can be performed using any of the wash methods and solutions described herein. In some embodiments, after the washing step, the first and second oligonucleotides (e.g., the first and second probes) are bound to (e.g., hybridized to) the analyte, and the third oligonucleotide is bound to (e.g., hybridized to) the first and second oligonucleotides (e.g., at portions of the first and second probes that are not bound to the analyte).

In some embodiments, the first oligonucleotide (e.g., the first probe), the second oligonucleotide (e.g., the second probe), and the third oligonucleotide are added to the biological sample at the same time. Then, in some embodiments, the temperature is adjusted to the first temperature to allow the first oligonucleotide (e.g., the first probe) and the second oligonucleotide (e.g., the second probe) to hybridize to the analyte in the biological sample. Next, the temperature is adjusted to the second temperature to allow the third oligonucleotide to hybridize to the first oligonucleotide and the second oligonucleotide.

In some embodiments where a third oligonucleotide hybridizes to a first probe and a second probe that are hybridized to targets sequences that are not directly adjacent in the analyte, the third oligonucleotide is extended to fill the gap between the first probe and the second probe. In some instances, a polymerase (e.g., a DNA polymerase) can extend one of the probes (e.g., the first probe) prior to ligation.

In some embodiments, a ligation step is performed. Ligation can be performed using any of the methods described herein. In some embodiments, the step includes ligation of the first oligonucleotide (e.g., the first probe) and the second oligonucleotide (e.g., the second probe), forming a ligation product. In some embodiments, the third oligonucleotide serves as an oligonucleotide splint to facilitate ligation of the first oligonucleotide (e.g., the first probe) and the second oligonucleotide (e.g., the second probe). In some embodiments, ligation is chemical ligation. In some embodiments, ligation is enzymatic ligation. In some embodiments, the ligase is a T4 RNA ligase (Rnl2), a splintR ligase, a single stranded DNA ligase, or a T4 DNA ligase.

(ii) Hybridization Buffer

In some embodiments, an undesirable RNA depletion probe, a first probe, and/or a second probe are hybridized to the analyte in a hybridization buffer. In some instances, the hybridization buffer contains formamide. In other instances the hybridization buffer is formamide free. Formamide is not human friendly and it is a known health hazard. Chemically, it can oxidize over time, thereby impacting reagent shelf life and, most importantly, reagent efficacy. As such, the methods described herein can include formamide-free buffers, including formamide-free hybridization buffer.

In some embodiments, the formamide-free hybridization buffer is a saline-sodium citrate (SSC) hybridization buffer. In some embodiment, the SSC is present in the SSC hybridization buffer from about 1×SSC to about 6×SSC (e.g., about 1×SSC to about 5×SSC, about 1×SSC to about 4×SSC, about 1×SSC to about 3×SSC, about 1×SSC to about 2×SSC, about 2×SSC to about 6×SSC, about 2×SSC to about 5×SSC, about 2×SSC to about 4×SSC, about 2×SSC to about 3×SSC, about 3×SSC to about 5×SSC, about 3×SSC to about 4×SSC, about 4×SSC to about 6×SSC, about 4×SSC to about 5×SSC, or about 5×SSC to about 6×SSC). In some embodiments, the SSC is present in the SSC hybridization buffer from about 2×SSC to about 4×SSC. In some embodiments, SSPE hybridization buffer can be used.

In some embodiments, the SSC hybridization buffer comprises a solvent. In some embodiments, the solvent comprises ethylene carbonate instead of formamide (2020, Kalinka et al., *Scientia Agricola* 78(4):e20190315). In some embodiments, ethylene carbonate is present in the SSC hybridization buffer from about 10% (w/v) to about 25% (w/v) (e.g., about 10% (w/v) to about 20% (w/v), about 10% (w/v) to about 15% (w/v), about 15% (w/v) to about 25% (w/v), about 15% (w/v) to about 20% (w/v), or about 20% (w/v) to about 25% (w/v)). In some embodiments, ethylene carbonate is present in the SSC hybridization buffer from about 15% (w/v) to about 20% (w/v). In some embodiments, ethylene carbonate is present in the SSC hybridization buffer at about 10% (w/v), about 11% (w/v), about 12% (w/v), about 13% (w/v), about 14% (w/v), about 15% (w/v), about 16% (w/v), about 17% (w/v), about 18% (w/v), about 19% (w/v), about 20% (w/v), about 21% (w/v), about 22% (w/v), about 23% (w/v), about 24% (w/v), or about 25% (w/v). In some embodiments, ethylene carbonate is present in the SSC hybridization buffer at about 13% (w/v).

In some embodiments, the SSC hybridization buffer is at a temperature from about 40° C. to about 60° C. (e.g., about 40° C. to about 55° C., about 40° C. to about 50° C., about 40° C. to about 45° C., about 45° C. to about 60° C., about 45° C. to about 55° C., about 45° C. to about 50° C., about 50° C. to about 60° C., about 50° C. to about 55° C., or about 55° C. to about 60° C.). In some embodiments, the SSC hybridization buffer is at temperature from about 45° C. to about 55° C., or any of the subranges described herein. In some embodiments, the SSC hybridization buffer is at a temperature of about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., or about 60° C. In some embodiments, the SSC hybridization buffer is at a temperature of about 50° C.

In some embodiments, the SSC hybridization buffer further comprises one or more of a carrier, a crowder, or an additive. Non-limiting examples of a carrier that can be included in the hybridization buffer include: yeast tRNA, salmon sperm DNA, lambda phage DNA, glycogen, and cholesterol. Non-limiting examples of a molecular crowder that can be included in the hybridization buffer include: Ficoll, dextran, Denhardt's solution, and PEG. Non-limiting examples of additives that can be included in the hybridization buffer include: binding blockers, RNase inhibitors, Tm adjustors and adjuvants for relaxing secondary nucleic acid structures (e.g., betaine, TMAC, and DMSO). Further, a hybridization buffer can include detergents such as SDS, Tween, Triton-X 100, and sarkosyl (e.g., N-Lauroylsarcosine sodium salt). A skilled artisan would understand that a buffer for hybridization of nucleic acids could include many different compounds that could enhance the hybridization reaction.

(j) Washing

In some embodiments, the methods disclosed herein also include a wash step. The wash step removes any unbound probes. Wash steps could be performed between any of the steps in the methods disclosed herein. For example, a wash step can be performed after adding probes (e.g., any of the undesirable RNA probes and/or RTL probe pairs described herein) to the biological sample. As such, free/unbound probes are washed away, leaving only probes that have hybridized to an analyte and/or undesirable RNA (e.g., rRNA). In some instances, multiple (i.e., at least 2, 3, 4, 5, or more) wash steps occur between the methods disclosed herein. Wash steps can be performed at times (e.g., 1, 2, 3, 4, or 5 minutes) and temperatures (e.g., room temperature; 4° C. known in the art and determined by a person of skill in the art.

In some instances, wash steps are performed using a wash buffer. In some instances, the wash buffer includes SSC (e.g., 1×SSC). In some instances, the wash buffer includes PBS (e.g., 1×PBS). In some instances, the wash buffer includes PBST (e.g., 1×PBST). In some instances, the wash buffer can also include formamide or be formamide free.

Additional embodiments regarding wash steps are provided herein.

(i) Formamide Free Wash Buffer

In some embodiments, after hybridizing and/or ligating the undesirable RNA depletion probe, one or more unhybridized undesirable RNA depletion probes are removed from the array. In some embodiments, after ligating a first probe and a second probe, the one or more unhybridized first probes, one or more unhybridized second probes, or both, are removed from the array. In some embodiments, after ligating a first probe, a second probe, and a third oligonucleotide, the one or more unhybridized first probes, one or more unhybridized second probes, or one or more third oligonucleotides, or all the above, are removed from the array.

In some embodiments, a pre-hybridization buffer is used to wash the sample. In some embodiments, a phosphate buffer is used. In some embodiments, multiple wash steps are performed to remove unbound oligonucleotides.

In some embodiments, removing includes washing the one or more unhybridized probes (e.g., an undesirable RNA depletion probe, a first probe, a second probe, and a third oligonucleotide) from the array in a formamide-free wash buffer.

In some embodiments, the formamide-free wash buffer is an SSC wash buffer. In some embodiments, SSC is present in the SSC wash buffer from about 0.01×SSC to about 1×SSC (e.g., about 0.01×SSC to about 0.5×SSC, 0.01×SSC to about 0.1×SSC, about 0.01×SSC to about 0.05×SSC, about 0.05×SSC to about 1×SSC, about 0.05×SSC to about 0.5×SSC, about 0.05×SSC to about 0.1×SSC, about 0.1× SSC to about 1×SSC, about 0.1×SSC to about 0.5×SSC, or about 0.5×SSC to about 1×SSC). In some embodiments, SSC is present in the SSC wash buffer at about 0.01×SSC, about 0.02×SSC, about 0.03×SSC, about 0.04×SSC, about 0.05×SSC, about 0.06×SSC, about 0.07×SSC, about 0.08× SSC, about 0.09×SSC, about 0.1×SSC, about 0.2×SSC, about 0.3×SSC, about 0.4×SSC, about 0.5×SSC, about 0.6× SSC, about 0.7×SSC, about 0.8×SSC, about 0.9×SSC, or about 0.1× SSC. In some embodiments, SSC is present in the SSC wash buffer at about 0.1×SSC.

In some embodiments, the SSC wash buffer comprises a detergent. In some embodiments, the detergent comprises sodium dodecyl sulfate (SDS). In some embodiments, SDS is present in the SSC wash buffer from about 0.01% (v/v) to about 0.5% (v/v) (e.g., about 0.01% (v/v) to about 0.4% (v/v), about 0.01% (v/v) to about 0.3% (v/v), about 0.01% (v/v) to about 0.2% (v/v), about 0.01% (v/v) to about 0.1% (v/v), about 0.05% (v/v) to about 0.5% (v/v), about 0.05% (v/v) to about 0.4% (v/v), about 0.05% (v/v) to about 0.3% (v/v), about 0.05% (v/v) to about 0.2% (v/v), about 0.05% (v/v) to about 0.1% (v/v), about 0.1% (v/v) to about 0.5% (v/v), about 0.1% (v/v) to about 0.4% (v/v), about 0.1% (v/v) to about 0.3% (v/v), about 0.1% (v/v) to about 0.2% (v/v), about 0.2% (v/v) to about 0.5% (v/v), about 0.2% (v/v) to about 0.4% (v/v), about 0.2% (v/v) to about 0.3% (v/v), about 0.3% (v/v) to about 0.5% (v/v), about 0.3% (v/v) to about 0.4% (v/v), or about 0.4% (v/v) to about 0.5% (v/v)). In some embodiments, the SDS is present the SSC wash buffer at about 0.01% (v/v), about 0.02% (v/v), about 0.03% (v/v), about 0.04% (v/v), about 0.05% (v/v), about 0.06% (v/v), about 0.07% (v/v), about 0.08% (v/v), about 0.09% (v/v), about 0.10% (v/v), about 0.2% (v/v), about 0.3% (v/v), about 0.4% (v/v), or about 0.5% (v/v), In some embodiments, the SDS is present in the SSC wash buffer at about 0.1% (v/v). In some embodiments, sarkosyl may be present in the SSC wash buffer.

In some embodiments, the SSC wash buffer comprises a solvent. In some embodiments, the solvent comprises formamide or ethylene carbonate. In some embodiments, ethylene carbonate is present in the SSC wash buffer from about 10% (w/v) to about 25% (w/v), or any of the subranges described herein. In some embodiments, ethylene carbonate is present in the SSC wash buffer from about 15% (w/v) to about 20% (w/v). In some embodiments, ethylene carbonate is present in the SSC wash buffer at about 16% (w/v).

In some embodiments, the SSC wash buffer is at a temperature from about 50° C. to about 70° C. (e.g., about 50° C. to about 65° C., about 50° C. to about 60° C., about 50° C. to about 55° C., about 55° C. to about 70° C., about 55° C. to about 65° C., about 55° C. to about 60° C., about 60° C. to about 70° C., about 60° C. to about 65° C., or about 65° C. to about 70° C.). In some embodiments, the SSC wash buffer is at a temperature from about 55° C. to about 65° C. In some embodiments, the SSC wash buffer is at a temperature about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., or about 70° C. In some embodiments, the SSC wash buffer is at a temperature of about 60° C.

In some embodiments, the method includes releasing the ligation product, where releasing is performed after the array is washed to remove the one or more unhybridized first and second probes.

(k) Ligation

In some embodiments, after hybridization of the probe oligonucleotides (e.g., a first probe, a second probe, and/or a third oligonucleotide) to the analyte, the probes (e.g., a first probe, a second probe, and/or a third oligonucleotide) can be ligated together, creating a single ligation product that includes one or more sequences that are complementary to the analyte. In some embodiments, after hybridization of the undesirable RNA depletion probes, the undesirable RNA depletion probes can be ligated together. Ligation can be performed enzymatically or chemically, as described herein.

In some instances, the ligation is an enzymatic ligation reaction, using a ligase (e.g., T4 RNA ligase (Rnl2), a SplintR ligase, a single stranded DNA ligase, or a T4 DNA ligase). See, e.g., Zhang et al.; *RNA Biol.* 2017; 14(1): 36-44, which is incorporated by reference in its entirety, for a description of KOD ligase. Following the enzymatic ligation reaction, the probes (e.g., a first probe, a second probe, and/or a third oligonucleotide) may be considered ligated.

In some embodiments, a polymerase catalyzes synthesis of a complementary strand of the ligation product, creating a double-stranded ligation product. In some instances, the polymerase is DNA polymerase. In some embodiments, the polymerase has 5' to 3' polymerase activity. In some embodiments, the polymerase has 3' to 5' exonuclease activity for proofreading. In some embodiments, the polymerase has 5' to 3' polymerase activity and 3' to 5' exonuclease activity for proofreading.

In some embodiments, the probe (e.g., a first probe, a second probe, and/or a third oligonucleotide) may each comprise a reactive moiety such that, upon hybridization to the target and exposure to appropriate ligation conditions, the probe oligonucleotides may ligate to one another. In some embodiments, probe oligonucleotides that include a reactive moiety are ligated chemically. For example, a first probe capable of hybridizing to a first target region (e.g., a first target sequence or a first portion) of a nucleic acid molecule may comprise a first reactive moiety, and a second probe oligonucleotide capable of hybridizing to a second target region (e.g., a second target sequence or a second portion) of the nucleic acid molecule may comprise a second reactive moiety. When the first and second probes are hybridized to the first and second target regions (e.g., first and second target sequences) of the nucleic acid molecule, the first and second reactive moieties may be adjacent to one another. A reactive moiety of a probe may be selected from the non-limiting group consisting of azides, alkynes, nitrones (e.g., 1,3-nitrones), strained alkenes (e.g., trans-cycloalkenes such as cyclooctenes or oxanorbornadiene), tetrazines, tetrazoles, iodides, thioates (e.g., phorphorothioate), acids, amines, and phosphates. For example, the first reactive moiety of a first probe may comprise an azide moiety, and a second reactive moiety of a second probe may comprise an alkyne moiety. The first and second reactive moieties may react to form a linking moiety. A reaction between the first and second reactive moieties may be, for example, a cycloaddition reaction such as a strain-promoted azide-alkyne cycloaddition, a copper-catalyzed azide-alkyne cycloaddition, a strain-promoted alkyne-nitrone cycloaddition, a Diels-Alder reaction, a [3+2] cycloaddition, a [4+2] cycloaddition, or a [4+1] cycloaddition; a thiol-ene reaction; a nucleophilic substation reaction; or another reaction. In some cases, reaction between the first and second reactive moieties may yield a triazole moiety or an isoxazoline moiety. A reaction between the first and second reactive moieties may involve subjecting the reactive moieties to suitable conditions such as a suitable temperature, pH, or pressure and providing one or more reagents or catalysts for the reaction. For example, a reaction between the first and second reactive moieties may be catalyzed by a copper catalyst, a ruthenium catalyst, or a strained species such as a difluorooctyne, dibenzylcyclooctyne, or biarylazacyclooctynone. Reaction between a first reactive moiety of a first probe hybridized to a first target region (e.g., a first target sequence or first portion) of the nucleic acid molecule and a second reactive moiety of a third probe oligonucleotide hybridized to a second target region (e.g., a first target sequence or first portion) of the nucleic acid molecule may link the first probe and the second probe to provide a ligated probe. Upon linking, the first and second probe may be considered ligated. Accordingly, reaction of the first and second reactive moieties may comprise a chemical ligation reaction such as a copper-catalyzed 5' azide to 3' alkyne "click" chemistry reaction to form a triazole linkage between two probe oligonucleotides. In other non-limiting examples, an iodide moiety may be chemically ligated to a phosphorothioate moiety to form a phosphorothioate bond, an acid may be ligated to an amine to form an amide bond, and/or a phosphate and amine may be ligated to form a phosphoramidate bond.

In some instances, ligation is performed in a ligation buffer. In instances where probe ligation is performed on diribo-containing probes, the ligation buffer can include T4 RNA Ligase Buffer 2, enzyme (e.g., RNL2 ligase), and nuclease free water. In instances where probe ligation is performed on DNA probes, the ligation buffer can include Tris-HCl pH7.5, MnCl2, ATP, DTT, surrogate fluid (e.g., glycerol), enzyme (e.g., SplintR ligase), and nuclease-free water.

In some embodiments, the ligation buffer includes additional reagents. In some instances, the ligation buffer includes adenosine triphosphate (ATP) is added during the ligation reaction. DNA ligase-catalyzed sealing of nicked DNA substrates is first activated through ATP hydrolysis, resulting in covalent addition of an AMP group to the enzyme. After binding to a nicked site in a DNA duplex, the ligase transfers the AMP to the phosphorylated 5'-end at the nick, forming a 5'-5' pyrophosphate bond. Finally, the ligase catalyzes an attack on this pyrophosphate bond by the OH group at the 3'-end of the nick, thereby sealing it, whereafter ligase and AMP are released. If the ligase detaches from the substrate before the 3' attack, e.g., because of premature AMP reloading of the enzyme, then the 5' AMP is left at the 5'-end, blocking further ligation attempts. In some instances, ATP is added at a concentration of about 1 µM, about 10 µM, about 100 µM, about 1000 µM, or about 10000 µM during the ligation reaction.

In some embodiments, cofactors that aid in joining of the probe oligonucleotides are added during the ligation process. In some instances, the cofactors include magnesium ions ($Mg^{2+}$). In some instances, the cofactors include manganese ions ($Mn^{2+}$). In some instances, $Mg^{2+}$ is added in the form of $MgCl_2$. In some instances, $Mn^{2+}$ is added in the form of $MnCl_2$. In some instances, the concentration of $MgCl_2$ is at about 1 mM, at about 10 mM, at about 100 mM, or at about 1000 mM. In some instances, the concentration of $MnCl_2$ is at about 1 mM, at about 10 mM, at about 100 mM, or at about 1000 mM.

In some embodiments, the ligation product includes a capture probe capture domain, which can bind to a capture probe (e.g., a capture probe immobilized, directly or indirectly, on a substrate). In some embodiments, methods provided herein include contacting a biological sample with a substrate, wherein the capture probe is affixed to the substrate (e.g., immobilized to the substrate, directly or indirectly). In some embodiments, the capture probe capture domain of the ligated probe specifically binds to the capture domain.

After ligation, in some instances, the biological sample is washed with a post-ligation wash buffer. In some instances, the post-ligation wash buffer includes one or more of SSC (e.g., 1×SSC), ethylene carbonate or formamide, and nuclease free water. In some instances, the biological sample is washed at this stage at about 50° C. to about 70° C. In some instances, the biological sample is washed at about 60° C.

(i) Ligation Including Pre-Adenylated 5' Phosphate on Second Probe

Provided herein are methods for determining a location of a target nucleic acid in a biological sample that include: (a) contacting the biological sample with a substrate comprising a plurality of capture probes, where a capture probe of the plurality of capture probes comprises a capture domain and a spatial barcode; (b) hybridizing a target nucleic acid in the biological sample with a first probe and a second probe, where the first probe comprises, from 3' to 5', a sequence substantially complementary to the capture domain and a sequence that is substantially complementary to a first sequence in the target nucleic acid and has a pre-adenylated phosphate group at its 5' end; the second probe comprises a sequence substantially complementary to a second sequence in the target nucleic acid; (c) generating a ligation product by ligating a 3' end of the second probe to the 5' end of the first probe using a ligase that does not require adenosine triphosphate for ligase activity; (d) releasing the ligation product from the target nucleic acid and binding the capture domain of the ligation product specifically to the capture domain of capture probe; and (e) determining (i) all or a part of a sequence corresponding to the ligation product, or a complement thereof, and (ii) all or a part of a sequence corresponding to the spatial barcode, or a complement thereof, and using the determined sequences of (i) and (ii) to identify the location of the target nucleic acid in the biological sample In some instances, the ligase that does not require adenosine triphosphate for ligase activity (e.g., thermostable 5' AppDNA/RNA Ligase, truncated T4 RNA Ligase 2 (trRnl2), truncated T4 RNA Ligase 2 K227Q, truncated T4 RNA Ligase 2 KQ, *Chlorella* Virus PBCV-DNA Ligase, and combinations thereof). See, e.g., Nichols et al., "RNA Ligases," Curr. Protocol. Molec. Biol. 84(1):3.15.1-.4 (2008); Viollet et al., "T4 RNA Ligase 2 Truncated Active Site Mutants: Improved Tools for RNA Analysis," BMC Biotechnol. 11: 72 (2011); and Ho et al., "Bacteriophage T4 RNA Ligase 2 (gp24.1) Exemplifies a Family of RNA Ligases Found in All Phylogenetic Domains," PNAS 99(20):12709-14 (2002), which are hereby incorporated by reference in their entirety for a description of T4 RNA Ligases and truncated T4 RNA Ligases. Thermostable 5' AppDNA/RNA Ligase is an enzyme belonging to the Ligase family that catalyzes the ligation of the 3' end of ssRNA or ssDNA to a 5'-adenylated ssDNA or 5'-adenylated ssRNA. Truncated T4 RNA Ligase 2 is an enzyme belonging to the Ligase family that catalyzes the ligation of dsRNA nicks and ssRNA to ssRNA. It can also ligate the 3' end of RNA or DNA to a 5'-pDNA when annealed to an RNA complement, and the 3' end of RNA to a 5'-pRNA when annealed to a DNA complement, with reduced efficiency. Truncated T4 RNA Ligase 2 K227Q is an enzyme belonging to the Ligase family that catalyzes the ligation of the 3' end of ssRNA to 5' adenylated ssDNA and 5' adenylated ssRNA. It has a reduction of side products as compared to truncated T4 RNA Ligase 2. Truncated T4 RNA Ligase 2 KQ is an enzyme belonging to the Ligase family that catalyzes the ligation of the 3' end of ssRNA to 5' adenylated ssDNA and 5' adenylated ssRNA. It is a preferred choice for ligation of ssRNA to preadenylated adapters and has a reduction of side products as compared to truncated T4 RNA Ligase 2.

In some embodiments, the T4 RNA Ligase comprises a K227Q mutation. See Viollet et al., "T4 RNA Ligase 2 Truncated Active Site Mutants: Improved Tools for RNA Analysis," *BMC Biotechnol.* 11, which is hereby incorporated by reference in its entirety.

In some instances, cofactors that aid in ligation of the first and second probe are added during ligation. In some instances, the cofactors include magnesium ions ($Mg^{2+}$). In some instances, the cofactors include manganese ions ($Mn^{2+}$). In some instances, $Mg^{2+}$ is added in the form of $MgCl_2$. In some instances, $Mn^{2+}$ is added in the form of $MnCl_2$. In some instances, the concentration of $MgCl_2$ is at about 1 mM to about 10 mM. In some instances, the concentration of $MnCl_2$ is at about 1 mM to about 10 mM.

In some instances, the ligation occurs at a pH in the range of about 6.5 to about 9.0, about 6.5 to about 8.0, or about 7.5 to about 8.0.

In some embodiments, the ligation buffer includes an enzyme storage buffer. In some embodiments, the enzymes storage buffer includes glycerol. In some embodiments, the ligation buffer is supplemented with glycerol. In some embodiments, the glycerol is present in the ligation buffer at a total volume of 15% v/v.

(l) Permeabilization and Releasing the Ligation Product

In some embodiments, the methods provided herein include a permeabilizing step. In some embodiments, permeabilization occurs using a protease. In some embodiments, the protease is an endopeptidase. Endopeptidases that can be used include but are not limited to trypsin, chymotrypsin, elastase, thermolysin, pepsin, clostripan, glutamyl endopeptidase (GluC), ArgC, peptidyl-asp endopeptidase (ApsN), endopeptidase LysC and endopeptidase LysN. In some embodiments, the endopeptidase is pepsin. In some embodiments, the biological sample is permeabilized contemporaneously with or prior to contacting the biological sample with undesirable RNA depletion probes. In some embodiments, the biological sample is permeabilized after the biological sample is contacted with undesirable RNA depletion probes. In some embodiments, the biological sample is permeabilized after the biological sample is contacted with undesirable RNA depletion probes but prior to contacting the array. In some embodiments, the biological sample is permeabilized after the biological sample is contacted with undesirable RNA depletion probes but prior to contacting a first probe oligonucleotide and a second probe oligonucleotide. In some embodiments, after creating a ligation product (e.g., by ligating a first probe and a second probe that are hybridized to adjacent sequences in the analyte), the biological sample is permeabilized. In some embodiments, the biological sample is permeabilized contemporaneously with or prior to contacting the biological sample with a first probe and a second probe, hybridizing the first probe and the second probe to the analyte, generating a ligation product by ligating the first probe and the second probe, and releasing the ligated product from the analyte.

In some embodiments, methods provided herein include permeabilization of the biological sample such that the capture probe can more easily bind to the captured ligated probe (i.e., compared to no permeabilization). In some embodiments, reverse transcription (RT) reagents can be added to permeabilized biological samples. Incubation with the RT reagents can produce spatially-barcoded full-length cDNA from the captured analytes (e.g., polyadenylated mRNA). Second strand reagents (e.g., second strand primers, enzymes) can be added to the biological sample on the slide to initiate second strand synthesis.

In some instances, the permeabilization step includes application of a permeabilization buffer to the biological sample. In some instances, the permeabilization buffer includes a buffer (e.g., Tris pH 7.5), MgCl2, sarkosyl detergent (e.g., sodium lauroyl sarcosinate), enzyme (e.g., proteinase K), and nuclease free water. In some instances, the permeabilization step is performed at 37° C. In some instances, the permeabilization step is performed for about 20 minutes to 2 hours (e.g., about 20 minutes, about 30 minutes, about 40 minutes, about 50 minutes, about 1 hour, about 1.5 hours, or about 2 hours). In some instances, the releasing step is performed for about 40 minutes.

In some embodiments, after generating a ligation product, the ligation product is released from the analyte. In some embodiments, a ligation product is released from the analyte using an endoribonuclease. In some embodiments, the endoribonuclease is RNase H, RNase A, RNase C, or RNase I. In some embodiments, the endoribonuclease is RNase H. RNase H is an endoribonuclease that specifically hydrolyzes the phosphodiester bonds of RNA, when hybridized to DNA. RNase H is part of a conserved family of ribonucleases which are present in many different organisms. There are two primary classes of RNase H: RNase H1 and RNase H2. Retroviral RNase H enzymes are similar to the prokaryotic RNase H1. All of these enzymes share the characteristic that they are able to cleave the RNA component of an RNA:DNA heteroduplex. In some embodiments, the RNase H is RNase H1, RNase H2, or RNase H1, or RNase H2. In some embodiments, the RNase H includes but is not limited to RNase HII from *Pyrococcus furiosus*, RNase HII from *Pyrococcus horikoshi*, RNase HI from *Thermococcus htorahs*, RNase HI from *Thermus thermophilus*, RNAse HI from *E. coli*, or RNase HII from *E. coli*.

In some instances, the releasing step is performed using a releasing buffer. In some instances, the release buffer includes one or more of a buffer (e.g., Tris pH 7.5), enzyme (e.g., RNAse H) and nuclease-free water. In some instances, the releasing step is performed at 37° C. In some instances, the releasing step is performed for about 20 minutes to 2 hours (e.g., about 20 minutes, about 30 minutes, about 40 minutes, about 50 minutes, about 1 hour, about 1.5 hours, or about 2 hours). In some instances, the releasing step is performed for about 30 minutes.

In some instances, the releasing step occurs before the permeabilization step. In some instances, the releasing step occurs after the permeabilization step. In some instances, the releasing step occurs at the same time as the permeabilization step (e.g., in the same buffer).

(m) Biological Samples

Methods disclosed herein can be performed on any type of sample. In some embodiments, the sample is a fresh tissue. In some embodiments, the sample is a frozen sample. In some embodiments, the sample was previously frozen. In some embodiments, the sample is a formalin-fixed, paraffin embedded (FFPE) sample.

Subjects from which biological samples can be obtained can be healthy or asymptomatic individuals, individuals that have or are suspected of having a disease (e.g., cancer) or a pre-disposition to a disease, and/or individuals that are in need of therapy or suspected of needing therapy. In some instances, the biological sample can include one or more diseased cells. A diseased cell can have altered metabolic properties, gene expression, protein expression, and/or morphologic features. Examples of diseases include inflammatory disorders, metabolic disorders, nervous system disorders, and cancer. In some instances, the biological sample includes cancer or tumor cells. Cancer cells can be derived from solid tumors, hematological malignancies, cell lines, or obtained as circulating tumor cells. In some instances, the biological sample is a heterogenous sample. In some instances, the biological sample is a heterogenous sample that includes tumor or cancer cells and/or stromal cells, In some instances, the cancer is breast cancer. In some instances, the breast cancer is triple positive breast cancer (TPBC). In some instances, the breast cancer is triple negative breast cancer (TNBC).

In some instances, the cancer is colorectal cancer. In some instances, the cancer is ovarian cancer. In certain embodiments, the cancer is squamous cell cancer, small-cell lung cancer, non-small cell lung cancer, gastrointestinal cancer, Hodgkin's or non-Hodgkin's lymphoma, pancreatic cancer, glioblastoma, glioma, cervical cancer, ovarian cancer, liver cancer, bladder cancer, breast cancer, colon cancer, colorectal cancer, endometrial carcinoma, myeloma, salivary gland carcinoma, kidney cancer, basal cell carcinoma, melanoma, prostate cancer, vulval cancer, thyroid cancer, testicular cancer, esophageal cancer, or a type of head or neck cancer. In certain embodiments, the cancer treated is desmoplastic melanoma, inflammatory breast cancer, thymoma, rectal cancer, anal cancer, or surgically treatable or non-surgically treatable brain stem glioma. In some embodiments, the subject is a human.

FFPE samples generally are heavily cross-linked and fragmented, and therefore this type of sample allows for limited RNA recovery using conventional detection techniques. In certain embodiments, methods of targeted RNA capture provided herein are less affected by RNA degradation associated with FFPE fixation than other methods (e.g., methods that take advantage of oligo-dT capture and reverse transcription of mRNA). In certain embodiments, methods provided herein enable sensitive measurement of specific genes of interest that otherwise might be missed with a whole transcriptomic approach.

In some instances, FFPE samples are stained (e.g., using H&E). The methods disclosed herein are compatible with H&E will allow for morphological context overlaid with transcriptomic analysis. However, depending on the need some samples may be stained with only a nuclear stain, such as staining a sample with only hematoxylin and not eosin, when location of a cell nucleus is needed.

In some embodiments, a biological sample (e.g., tissue section) can be fixed with methanol, stained with hematoxylin and eosin, and imaged. In some embodiments, fixing, staining, and imaging occurs before one or more probes are hybridized to the sample. Some embodiments of any of the workflows described herein can further include a destaining step (e.g., a hematoxylin and eosin destaining step), after imaging of the sample and prior to permeabilizing the sample. For example, destaining can be performed by performing one or more (e.g., one, two, three, four, or five) washing steps (e.g., one or more (e.g., one, two, three, four, or five) washing steps performed using a buffer including HCl). The images can be used to map spatial gene expression patterns back to the biological sample. A permeabilization enzyme can be used to permeabilize the biological sample directly on the slide.

In some embodiments, the FFPE sample is deparaffinized, permeabilized, equilibrated, and blocked before target probe oligonucleotides are added. In some embodiments, deparaffinization using xylenes. In some embodiments, deparaffinization includes multiple washes with xylenes. In some embodiments, deparaffinization includes multiple washes with xylenes followed by removal of xylenes using multiple rounds of graded alcohol followed by washing the sample with water. In some aspects, the water is deionized water. In some embodiments, equilibrating and blocking includes incubating the sample in a pre-Hyb buffer. In some embodiments, the pre-Hyb buffer includes yeast tRNA. In some embodiments, permeabilizing a sample includes washing the sample with a phosphate buffer. In some embodiments, the buffer is PBS. In some embodiments, the buffer is PBST.

(n) Determining the Sequence of the Ligation Product

After an analyte (e.g., mRNA molecule) or a ligation product from the sample has hybridized or otherwise been associated with a capture probe according to any of the methods described above in connection with the general spatial cell-based analytical methodology, the barcoded constructs that result from hybridization/association are analyzed.

In some embodiments, after contacting a biological sample with a substrate that includes capture probes, a removal step can optionally be performed to remove all or a portion of the biological sample from the substrate. In some embodiments, the removal step includes enzymatic and/or chemical degradation of cells of the biological sample. For example, the removal step can include treating the biological sample with an enzyme (e.g., a proteinase, e.g., proteinase K) to remove at least a portion of the biological sample from the substrate. In some embodiments, the removal step can include ablation of the tissue (e.g., laser ablation).

In some embodiments, provided herein are methods for spatially detecting an analyte (e.g., detecting the location of an analyte, e.g., a biological analyte) from a biological sample (e.g., present in a biological sample), the method comprising: (a) optionally staining and/or imaging a biological sample on a substrate; (b) permeabilizing (e.g., providing a solution comprising a permeabilization reagent to) the biological sample on the substrate; (c) contacting the biological sample with an array comprising a plurality of capture probes, wherein a capture probe of the plurality captures the biological analyte; (d) hybridizing an undesirable RNA depletion probe to an undesirable RNA; (e) removing the plurality of undesirable RNA depletion probe-undesirable RNA complexes; (f) hybridizing the analyte to a capture domain of a capture probe that is affixed to the substrate; and (g) analyzing the captured biological analyte, thereby spatially detecting the biological analyte; wherein the biological sample is fully or partially removed from the substrate.

In some embodiments, a biological sample is not removed from the substrate. For example, the biological sample is not removed from the substrate prior to releasing a capture probe (e.g., a capture probe bound to an analyte) from the substrate. In some embodiments, such releasing comprises cleavage of the capture probe from the substrate (e.g., via a cleavage domain). In some embodiments, such releasing does not comprise releasing the capture probe from the substrate (e.g., a copy of the capture probe bound to an analyte can be made and the copy can be released from the substrate, e.g., via denaturation). In some embodiments, the biological sample is not removed from the substrate prior to analysis of an analyte bound to a capture probe after it is released from the substrate. In some embodiments, the biological sample remains on the substrate during removal of a capture probe from the substrate and/or analysis of an analyte bound to the capture probe after it is released from the substrate. In some embodiments, the biological sample remains on the substrate during removal (e.g., via denaturation) of a copy of the capture probe (e.g., complement). In some embodiments, analysis of an analyte bound to capture probe from the substrate can be performed without subjecting the biological sample to enzymatic and/or chemical degradation of the cells (e.g., permeabilized cells) or ablation of the tissue (e.g., laser ablation).

In some embodiments, at least a portion of the biological sample is not removed from the substrate. For example, a portion of the biological sample can remain on the substrate prior to releasing a capture probe (e.g., a capture prove bound to an analyte) from the substrate and/or analyzing an analyte bound to a capture probe released from the substrate. In some embodiments, at least a portion of the biological sample is not subjected to enzymatic and/or chemical degradation of the cells (e.g., permeabilized cells) or ablation of the tissue (e.g., laser ablation) prior to analysis of an analyte bound to a capture probe from the substrate.

In some embodiments, provided herein are methods for spatially detecting an analyte (e.g., detecting the location of an analyte, e.g., a biological analyte) from a biological sample (e.g., present in a biological sample) that include: (a) optionally staining and/or imaging a biological sample on a substrate; (b) permeabilizing (e.g., providing a solution comprising a permeabilization reagent to) the biological sample on the substrate; (c) contacting the biological sample with an array comprising a plurality of capture probes, wherein a capture probe of the plurality captures the biological analyte; (d) hybridizing an undesirable RNA depletion probe to an undesirable RNA; (e) removing the plurality of undesirable RNA depletion probe-undesirable RNA complexes; (f) hybridizing the analyte to a capture domain of a capture probe that is affixed to the substrate; and (g) analyzing the captured biological analyte, thereby spatially detecting the biological analyte; where the biological sample is not removed from the substrate.

In some embodiments, provided herein are methods for spatially detecting a biological analyte of interest from a biological sample that include: (a) staining and imaging a biological sample on a substrate; (b) providing a solution comprising a permeabilization reagent to the biological sample on the substrate; (c) contacting the biological sample with an array on a substrate, wherein the array comprises one or more capture probe pluralities thereby allowing the one or more pluralities of capture probes to capture the biological analyte of interest; (d) hybridizing an undesirable RNA depletion probe to an undesirable RNA; (e) removing the plurality of undesirable RNA depletion probe-undesirable RNA complexes; (f) hybridizing the analyte to a capture domain of a capture probe that is affixed to the substrate; and (g) analyzing the captured biological analyte, thereby spatially detecting the biological analyte of interest; where the biological sample is not removed from the substrate.

In some embodiments, the method further includes subjecting a region of interest in the biological sample to spatial transcriptomic analysis. In some embodiments, one or more of the capture probes includes a capture domain. In some embodiments, one or more of the capture probes comprises a unique molecular identifier (UMI). In some embodiments, one or more of the capture probes comprises a cleavage domain. In some embodiments, the cleavage domain comprises a sequence recognized and cleaved by uracil-DNA glycosylase, apurinic/apyrimidinic (AP) endonuclease (APE1), U uracil-specific excision reagent (USER), and/or an endonuclease VIII. In some embodiments, one or more capture probes do not comprise a cleavage domain and is not cleaved from the array.

In some embodiments, a capture probe can be extended (an "extended capture probe," e.g., as described herein). For example, extending a capture probe can include generating cDNA from a captured (hybridized) RNA. This process involves synthesis of a complementary strand of the hybridized nucleic acid, e.g., generating cDNA based on the captured RNA template (the RNA hybridized to the capture domain of the capture probe). Thus, in an initial step of extending a capture probe, e.g., the cDNA generation, the captured (hybridized) nucleic acid, e.g., RNA, acts as a template for the extension, e.g., reverse transcription, step. In some embodiments, the capture probe is extended after hybridizing an undesirable RNA depletion probe to an undesirable RNA and removing the plurality of undesirable RNA depletion probe-undesirable RNA complexes.

In some embodiments, the capture probe is extended using reverse transcription. For example, reverse transcription includes synthesizing cDNA (complementary or copy DNA) from RNA, e.g., (messenger RNA), using a reverse transcriptase. In some embodiments, reverse transcription is performed while the tissue is still in place, generating an analyte library, where the analyte library includes the spatial barcodes from the adjacent capture probes. In some embodiments, the capture probe is extended using one or more DNA polymerases.

In some embodiments, a capture domain of a capture probe includes a primer for producing the complementary strand of a nucleic acid hybridized to the capture probe, e.g., a primer for DNA polymerase and/or reverse transcription. The nucleic acid, e.g., DNA and/or cDNA, molecules generated by the extension reaction incorporate the sequence of the capture probe. The extension of the capture probe, e.g., a DNA polymerase and/or reverse transcription reaction, can be performed using a variety of suitable enzymes and protocols.

In some embodiments, a full-length DNA (e.g., cDNA) molecule is generated. In some embodiments, a "full-length" DNA molecule refers to the whole of the captured nucleic acid molecule. However, if a nucleic acid (e.g., RNA) was partially degraded in the tissue sample, then the captured nucleic acid molecules will not be the same length as the initial RNA in the tissue sample. In some embodiments, the 3' end of the extended probes, e.g., first strand cDNA molecules, is modified. For example, a linker or adaptor can be ligated to the 3' end of the extended probes. This can be achieved using single stranded ligation enzymes such as T4 RNA ligase or Circligase™ (available from Lucigen, Middleton, Wis.). In some embodiments, template switching oligonucleotides are used to extend cDNA in order to generate a full-length cDNA (or as close to a full-length cDNA as possible). In some embodiments, a second strand synthesis helper probe (a partially double stranded DNA molecule capable of hybridizing to the 3' end of the extended capture probe), can be ligated to the 3' end of the extended probe, e.g., first strand cDNA, molecule using a double stranded ligation enzyme such as T4 DNA ligase. Other enzymes appropriate for the ligation step are known in the art and include, e.g., Tth DNA ligase, Taq DNA ligase, *Thermococcus* sp. (strain 9° N) DNA ligase (9° N™ DNA ligase, New England Biolabs), Ampligase™ (available from Lucigen, Middleton, Wis.), and SplintR (available from New England Biolabs, Ipswich, Mass.). In some embodiments, a polynucleotide tail, e.g., a poly(A) tail, is incorporated at the 3' end of the extended probe molecules. In some embodiments, the polynucleotide tail is incorporated using a terminal transferase active enzyme.

In some embodiments, double-stranded extended capture probes are treated to remove any unextended capture probes prior to amplification and/or analysis, e.g., sequence analysis. This can be achieved by a variety of methods, e.g., using an enzyme to degrade the unextended probes, such as an exonuclease enzyme, or purification columns.

In some embodiments, extended capture probes are amplified to yield quantities that are sufficient for analysis, e.g., via DNA sequencing. In some embodiments, the first strand of the extended capture probes (e.g., DNA and/or cDNA molecules) acts as a template for the amplification reaction (e.g., a polymerase chain reaction).

In some embodiments, the amplification reaction incorporates an affinity group onto the extended capture probe (e.g., RNA-cDNA hybrid) using a primer including the affinity group. In some embodiments, the primer includes an affinity group and the extended capture probes includes the affinity group. The affinity group can correspond to any of the affinity groups described previously.

In some embodiments, the extended capture probes including the affinity group can be coupled to a substrate specific for the affinity group. In some embodiments, the substrate can include an antibody or antibody fragment. In some embodiments, the substrate includes avidin or streptavidin and the affinity group includes biotin. In some embodiments, the substrate includes maltose and the affinity group includes maltose-binding protein. In some embodiments, the substrate includes maltose-binding protein and the affinity group includes maltose. In some embodiments, amplifying the extended capture probes can function to release the extended probes from the surface of the substrate, insofar as copies of the extended probes are not immobilized on the substrate.

In some embodiments, the extended capture probe or complement or amplicon thereof is released. The step of releasing the extended capture probe or complement or amplicon thereof from the surface of the substrate can be achieved in a number of ways. In some embodiments, an extended capture probe or a complement thereof is released from the array by nucleic acid cleavage and/or by denaturation (e.g., by heating to denature a double-stranded molecule).

In some embodiments, the extended capture probe or complement or amplicon thereof is released from the surface of the substrate (e.g., array) by physical means. For example, where the extended capture probe is indirectly immobilized on the array substrate, e.g., via hybridization to a surface probe, it can be sufficient to disrupt the interaction between the extended capture probe and the surface probe. Methods for disrupting the interaction between nucleic acid molecules include denaturing double stranded nucleic acid molecules are known in the art. A straightforward method for releasing the DNA molecules (i.e., of stripping the array of extended probes) is to use a solution that interferes with the hydrogen bonds of the double stranded molecules. In some embodiments, the extended capture probe is released by an applying heated solution, such as water or buffer, of at least 85° C., e.g., at least 90, 91, 92, 93, 94, 95, 96, 97, 98, or 99° C. In some embodiments, a solution including salts, surfactants, etc. that can further destabilize the interaction between the nucleic acid molecules is added to release the extended capture probe from the substrate.

In some embodiments, where the extended capture probe includes a cleavage domain, the extended capture probe is released from the surface of the substrate by cleavage. For example, the cleavage domain of the extended capture probe can be cleaved by any of the methods described herein. In some embodiments, the extended capture probe is released from the surface of the substrate, e.g., via cleavage of a cleavage domain in the extended capture probe, prior to the step of amplifying the extended capture probe.

In some embodiments, probes complementary to the extended capture probe can be contacted with the substrate. In some embodiments, the biological sample can be in contact with the substrate when the probes are contacted with the substrate. In some embodiments, the biological sample can be removed from the substrate prior to contacting the substrate with probes. In some embodiments, the probes can be labeled with a detectable label (e.g., any of the detectable labels described herein). In some embodiments, probes that do not specially bind (e.g., hybridize) to an extended capture probe can be washed away. In some embodiments, probes complementary to the extended capture probe can be detected on the substrate (e.g., imaging, any of the detection methods described herein).

In some embodiments, probes complementary to an extended capture probe can be about 4 nucleotides to about 100 nucleotides long. In some embodiments, probes (e.g., detectable probes) complementary to an extended capture probe can be about 10 nucleotides to about 90 nucleotides long. In some embodiments, probes (e.g., detectable probes) complementary to an extended capture probe can be about 20 nucleotides to about 80 nucleotides long. In some embodiments, probes (e.g., detectable probes) complementary to an extended capture probe can be about 30 nucleotides to about 60 nucleotides long. In some embodiments, probes (e.g., detectable probes) complementary to an extended capture probe can be about 40 nucleotides to about 50 nucleotides long. In some embodiments, probes (e.g., detectable probes) complementary to an extended capture probe can be about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, and about 99 nucleotides long.

In some embodiments, about 1 to about 100 probes can be contacted to the substrate and specifically bind (e.g., hybridize) to an extended capture probe. In some embodiments, about 1 to about 10 probes can be contacted to the substrate and specifically bind (e.g., hybridize) to an extended capture probe. In some embodiments, about 10 to about 100 probes can be contacted to the substrate and specifically bind (e.g., hybridize) to an extended capture probe. In some embodiments, about 20 to about 90 probes can be contacted to the substrate and specifically bind (e.g., hybridize) to an extended capture probe. In some embodiments, about 30 to about 80 probes (e.g., detectable probes) can be contacted to the substrate and specifically bind (e.g., hybridize) to an extended capture probe. In some embodiments, about 40 to about 70 probes can be contacted to the substrate and specifically bind (e.g., hybridize) to an extended capture probe. In some embodiments, about 50 to about 60 probes can be contacted to the substrate and specifically bind (e.g., hybridize) to an extended capture probe. In some embodiments, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, and about 99 probes can be contacted to the substrate and specifically bind (e.g., hybridize) to an extended capture probe.

In some embodiments, the probes can be complementary to a single analyte (e.g., a single gene). In some embodiments, the probes can be complementary to one or more analytes (e.g., analytes in a family of genes). In some embodiments, the probes (e.g., detectable probes) can be for a panel of genes associated with a disease (e.g., cancer, Alzheimer's disease, Parkinson's disease).

In some instances, the analyte and capture probe can be amplified or copied, creating a plurality of cDNA molecules. In some instances, the ligated probe and capture probe can be amplified or copied, creating a plurality of cDNA molecules. In some embodiments, cDNA can be denatured from the capture probe template and transferred (e.g., to a clean tube) for amplification, and/or library construction. The spatially-barcoded cDNA can be amplified via PCR prior to library construction. The cDNA can then be enzymatically fragmented and size-selected in order to optimize for cDNA amplicon size. P5 and P7 sequences directed to capturing the amplicons on a sequencing flowcell (Illumina sequencing instruments) can be appended to the amplicons, i7, and i5 can be used as sample indexes, and TruSeq Read 2 can be added via End Repair, A-tailing, Adaptor Ligation, and PCR. The cDNA fragments can then be sequenced using paired-end sequencing using TruSeq Read 1 and TruSeq Read 2 as sequencing primer sites. The additional sequences are directed toward Illumina sequencing instruments or sequencing instruments that utilize those sequences; however a skilled artisan will understand that additional or alternative sequences used by other sequencing instruments or technologies are also equally applicable for use in the aforementioned methods. In some embodiments, where a sample is barcoded directly via hybridization with capture probes or analyte capture agents hybridized, bound, or associated with either the cell surface, or introduced into the cell, as described above, sequencing can be performed on the intact sample.

A wide variety of different sequencing methods can be used to analyze barcoded analytes (e.g., an analyte and/or the ligation product). In general, sequenced polynucleotides can be, for example, nucleic acid molecules such as deoxyribonucleic acid (DNA) or ribonucleic acid (RNA), including variants or derivatives thereof (e.g., single stranded DNA or DNA/RNA hybrids, and nucleic acid molecules with a nucleotide analog).

Sequencing of polynucleotides can be performed by various systems. More generally, sequencing can be performed using nucleic acid amplification, polymerase chain reaction (PCR) (e.g., digital PCR and droplet digital PCR (ddPCR), quantitative PCR, real time PCR, multiplex PCR, PCR-based single plex methods, emulsion PCR), and/or isothermal amplification. Non-limiting examples of methods for sequencing genetic material include, but are not limited to, DNA hybridization methods (e.g., Southern blotting), restriction enzyme digestion methods, Sanger sequencing methods, next-generation sequencing methods (e.g., single-molecule real-time sequencing, nanopore sequencing, and Polony sequencing), ligation methods, and microarray methods.

(o) Kits

In some embodiments, also provided herein are kits that include one or more reagents to detect one or more analytes described herein. In some instances, the kit includes a substrate comprising a plurality of capture probes comprising a spatial barcode and the capture domain. In some instances, the kit includes a plurality of probes (e.g., a first probe, a second probe, one or more spanning probes, and/or a third oligonucleotide).

A non-limiting example of a kit used to perform any of the methods described herein includes: (a) a substrate comprising a plurality of capture probes comprising a spatial barcode and a capture domain; (b) a system comprising: a plurality of undesirable RNA depletion probes, wherein an undesirable RNA depletion probe of the plurality of undesirable RNA depletion probes is substantially complementary to a sequence of an undesirable RNA molecule in the biological sample; and (c) instructions for performing the method of any one of the preceding claims.

A non-limiting example of a kit used to perform any of the methods described herein includes: (a) a substrate comprising a plurality of capture probes comprising a spatial barcode and a capture domain; (b) a system comprising: a first probe oligonucleotide, a second probe oligonucleotide, and a plurality of undesirable RNA depletion probes, wherein the first probe oligonucleotide and the second probe oligonucleotide are substantially complementary to adjacent sequences of the analyte, wherein the second probe oligonucleotide comprises a capture probe binding domain that is capable of binding to a capture domain of a capture probe, and wherein an undesirable RNA depletion probe of the plurality of undesirable RNA depletion probes is substantially complementary to a sequence of an undesirable RNA molecule in the biological sample; and (c) instructions for performing the method of any one of the preceding claims.

In some embodiments of any of the kits described herein, the kit includes a second probe that includes a preadenylated phosphate group at its 5' end and a first probe comprising at least two ribonucleic acid bases at the 3' end.

EXAMPLES

Example 1. Workflow of In Situ Spatial RTL (RNA-Templated Ligation) Ribosomal Depletion Others have reported ribosomal probe designs and their application to ribosomal depletion from purified total RNA. See Morlan et al., "Selective depletion of rRNA enables whole transcriptome profiling of archival fixed tissue." PloS one 7.8 (2012); US patent application publication No. 20110111409 A1; U.S. patent application No. 62/860,993; and Adiconis et al., "Comparative analysis of RNA sequencing methods for degraded or low-input samples." Nature methods 10.7 (2013): 623; each of which is incorporated herein in its entirety by reference. Here, the RNA depletion procedure is incorporated into the workflow of RNA-templated ligation in a biological sample, wherein the ribosomal RNA for depletion is not purified, but located in a sample, such as a tissue.

As a non-limiting example, and as shown in FIG. 7, the RNA depletion procedure can be performed using a biological tissue sample comprising mRNA and ribosomal RNA (rRNA), where the rRNA is to be depleted from the sample. A plurality of ribosomal depletion probes can be added simultaneously to specifically hybridize with rRNA, forming RNA:DNA duplex structures. The ribosomal depletion probes can be designed to hybridize to the complete or partial sequence of the rRNA molecule. After hybridization, RNase H can be added to digest the RNA strand of the hybridized RNA:DNA duplex, such that the rRNA can be digested. The biological sample can then be permeabilized to release the ligated RTL probes. In this example, the capture of target mRNA can also be performed concurrently with the rRNA depletion method. To perform concurrent rRNA depletion and target mRNA capture, two RTL probes (i.e., LHS and RHS probes) can be applied to the sample simultaneously with the rRNA depletion probes. The probes are allowed to hybridize to their targets during a hybridization reaction and a ligation step ligates the RTL probes together, followed by RNase H digestion of the RNA of the DNA:RNA formed hybrids, thereby digesting the rRNA and depleting those molecules while at the same time releasing the RTL ligation product. The sample can be permeabilized, thereby contacting the RTL ligation products with a plurality of capture probes attached to a slide. The ligated RTL probes can diffuse and bind to a capture probe affixed to the surface of the slide, wherein the capture probe comprises a complementary sequence to a sequence on the RHS ligation product. After hybridization, the 3' end of the capture probe can be extended using the ligated RTL probes as a template. The extended and ligated RTL probes can then be collected for downstream library preparation and subsequent spatial expression analysis.

As another non-limiting example, RNA depletion probes can be added to a biological sample to specifically hybridize with unwanted RNA molecules. RNase H can then be added to digest the RNA strand of the hybridized RNA:DNA duplex, such that the unwanted RNA molecules can be digested. The RNA depletion probes can also be removed using RecJ exonuclease. The biological sample can then be subjected to a spatial analysis workflow as described herein.

Figure 8A:
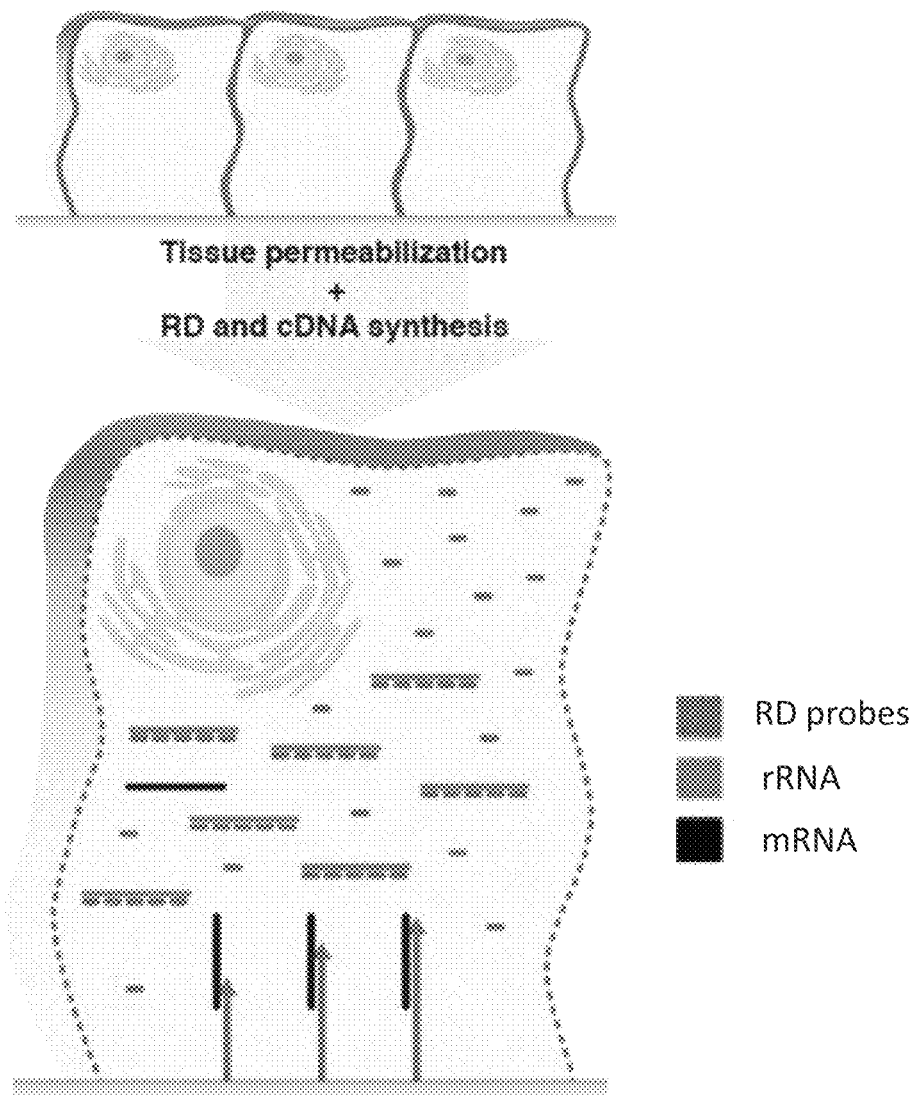
FIG. 8A shows a schematic illustrating an exemplary workflow for ribosomal depletion (RD).

Example 2. In Situ Ribosomal Depletion Increases mRNA Capture with Spatial Transcriptomics in Clinical Samples In general, ribosomal depletion can be performed by adding rRNA specific probes before permeabilizing tissue samples. As shown in FIG. 8A, ribosomal depletion probes (RD probes) can specifically hybridize to and inhibit rRNA molecules from non-specifically binding to capture probes on a substrate, thereby increasing mRNA capture with spatial transcriptomics in clinical samples. After rRNA molecules are removed, the tissue sample can be permeabilized by any permeabilization methods as described herein. Ribosomal depletion probes were designed to block cytoplasmic 18S, 28S, 5S and 5.8S rRNA, as well as mitochondrial 16S and 12S rRNA. For these set of experiments, the ribosomal depletion probes include the nucleic acid sequences of SEQ ID NOs: 1-195. The ribosomal depletion probes (e.g., SEQ ID NOs: 1-195) were combined into a pool including a concentration of 2 μM of each probe in IDTE buffer (10 mM Tris, 0.1 mM EDTA, pH 7.5-8.0). For spatial transcriptomic analysis, in the reverse transcription (RT) step, $H_2O$ (166.3 μl) was replaced with an equivalent volume (166.3 μl) of the pooled ribosomal depletion probes in IDTE buffer. The final concentration of each ribosomal depletion probe in the RT reaction mixture was about 1 μM.

Figures 8B, 8C:
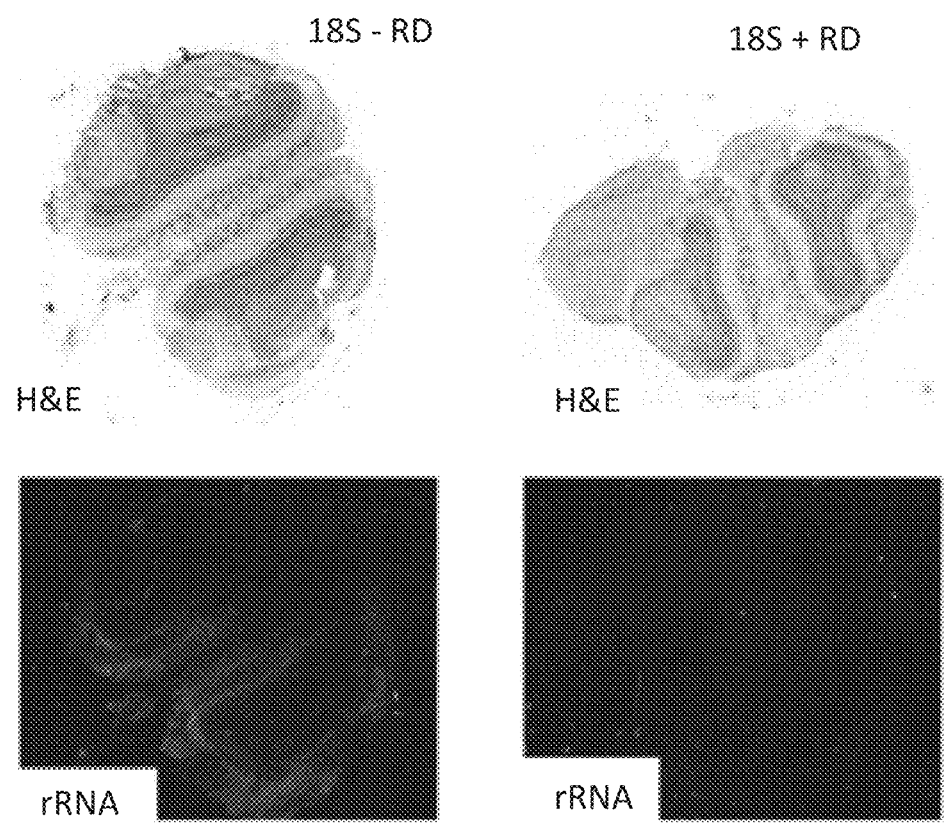
FIG. 8B shows an H&E staining image and an 18S rRNA staining image. No ribosomal depletion was performed.
FIG. 8C shows an H&E staining image and an 18S rRNA staining image. Ribosomal depletion was performed using RD probes designed to block both the cytoplasmic RNA (18S, 28S, 5S and 5.8S) and mitochondrial RNA (16S and 12S).
Figures 8D, 8E:
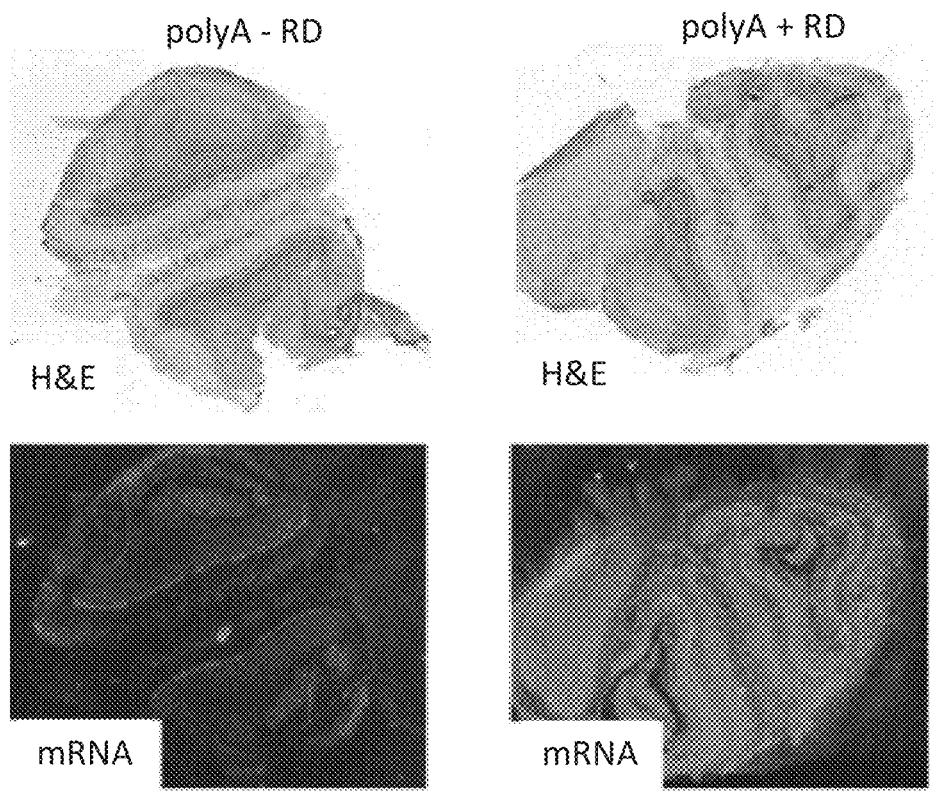
FIG. 8D shows an H&E staining image and an mRNA staining image using polyA probes. No ribosomal depletion was performed.
FIG. 8E shows an H&E staining image and an mRNA staining image using polyA probes. Ribosomal depletion was performed using RD probes designed to block both the cytoplasmic RNA (18S, 28S, 5S and 5.8S) and mitochondrial RNA (16S and 12S).

As shown in FIGS. 8B-8C, ribosomal depletion using the probes described herein reduced the 18S rRNA level in the tissue sample. The results of FIGS. 8D-8E also indicated that ribosomal depletion increased polyA-specific probe binding to mRNA.

Figure 9A:
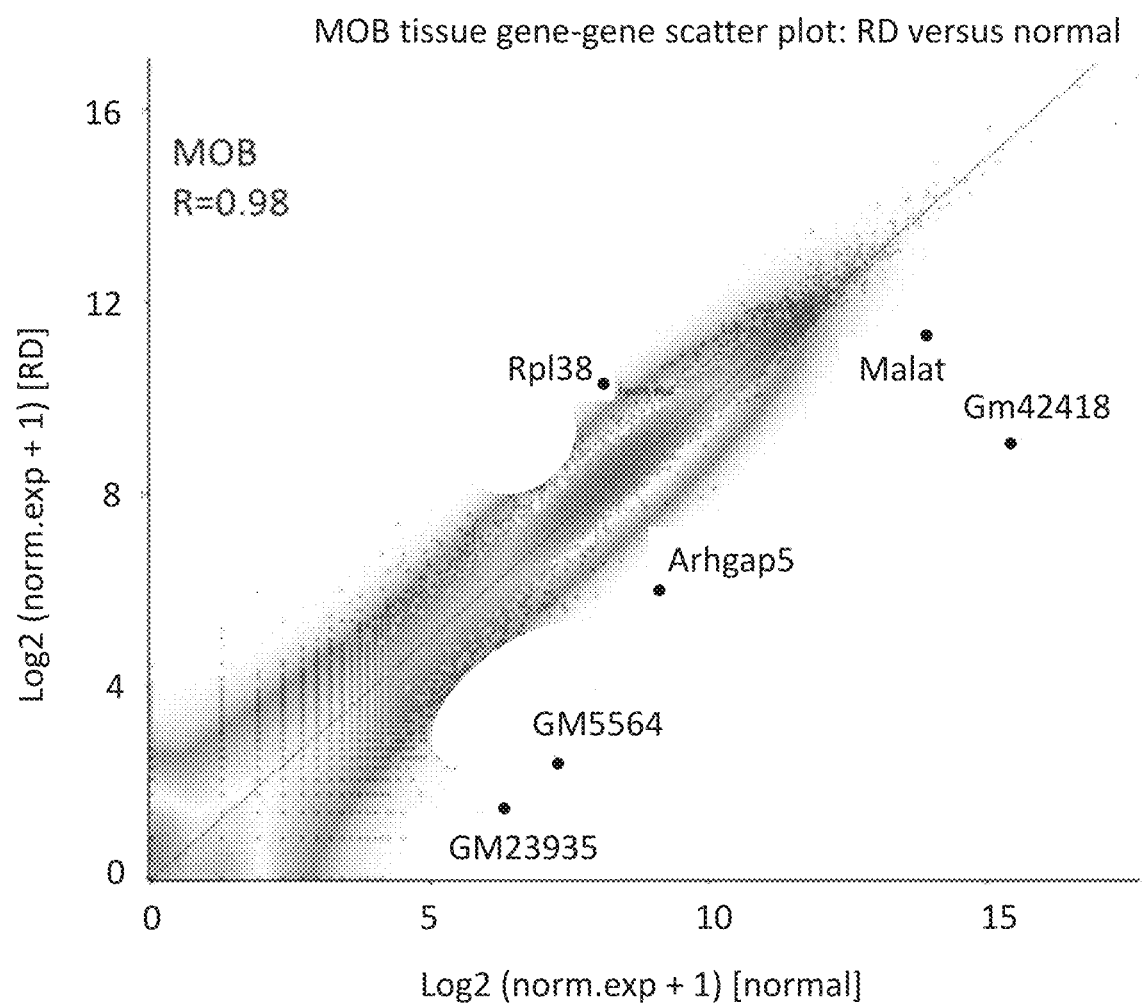
FIG. 9A shows the gene-gene scatter plot between normal and ribosomal depleted mouse olfactory bulb (MOB) tissues. Ribosomal depletion was performed using RD probes designed to block both the cytoplasmic RNA (18S, 28S, 5S and 5.8S) and mitochondrial RNA (16S and 12S).
Figure 9B:
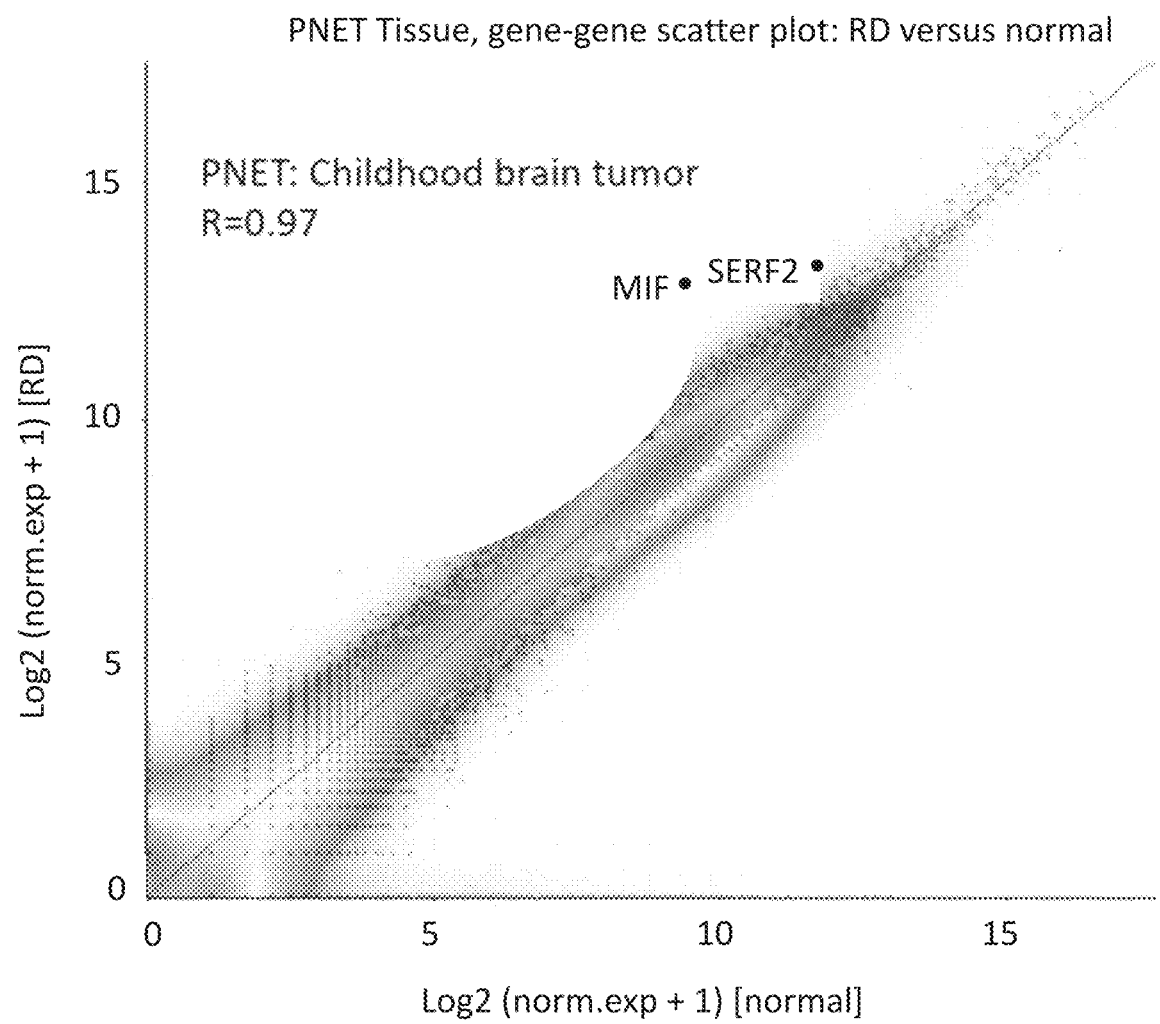
FIG. 9B shows the gene-gene scatter plot between normal and ribosomal depleted childhood brain cancer (PNET) tissues. Ribosomal depletion was performed using RD probes designed to block both the cytoplasmic RNA (18S, 28S, 5S and 5.8S) and mitochondrial RNA (16S and 12S).
Figure 9C:
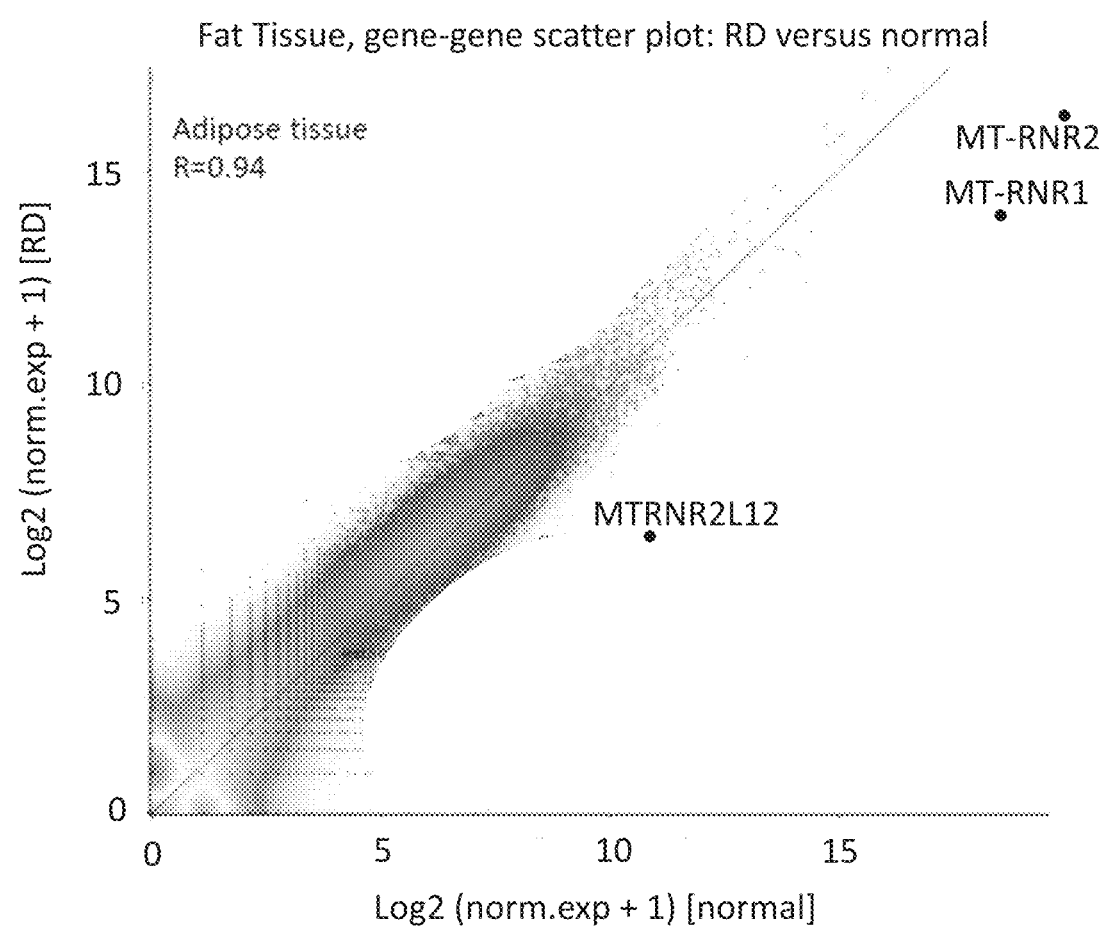
FIG. 9C shows the gene-gene scatter plot between normal and ribosomal depleted adipose (fat) tissues. Ribosomal depletion was performed using RD probes designed to block both the cytoplasmic RNA (18S, 28S, 5S and 5.8S) and mitochondrial RNA (16S and 12S).

Effects of ribosomal depletion on gene expression were assessed. The gene expression levels were compared between normal tissue and ribosomal depleted tissue samples. Mouse olfactory bulb (MOB), childhood brain tumor (PNET) and adipose tissues were analyzed and results are shown in FIGS. 9A-9C, respectively. The results show that most genes exhibited similar expression levels upon ribosomal depletion, as indicated by the $R^2$ values. MT-RNR1 and MT-RNR2, which encodes mitochondrial 12S and 16S rRNA, respectively, exhibited reduced expression levels in ribosomal depleted tissue samples.

Figure 10:
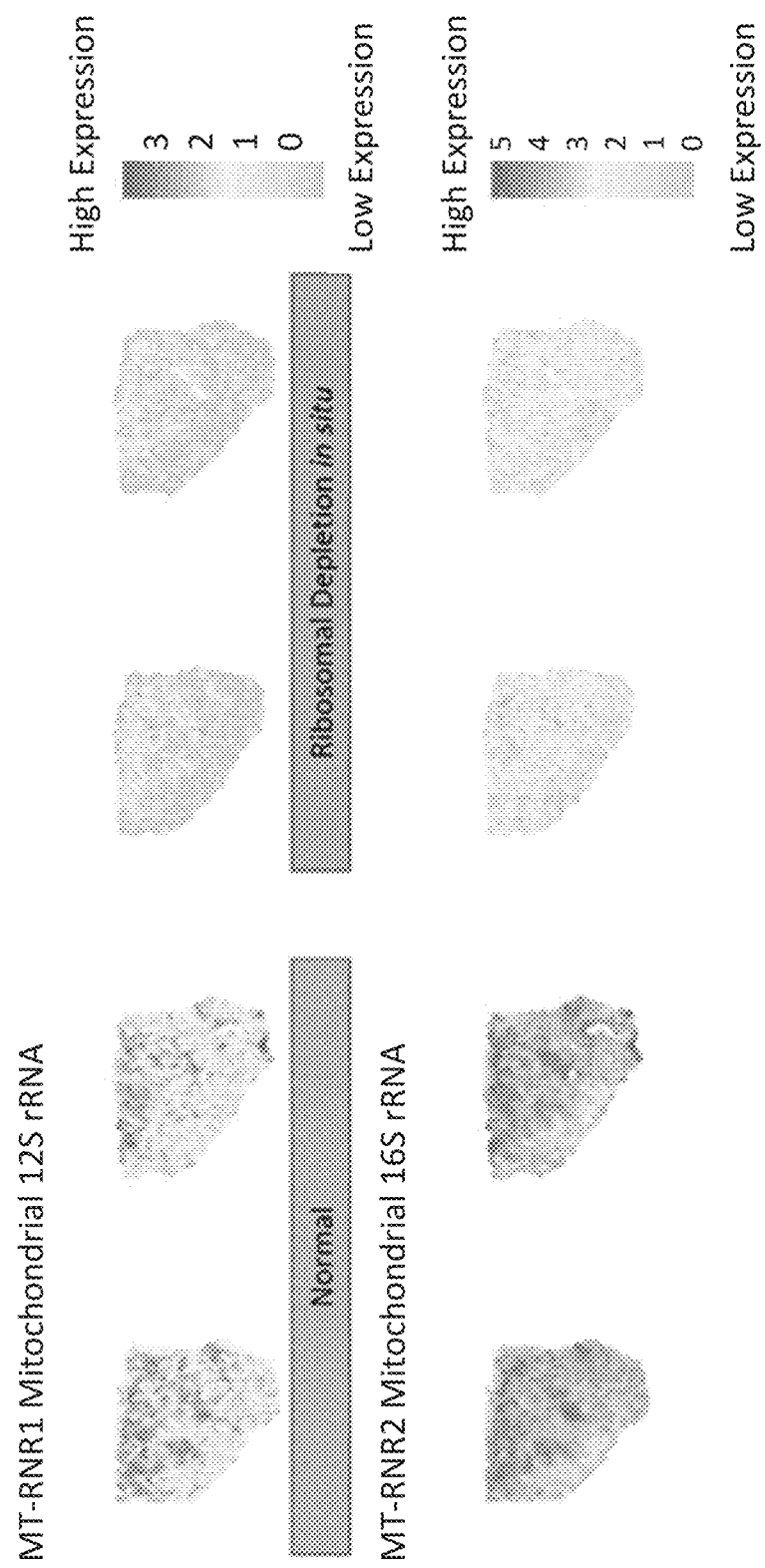
FIG. 10 shows tissue plots illustrating the gene expression level of MT-RNR1 or MT-RNR2 of normal or ribosomal depleted tissues. Ribosomal depletion was performed using RD probes designed to block both the cytoplasmic RNA (18S, 28S, 5S and 5.8S) and mitochondrial RNA (16S and 12S).
Figure 11:
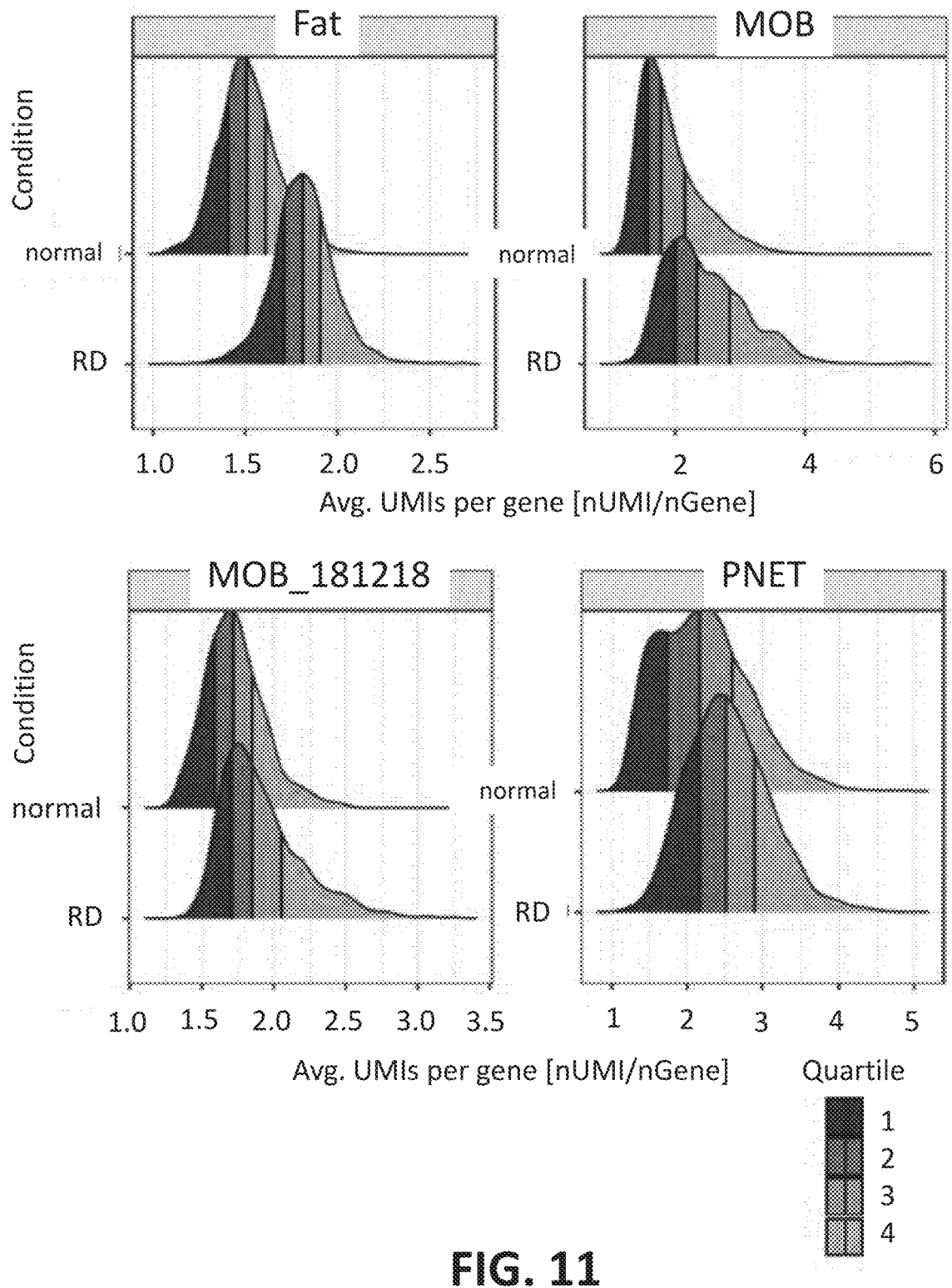
FIG. 11 shows the UMIs per gene in normal or ribosomal depleted tissues. The tissues include adipose (fat), mouse olfactory bulb (MOB), MOB-181218, and childhood brain cancer (PNET) tissues.
Figure 12:
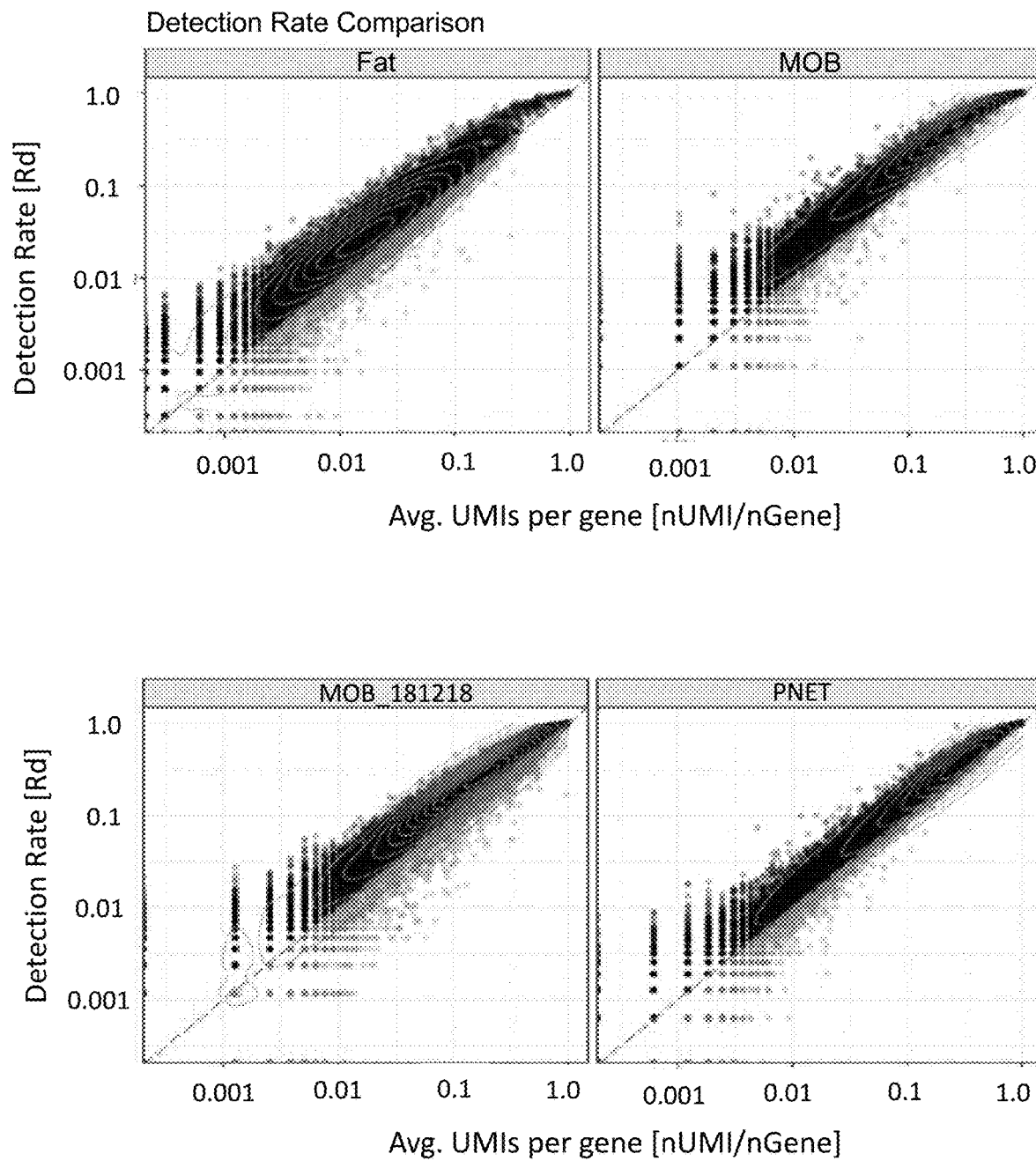
FIG. 12 shows the detection rate comparison between normal and ribosomal depleted tissues. The tissues include adipose (fat), mouse olfactory bulb (MOB), MOB-181218, and childhood brain cancer (PNET) tissues.

Tissue plots indicating the gene expression levels of mitochondrial 12S and 16S rRNA are shown in FIG. 10. Both rRNA molecules presented a reduced expression level upon ribosomal depletion in a tissue. As shown in FIGS. 11-12, more UMIs per gene, as well as an increased detection rate, were observed with in tissue ribosomal depletion in adipose (fat), mouse olfactory bulb (MOB), MOB-181218, and childhood brain cancer (PNET) tissues.

Figures 13A, 13B:
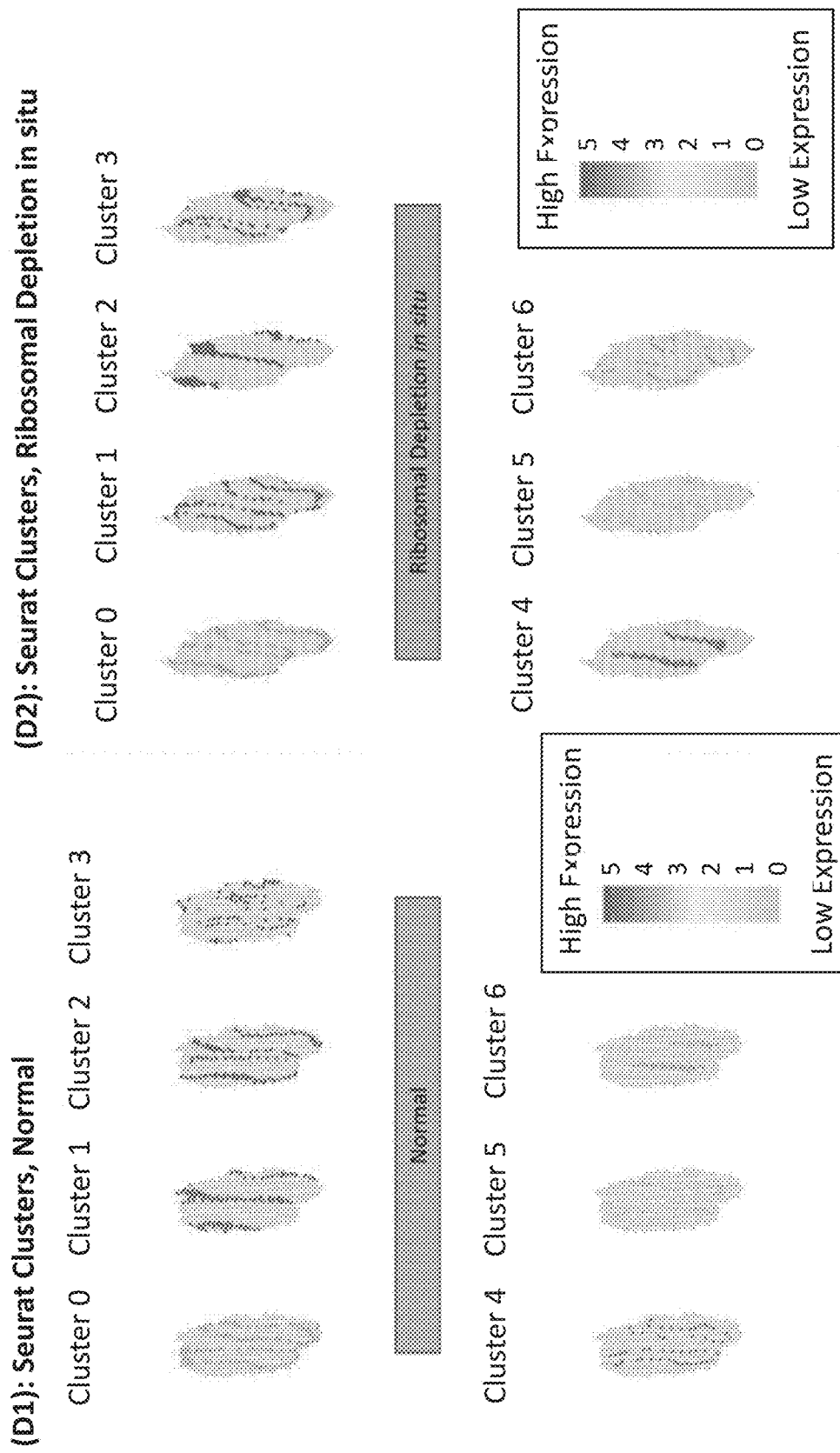
FIG. 13A shows tissue plots by Seurat clustering for 7 clusters from a normal tissue.
FIG. 13B shows tissue plots by Seurat clustering for 7 clusters from a ribosomal depleted tissue.
Figures 14A, 14B:
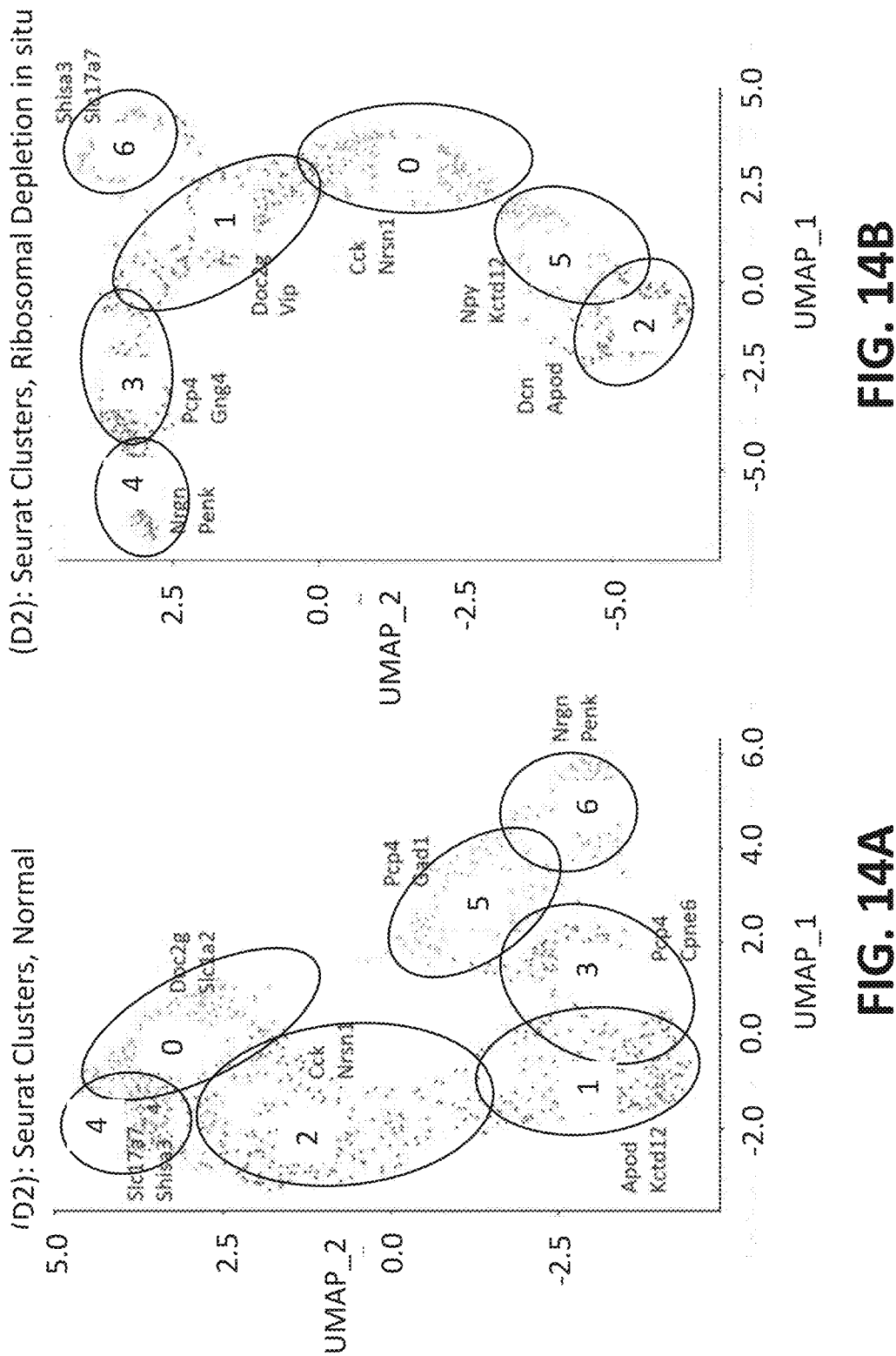
FIG. 14A shows a tSNE plot of Seurat clustering corresponding to the tissue plots in FIG. 13A.
FIG. 14B shows a tSNE plot of Seurat clustering corresponding to the tissue plots in FIG. 13B.
Figure 15:
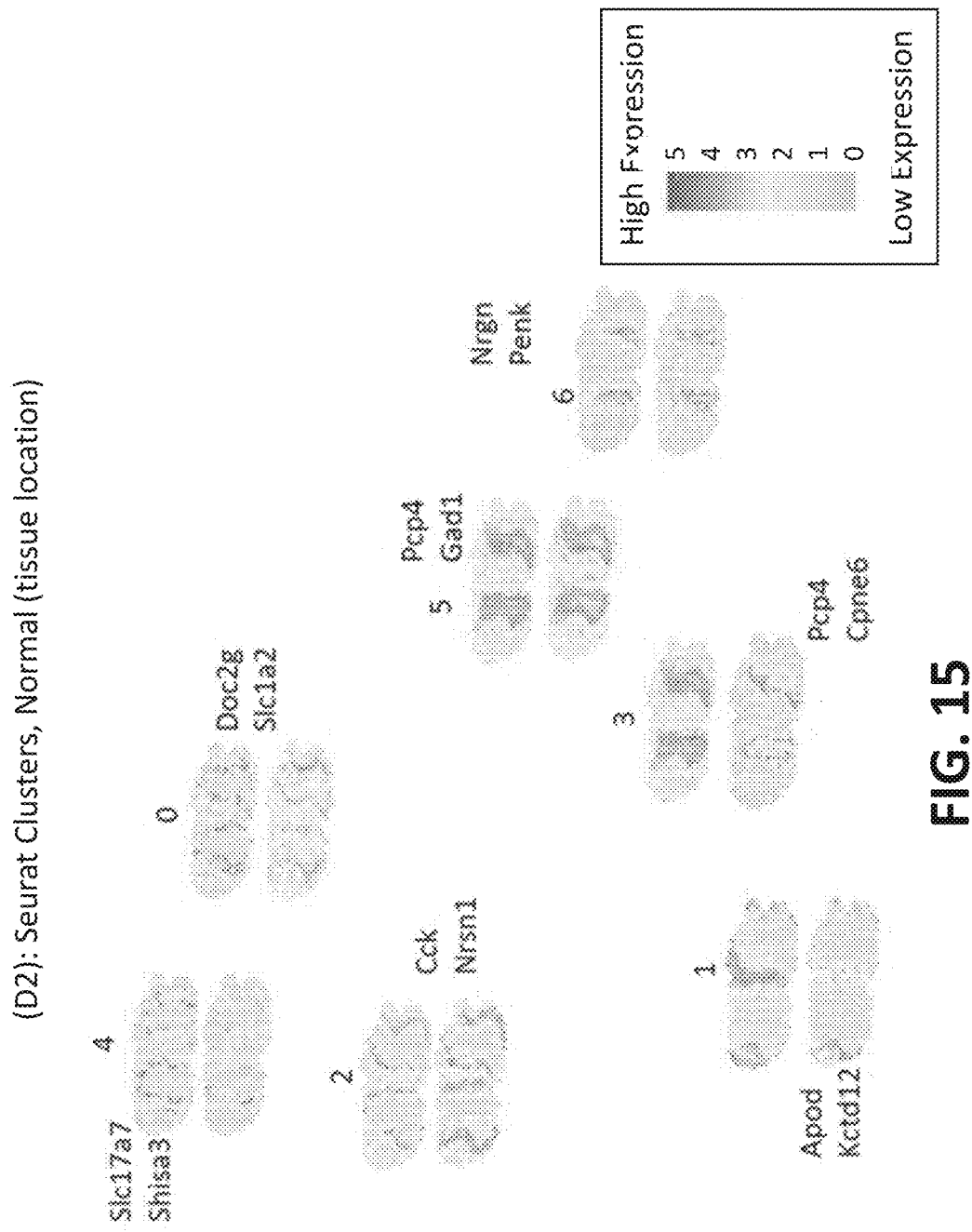
FIG. 15 shows tissue plots of 7 clusters from a normal tissue (same clusters from FIG. 14A).
Figure 16:
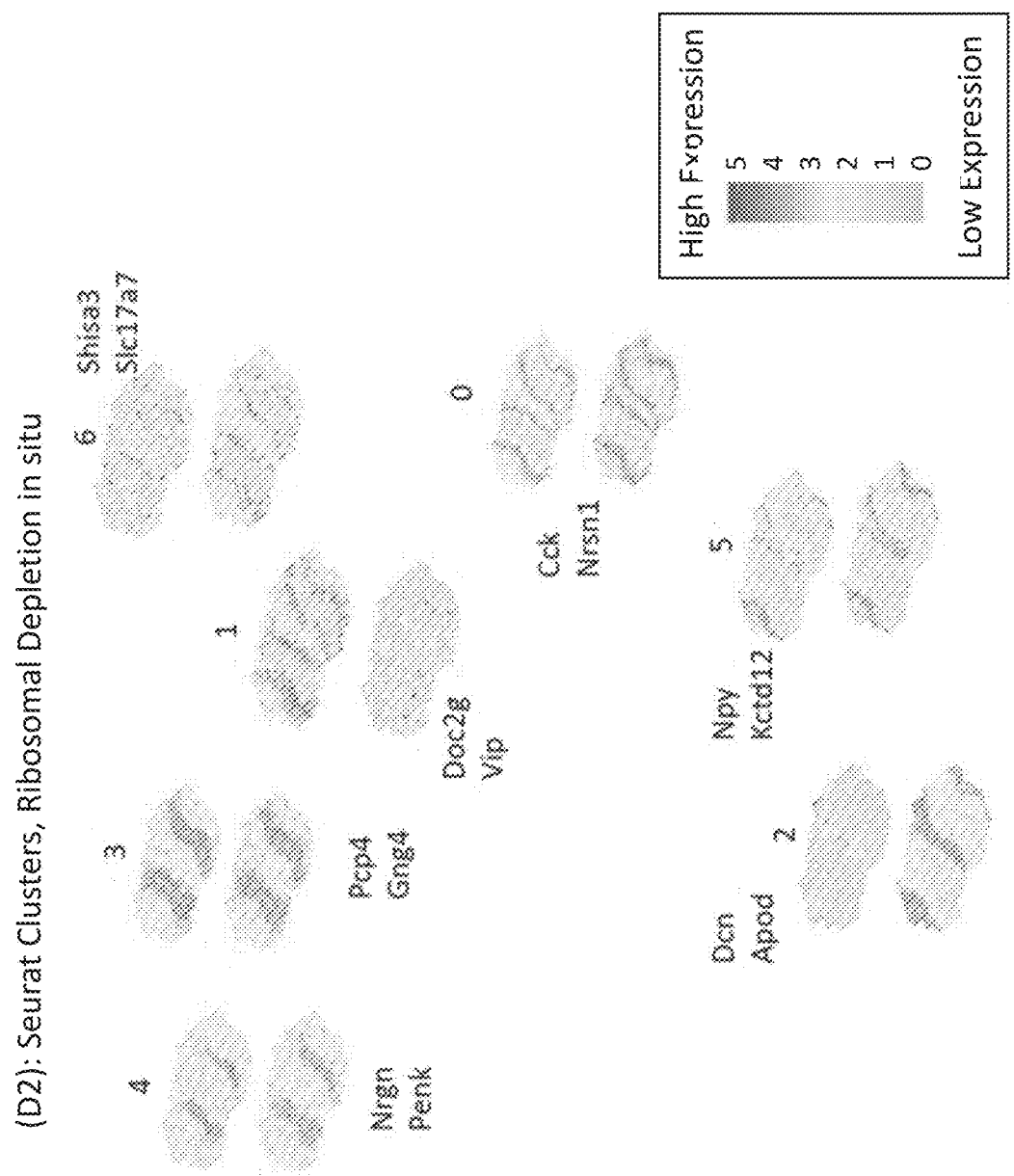
FIG. 16 shows tissue plots of 7 clusters from a ribosomal depleted tissue (same clusters from FIG. 14B).

Spatial expression patterns of different Seurat clusters were compared between a normal tissue and a ribosomal depleted tissue in FIG. 13A and FIG. 13B, respectively. The results show that the ribosomal depleted tissue samples exhibited more clear patterns than the normal tissue samples (see, e.g., FIGS. 13A-B). Analysis of additional normal tissue and ribosomal depleted tissue in FIGS. 14A-14B show that in a tSNE plot each Seurat cluster from the ribosomal depleted tissue presented clearer boundaries between Seurat clusters as compared to normal tissue samples, indicating an improved dataset quality. The spatial expression patterns for each of the Seurat clusters from FIG. 14A (normal tissue) and FIG. 14B (ribosomal depleted tissue) are shown in FIG. 15 and FIG. 16, respectively. These results indicate that ribosomal depletion improved the overall analyzing capability and accuracy of the spatial gene expression analysis methods as described herein.

Figures 17A, 17B:
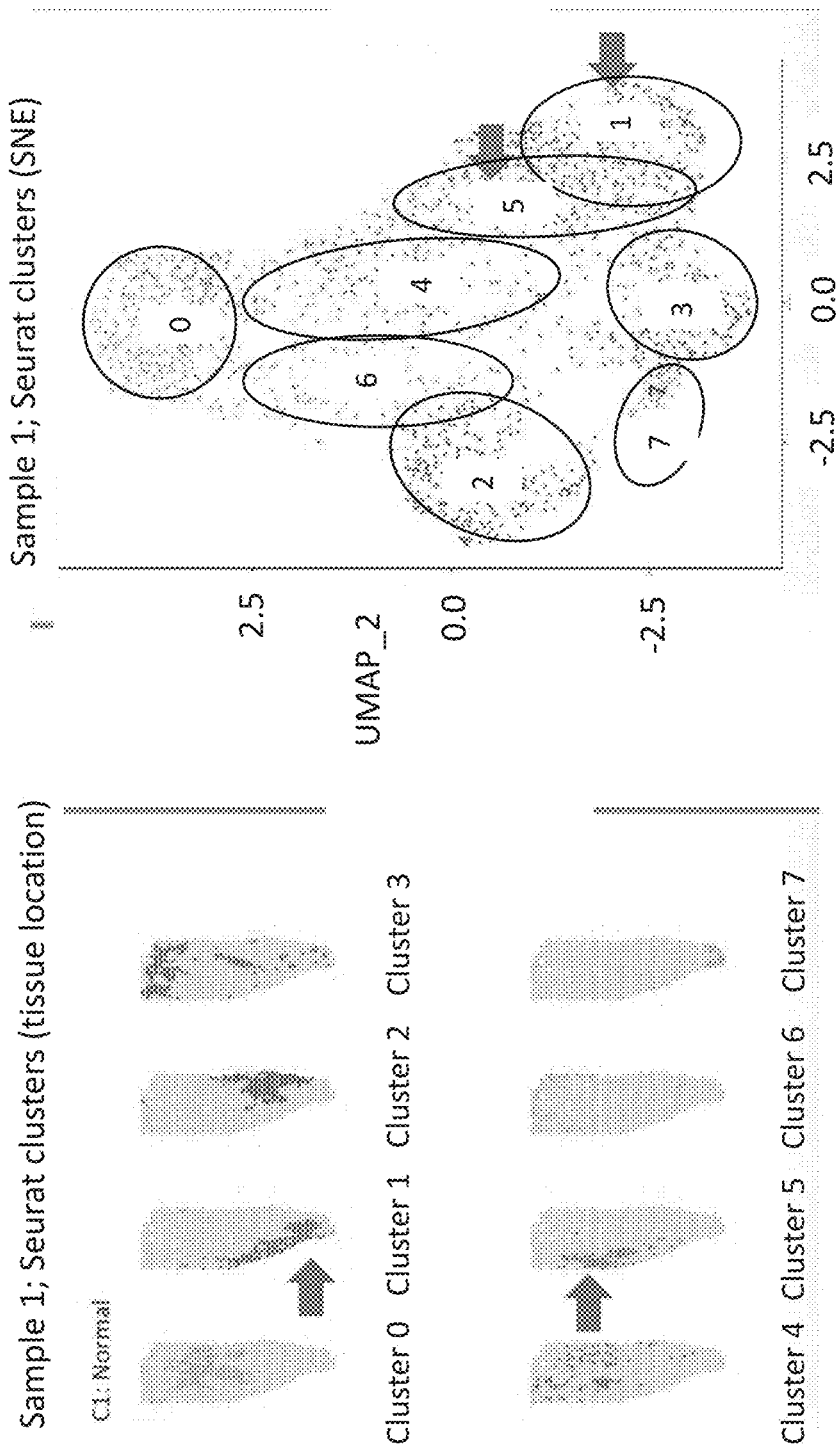
FIG. 17A shows tissue plots of 8 clusters from a normal tissue corresponding to the Seurat clusters in the tSNE plot in FIG. 17B. The two arrows indicate clusters 1 and 5 (also indicated by numerals).
FIG. 17B shows a tSNE plot of Seurat clustering corresponding to the indicated tissue plots in FIG. 17A. The two arrows indicate clusters 1 and 5 (also indicated by numerals).
Figures 18A, 18B:
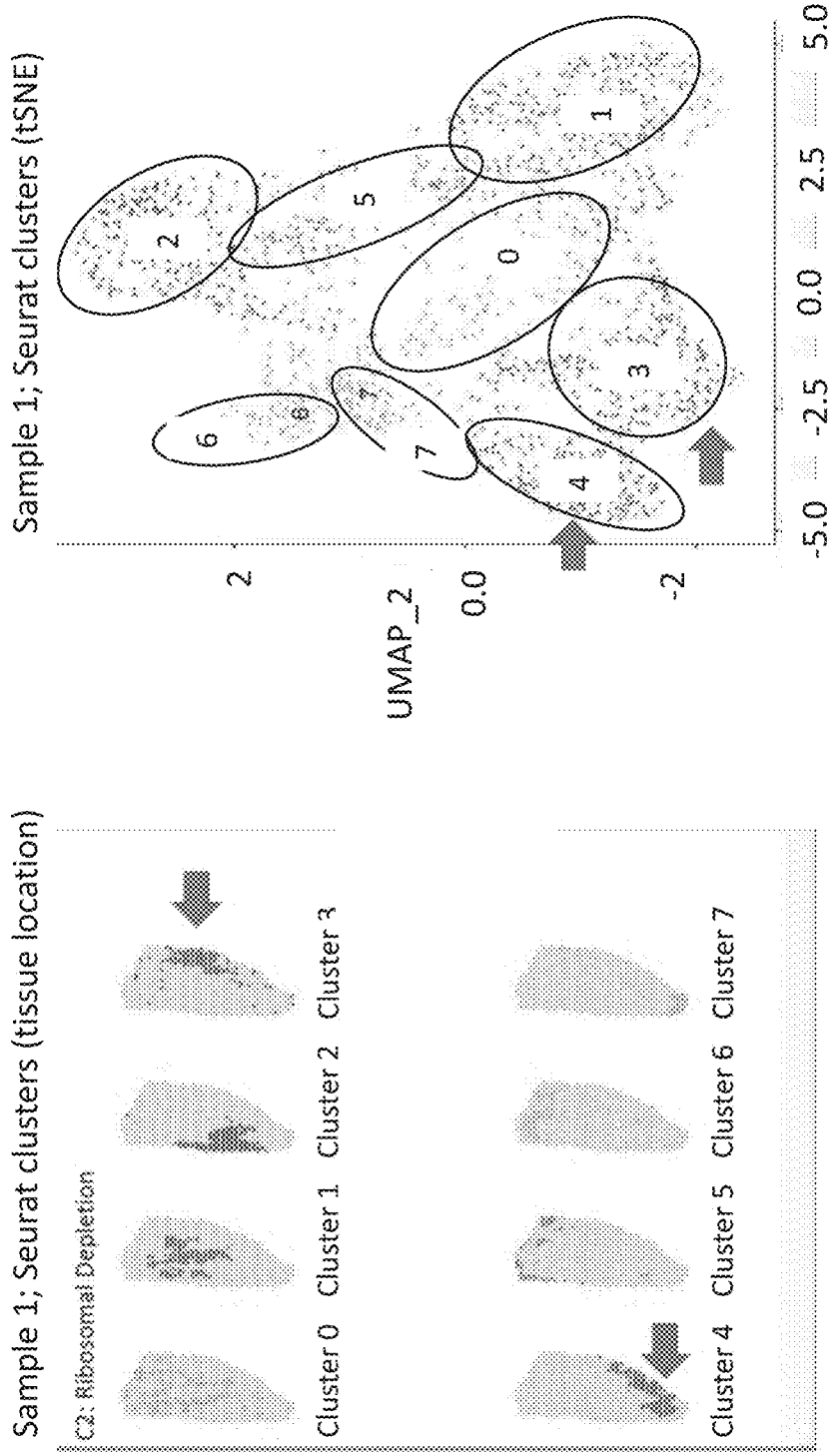
FIG. 18A shows tissue plots of 8 clusters from a ribosomal depleted tissue corresponding to the Seurat clusters in the tSNE plot in FIG. 18B. The two arrows indicate clusters 3 and 4, (also indicated by numerals).
FIG. 18B shows a tSNE plot of Seurat clustering corresponding to the indicated tissue plots in FIG. 18A. The two arrows indicate clusters 3 and 4 (also indicated by numerals).
Figure 19A:
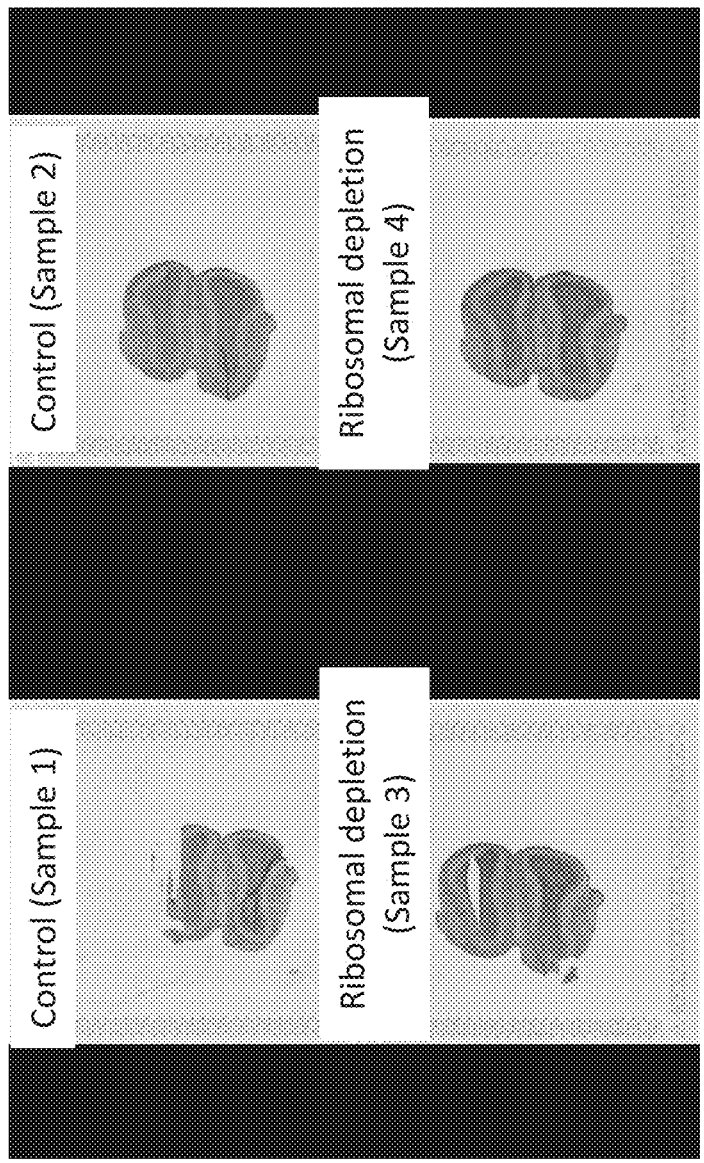
FIGS. 19A-19D show H&E staining images and gene expression heat maps for control samples (samples 1 and 2) and ribosomal depletion samples (samples 3 and 4).
Figure 19B:
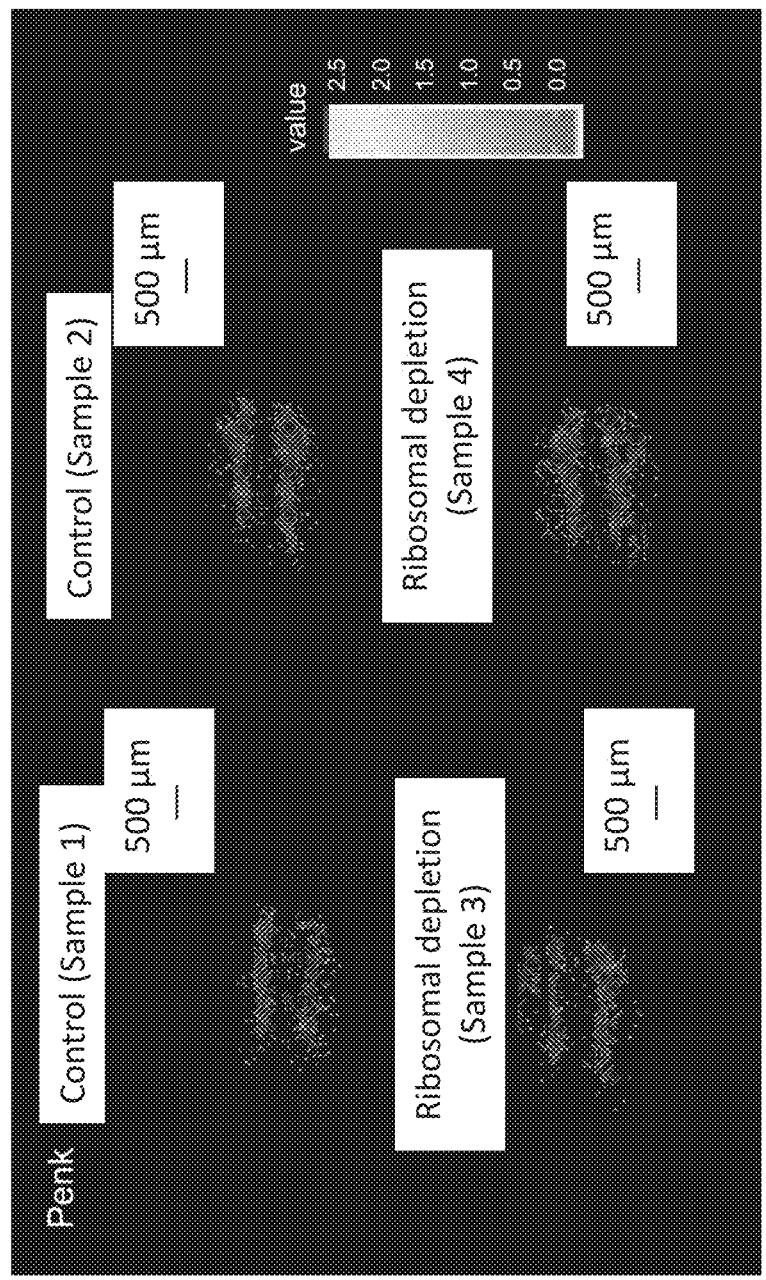
Figure 19C:
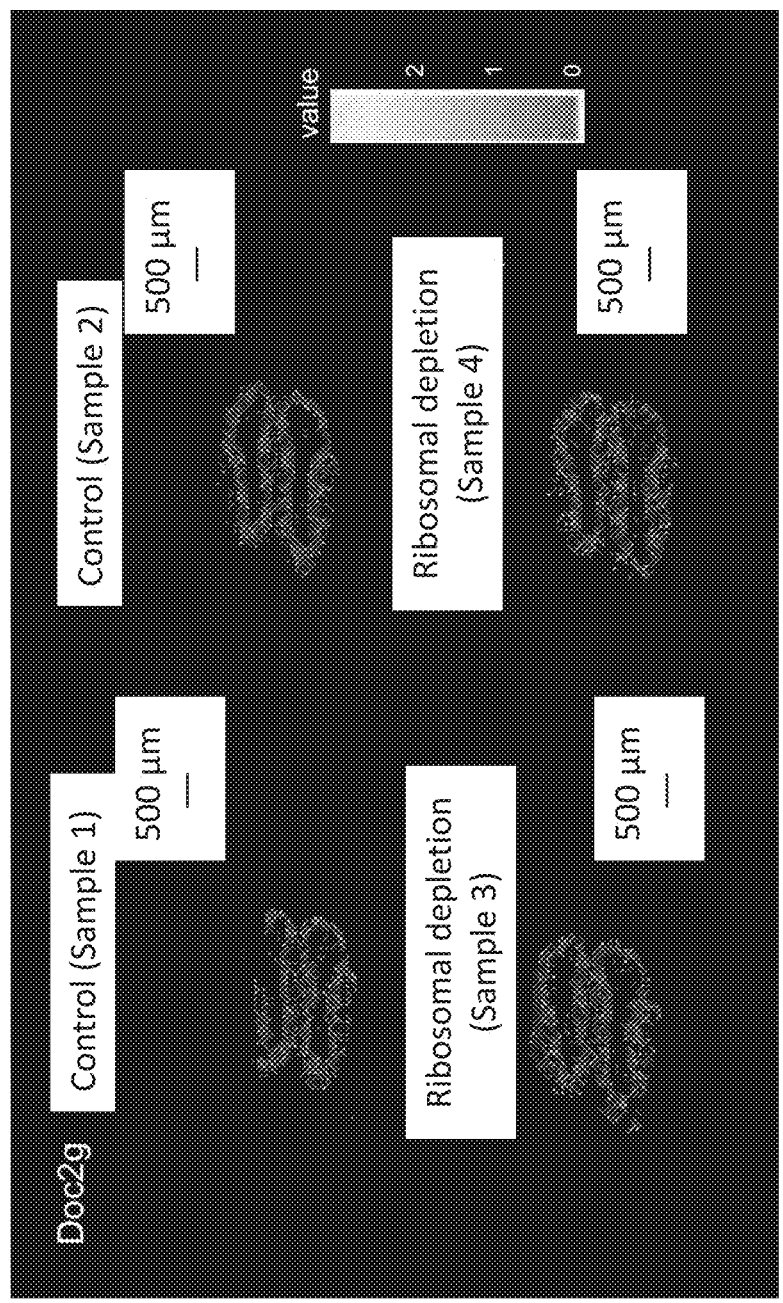
Figure 19D:
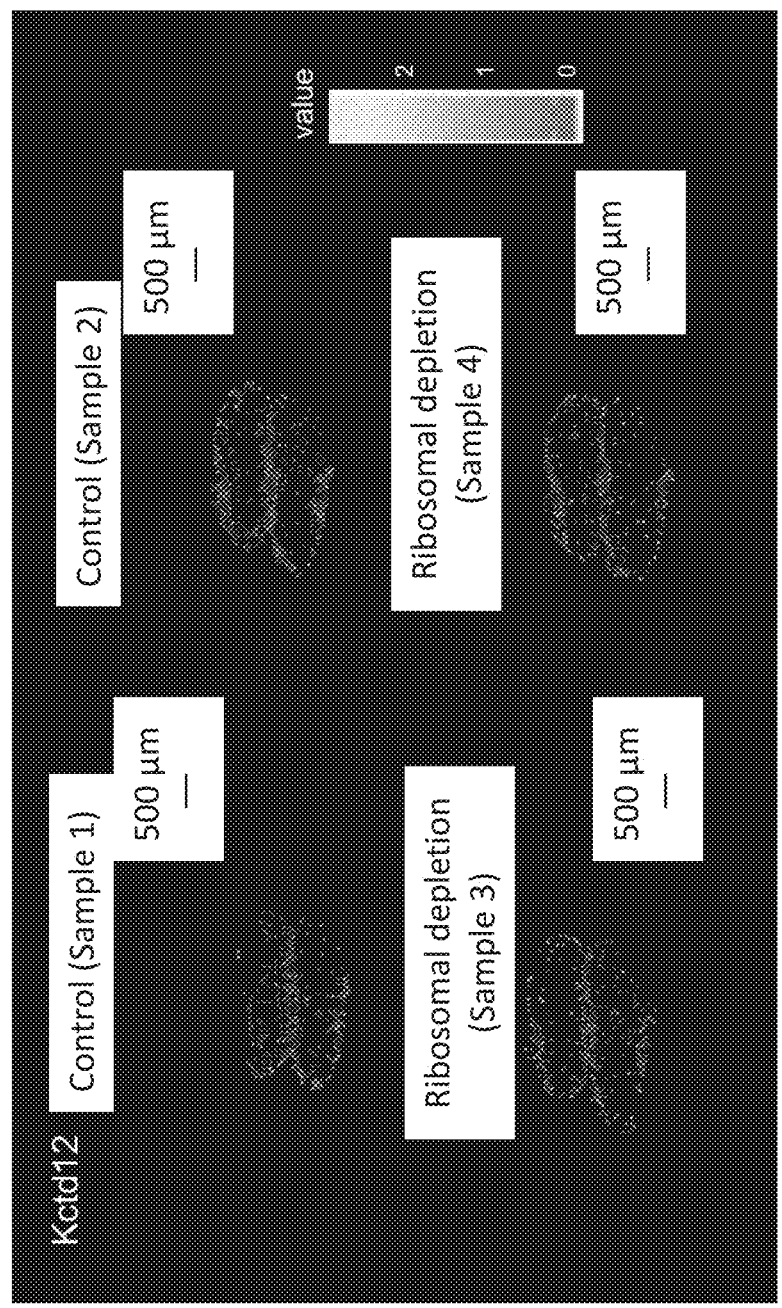
Figure 20A:
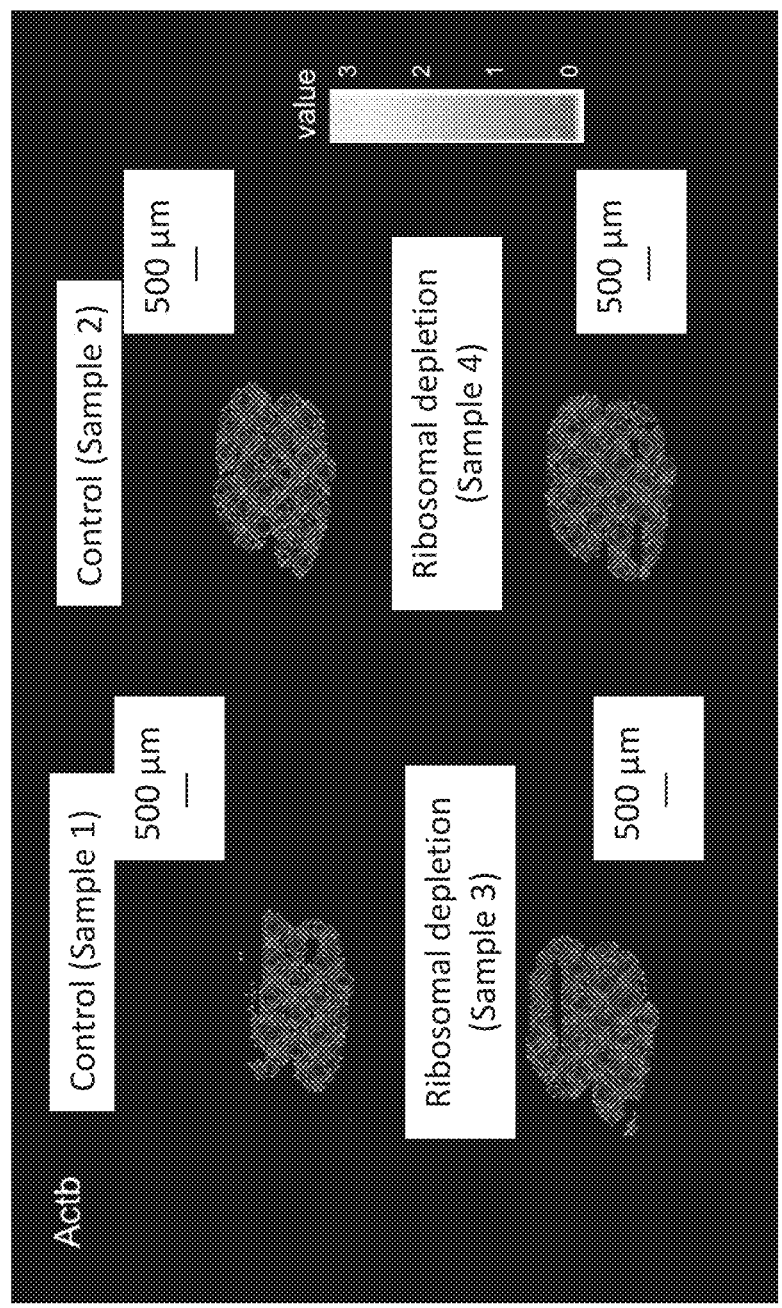
FIGS. 20A-20D show gene expression heat maps for control samples (sample 1 and 2) and ribosomal depletion samples (samples 3 and 4).
Figure 20B:
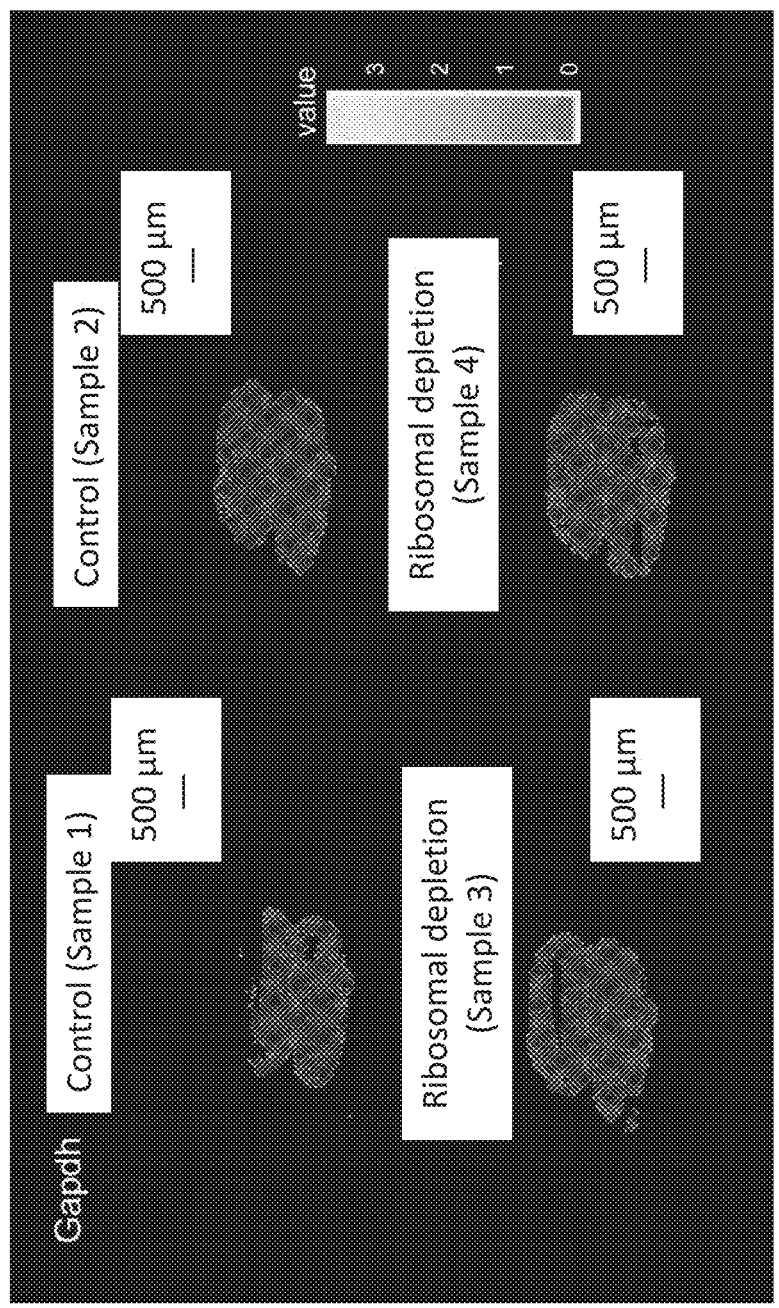
Figure 20C:
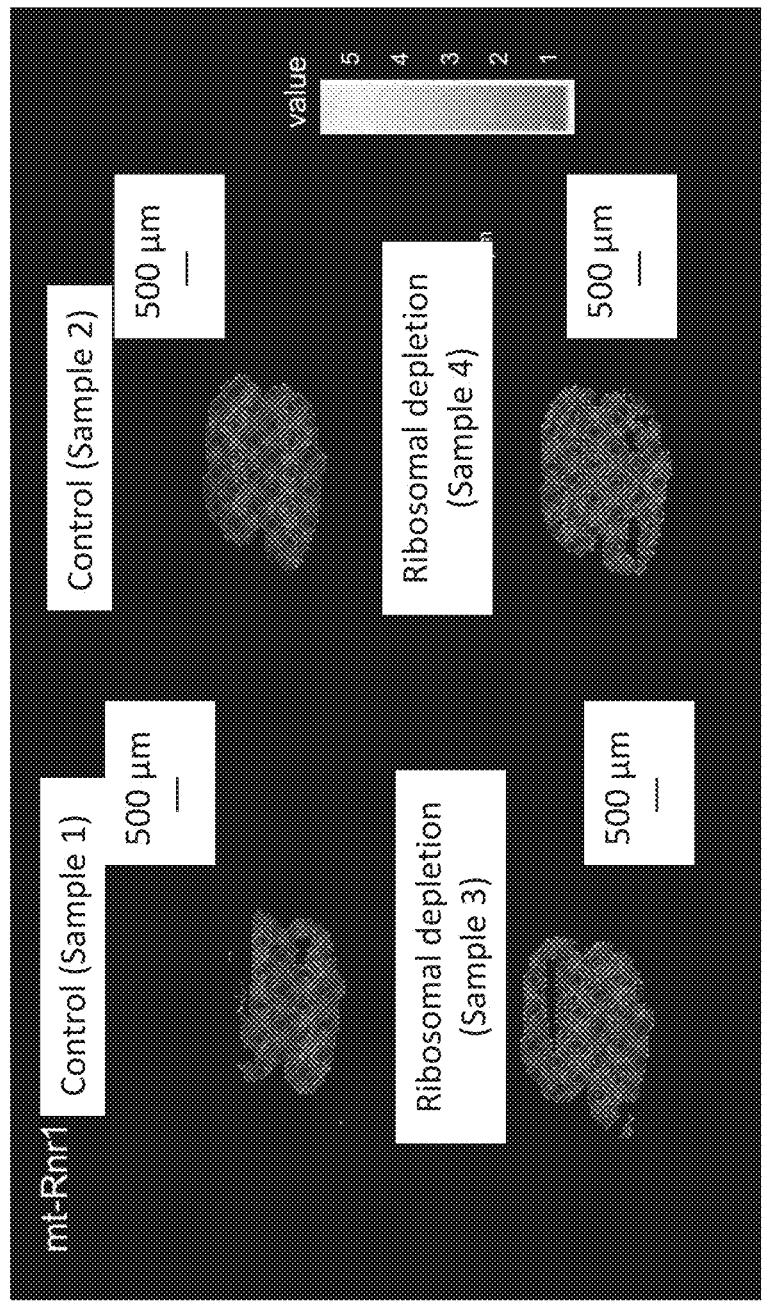
Figure 20D:
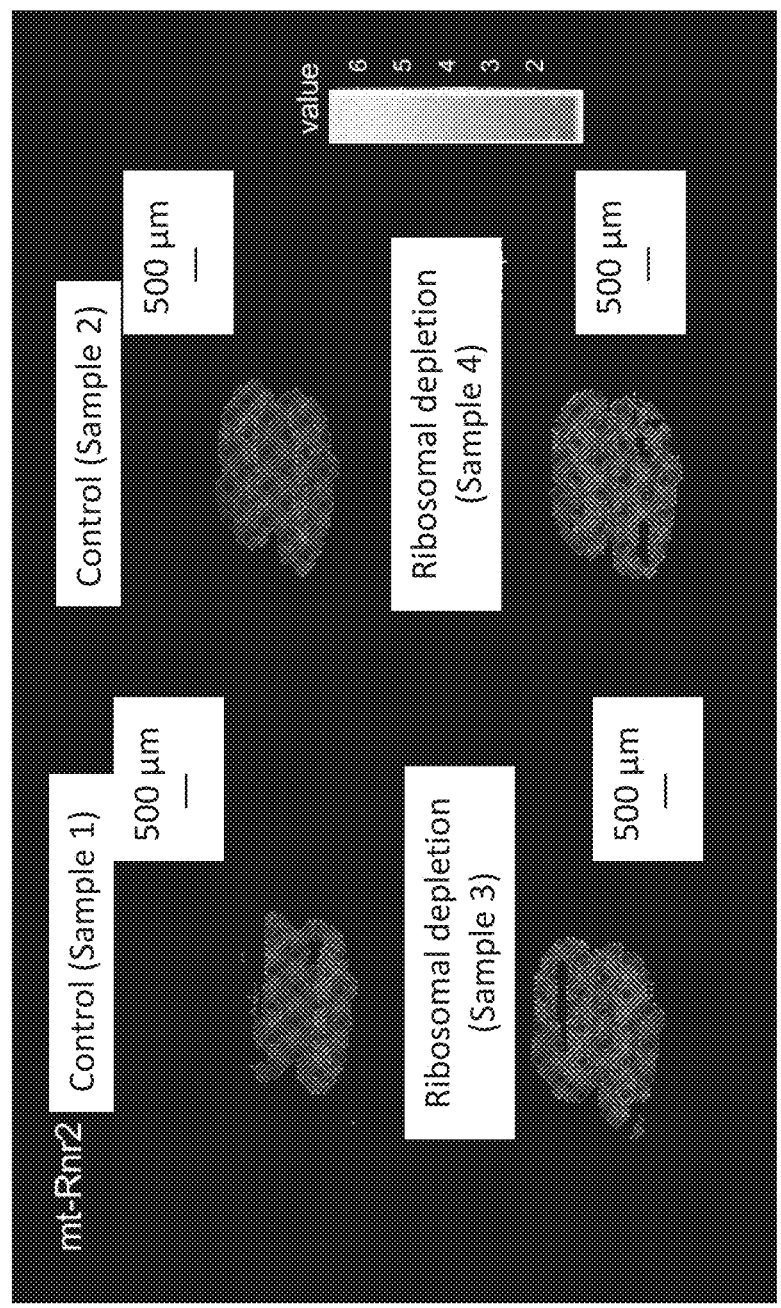

Another example is shown in FIGS. 17A-17B and FIGS. 18A-18B, which further supported the conclusions above. In the normal tissue sample (see FIGS. 17A-17B), clusters 1 and 5 (indicated by arrows) had high expression levels on substantially separate regions of the tissue sample (FIG. 17A). However, these two clusters present interpenetrated patterns in the tSNE plot (see FIG. 17B, indicated by arrows). In contrast, clusters 3 and 4 (indicated by arrows) in the ribosomal depleted tissue sample (see FIG. 18A) also had separate expression patterns, but presented a clearer boundary in the tSNE plot (FIG. 18B, indicated by arrows).

Thus, ribosomal depletion improved the overall dataset quality to reflect a more accurate spatial gene expression pattern.

An additional example of using ribosomal depletion probes in a spatial transcriptomic workflow is shown in FIGS. 19-21, which provides data for both global gene expression and an exemplary set of individual genes, comparing the control samples to ribosomal depleted samples. As noted above, each of the 195 ribosomal depletion probes (e.g., the ribosomal depletion probes of SEQ ID NOs: 1-195) were included at 1 μM final concentration in the spatial transcriptomics RT reaction mix. As shown in FIGS. 19A-19D, ribosomal depletion improved detection of an exemplary subset of mRNA molecules, including Perk, Doc2g, and Kctd12, FIGS. 19B-19D, respectively. As the pool of ribosomal depletion probes included probes targeting MT-RNR1 and MT-RNR2, depletion of undesirable RNAs was confirmed by comparing detection of housekeeping genes (e.g., Actb and Gapdh) with detection of MT-RNR1 and MT-RNR2. As shown in FIGS. 20A-20D, there was no change in detection of the housekeeping genes but a reduction in detection of MT-RNR1 and MT-RNR2 when samples were exposed to the ribosomal depletion probes. Additionally, global gene expression was not affected by the inclusion of the ribosomal depletion probes in the spatial transcriptomics workflow. Comparison of global gene expression between control samples and ribosomal depleted samples showed significant correlation for all comparisons (Pearson's r>0.97; p<2.2e-16)). Thus, as noted above, this data shows that ribosomal depletion probes included in the spatial transcriptomics workflow increased resolution of spatial gene expression patterns by improving capture of mRNA molecules while not limiting analysis of global gene expression.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

| | | Sequence Listing |
|---|---|---|
| SEQ ID NO: | Oligo Name | Sequence (5' to 3') |
| 1 | AG9327_18_1 | TAATGATCCTTCCGCAGGTTCACCTACGGAAACCTTGTTACGACTTTTAC |
| 2 | AG9328_18_2 | TTCCTCTAGATAGTCAAGTTCGACCGTCTTCTCAGCGCTCCGCCAGGGCC |
| 3 | AG9329_18_3 | GTGGGCCGACCCCGGCGGGGCCGATCCGAGGGCCTCACTAAACCATCCAA |
| 4 | AG9330_18_4 | TCGGTAGTAGCGACGGGCGGTGTGTACAAAGGGCAGGGACTTAATCAACG |
| 5 | AG9331_18_5 | CAAGCTTATGACCCGCACTTACTCGGGAATTCCCTCGTTCATGGGAATA |
| 6 | AG9332_18_6 | ATTGCAATCCCCGATCCCCATCACGAATGGGGTTCAACGGGTTACCCGCG |
| 7 | AG9333_18_7 | CCTGCCGGCGTAGGGTAGGCACACGCTGAGCCAGTCAGTGTAGCGCGCGT |
| 8 | AG9334_18_8 | GCAGCCCCGGACATCTAAGGGCATCACAGACCTGTTATTGCTCAATCTCG |

-continued

| SEQ ID NO: | Oligo Name | Sequence (5' to 3') |
|---|---|---|
| 9 | AG9335_18_9 | GGTGGCTGAACGCCACTTGTCCCTCTAAGAAGTTGGGGG ACGCCGACCGC |
| 10 | AG9336_18_10 | TCGGGGGTCGCGTAACTAGTTAGCATGCCAGAGTCTCGT TCGTTATCGGA |
| 11 | AG9337_18_11 | ATTAACCAGACAAATCGCTCCACCAACTAAGAACGGCCA TGCACCACCAC |
| 12 | AG9338_18_12 | CCACGGAATCGAGAAAGAGCTATCAATCTGTCAATCCTG TCCGTGTCCGG |
| 13 | AG9339_18_13 | GCCGGGTGAGGTTTCCCGTGTTGAGTCAAATTAAGCCGC AGGCTCCACTC |
| 14 | AG9340_18_14 | CTGGTGGTGCCCTTCCGTCAATTCCTTTAAGTTTCAGCTTT GCAACCATA |
| 15 | AG9341_18_15 | CTCCCCCCGGAACCCAAAGACTTTGGTTTCCCGGAAGCT GCCCGGCGGGT |
| 16 | AG9342_18_16 | CATGGGAATAACGCCGCCGCATCGCCGGTCGGCATCGTT TATGGTCGGAA |
| 17 | AG9343_18_17 | CTACGACGGTATCTGATCGTCTTCGAACCTCCGACTTTCG TTCTTGATTA |
| 18 | AG9344_18_18 | ATGAAAACATTCTTGGCAAATGCTTTCGCTCTGGTCCGTC TTGCGCCGGT |
| 19 | AG9345_18_19 | CCAAGAATTTCACCTCTAGCGGCGCAATACGAATGCCCC CGGCCGTCCCT |
| 20 | AG9346_18_20 | CTTAATCATGGCCTCAGTTCCGAAAACCAACAAAATAGA ACCGCGGTCCT |
| 21 | AG9347_18_21 | ATTCCATTATTCCTAGCTGCGGTATCCAGGCGGCTCGGGC CTGCTTTGAA |
| 22 | AG9348_18_22 | CACTCTAATTTTTTCAAAGTAAACGCTTCGGGCCCCGCGG GACACTCAGC |
| 23 | AG9349_18_23 | TAAGAGCATCGAGGGGGCGCCGAGAGGCAAGGGGCGGG GACGGGCGGTGG |
| 24 | AG9350_18_24 | CTCGCCTCGCGGCGGACCGCCCGCCCGCTCCCAAGATCC AACTACGAGCT |
| 25 | AG9351_18_25 | TTTTAACTGCAGCAACTTTAATATACGCTATTGGAGCTGG AATTACCGCG |
| 26 | AG9352_18_26 | GCTGCTGGCACCAGACTTGCCCTCCAATGGATCCTCGTTA AAGGATTTAA |
| 27 | AG9353_18_27 | AGTGGACTCATTCCAATTACAGGGCCTCGAAAGAGTCCT GTATTGTTATT |
| 28 | AG9354_18_28 | TTTCGTCACTACCTCCCCGGGTCGGGAGTGGGTAATTTGC GCGCCTGCTG |
| 29 | AG9355_18_29 | CCTTCCTTGGATGTGGTAGCCGTTTCTCAGGCTCCCTCTC CGGAATCGAA |
| 30 | AG9356_18_30 | CCCTGATTCCCCGTCACCCGTGGTCACCATGGTAGGCACG GCGACTACCA |
| 31 | AG9357_18_31 | TCGAAAGTTGATAGGGCAGACGTTCGAATGGGTCGTCGC CGCCACGGG |
| 32 | AG9358_18_32 | GCGTGCGATCGGCCCGAGGTTATCTAGAGTCACCAAAGC CGCCGGCGCCC |
| 33 | AG9359_18_33 | GCCCCCGGCCGGGGCCGGAGAGGGGCTGACCGGGTTGG TTTTGATCTGA |
| 34 | AG9360_18_34 | TAAATGCACGCATCCCCCCCGCGAAGGGGGTCAGCGCCC GTCGGCATGTA |
| 35 | AG9361_18_35 | TTAGCTCTAGAATTACCACAGTTATCCAAGTAGGAGAGG AGCGAGCGACC |
| 36 | AG9362_18_36 | AAAGGAACCATAACTGATTTAATGAGCCATTCGCAGTTT CACTGTACCGG |
| 37 | AG9363_18_37 | CCGTGCGTACTTAGACATGCATGGCTTAATCTTTGAGACA AGCATATGCT |
| 38 | AG9364_18_38 | TGGCTTAATCTTTGAGACAAGCATATGCTACTGGCAGGA TCAACCAGGTA |
| 39 | AG9365_28_1 | GACAAACCCTTGTGTCGAGGGCTGACTTTCAATAGATCG CAGCGAGGGAG |
| 40 | AG9366_28_2 | CTGCTCTGCTACGTACGAAACCCCGACCCAGAAGCAGGT CGTCTACGAAT |
| 41 | AG9367_28_3 | GGTTTAGCGCCAGGTTCCCCACGAACGTGCGGTGCGTGA CGGGCGAGGG |
| 42 | AG9368_28_4 | GCGGCCGCCTTTCCGGCCGCGCCCCGTTTCCCAGGACGA AGGGCACTCCG |

-continued

Sequence Listing

| SEQ ID NO: | Oligo Name | Sequence (5' to 3') |
|---|---|---|
| 43 | AG9369_28_5 | CACCGGACCCCGGTCCCGGCGCGCGGCGGGGCACGCGCCCTCCCGCGGCG |
| 44 | AG9370_28_6 | GGGCGCGTGGAGGGGIGGGCGGCCCGCCGGCGGGGACAGGCGGGGGACCG |
| 45 | AG9371_28_7 | GCTATCCGAGGCCAACCGAGGCTCCGCGGCCGCTGCCGTATCGTTCGCCTG |
| 46 | AG9372_28_8 | GGCGGGATTCTGACTTAGAGGCGTTCAGTCATAATCCCACAGATGGTAGC |
| 47 | AG9373_28_9 | TTCGCCCCATTGGCTCCTCAGCCAAGCACATACACCAAATGTCTGAACCT |
| 48 | AG9374_28_10 | GCGGTTCCTCTCGTACTGAGCAGGATTACCATGGCAACAACACATCATCA |
| 49 | AG9375_28_11 | GTAGGGTAAAACTAACCTGTCTCACGACGGTCTAAACCCAGCTCACGTTC |
| 50 | AG9376_28_12 | CCTATTAGTGGGTGAACAATCCAACGCTTGGCGAATTCTGCTTCACAATG |
| 51 | AG9377_28_13 | ATAGGAAGAGCCGACATCGAAGGATCAAAAAGCGACGTCGCTATGAACGC |
| 52 | AG9378_28_14 | TTGGCCGCCACAAGCCAGTTATCCCTGTGGTAACTTTTCTGACACCTCCT |
| 53 | AG9379_28_15 | GCTTAAAACCCAAAAGGTCAGAAGGATCGTGAGGCCCCGCTTTCACGGTC |
| 54 | AG9380_28_16 | TGTATTCGTACTGAAAATCAAGATCAAGCGAGCTTTTGCCCTTCTGCTCC |
| 55 | AG9381_28_17 | ACGGGAGGTTTCTGTCCTCCCTGAGCTCGCCTTAGGACACCTGCGTTACC |
| 56 | AG9382_28_18 | GTTTGACAGGTGTACCGCCCCAGTCAAACTCCCCACCTGGCACTGTCCCC |
| 57 | AG9383_28_19 | GGAGCGGGTCGCGCCCGGCCGGGCGGGCGCTTGGCGCCAGAAGCGAGAGC |
| 58 | AG9384_28_20 | CCCTCGGGCTCGCCCCCCCGCCTCACCGGGTCAGTGAAAAAACGATCAGA |
| 59 | AG9385_28_21 | GTAGTGGTATTTCACCGGCGGCCCGCAGGGCCGCGGACCCCGCCCCGGGC |
| 60 | AG9386_28_22 | CCCTCGCGGGGACACCGGGIGGGCGCCGGGGGCCTCCCACTTATTCTACA |
| 61 | AG9387_28_23 | CCTCTCATGTCTCTTCACCGTGCCAGACTAGAGTCAAGCTCAACAGGGTC |
| 62 | AG9388_28_24 | TTCTTTCCCCGCTGATTCCGCCAAGCCCGTTCCCTTGGCTGTGGTTTCGC |
| 63 | AG9389_28_25 | TGGATAGTAGGTAGGGACAGTGGGAATCTCGTTCATCCATTCATGCGCGT |
| 64 | AG9390_28_26 | CACTAATTAGATGACGAGGCATTTGGCTACCTTAAGAGAGTCATAGTTAC |
| 65 | AG9391_28_27 | TCCCGCCGTTTACCCGCGCTTCATTGAATTTCTTCACTTTGACATTCAGA |
| 66 | AG9392_28_28 | GCACTGGGCAGAAATCACATCGCGTCAACACCCGCCGCGGGCCTTCGCGA |
| 67 | AG9393_28_29 | TGCTTTGTTTTAATTAAACAGTCGGATTCCCCTGGTCCGCACCAGTTCTA |
| 68 | AG9394_28_30 | AGTCGGCTGCTAGGCGCCGGCCGAGGCGAGGCGCGCGGGAACCGCGGCC |
| 69 | AG9395_28_31 | CCGGGGCGGACCCGGCGGGIGGGACCGGCCCGCGGCCCCTCCGCCGCCT |
| 70 | AG9396_28_32 | GCCGCCGCCGCCGCCGCGCGCCGAGGAGGAGGGGGAACGGGGGGCGGAC |
| 71 | AG9397_28_33 | GGGCCGGGIGGGTAGGGCGGGGGGACGAACCGCCCCGCCCCGCCGCCCG |
| 72 | AG9398_28_34 | CCGACCGCCGCCGCCCGACCGCTCCCGCCCCCAGCGGACGCGCGCGCGAC |
| 73 | AG9399_28_35 | CGAGACGTGGGGTGGGGGTGGGGGGCGCGCCGCGCCGCCGCCGGGCTCCC |
| 74 | AG9400_28_36 | CGGGGGCGGCCGCGACGCCCGCCGCAGCTGGGCGATCCACGGGAAGGGC |
| 75 | AG9401_28_37 | CCCGGCTCGCGTCCAGAGTCCGCGCCGCCGCCGGCCCCCCGGGTCCCCGGG |
| 76 | AG9402_28_38 | GCCCCCCTCGCGGGGACCTGCCCCCGCCGGCCGCCCCGGCGGCCGCCGCG |
| 77 | AG9403_28_39 | CGGCCCCTGCCGCCCCGACCCTTCTCCCCCCGCCGCGCCCCCACGCGGCG |

-continued

Sequence Listing

| SEQ ID NO: | Oligo Name | Sequence (5' to 3') |
|---|---|---|
| 78 | AG9404_28_40 | CTCCCCCGGGGAGGGGGGAGGACGGGGAGCGGGGGAGAGAGAGAGAGA |
| 79 | AG9405_28_41 | GGGCGCGGGGTGGGGAGGGAGCGAGCGGCGCGCGCGGGTGGGGCGGGGGA |
| 80 | AG9406_28_42 | GGGCCGCGAGGGGGGTGCCCCGGGCGTGGGGIGGGCGCGCGCCTCGTCCA |
| 81 | AG9407_28_43 | GCCGCGGCGCGCGCCCAGCCCCGCTTCGCGCCCCAGCCCGACCGACCCAG |
| 82 | AG9408_28_44 | CCCTTAGAGCCAATCCTTATCCCGAAGTTACGGATCCGGCTTGCCGACTT |
| 83 | AG9409_28_45 | CCCTTACCTACATTGTTCCAACATGCCAGAGGCTGTTCACCTTGGAGACC |
| 84 | AG9410_28_46 | TGCTGCGGATATGGGTACGGCCCGGCGCGAGATTTACACCCTCTCCCCCG |
| 85 | AG9411_28_47 | GATTTTCAAGGGCCAGCGAGAGCTCACCGGACGCCGCCGGAACCGCGACG |
| 86 | AG9412_28_48 | CTTTCCAAGGCACGGGCCCCTCTCTCGGGGCGAACCCATTCCAGGGCGCC |
| 87 | AG9413_28_49 | CTGCCCTTCACAAAGAAAAGAGAACTCTCCCCGGGGCTCCCGCCGGCTTC |
| 88 | AG9414_28_50 | TCCGGGATCGGTCGCGTTACCGCACTGGACGCCTCGCGGCGCCCATCTCC |
| 89 | AG9415_28_51 | GCCACTCCGGATTCGGGGATCTGAACCCGACTCCCTTTCGATCGGCCGAG |
| 90 | AG9416_28_52 | GGCAACGGAGGCCATCGCCCGTCCCTTCGGAACGGCGCTCGCCCATCTCT |
| 91 | AG9417_28_53 | CAGGACCGACTGACCCATGTTCAACTGCTGTTCACATGGAACCCTTCTCC |
| 92 | AG9418_28_54 | ACTTCGGCCTTCAAAGTTCTCGTTTGAATATTTGCTACTACCACCAAGAT |
| 93 | AG9419_28_55 | CTGCACCTGCGGCGGCTCCACCCGGGCCCGCGCCCTAGGCTTCAAGGCTC |
| 94 | AG9420_28_56 | ACCGCAGCGGCCCTCCTACTCGTCGCGGCGTAGCGTCCGCGGGGCTCCGG |
| 95 | AG9421_28_57 | GGGCGGGGAGCGGGGCGTGGGCGGGAGGAGGGGAGGAGGCGTGGG |
| 96 | AG9422_28_58 | GGGCGGGGGAAGGACCCCACACCCCCGCCGCCGCCGCCGCCGCCCTC |
| 97 | AG9423_28_59 | CGACGCACACCACACGCGCGCGCGCGCGCCGCCCCCGCCGCTCCCGTC |
| 98 | AG9424_28_60 | CACTCTCGACTGCCGGCGACGGCCGGGTATGGGCCCGACGCTCCAGCGCC |
| 99 | AG9425_28_61 | ATCCATTTTCAGGGCTAGTTGATTCGGCAGGTGAGTTGTTACACACTCCT |
| 100 | AG9426_28_62 | TAGCGGATTCCGACTTCCATGGCCACCGTCCTGCTGTCTATATCAACCAA |
| 101 | AG9427_28_63 | CACCTTTTCTGGGGTCTGATGAGCGTCGGCATCGGGCGCCTTAACCCGGC |
| 102 | AG9428_28_64 | GTTCGGTTCATCCCGCAGCGCCAGTTCTGCTTACCAAAAGTGGCCCACTA |
| 103 | AG9429_28_65 | GGCACTCGCATTCCACGCCCGGCTCCACGCCAGCGAGCCGGGCTTCTTAC |
| 104 | AG9430_28_66 | CCATTTAAAGTTTGAGAATAGGTTGAGATCGTTTCGGCCCCAAGACCTCT |
| 105 | AG9431_28_67 | AATCATTCGCTTTACCGGATAAAACTGCGTGGCGGGGTGCGTCGGGTCT |
| 106 | AG9432_28_68 | GCGAGAGCGCCAGCTATCCTGAGGGAAACTTCGGAGGGAACCAGCTACTA |
| 107 | AG9433_28_69 | GATGGTTCGATTAGTCTTTCGCCCCTATACCCAGGTCGGACGACCGATTT |
| 108 | AG9434_28_70 | GCACGTCAGGACCGCTACGGACCTCCACCAGAGTTTCCTCTGGCTTCGCC |
| 109 | AG9435_28_71 | CTGCCCAGGCATAGTTCACCATCTTTCGGGTCCTAACACGTGCGCTCGTG |
| 110 | AG9436_28_72 | CTCCACCTCCCCGGCGCGGCGGGCGAGACGGGCCGGTGGTGCGCCCTCGG |
| 111 | AG9437_28_73 | CGGACTGGAGAGGCCTCGGGATCCCACCTCGGCCGGCGAGCGCGCCGGCC |
| 112 | AG9438_28_74 | TTCACCTTCATTGCGCCACGGCGGCTTTCGTGCGAGCCCCCGACTCGCGC |

-continued

| SEQ ID NO: | Oligo Name | Sequence (5' to 3') |
|---|---|---|
| 113 | AG9439_28_75 | ACGTGTTAGACTCCTTGGTCCGTGTTTCAAGACGGGTCGGGTGGGTAGCC |
| 114 | AG9440_28_76 | GACGTCGCCGCCGACCCCGTGCGCTCGCTCCGCCGTCCCCCTCTTCGGG |
| 115 | AG9441_28_77 | GACGCGCGCGTGGCCCCGAGAGAACCTCCCCCGGGCCCGACGGCGCGACC |
| 116 | AG9442_28_78 | CGCCCGGGGCGCACTGGGGACAGTCCGCCCCGCCCCCCGACCCGCGCGCG |
| 117 | AG9443_28_79 | GCACCCCCCCCGTCGCCGGGGCGGGGCGCGGGGAGGAGGGGTGGGAGAG |
| 118 | AG9444_28_80 | CGGTCGCGCCGTGGGAGGGGTGGCCCGGCCCCCCACGAGGAGACGCCGG |
| 119 | AG9445_28_81 | CGCGCCCCCGCGGGGGAGACCCCCCTCGCGGGGGATTCCCCGCGGGGTG |
| 120 | AG9446_28_82 | GGCGCCGGGAGGGGGGAGAGCGCGGCGACGGGTCTCGCTCCCTCGGCCCC |
| 121 | AG9447_28_83 | GGGATTCGGCGAGTGCTGCTGCCGGGGGGGCTGTAACACTCGGGGIGGGT |
| 122 | AG9448_28_84 | TTCGGTCCCGCCGCCCCGCCGCCGCCGCCACCGCCGCCGCCGCCGCC |
| 123 | AG9449_28_85 | CCCGACCCGCGCGCCCTCCCGAGGGAGGACGCGGGGCCGGGGGCGGAGA |
| 124 | AG9450_28_86 | CGGGGGAGGAGGAGGACGGACGGACGGACGGGGCCCCCCGAGCCACCTTC |
| 125 | AG9451_28_87 | CCCGCCGGGCCTTCCCAGCCGTCCCGGAGCCGGTCGCGGCGCACCGCCGC |
| 126 | AG9452_28_88 | GGTGGAAATGCGCCCGGCGGCGGCCGGTCGCCGGTCGGGGGACGGTCCCC |
| 127 | AG9453_28_89 | CGCCGACCCCACCCCCGGCCCCGCCCGCCCACCCCCGCACCCGCCGGAGC |
| 128 | AG9454_28_90 | CCGCCCCCTCCGGGGAGGAGGAGGAGGGGCGGCGGGGGAAGGGAGGGCGG |
| 129 | AG9455_28_91 | GTGGAGGGGTCGGGAGGAACGGGGGGCGGGAAAGATCCGCCGGGCCGCCG |
| 130 | AG9456_28_92 | ACACGGCCGGACCCGCCGCCGGGTTGAATCCTCCGGGCGGACTGCGCGGA |
| 131 | AG9457_28_93 | CCCCACCCGTTTACCTCTTAACGGTTTCACGCCCTCTTGAACTCTCTCTT |
| 132 | AG9458_28_94 | CAAAGTTCTTTTCAACTTTCCCTTACGGTACTTGTTGACTATCGGTCTCG |
| 133 | AG9459_28_95 | TGCCGGTATTTAGCCTTAGATGGAGTTTACCACCCGCTTTGGGCTGCATT |
| 134 | AG9460_28_96 | CCCAAGCAACCCGACTCCGGGAAGACCCGGGCGCGCGCCGGCCGCTACCG |
| 135 | AG9461_28_97 | GCCTCACACCGTCCACGGGCTGGGCCTCGATCAGAAGGACTTGGGCCCCC |
| 136 | AG9462_28_98 | CACGAGCGGCGCCGGGGAGCGGGTCTTCCGTACGCCACATGTCCCGCGCC |
| 137 | AG9463_28_99 | CCGCGGGGCGGGGATTCGGCGCTGGGCTCTTCCCTGTTCACTCGCCGTTA |
| 138 | AG9464_28_100 | CTGAGGGAATCCTGGTTAGTTTCTTTTCCTCCGCTGACTAATATGCTTAA |
| 139 | AG9465_28_101 | GACTAATATGCTTAAATTCAGCGGGTCGCCACGTCTGATCTGAGGTCGCG |
| 140 | AG9466_5.8_1 | AAGCGACGCTCAGACAGGCGTAGCCCCGGGAGGAACCCGGGGCCGCAAGT |
| 141 | AG9467_5.8_2 | GCGTTCGAAGTGTCGATGATCAATGTGTCCTGCAATTCACATTAATTCTC |
| 142 | AG9468_5.8_3 | GCAGCTAGCTGCGTTCTTCATCGACGCACGAGCCGAGTGATCCACCGCTA |
| 143 | AG9469_16_1 | AAACCCTGTTCTTGGGTGGGTGTGGGTATAATACTAAGTTGAGATGATAT |
| 144 | AG9470_16_2 | CATTTACGGGGAAGGCGCTTTGTGAAGTAGGCCTTATTTCTCTTGTCCT |
| 145 | AG9471_16_3 | TTCGTACAGGGAGGAATTTGAANGTAGATAGAAACCGACCTGGATTACTC |
| 146 | AG9472_16_4 | CGGTCTGAACTCAGATCACGTAGGACTTTAATCGTTGAACAAACGAACCT |
| 147 | AG9473_16_5 | TTAATAGCGGCTGCACCATCGGGATGTCCTGATCCAACATCGAGGTCGTA |

-continued

Sequence Listing

| SEQ ID NO: | Oligo Name | Sequence (5' to 3') |
|---|---|---|
| 148 | AG9474_16_6 | AACCCTATTGTTGATATGGACTCTAGAATAGGATTGCGCTGTTATCCCTA |
| 149 | AG9475_16_7 | GGGTAACTTGTTCCGTTGGTCAAGTTATTGGATCAATTGAGTATAGTAGT |
| 150 | AG9476_16_8 | TCGCTTTGACTGGTGAAGTCTTAGCATGTACTGCTCGGAGGTTGGGTTCT |
| 151 | AG9477_16_9 | GCTCCGAGGTCGCCCCAACCGAAATTTTTAATGCAGGTTTGGTAGTTTAG |
| 152 | AG9478_16_10 | GACCTGTGGGTTTGTTAGGTACTGTTTGCATTAATAAATTAAAGCTCCAT |
| 153 | AG9479_16_11 | AGGGTCTTCTCGTCTTGCTGTGTTATGCCCGCCTCTTCACGGGCAGGTCA |
| 154 | AG9480_16_12 | ATTTCACTGGTTAAAAGTAAGAGACAGCTGAACCCTCGTGGAGCCATTCA |
| 155 | AG9481_16_13 | TACAGGTCCCTATTTAAGGAACAAGTGATTATGCTACCTTTGCACGGTTA |
| 156 | AG9482_16_14 | GGGTACCGCGGCCGTTAAACATGTGTCACTGGGCAGGCGGTGCCTCTAAT |
| 157 | AG9483_16_15 | ACTGGTGATGCTAGAGGTGATGTTTTTGGTAAACAGGCGGGGTAAGATTT |
| 158 | AG9484_16_16 | GCCGAGTTCCTTTTACTTTTTTTAACCTTTCCTTATGAGCATGCCTGTGT |
| 159 | AG9485_16_17 | TGGGTTGACAGTGAGGGTAATAATGACTTGTTGGTTGATTGTAGATATTG |
| 160 | AG9486_16_18 | GGCTGTTAATTGTCAGTTCAGTGTTTTAATCTGACGCAGGCTTATGCGGA |
| 161 | AG9487_16_19 | GGAGAATGTTTTCATGTTACTTATACTAACATTAGTTCTTCTATAGGGTG |
| 162 | AG9488_16_20 | ATAGATTGGTCCAATTGGGTGTGAGGAGTTCAGTTATATGTTTGGGATTT |
| 163 | AG9489_16_21 | TTTAGGTAGTGGGTGTTGAGCTTGAACGCTTTCTTAATTGGTGGCTGCTT |
| 164 | AG9490_16_22 | TTAGGCCTACTATGGGTGTTAAATTTTTACTCTCTCTACAAGGTTTTTT |
| 165 | AG9491_16_23 | CCTAGTGTCCAAAGAGCTGTTCCTCTTTGGACTAACAGTTAAATTTACAA |
| 166 | AG9492_16_24 | GGGATTTAGAGGGTTCTGTGGGCAAATTTAAAGTTGAACTAAGATTCTA |
| 167 | AG9493_16_25 | TCTTGGACAACCAGCTATCACCAGGCTCGGTAGGTTTGTCGCCTCTACCT |
| 168 | AG9494_16_26 | ATAAATCTTCCCACTATTTTGCTACATAGACGGGTGTGCTCTTTTAGCTG |
| 169 | AG9495_16_27 | TTCTTAGGTAGCTCGTCTGGTTTCGGGGTCTTAGCTTTGGCTCTCCTTG |
| 170 | AG9496_16_28 | CAAAGTTATTTCTAGTTAATTCATTATGCAGAAGGTATAGGGGTTAGTCC |
| 171 | AG9497_16_29 | TTGCTATATTATGCTTGGTTATAATTTTTCATCTTTCCCTTGCGGTACTA |
| 172 | AG9498_16_30 | TATCTATTGCGCCAGGTTTCAATTTCTATCGCCTATACTTTATTTGGGTA |
| 173 | AG9499_16_31 | AATGGTTTGGCTAAGGTTGTCTGGTAGTAAGGTGGAGTGGGTTTGGGGCT |
| 174 | AG9500_12_1 | GTTCGTCCAAGTGCACTTTCCAGTACACTTACCATGTTACGACTTGTCTC |
| 175 | AG9501_12_2 | CTCTATATAAATGCGTAGGGGTTTTAGTTAAATGTCCTTTGAAGTATACT |
| 176 | AG9502_12_3 | TGAGGAGGGTGACGGGCGGTGTGTACGCGCTTCAGGGCCCTGTTCAACTA |
| 177 | AG9503_12_4 | AGCACTCTACTCTTAGTTTACTGCTAAATCCACCTTCGACCCTTAAGTTT |
| 178 | AG9504_12_5 | CATAAGGGCTATCGTAGTTTTCTGGGGTAGAAAATGTAGCCCATTTCTTG |
| 179 | AG9505_12_6 | CCACCTCATGGGCTACACCTTGACCTAACGTCTTTACGTGGGTACTTGCG |
| 180 | AG9506_12_7 | CTTACTTTGTAGCCTTCATCAGGGTTTGCTGAAGATGGCGGTATATAGGC |
| 181 | AG9507_12_8 | TGAGCAAGAGGTGGTGAGGTTGATCGGGGTTTATCGATTACAGAACAGGC |
| 182 | AG9508_12_9 | TCCTCTAGAGGGATATGAAGCACCGCCAGGTCCTTTGAGTTTTAAGCTGT |

Sequence Listing

| SEQ ID NO: | Oligo Name | Sequence (5' to 3') |
|---|---|---|
| 183 | AG9509_12_10 | GGCTCGTAGTGTTCTGGCGAGCAGTTTTGTTGATTTAACTGTTGAGGTTT |
| 184 | AG9510_12_11 | AGGGCTAAGCATAGTGGGGTATCTAATCCCAGTTTGGGTCTTAGCTATTG |
| 185 | AG9511_12_12 | TGTGTTCAGATATGTTAAAGCCACTTTCGTAGTCTATTTTGTGTCAACTG |
| 186 | AG9512_12_13 | GAGTTTTTTACAACTCAGGTGAGTTTTAGCTTTATTGGGGAGGGGGTGAT |
| 187 | AG9513_12_14 | CTAAAACACTCTTTACGCCGGCTTCTATTGACTTGGGTTAATCGTGTGAC |
| 188 | AG9514_12_15 | CGCGGTGGCTGGCACGAAATTGACCAACCCTGGGGTTAGTATAGCTTAGT |
| 189 | AG9515_12_16 | TAAACTTTCGTTTATTGCTAAAGGTTAATCACTGCTGTTTCCCGTGGG |
| 190 | AG9516_12_17 | TGTGGCTAGGCTAAGCGTTTTGAGCTGCATTGCTGCGTGCTTGATGCTTG |
| 191 | AG9517_12_18 | TTCCTTTTGATCGTGGTGATTTAGAGGGTGAACTCACTGGAACGGGGATG |
| 192 | AG9518_12_19 | CTTGCATGTGTAATCTTACTAAGAGCTAATAGAAAGGCTAGGACCAAACC |
| 193 | AG9519_5_1 | AAAGCCTACAGCACCCGGTATTCCCAGGCGGTCTCCCATCCAAGTACTAA |
| 194 | AG9520_5_2 | CCAGGCCCGACCCTGCTTAGCTTCCGAGATCAGACGAGATCGGGCGCGTT |
| 195 | AG9521_5_3 | TTCCGAGATCAGACGAGATCGGGCGCGTTCAGGGTGGTATGGCCGTAGAC |

What is claimed is:

1. A method for depleting an undesirable RNA molecule in a biological sample on a spatial array, the method comprising:
   (a) providing the biological sample on the spatial array, wherein the spatial array comprises a plurality of attached capture probes, wherein a capture probe of the plurality of capture probes comprises (i) a spatial barcode and (ii) a capture domain that is substantially complementary to an analyte of a plurality of analytes in the biological sample;
   (b) adding a plurality of undesirable RNA depletion probes to the biological sample, wherein an undesirable RNA depletion probe of the plurality of undesirable RNA depletion probes comprises a sequence that is substantially complementary to a sequence of the undesirable RNA molecule;
   (c) hybridizing the undesirable RNA depletion probe to the undesirable RNA molecule, thereby generating an undesirable RNA depletion probe-undesirable RNA molecule complex; and
   (d) removing the undesirable RNA depletion probe-undesirable RNA molecule complex to deplete the undesirable RNA molecule in the biological sample on the spatial array.

2. The method of claim 1, wherein the undesirable RNA depletion probe is a DNA probe.

3. The method of claim 1, wherein the removing step comprises contacting the undesirable RNA depletion probe-undesirable RNA molecule complex with a ribonuclease.

4. The method of claim 1, wherein the ribonuclease is RNase H.

5. The method of claim 4, wherein the RNase H is RNase H1, RNase H2, or a thermostable RNase H.

6. The method of claim 1, wherein the undesirable RNA depletion probe is substantially complementary to all or a portion of the sequence of the undesirable RNA molecule.

7. The method of claim 1, wherein multiple undesirable RNA depletion probes of the plurality of undesirable RNA depletion probes hybridizes to one or more undesirable RNA molecules in the biological sample.

8. The method of claim 1, wherein the undesirable RNA molecule is a transfer RNA (tRNA), a ribosomal RNA (rRNA), a messenger RNA (mRNA), a mitochondrial RNA, a nuclear RNA, or a cytoplasmic RNA, or combinations thereof.

9. The method of claim 8, wherein the undesirable RNA molecule is rRNA.

10. The method of claim 1, wherein the analyte is a ribonucleic acid (RNA).

11. The method of claim 10, wherein the RNA is mRNA.

12. The method of claim 1, further comprising:
   hybridizing the analyte to the capture domain of the capture probe; and
   determining (i) all or a part of the sequence of the analyte hybridized to the capture domain, or a complement thereof, and (ii) the spatial barcode, or a complement thereof, and using the determined sequence of (i) and (ii) to identify the location or abundance of the analyte in the biological sample.

13. The method of claim 12, further comprising extending a 3' end of the capture probe using the analyte as a template to generate an extended capture probe.

14. The method of claim 13, further comprising generating a nucleic acid molecule that is complementary to all or a part of the extended capture probe.

15. The method of claim 12, wherein determining (i) and (ii) comprises sequencing.

16. The method of claim 12, wherein the analyte is amplified after hybridization to the capture domain of the capture probe and prior to determining (i) all or part of the sequence of the analyte hybridized to the capture domain and (ii) the spatial barcode.

17. The method of claim 1, wherein the capture probe further comprises one or more functional domains, a unique molecular identifier, a cleavage domain, or combinations thereof.

18. The method of claim 1, wherein the capture domain comprises a poly-uridine sequence or a poly-thymidine sequence.

19. The method of claim 1, wherein the biological sample is a tissue section sample.

20. The method of claim 1, wherein the biological sample is an FFPE tissue sample.

21. The method of claim 1, wherein the biological sample is decrosslinked.

22. The method of claim 1, wherein the biological sample is previously stained.

23. The method of claim 22, wherein the biological sample is stained using hematoxylin and eosin (H&E).

24. The method of claim 22, wherein the biological sample is stained using immunofluorescence or immunohistochemistry.

25. The method of claim 1, further comprising imaging the biological sample on the spatial array.

26. The method of claim 1, further comprising contacting the biological sample with a permeabilization agent.

27. The method of claim 26, wherein the permeabilization agent comprises proteinase K or pepsin.

28. The method of claim 1, wherein the undesirable RNA depletion probe further comprises a capture moiety, wherein the removing step comprises using a capture moiety-binding agent that binds specifically to the capture moiety.

29. The method of claim 28, wherein the capture moiety is streptavidin, avidin, biotin, or a fluorophore.

30. The method of claim 28, wherein the capture moiety is positioned 5' or 3' to the sequence that is substantially complementary to the sequence of the undesirable RNA molecule.

* * * * *

UNITED STATES PATENT AND TRADEMARK OFFICE
CERTIFICATE OF CORRECTION

PATENT NO. : 11,535,887 B2
APPLICATION NO. : 17/546625
DATED : December 27, 2022
INVENTOR(S) : Caroline Julie Gallant and Linda Kvastad It is certified that error appears in the above-identified patent and that said Letters Patent is hereby corrected as shown below:

On the Title Page

Column 2 (item (56), U.S. Patent Documents), Line 18, delete "Kura" and insert -- Kurn --.

Signed and Sealed this
Twenty-first Day of February, 2023

Katherine Kelly Vidal
*Director of the United States Patent and Trademark Office*